(12) United States Patent
Sandanayaka et al.

(10) Patent No.: US 9,428,490 B2
(45) Date of Patent: *Aug. 30, 2016

(54) NUCLEAR TRANSPORT MODULATORS AND USES THEREOF

(75) Inventors: Vincent P. Sandanayaka, Northboro, MA (US); Sharon Shacham, Newton, MA (US); Michael Kauffman, Newton, MA (US); Sharon Shechter, Andover, MA (US); Dilara McCauley, Arlington, MA (US); Yosef Landesman, Brookline, MA (US); William Senapedis, Millis, MA (US); Jean-Richard Saint-Martin, Walpole, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/235,342

(22) PCT Filed: Jul. 26, 2012

(86) PCT No.: PCT/US2012/048368
§ 371 (c)(1),
(2), (4) Date: Sep. 9, 2014

(87) PCT Pub. No.: WO2013/019561
PCT Pub. Date: Feb. 7, 2013

(65) Prior Publication Data
US 2015/0018332 A1    Jan. 15, 2015

Related U.S. Application Data

(60) Provisional application No. 61/513,432, filed on Jul. 29, 2011, provisional application No. 61/513,428, filed on Jul. 29, 2011, provisional application No. 61/653,588, filed on May 31, 2012.

(51) Int. Cl.

| | |
|---|---|
| *C07D 403/06* | (2006.01) |
| *C07D 403/12* | (2006.01) |
| *C07D 401/14* | (2006.01) |
| *C07D 405/14* | (2006.01) |
| *C07D 401/08* | (2006.01) |
| *C07D 401/12* | (2006.01) |
| *C07D 403/14* | (2006.01) |
| *C07D 413/12* | (2006.01) |
| *C07D 487/10* | (2006.01) |
| *C07D 401/06* | (2006.01) |

(52) U.S. Cl.
CPC .......... *C07D 403/06* (2013.01); *C07D 401/06* (2013.01); *C07D 401/08* (2013.01); *C07D 401/12* (2013.01); *C07D 401/14* (2013.01); *C07D 403/12* (2013.01); *C07D 403/14* (2013.01); *C07D 405/14* (2013.01); *C07D 413/12* (2013.01); *C07D 487/10* (2013.01)

(58) Field of Classification Search
CPC .................................................... C07D 403/06
See application file for complete search history.

(56) References Cited

U.S. PATENT DOCUMENTS

| | | |
|---|---|---|
| 5,153,201 A | 10/1992 | Aono et al. |
| 6,462,049 B1 | 10/2002 | Ogura et al. |
| 8,304,438 B2 * | 11/2012 | Strobel et al. ................ 514/357 |
| 8,513,230 B2 | 8/2013 | Shacham et al. |
| 8,999,996 B2 | 4/2015 | Sandanayaka et al. |
| 9,079,865 B2 * | 7/2015 | Sandanayaka et al. |
| 2003/0018025 A1 | 1/2003 | Thurkauf et al. |
| 2009/0221586 A1 | 9/2009 | Okada et al. |
| 2009/0298896 A1 | 12/2009 | Sakuma et al. |
| 2010/0016272 A1 * | 1/2010 | Strobel et al. ........... 514/210.01 |
| 2010/0056569 A1 | 3/2010 | Nan et al. |
| 2011/0275607 A1 * | 11/2011 | Shacham et al. .......... 514/210.2 |
| 2012/0258986 A1 | 10/2012 | Sandanayaka et al. |

(Continued)

FOREIGN PATENT DOCUMENTS

| | | |
|---|---|---|
| CN | 101309912 | 11/2008 |
| CN | 101466687 | 6/2009 |

(Continued)

OTHER PUBLICATIONS

Brekhov, Y., et al.,"Cyanomethyltetrazoles II reactions of the methylene Moiety", *Zhurnal organicheskoi Khimii*, 28(9): 1921-1925 (1992).

(Continued)

*Primary Examiner* — Valerie Rodriguez-Garcia
(74) *Attorney, Agent, or Firm* — Foley Hoag LLP

(57) ABSTRACT

The invention generally relates to nuclear transport modulators, e.g CRM1 inhibitors, and more particularly to a compound represented by formula (I): or a pharmaceutically acceptable salt thereof, wherein the variables are as defined and described herein. The invention also includes the synthesis and use of a compound of structural formula (I), or a pharmaceutically acceptable salt or composition thereof, e.g, in the treatment, modulation and/or prevention of physiological conditions associated with CRM1 activity.

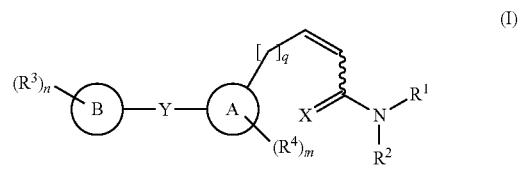

8 Claims, 7 Drawing Sheets

(56) References Cited

U.S. PATENT DOCUMENTS

| | | |
|---|---|---|
| 2013/0317031 A1 | 11/2013 | Sandanayaka et al. |
| 2014/0155370 A1 | 6/2014 | Shacham et al. |
| 2014/0235653 A1 | 8/2014 | Sandanayaka et al. |
| 2014/0364408 A1 | 12/2014 | Sandanayaka et al. |
| 2015/0111893 A1 | 4/2015 | Sandanayaka et al. |

FOREIGN PATENT DOCUMENTS

| | | |
|---|---|---|
| EP | 1 939 180 A1 | 7/2008 |
| EP | 1992618 A1 | 11/2008 |
| EP | 2 090 570 A1 | 8/2009 |
| WO | WO 2007/147336 A1 | 12/2007 |
| WO | WO 2011/109799 A1 | 9/2011 |
| WO | WO 2012/099807 | 7/2012 |
| WO | WO 2013/019548 | 2/2013 |
| WO | WO 2013/019561 A1 | 2/2013 |
| WO | WO 2013/0170068 | 11/2013 |
| WO | WO 2014/144772 A1 | 9/2014 |
| WO | WO 2014/152263 A1 | 9/2014 |
| WO | WO 2014/205389 A1 | 12/2014 |
| WO | WO 2014/205393 A1 | 12/2014 |

OTHER PUBLICATIONS

Buckler, R.T., et al., "Synthesis and Antiinflammatory Activity of Some 1,2,3- and 1,2,4-Triazolerpropionic Acids", *Journal of Medicinal Chemistry*, 21(12): 1254-1260 (1978).

Extended Search Report for EP Application No. 11751491.9, "Nuclear Transport Modulators and Uses Thereof", Date of Completion of the Search: Dec. 17, 2013.

Extended Search Report for EP Application No. 12736172.3, "Olefin Containing Nuclear Transport Modulators and Uses Thereof", Date of Completion of the Search: May 8, 2014.

Final Office Action dated Feb. 27, 2015 for U.S. Appl. No. 13/350,864, "Olefin Containing Nuclear Transport Modulators and Uses Thereof".

Golub, T.R., et al., "Molecular Classification of Cancer: Class Discovery and Class Prediction by Gene Expression Monitoring", *Science*, 286: 531-536 (1999).

Huff, J., "HIV Protease: A Novel Chemotherapeutic Target for AIDS", *Journal of Medicinal Chemistry*, 34(8): 2305-2314 (1991).

Lala, P.K., et al., "Role of nitric oxide in tumor progression: Lessons from experimental tumors", *Cancer and Metastasis Reviews*, 17: 91-106 (1998).

Lapalombella, R., et al., "Selective Inhibitors of nuclear exports show that CRM1/XPO1 is a target in chronic lymphocytic leukemia", *Blood*, 120(23): 4621-4634 (Nov. 29, 2012).

Non-Final Office Action dated Jul. 3, 2014 for U.S. Appl. No. 14/219,638 "Hydrazide Containing Nuclear Transport Modulators and Uses Thereof".

Non-Final Office Action dated May 27, 2014 for U.S. Appl. No. 13/350,864 "Olefin Containing Nuclear Transport Modulators and Uses Thereof".

Non-Final Office Action dated Oct. 21, 2014 for U.S. Appl. No. 13/891,044 "Nuclear Transport Modulators and Uses Thereof".

Non-Final Office Action for U.S. Appl. No. 13/931,372 "Nuclear Transport Modulators and Uses Thereof" dated Feb. 9, 2015.

Non-Final Office Action for U.S. Appl. No. 14/399,868 "Nuclear Transport Modulators and Uses Thereof" dated Feb. 13, 2015.

Notice of Allowability for U.S. Appl. No. 14/219,638 "Hydrazide Containing Nuclear Transport Modulators and Uses Thereof" mailed Oct. 10, 2014.

Notification Concerning Transmittal of International Preliminary Report on Patentability for International Application No. PCT/US2012/048368, Nuclear Transport "Modulators and Uses Thereof"; Date of Issuance of the Report: Feb. 4, 2014.

Notification Concerning Transmittal of International Preliminary Report on Patentability for International Application No. PCT/US2012/048319, "Hydrazide Containing Nuclear Transport Modulators and Uses Thereof"; Date of Issuance of the Report: Feb. 4, 2014.

Notification Concerning Transmittal of International Preliminary Report on Patentability for International Application No. PCT/US2013/040404, "Nuclear Transport Modulators and Uses Thereof"; Date of Issuance of the Report: Nov. 11, 2014.

Notification of Transmittal of the International Search Report and the Written Opinion of the International Searching Authority, or the Declaration for International Application No. PCT/US2014/027136 "Exo Olefin-Containing Nuclear Transport Modulators and Uses Thereof"; Date of Mailing: Jul. 11, 2014.

Notification of Transmittal of the International Search Report and the Written Opinion of the International Searching Authority, or the Declaration for International Application No. PCT/US2014/029322 "Methods of Promoting Wound Healing Using CRM1 Inhibitors"; Date of Mailing: May 28, 2014.

Notification of Transmittal of the International Search Report and the Written Opinion of the International Searching Authority, or the Declaration for International Application No. PCT/US2014/043484 "Nuclear Transport Modulators and Uses Thereof"; Date of Mailing: Sep. 2, 2014.

Notification of Transmittal of the International Search Report and the Written Opinion of the International Searching Authority, or the Declaration for International Application No. PCT/US2014/043479 "Nuclear Transport Modulators and Uses Thereof"; Date of Mailing: Sep. 17, 2014.

Quan, M.L., et al., "Design and Synthesis of Isoxazoline Derivatives as Factor Xa lhibitors", *J. Med. Chem.* 42: 2760-2773 (1999).

Shaoyong, Ke., et al., "Research Advance of Acylhydrazine Derivatives with Biological Activities", *Chinese Journal of Organic Chemistry* 30(12): 1820-1830 (2010).

Sun Q., et al., "Nuclear export inhibition through covalent conjugation and hydrolysis of Leptomycin B by CRM1", *PNAS*, 110(4): 1303-1308 (Jan. 22, 2013).

Yu, E., "Reactions of Hydroxyphenyl-Substituted 1,2,4-Triazoles with Electrophylic Reagents", *Russian Journal of General Chemistry*, 79(10): 2234-2243 (2009).

Notice of Allowance, U.S. Appl. No. 14/235,306, "Hydrazine Containing Nuclear Transport Modulators and Uses Thereof," Dated: Apr. 6, 2015.

Notice of Allowance, U.S. Appl. No. 13/891,044, "Nuclear Transport Modulators and Uses Thereof," Dated: Apr. 7, 2015.

Balsamini, "(E)-3-(2-(N-Phenylcarbamoyl)vinyl)pyrrole-2-carboxylic Acid Derivatives. A Novel Class of Glycine Site Antagonists", *Journal of Medicinal Chemistry*, 41(6):808-820 (Jan. 1, 1998).

Cai, X., et al., "Inhibition of Thr-55 phosphorylation restores p53 nuclear localization and sensitizes cancer cells to DNA damage", *PNAS*, 105(44):16958-16963 (Nov. 4, 2008).

Cronshaw, J.M., et al., "The nuclear pore complex: disease associations and functional correlations", *TRENDS Endocrin Metab.* 15:34-39 (2004).

Daelemans, D., et al., "A synthetic HIV-1 Rev inhibitor interfering with the CRM1-mediated nuclear export", *PNAS*, 99(22):14440-14445 (Oct. 29, 2002).

Davis, J.R., et al., "Controlling protein compartmentalization to overcome disease" *Pharmaceut Res.*, 24:17-27 (2007).

Falini, B., et al., "Both carboxy-terminus NES motif and mutated tryptophan(2) are crucial for aberrant nuclear export of nucleophosmin leukemic mutants in NPMc+ AML", *Blood Journal*, 107(11):45144523.

Freundt, E.C., et al., "Molecular Determinants for Subcellular Localization of the Severe Acute Respiratory Syndrome Coronavirus Open Reading Frame 3b Protein", *Journal of Virology*, 83(13):6631-6640 (Jul. 2009).

Ghildyal, R., et al., "The Respiratory Syncytial Virus Matrix Protein Possesses a Crm1-Mediated Nuclear Export Mechanism", *Journal of Virology*, 83(11):5353-5362 (Jun. 2009).

Ghosh, C.C., et al., "Analysis of nucleocytoplasmic shuttling of NF kappa B proteins in human leukocytes", *Methods Mol. Biol.* 457:279-92 (2008).

Gupta, N., et. al., "Retinal tau pathology in human glaucomas" *Can J Ophthalmol.* 43(1):53-60 (Feb. 2008).

Hoffman, Thomas J., et al., "Synthesis of Vinyl-Functionalized Oxazoles by Olefin Cross-Metathesis", *J. Org. Chem.* 73: 2400-2403 (2008).

(56) References Cited

OTHER PUBLICATIONS

Hoshino, L., et al., "Combined effects of p53 gene therapy and leptomycin B in human esophageal squamous cell carcinoma", *Oncology*, 75:113-119 (2008).
International Search Report for International Application No. PCT/US2011/027328, "Nuclear Transport Modulators and Uses Thereof" dated Apr. 29, 2011.
International Search Report for International Application No. PCT/US2012/048368, "Nuclear Transport Modulators and Uses Thereof" dated Sep. 21, 2012.
International Search Report for International Application No. PCT/US2012/048319, "Hydrazide Containing Nuclear Transport Modulators and Uses Thereof" dated Jul. 29, 2011.
Kau, T.R., et al., "A chemical genetic screen identifies inhibitors of regulated nuclear export of a Forkhead transcription factor in PTEN-deficient tumor cells", *Cancer Cell*, pp. 463-476 (2003).
Lain, S. et al., "Accumulating active p53 in the nucleus by inhibition of nuclear export: a novel strategy to promote the p53 tumor suppressor function", *Exp Cell Res*. 253:315 (1999).
Lain, S. et al., "An inhibitor of nuclear export activates the p53 response and induces the localization of HDM2 and p53 to U1A-positive nuclear bodies associated with the PODs", *Exp Cell Res*. 248:457-472 (1999).
Li, A., et al., "Upregulation of CRM1 Relates to Neuronal Apoptosis after Traumatic Brain Injury in Adult Rats", *J Mol Neurosci*, DOI 10.1007/s12031-013-9994-7, Published online Mar. 15, 2013.
Modzelewska-Banachiewicz, B., et al., "Synthesis and biological activity of (Z) and (E) isomers of 3-(3,4-diaryl-1-1,2,4-triazole-5-yl)prop-2-enoic acid" *Monatsh Chem*. 140:439-444 (2009).
Modzelewska-Banachiewicz, B., et al., "Synthesis and biological activity of new derivatives of 3-(3,4-diaryl-1-1,2,4-triazole-5-yl)propenoic acid" *European Journal of Medicinal Chemistry*, 39:873-877 (2004).
Monecke, T., et al., "Crystal Structure of the Nuclear Export Receptor CRM1 in Complex with Snurportin1 and RanGTP", *Science*, 324:1087-1091 (May 22, 2009).
Muller, P.A.J., et al., "Nuclear-Cytosolic Transport of COMMD1 Regulates NF-κB and HIF-1 Activity", *Traffic*, 10:514-527 (2009).
Mutka, S., et al., "Nuclear export inhibitors (NEIs) as novel cancer therapeutics", *98th AACr Ann. Mtg*., 2 pgs (Apr. 14-18, 2007).
Nakahara, J., et al., "Abnormal expression of TIP30 and arrested nucleocytoplasmic transport within oligodendrocyte precursor cells in multiple sclerosis", *Journal of Clinical Investigation*, 119(1):169-181 (Jan. 2009).
Non-Final Office Action dated Sep. 21, 2012 for U.S. Appl. No. 13/041,377 "Nuclear Transport Modulators and Uses Thereof".
Noske, A., et al., "Expression of the Nuclear Export Protein Chromosomal Region Maintenance/Exportin 1/Xpo1 Is a Prognostic Factor in Human Ovarian Cancer", *Cancer*, 112(8):1733-1743 (Apr. 15, 2008).
Notice of Allowability for U.S. Appl. No. 13/041,377 "Nuclear Transport Modulators and Uses Thereof", mailed May 2, 2013.
Notification Concerning Transmittal of International Preliminary Report on Patentability for International Application No. PCT/US2011/027328, "Nuclear Transport Modulators and Uses Thereof" dated Sep. 11, 2012.
Notification Concerning Transmittal of International Preliminary Report on Patentability for International Application No. PCT/US2012/021406, "Olefin Containing Nuclear Transport Modulators and Uses Thereof" dated Jul. 17, 2013.
Notification of Transmittal of the International Search Report and the Written Opinion of the International Searching Authority for International Application No. PCT/US2012/021406, "Olefin Containing Nuclear Transport Modulators and Uses Thereof" dated Apr. 30, 2012.
Notification of Transmittal of the International Search Report and The Written Opinion of the International Searching Authority for International Application No. PCT/US2013/040404, "Nuclear Transport Modulators and Uses Thereof"; Date of Mailing: Nov. 18, 2013.
Patani, G.A., et al., "Bioisosterism: A Rational Approach in Drug Design", *Amer. Chem. Soc.*, 96:3147-3176 (1996).
Rawlinson, S.M., et al., "CRM1-mediated Nuclear Export of Dengue Virus RNA Polymerase NS5 Modulates Interleukin-8 Induction and Virus Production", *Journal of Biological Chemistry*, 284(23):15589-15597 (Jun. 5, 2009).
Sanchez, V., et al., "Nuclear Export of the Human Cytomegalovirus Tegument Protein pp65 Requires Cyclin-Dependent Kinase Activity and the Crm1 Exporter", *Journal of Virology*, 81(21):11730-11736 (Nov. 2007).
Sorokin, A.V., et al., "Nucleocytoplasmic Transport of Proteins", *Biochemistry*, 72(13):1439-1457 (2007).
Terry, L.J., et al., "Crossing the Nuclear Envelope: Hierarchical Regulation of Nucleocytoplasmic Transport", *Science*, 318:1412-1416(Nov. 30, 2007).
van der Watt, P.J., et al., "The Karyopherin proteins, Crm1 and Karyopherin β1, are overexpressed in cervical cancer and are critical for cancer cell survival and proliferation", *Int. J. Cancer*, 124:1829-1840 (2009).
Van Neck, T., et al., "Inhibition of the CRM1-mediated nucleocytoplasmic transport by N-azolylacrylates: Structure-activity relationship and mechanism of action", Biorganic & Medicinal Chemistry 16:9487-9497 (2008).
Walsh, Jr., M.D., et al., Exportin 1 Inhibition Attenuates Nuclear Factor-κB-Dependent Gene Expression, *Shock*, 29(2):160-166 (2008).
Williams, P., et al., "Characterization of a CRM1-Dependent Nuclear Export Signal in the C Terminus of Herpes Simplex Virus Type 1 Tegument Protein UL47", *Journal of Virology*, 82(21):10946-10952.
Written Opinion of the International Searching Authority for International Application No. PCT/US2011/027328, "Nuclear Transport Modulators and Uses Thereof" dated Apr. 29, 2011.
Written Opinion of the International Searching Authority for International Application No. PCT/US2012/048368, "Nuclear Transport Modulators and Uses Thereof" dated Sep. 21, 2012.
Written Opinion of the International Searching Authority for International Application No. PCT/US2012/048319, "Hydrazide Containing Nuclear Transport Modulators and Uses Thereof" dated Nov. 9, 2012.
Yao, Y., et al., "The expression of CRM1 is associated with prognosis in human osteosarcoma", *Oncology Reports*, 21:229-235 (2009).
Zimmerman, T.L., et al., "Nuclear Export of Retinoid X Receptor α in Response to Interleukin-1β-mediated Cell Signaling", *The Journal of Biological Chemistry*, 281(22):15434-15440 (Jun. 2, 2006.

\* cited by examiner

NUCLEAR TRANSPORT MODULATORS AND USES THEREOF

RELATED APPLICATIONS

This application is the U.S. National Stage of International Application No. PCT/US2012/048368, which designated the United States and was filed Jul. 26, 2012, published in English, which claims the benefit of U.S. Provisional Application No. 61/513,428, filed Jul. 29, 2011, U.S. Provisional Application No. 61/513,432, filed Jul. 29, 2011, and U.S. Provisional Application No. 61/653,588, filed May 31, 2012. The contents of the above applications are incorporated herein by reference in their entirety.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al. 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al. 2008; Hoshino et al. 2008; Lain et al. 1999a; Lain et al. 1999b; Smart et al. 1999), can restore sensitivity of cancer cells to DNA damaging agents (Cai et al. 2008), and can lead to regression of established tumors (Sharpless & DePinho 2007, Xue et al. 2007). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009). CRM1 inhibition may provide particularly interesting utility in familial cancer syndromes (e.g., Li-Fraumeni Syndrome due to loss of one p53 allele, BRCA1 or 2 cancer syndromes), where specific tumor suppressor proteins (TSP) are deleted or dysfunctional and where increasing TSP levels by systemic (or local) administration of CRM1 inhibitors could help restore normal tumor suppressor function.

Specific proteins and RNAs are carried into and out of the nucleus by specialized transport molecules, which are classified as importins if they transport molecules into the nucleus, and exportins if they transport molecules out of the nucleus (Terry et al. 2007; Sorokin et al. 2007). Proteins that are transported into or out of the nucleus contain nuclear import/localization (NLS) or export (NES) sequences that allow them to interact with the relevant transporters. Chromosomal Region Maintenance 1 (Crm1 or CRM1), which is also called exportin-1 or Xpo1, is a major exportin.

Overexpression of Crm1 has been reported in several tumors, including human ovarian cancer (Noske et al. 2008), cervical cancer (van der Watt et al. 2009), pancreatic cancer (Huang et al. 2009), hepatocellular carcinoma (Pascale et al. 2005) and osteosarcoma (Yao et al. 2009) and is independently correlated with poor clinical outcomes in these tumor types.

Inhibition of Crm1 blocks the exodus of tumor suppressor proteins and/or growth regulators such as p53, c-Abl, p21, p27, pRb, BRCA1, IkB, ICp27, E2F4, KLF5, YAP1, ZAP, KLF5, HDAC4, HDAC5 or forkhead proteins (e.g., FOXO3a) from the nucleus that are associated with gene expression, cell proliferation, angiogenesis and epigenetics. Crm1 inhibitors have been shown to induce apoptosis in cancer cells even in the presence of activating oncogenic or growth stimulating signals, while sparing normal (untransformed) cells. Most studies of Crm1 inhibition have utilized the natural product Crm1 inhibitor Leptomycin B (LMB). LMB itself is highly toxic to neoplastic cells, but poorly tolerated with marked gastrointestinal toxicity in animals (Roberts et al. 1986) and humans (Newlands et al. 1996). Derivatization of LMB to improve drug-like properties leads to compounds that retain antitumor activity and are better tolerated in animal tumor models (Yang et al. 2007, Yang et al. 2008, Mutka et al. 2009). Therefore, nuclear export inhibitors could have beneficial effects in neoplastic and other proliferative disorders.

In addition to tumor suppressor proteins, Crm1 also exports several key proteins that are involved in many inflammatory processes. These include IkB, NF-kB, Cox-2, RXRα, Commd1, HIF1, HMGB1, FOXO, FOXP and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LMB not only results in accumulation of transcriptionally inactive, nuclear IkBa-NF-kB complex but also prevents the initial activation of NF-kB even upon cell stimulation (Ghosh 2008, Huang 2000). In a different study, treatment with LMB inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB and hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

Crm1 also mediates retinoid X receptor α (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. LMB is able to prevent IL-1β induced cytoplasmic increase in RXRα levels in human liver derived cells (Zimmerman 2006).

The role of Crm1-mediated nuclear export in NF-kB, HIF-1 and RXRα signalling suggests that blocking nuclear export can be potentially beneficial in many inflammatory processes across multiple tissues and organs including the vasculature (vasculitis, arteritis, polymyalgia rheumatic, atherosclerosis), dermatologic (see below), rheumatologic (rheumatoid and related arthritis, psoriatic arthritis, spondyloarthropathies, crystal arthropathies, systemic lupus erythematosus, mixed connective tissue disease, myositis syndromes, dermatomyositis, inclusion body myositis, undifferentiated connective tissue disease, Sjogren's syndrome, scleroderma and overlap syndromes, etc.).

CRM1 inhibition affects gene expression by inhibiting/activating a series of transcription factors like ICp27, E2F4, KLF5, YAP1, and ZAP.

Crm1 inhibition has potential therapeutic effects across many dermatologic syndromes including inflammatory dermatoses (atopy, allergic dermatitis, chemical dermatitis, psoriasis), sun-damage (ultraviolet (UV) damage), and infections. CRM1 inhibition, best studied with LMB, showed minimal effects on normal keratinocytes, and exerted anti-inflammatory activity on keratinocytes subjected to UV, TNFα, or other inflammatory stimuli (Kobayashi & Shinkai 2005, Kannan & Jaiswal 2006). Crm1 inhibition also upregulates NRF2 (nuclear factor erythroid-related factor 2) activity, which protects keratinocytes (Schafer et al. 2010, Kannan & Jaiswal 2006) and other cell types (Wang et al. 2009) from oxidative damage. LMB induces apoptosis in keratinocytes infected with oncogenic human papillomavirus (HPV) strains such as HPV16, but not in uninfected keratinocytes (Jolly et al. 2009).

Crm1 also mediates the transport of key neuroprotectant proteins that may be useful in neurodegenerative diseases including Parkinson's disease (PD), Alzheimer's disease, and amyotrophic lateral sclerosis (ALS). For example, by (1) forcing nuclear retention of key neuroprotective regulators such as NRF2 (Wang 2009), FOXA2 (Kittappa et al. 2007), parking in neuronal cells, and/or (2) inhibiting NFκB transcriptional activity by sequestering IκB to the nucleus in glial cells, Crm1 inhibition could slow or prevent neuronal cell death found in these disorders. There is also evidence linking abnormal glial cell proliferation to abnormalities in CRM1 levels or CRM1 function (Shen 2008).

Intact nuclear export, primarily mediated through CRM1, is also required for the intact maturation of many viruses. Viruses where nuclear export, and/or CRM1 itself, has been implicated in their lifecycle include human immunodeficiency virus (HIV), adenovirus, simian retrovirus type 1, Borna disease virus, influenza (usual strains as well as H1N1 and avian H5N1 strains), hepatitis B (HBV) and C(HCV) viruses, human papillomavirus (HPV), respiratory syncytial virus (RSV), Dungee, Severe Acute Respiratory Syndrome coronavirus, yellow fever virus, West Nile virus, herpes simplex virus (HSV), cytomegalovirus (CMV), and Merkel cell polyomavirus (MCV). (Bhuvanakantham 2010, Cohen 2010, Whittaker 1998). It is anticipated that additional viral infections reliant on intact nuclear export will be uncovered in the future.

The HIV-1 Rev protein, which traffics through nucleolus and shuttles between the nucleus and cytoplasm, facilitates export of unspliced and singly spliced HIV transcripts containing Rev Response Elements (RRE) RNA by the CRM1 export pathway. Inhibition of Rev-mediated RNA transport using CRM1 inhibitors such as LMBor PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, Dengue fever (DF), and its more severe and potentially deadly Dengue hemorrhagic fever (DHF). DHF appears to be the result of an over exuberant inflammatory response to DENV. NS5 is the largest and most conserved protein of DENV. CRM1 regulates the transport of NS5 from the nucleus to the cytoplasm, where most of the NS5 functions are mediated Inhibition of CRM1-mediated export of NS5 results in altered kinetics of virus production and reduces induction of the inflammatory chemokine interleukin-8 (IL-8), presenting a new avenue for the treatment of diseases caused by DENV and other medically important flaviviruses including hepatitis C virus (Rawlinson 2009).

Other virus-encoded RNA-binding proteins that use CRM1 to exit the nucleus include the HSV type 1 tegument protein (VP13/14, or hUL47), human CMV protein pp 65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. CRM1 inhibitors could therefore have beneficial effects on both the viral infectious process as well as on the process of neoplastic transformation due to these viruses.

CRM1 controls the nuclear localization and therefore activity of multiple DNA metabolizing enzymes including histone deacetylases (HDAC), histone acetyltransferases (HAT), and histone methyltransferases (HMT). Suppression of cardiomyocyte hypertrophy with irreversible CRM1 inhibitors has been demonstrated and is believed to be linked to nuclear retention (and activation) of HDAC 5, an enzyme known to suppress a hypertrophic genetic program (Monovich et al. 2009). Thus, CRM1 inhibition may have beneficial effects in hypertrophic syndromes, including certain forms of congestive heart failure and hypertrophic cardiomyopathies.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

To date, however, small-molecule, drug-like Crm1 inhibitors for use in vitro and in vivo are uncommon.

SUMMARY OF THE INVENTION

The present invention relates to compounds, or pharmaceutically acceptable salts thereof, useful as nuclear transport modulators. The invention also provides pharmaceutically acceptable compositions comprising compounds of the present invention and methods of using said compounds and compositions in the treatment of various disorders, such as disorders or conditions associated with abnormal cellular responses triggered by improper nuclear transport.

In one embodiment of the invention, the compounds useful as nuclear transport modulators are represented by formula I:

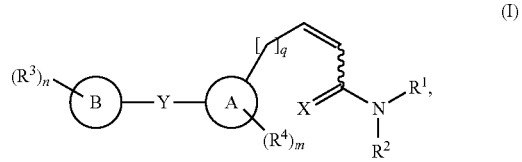

or a pharmaceutically acceptable salt thereof, wherein each variable is as defined and described herein.

Another embodiment of the invention is a composition comprising a compound of the invention, or a pharmaceutically acceptable salt thereof, and a pharmaceutically acceptable carrier.

Yet another embodiment of the invention is a method for treating a disorder associated with CRM1 activity, the method comprising administering to a subject in need thereof a therapeutically effective amount of a compound of the invention, or a pharmaceutically acceptable salt thereof, or a composition comprising a compound of the invention, or a pharmaceutically acceptable salt thereof.

Another embodiment of the invention is use of a compound of the invention for treating a disorder associated with CRM1 activity in a subject.

Another embodiment of the invention is use of a compound of the invention for the manufacture of a medicament for treating a disorder associated with CRM1 activity in a subject.

The nuclear transport modulators of the present invention, and pharmaceutically acceptable salts and/or compositions thereof, provide excellent in vivo exposure as measured by AUC in mouse, rat, dog and monkey, while exhibiting low levels of brain penetration. Therefore, compounds of the present invention, and pharmaceutically acceptable salts and/or compositions thereof, are useful for treating a variety of diseases, disorders or conditions, associated with abnormal cellular responses triggered by improper nuclear transport, such as those diseases, disorders, or conditions described herein. Compounds provided by this invention are also useful for the study of nuclear transport modulation in biological and pathological phenomena; the study of intracellular signal transduction pathways mediated by kinases; and the comparative evaluation of nuclear transport modulators.

DETAILED DESCRIPTION OF THE INVENTION

Figure 1:
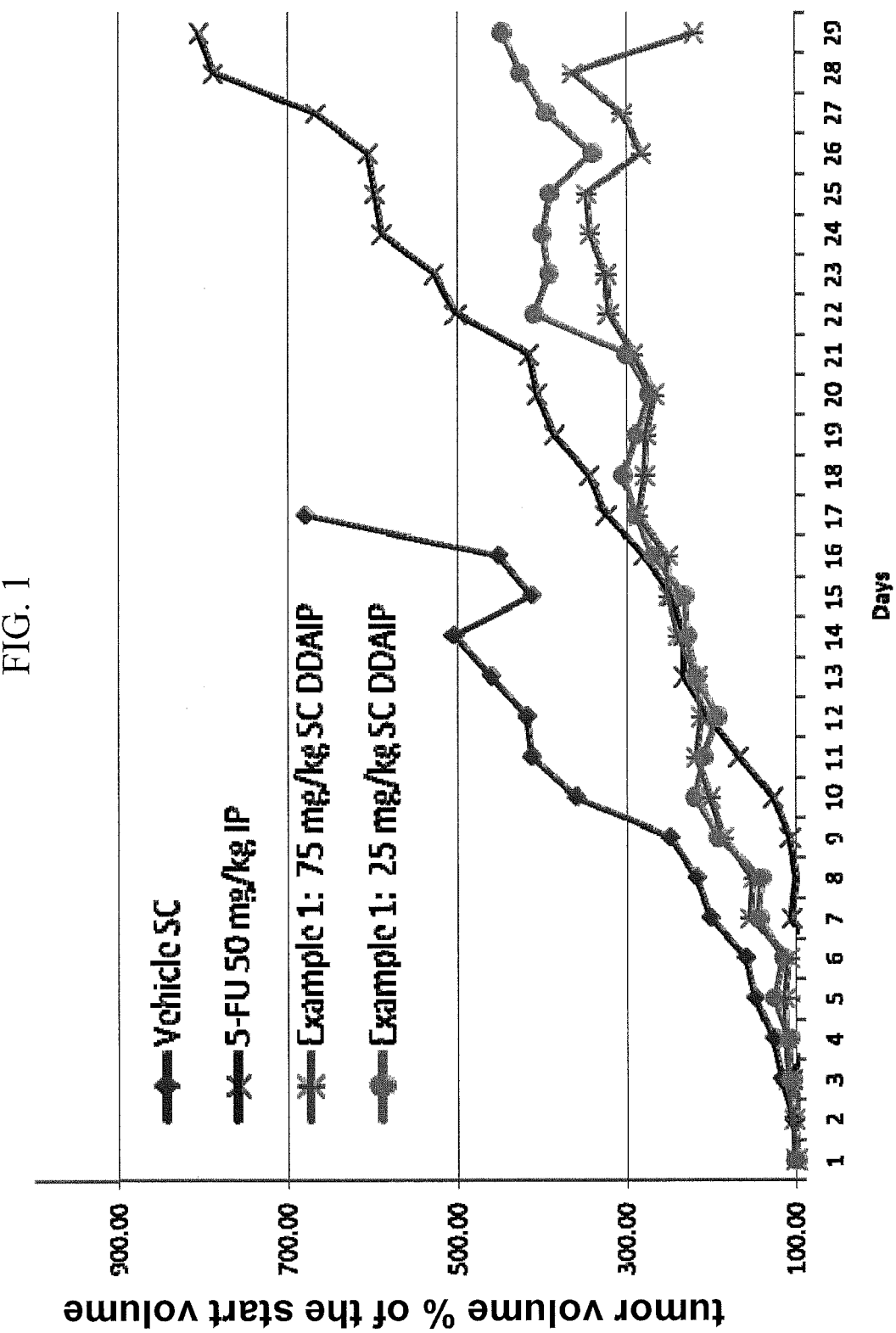
FIG. 1 is a graph of mean tumor volume as a function of time and shows the effect of (Z)-3-(3-(3,5-bis(trifluoromethyl)phenyl)-1H-1,2,4-triazol-1-yl)-1-(3,3-difluoroazetidin-1-yl)prop-2-en-1-one (Compound 1) on tumor volume in a mouse xenograft model of HCT-116.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

The term "aliphatic" or "aliphatic group," as used herein, denotes a monovalent hydrocarbon radical that is straight-chain (i.e., unbranched), branched, or cyclic (including fused, bridged, and spiro-fused polycyclic). An aliphatic group can be saturated or can contain one or more units of unsaturation, but is not aromatic. Unless otherwise specified, aliphatic groups contain 1-6 carbon atoms. However, in some embodiments, an aliphatic group contains 1-10 or 2-8 carbon atoms. In some embodiments, aliphatic groups contain 1-4 carbon atoms and, in yet other embodiments, aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl," as used herein, means a saturated, straight-chain or branched aliphatic group. In one aspect, an alkyl group contains 1-10 or 2-8 carbon atoms. Alkyl includes, but is not limited to, methyl, ethyl, propyl, isopropyl, n-butyl, sec-butyl, t-butyl, and the like.

The term "alkenyl," as used herein, means a straight-chain or branched aliphatic group having one or more carbon-carbon double bonds (i.e., —CH═CH—). In one aspect, an alkenyl group has from two to eight carbon atoms, and includes, for example, and without being limited thereto, ethenyl, 1-propenyl, 1-butenyl and the like. The term "alkenyl" encompasses radicals having carbon-carbon double bonds in the "cis" and "trans" or, alternatively, the "E" and "Z" configurations. If an alkenyl group includes more than one carbon-carbon double bond, each carbon-carbon double bond is independently a cis or trans double bond, or a mixture thereof.

The term "alkynyl," as used herein, means a straight-chain or branched aliphatic radical having one or more carbon-carbon triple bonds (i.e., —C≡C—). In one aspect, an alkyl group has from two to eight carbon atoms, and includes, for example, and without being limited thereto, 1-propynyl (propargyl), 1-butynyl and the like.

The terms "cycloaliphatic," "carbocyclyl," "carbocyclo," and "carbocyclic," used alone or as part of a larger moiety, refer to a saturated or partially unsaturated cyclic aliphatic monocyclic or bicyclic ring system, as described herein, having from 3 to 10 members, wherein the aliphatic ring system is optionally substituted as defined above and described herein. In some embodiments, a cycloaliphatic group has 3-6 carbon atoms. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. The terms "cycloaliphatic," "carbocyclyl," "carbocyclo," and "carbocyclic" also include aliphatic rings that are fused to one or more aromatic or nonaromatic rings, such as decahydronaphthyl, tetrahydronaphthyl, decalin, or bicyclo [2.2.2]octane.

The term "cycloalkyl," as used herein, means a saturated cyclic aliphatic monocyclic or bicyclic ring system having from 3-10 members. A cycloalkyl can be optionally substituted as described herein. In some embodiments, a cycloalkyl has 3-6 carbons.

The term "heterocycloalkyl," as used herein, means a saturated or unsaturated aliphatic ring system in which at least one carbon atom is replaced with a heteroatom selected from N, S and O. A heterocycloalkyl can contain one or more rings, which may be attached together in a pendent manner or may be fused. In one aspect, a heterocycloalkyl is a three- to seven-membered ring system and includes, for example, and without being limited thereto, piperidinyl, piperazinyl, pyrrolidinyl, tetrahydrofuranyl and the like.

The term "heteroatom" means one or more of oxygen, sulfur, nitrogen, phosphorus, or silicon, and includes any oxidized form of nitrogen, sulfur, phosphorus, or silicon; the quaternized form of any basic nitrogen; and a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," as used herein, means —O-alkyl. "Alkoxy" can include a straight-chained or branched alkyl.

In one aspect, "alkoxy" has from one to eight carbon atoms and includes, for example, and without being limited thereto, methoxy, ethoxy, propyloxy, isopropyloxy, t-butoxy and the like.

The term "halo" or "halogen" as used herein means halogen and includes, for example, and without being limited thereto, fluoro, chloro, bromo, iodo and the like, in both radioactive and non-radioactive forms.

The term "haloalkyl," as used herein, means an alkyl group that is substituted with one or more halogen atoms. In some embodiments, haloalkyl refers to a perhalogenated alkyl group. In some embodiments, haloalkyl refers to an alkyl group which is substituted with one or more halogen atoms. Exemplary haloalkyl groups include —CF$_3$, —CCl$_3$, —CF$_2$CH$_3$, —CH$_2$CF$_3$, —CH$_2$(CF$_3$)$_2$, —CF$_2$(CF$_3$)$_2$, and the like.

The term "alkylene," as used herein, means a bivalent branched or unbranched saturated hydrocarbon radical. In one aspect, "alkylene" has one to eight carbon atoms, and includes, for example, and without being limited thereto, methylene, ethylene, n-propylene, n-butylene and the like.

The term "alkenylene," as used herein, means a bivalent branched or unbranched hydrocarbon radical having one or more carbon-carbon double bonds (i.e., —CH═CH—). In one aspect, "alkenylene" has two to eight carbon atoms, and includes, for example, and without being limited thereto, ethenylene, n-propenylene, n-butenylene and the like.

The term "alkynylene," as used herein, means a bivalent branched or unbranched hydrocarbon radical having one or more carbon-carbon triple bonds (i.e., —C≡C—). In one aspect, "alkynylene" has two to eight carbon atoms, and includes, for example, and without being limited thereto, ethynylene, n-propynylene, n-butynylene and the like.

The term "aryl," alone or in combination, as used herein, means a carbocyclic aromatic system containing one or more rings, which may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl and acenaphthyl. An "aryl" group can have 1 to 4 substituents, such as lower alkyl, hydroxyl, halo, haloalkyl, nitro, cyano, alkoxy, lower alkylamino and the like.

The term "heteroaryl," alone or in combination, as used herein, means an aromatic system wherein at least one carbon atom is replaced by a heteroatom selected from N, S and O. A heteroaryl can contain one or more rings, which may be attached together in a pendent manner or may be fused. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, pyrazolyl, tetrazolyl, pyridyl, pyrimidinyl, pyrazinyl, pyridazinyl, indolyl, furyl, benzofuryl, thienyl, benzothienyl, quinolyl, oxazolyl, oxadiazolyl, isoxazolyl, and the like. A "heteroaryl" group can have 1 to 4 substituents, such as lower alkyl, hydroxyl, halo, haloalkyl, nitro, cyano, alkoxy, lower alkylamino and the like.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstituted.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched)alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R$^\circ$, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur. Suitable divalent substituents on a saturated carbon atom of R$^\circ$ include =O and =S.

Suitable divalent substituents on a saturated carbon atom of an "optionally substituted group" include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, and —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, and —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, and —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^\dagger$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers).

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a patient. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds of the Invention

One embodiment of the invention is a compound of formula I:

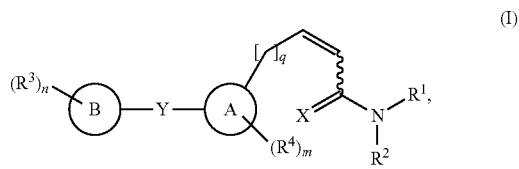

or a pharmaceutically acceptable salt thereof, wherein:

Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur;

Ring B is an optionally substituted ring selected from a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur;

X is selected from O, S, N—CN, and NR;

R is hydrogen or an optionally substituted group selected from $C_{1-6}$ aliphatic, 3-8 membered saturated or partially unsaturated heterocyclic ring having 1-2 heteroatoms independently selected from nitrogen, oxygen, and sulfur, phenyl, and a 5-6 membered heteroaryl ring having 1-4 heteroatoms independently selected from nitrogen, oxygen, and sulfur;

Y is a covalent bond or an optionally substituted bivalent $C_{1-4}$ hydrocarbon group, wherein one methylene unit of Y is optionally replaced by —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—;

each of $R^1$ and $R^2$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or:

$R^1$ and $R^2$ are taken together with their intervening atoms to form a 4-8 membered saturated, partially unsaturated, or aromatic heterocyclic ring having 1-3 heteroatoms independently selected from nitrogen, oxygen, and sulfur, wherein the ring formed thereby is substituted with —($R^5$)$_p$;

each of n, m, and p is independently an integer selected from 0, 1, 2, 3 and 4;

q is an integer selected from 0, 1 and 2;

each of $R^3$, $R^4$, and $R^5$ is independently halogen, —NO$_2$, —CN, —N$_3$, -L-$R^6$, or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or:

two $R^3$ groups on Ring B are taken together with their intervening atoms to form a fused 4-8 membered saturated, partially unsaturated, or aryl ring having 0-3 heteroatoms independently selected from nitrogen, oxygen, and sulfur; or:

two $R^4$ groups on Ring A are taken together with their intervening atoms to form a fused 4-8 membered saturated, partially unsaturated, or aryl ring having 0-3 heteroatoms independently selected from nitrogen, oxygen, and sulfur; or:

two $R^5$ groups on the ring formed by $R^1$ and $R^2$ are taken together with their intervening atoms to form a fused 4-8 membered saturated, partially unsaturated, or aryl ring having 0-3 heteroatoms independently selected from nitrogen, oxygen, and sulfur;

L is a covalent bond or an optionally substituted bivalent $C_{1-6}$ hydrocarbon group, wherein one or two methylene units of L is optionally and independently replaced by -Cy-, —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—;

-Cy- is an optionally substituted bivalent ring selected from a 3-7 membered saturated or partially unsaturated cycloalkylenylene ring, a 4-7-membered saturated or partially unsaturated heterocycloalkylene ring having 1-4 heteroatoms independently selected from nitrogen, oxygen, and sulfur, phenylene, a 5-6 membered monocyclic heteroarylene having 1-4 heteroatoms independently selected from nitrogen, oxygen, and sulfur, an 8-10 membered bicyclic arylene, and an 8-10 membered bicyclic heteroarylene having 1-4 heteroatoms independently selected from nitrogen, oxygen, and sulfur; and each $R^6$ is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 4-7-membered saturated or partially unsaturated heterocyclic ring having 1-4 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur; or:

two $R^6$ on the same nitrogen are taken together with their intervening atoms to form a 4-7 membered saturated, partially unsaturated, or aromatic heterocyclic ring having 1-2 heteroatoms independently selected from nitrogen, oxygen, and sulfur.

As described generally above, Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur.

In some embodiments, Ring A is an optionally substituted phenyl ring.

In some embodiments, Ring A is an optionally substituted 8-10 membered bicyclic aryl ring. In some embodiments, Ring A is an optionally substituted naphthyl ring.

In some embodiments, Ring A is an optionally substituted 5-6 membered monocyclic heteroaryl ring having 1-4 heteroatoms independently selected from nitrogen, oxygen, and sulfur. In some embodiments, Ring A is an optionally substituted 5-membered monocyclic heteroaryl ring having 1-4 heteroatoms independently selected from nitrogen, oxygen, and sulfur. In some embodiments, Ring A is an optionally substituted 5-membered heteroaryl ring having 1-3 heteroatoms independently selected from nitrogen, oxygen, and sulfur. In some embodiments, Ring A is an optionally substituted 5-membered heteroaryl ring having 1-2 heteroatoms independently selected from nitrogen, oxygen, and sulfur. In some embodiments, Ring A is an optionally substituted 5-membered heteroaryl ring having 3 heteroatoms independently selected from nitrogen, oxygen, and sulfur. In some embodiments, Ring A is an optionally substituted 5-membered heteroaryl ring having 2 heteroatoms independently selected from nitrogen, oxygen, and sulfur. In some embodiments, Ring A is an optionally substituted 5-membered heteroaryl ring having 1 heteroatom selected from nitrogen, oxygen, and sulfur. In some embodiments, Ring A is an optionally substituted 5-membered heteroaryl ring having 1-3 nitrogen atoms. In some embodiments, Ring A is an optionally substituted group selected from pyrrolyl, furanyl, thiophenyl, pyrazolyl, imidazolyl, triazolyl, tetrazolyl, oxazolyl, isoxazolyl, thiazolyl, isothiazolyl, oxadiazolyl and thiadiazolyl.

In some embodiments, Ring A is selected from:

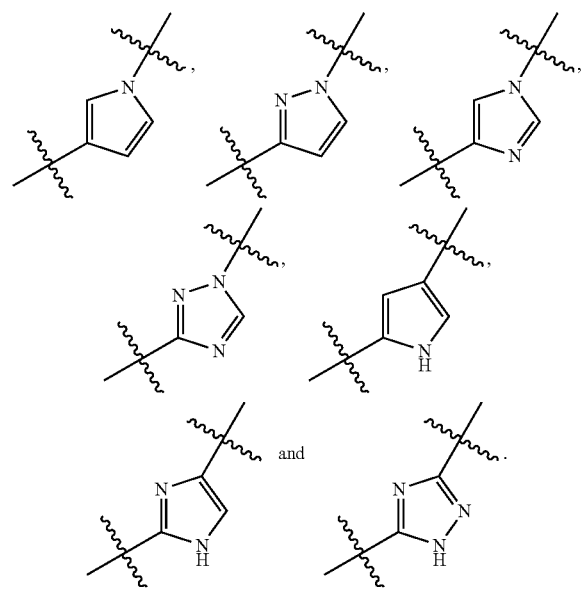

In some embodiments, Ring A is:

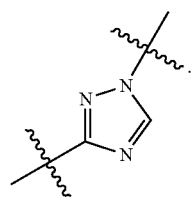 [SMILES: *c1ncn(*)n1]

In some embodiments, Ring A is an optionally substituted 6-membered heteroaryl ring having 1-4 nitrogen atoms. In some embodiments, Ring A is an optionally substituted 6-membered heteroaryl ring having 1-3 nitrogen atoms. In some embodiments, Ring A is an optionally substituted 6-membered heteroaryl ring having 1-2 nitrogen atoms. In some embodiments, Ring A is an optionally substituted 6-membered heteroaryl ring having 2 nitrogen atoms. In some embodiments, Ring A is an optionally substituted 6-membered heteroaryl ring having 1 nitrogen atom. In some embodiments, Ring A is an optionally substituted group selected from pyridinyl, pyrazinyl, pyridizinyl, pyrimidinyl, triazinyl and tetrazinyl.

In some embodiments, Ring A is an optionally substituted pyridyl ring. In some embodiments, Ring A is an optionally substituted 1,6-pyridyl ring. In some embodiments, Ring A is:

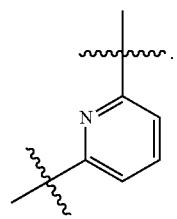 [SMILES: *c1cccc(*)n1]

As described generally above, Ring B is an optionally substituted ring selected from a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur.

In some embodiments, Ring B is an optionally substituted 3-8 membered saturated or partially unsaturated monocyclic carbocyclic ring. In some embodiments, Ring B is an optionally substituted 3-8 membered saturated monocyclic carbocyclic ring. In some embodiments, Ring B is selected from an optionally substituted cyclopropyl, cyclobutyl, cyclopentyl, cyclohexyl, cycloheptyl and cyclooctyl.

In some embodiments, Ring B is an optionally substituted 3-8 membered partially unsaturated monocyclic carbocyclic ring. In some embodiments, Ring B is selected from an optionally substituted cyclopropenyl, cyclobutenyl, cyclopentenyl, cyclohexenyl, cycloheptenyl, cyclooctenyl, cyclohexadienyl and cyclooctadienyl.

In some embodiments, Ring B is an optionally substituted phenyl ring.

In some embodiments, Ring B is a phenyl ring substituted with one or more groups independently selected from halogen, hydroxy or trifluoromethyl.

In some embodiments, Ring B is phenyl substituted with one or more optionally substituted methyl groups. In some embodiments, Ring B is phenyl substituted with one optionally substituted methyl group. In some embodiments, Ring B is phenyl substituted with two optionally substituted methyl groups.

In some embodiments, Ring B is phenyl substituted with one or more methyl groups substituted with at least one halogen. In some embodiments, Ring B is phenyl substituted with one or more methyl groups substituted with at least two halogens. In some embodiments, Ring B is phenyl substituted with one or more methyl groups substituted with three halogens.

In some embodiments, Ring B is phenyl substituted with one or more —CF$_3$ groups. In some embodiments, Ring B is phenyl substituted with two —CF$_3$ groups.

In some embodiments, Ring B is:

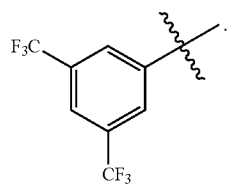

In some embodiments, Ring B is an optionally substituted 8-10 membered bicyclic aryl ring. In some embodiments, Ring B is an optionally substituted naphthyl.

In some embodiments, Ring B is an optionally substituted 3-8 membered saturated or partially unsaturated monocyclic heterocyclic ring having 1-2 heteroatoms independently selected from nitrogen, oxygen, and sulfur. In some embodiments, Ring B is an optionally substituted 3-8 membered saturated monocyclic heterocyclic ring having 1-2 heteroatoms independently selected from nitrogen, oxygen, and sulfur. In some embodiments, Ring B is an optionally substituted 3-8 membered saturated monocyclic heterocyclic ring having 2 heteroatoms independently selected from nitrogen, oxygen, and sulfur. In some embodiments, Ring B is an optionally substituted 3-8 membered saturated monocyclic heterocyclic ring having 1 heteroatom selected from nitrogen, oxygen, and sulfur. In some embodiments, Ring B is selected from an optionally substituted aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl and homopiperazinyl.

In some embodiments, Ring B is an optionally substituted 3-8 membered partially unsaturated monocyclic heterocyclic ring having 1-2 heteroatoms independently selected from nitrogen, oxygen, and sulfur. In some embodiments, Ring B is selected from an optionally substituted azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, Ring B is an optionally substituted 5-6 membered monocyclic heteroaryl ring having 1-4 heteroatoms independently selected from nitrogen, oxygen, and sulfur. In some embodiments, Ring B is an optionally substituted 5-membered monocyclic heteroaryl ring having 1-4 heteroatoms independently selected from nitrogen, oxygen, and sulfur. In some embodiments, Ring B is an optionally substituted 5-membered monocyclic heteroaryl ring having 1-3 heteroatoms independently selected from nitrogen, oxygen, and sulfur. In some embodiments, Ring B is an optionally substituted 5-membered monocyclic heteroaryl ring having 1-2 heteroatoms independently selected from nitrogen, oxygen, and sulfur. In some embodiments, Ring B is an optionally substituted 5-membered monocyclic heteroaryl ring having 2 heteroatoms independently selected from nitrogen, oxygen, and sulfur. In some embodiments, Ring B is an optionally substituted 5-membered monocyclic heteroaryl ring having 1 heteroatom selected from nitrogen, oxygen, and sulfur. In some embodiments, Ring B is an optionally substituted pyrrolyl, furanyl, thiophenyl, pyrazolyl, imidazolyl, triazolyl, tetrazolyl, oxazolyl, isoxazolyl, thiazolyl, isothiazolyl, oxadiazolyl or thiadiazolyl.

In some embodiments, Ring B is an optionally substituted 6-membered monocyclic heteroaryl ring having 1-4 nitrogen atoms. In some embodiments, Ring B is an optionally substituted 6-membered monocyclic heteroaryl ring having 1-3 nitrogen atoms. In some embodiments, Ring B is an optionally substituted 6-membered monocyclic heteroaryl ring having 1-2 nitrogen atoms. In some embodiments, Ring B is an optionally substituted 6-membered monocyclic heteroaryl ring having 2 nitrogen atoms. In some embodiments, Ring B is an optionally substituted 6-membered monocyclic heteroaryl ring having 1 nitrogen atom. In some embodiments, Ring B is an optionally substituted pyridinyl, pyrimidinyl, pyrizinyl, pyridizinyl, triazinyl or tetrazinyl.

In some embodiments, Ring B is an optionally substituted pyridyl ring. In some embodiments, Ring B is a pyridyl ring substituted with one or more optionally substituted C$_{1-6}$ aliphatic groups. In some embodiments, Ring B is a pyridyl ring substituted with one or more optionally substituted C$_{1-4}$ aliphatic groups. In some embodiments, Ring B is a pyridyl ring substituted with one or more optionally substituted C$_{1-2}$ aliphatic groups. In some embodiments, Ring B is a pyridyl ring substituted with one or more optionally substituted methyl groups. In some embodiments, Ring B is a pyridyl ring substituted with one or more methyl groups which are further substituted with one or more halogens. In some embodiments, Ring B is a pyridyl ring substituted with one or more methyl groups substituted with one halogen. In some embodiments, Ring B is a pyridyl ring substituted with one or more methyl groups substituted with at least two halogens. In some embodiments, Ring B is a pyridyl ring substituted with one or more methyl groups substituted with three halogens. In some embodiments, Ring B is a pyridyl ring substituted with one or more —CF$_3$ groups. In some embodiments, Ring B is a pyridyl ring substituted with two —CF$_3$ groups. In some embodiments, Ring B is:

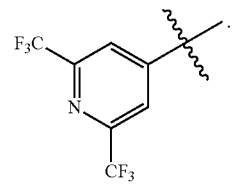

In some embodiments, Ring B is an optionally substituted 8-10 membered bicyclic heteroaryl ring having 1-4 heteroatoms independently selected from nitrogen, oxygen, and sulfur. In some embodiments, Ring B is an optionally substituted 8-10 membered bicyclic heteroaryl ring having 1-3 heteroatoms independently selected from nitrogen, oxygen, and sulfur. In some embodiments, Ring B is an optionally substituted 8-10 membered bicyclic heteroaryl ring having 1-2 heteroatoms independently selected from nitrogen, oxygen, and sulfur. In some embodiments, Ring B is an optionally substituted 8-10 membered bicyclic heteroaryl ring having 1 heteroatom selected from nitrogen, oxygen, and sulfur. In some embodiments, Ring B is an optionally substituted benzofuranyl, benzothiophenyl, indolyl, indazolyl, benzothiazolyl, benzoxazolyl, benzisoxazolyl, benzimidazolyl, benzotriazolyl, azaindolyl, quinolinyl, isoquinolinyl, quinazolinyl, quinoxalinyl or cinnolinyl.

As described generally above, X is selected from O, S, N—CN and NR, wherein R is hydrogen or an optionally substituted group selected from $C_{1-6}$ aliphatic, 3-8 membered saturated or partially unsaturated heterocyclic ring having 1-2 heteroatoms independently selected from nitrogen, oxygen, and sulfur, phenyl, and a 5-6 membered heteroaryl ring having 1-4 heteroatoms independently selected from nitrogen, oxygen, and sulfur.

In some embodiments, X is O.

In some embodiments, X is S.

In some embodiments, X is N—CN.

In some embodiments, X is NR. More specifically, X is NH. Alternatively, X is $NCH_3$.

As described generally above, R is hydrogen or an optionally substituted group selected from $C_{1-6}$ aliphatic, 3-8 membered saturated or partially unsaturated heterocyclic ring having 1-2 heteroatoms independently selected from nitrogen, oxygen and sulfur, and a 5-6 membered heteroaryl ring having 1-4 heteroatoms independently selected from nitrogen, oxygen and sulphur.

In some embodiments, R is hydrogen.

In some embodiments, R is optionally substituted $C_{1-6}$ aliphatic. In some embodiments, R is optionally substituted $C_{1-5}$ aliphatic. In some embodiments, R is optionally substituted $C_{1-4}$ aliphatic. In some embodiments, R is optionally substituted $C_{1-3}$ aliphatic. In some embodiments, R is optionally substituted $C_{1-2}$ aliphatic. In some embodiments, R is selected from optionally substituted methyl, ethyl, propyl, isopropyl, butyl, isobutyl, tert-butyl, pentyl, neopentyl, isopentyl, hexyl, ethenyl, propenyl, butenyl, pentenyl, hexenyl and isobutenyl.

In some embodiments, R is optionally substituted 3-8 membered saturated or partially unsaturated heterocyclic ring having 1-2 heteroatoms independently selected from nitrogen, oxygen, and sulfur. In some embodiments, R is optionally substituted 3-8 membered saturated heterocyclic ring having 1-2 heteroatoms independently selected from nitrogen, oxygen, and sulfur. In some embodiments, R is optionally substituted 3-8 membered saturated heterocyclic ring having 2 heteroatoms independently selected from nitrogen, oxygen, and sulfur. In some embodiments, R is optionally substituted 3-8 membered saturated heterocyclic ring having 1 heteroatom selected from nitrogen, oxygen, and sulfur. In some embodiments, R is optionally substituted aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl or homopiperazinyl.

In some embodiments, R is optionally substituted 3-8 membered partially unsaturated heterocyclic ring having 1-2 heteroatoms independently selected from nitrogen, oxygen, and sulfur. In some embodiments, R is optionally substituted 3-8 membered partially unsaturated heterocyclic ring having 2 heteroatoms independently selected from nitrogen, oxygen, and sulfur. In some embodiments, R is optionally substituted 3-8 membered partially unsaturated heterocyclic ring having 1 heteroatom selected from nitrogen, oxygen, and sulfur. In some embodiments, R is optionally substituted azirinyl, oxirenyl, thiirenyl, diazirinyl, azetyl, oxetyl, thietyl, dioxetyl, dithietyl, imidazolinyl, pyrazolinyl, oxazolinyl or thiazolinyl.

In some embodiments, R is an optionally substituted 5-6 membered heteroaryl ring having 1-4 heteroatoms independently selected from nitrogen, oxygen, and sulfur. In some embodiments, R is an optionally substituted 5-membered heteroaryl ring having 1-4 heteroatoms independently selected from nitrogen, oxygen, and sulfur. In some embodiments, R is an optionally substituted 5-membered heteroaryl ring having 1-3 heteroatoms independently selected from nitrogen, oxygen, and sulfur. In some embodiments, R is an optionally substituted 5-membered heteroaryl ring having 1-2 heteroatoms independently selected from nitrogen, oxygen, and sulfur. In some embodiments, R is an optionally substituted 5-membered heteroaryl ring having 2 heteroatoms independently selected from nitrogen, oxygen, and sulfur. In some embodiments, R is an optionally substituted 5-membered heteroaryl ring having 1 heteroatom selected from nitrogen, oxygen, and sulfur. In some embodiments, R is selected from optionally substituted pyrrolyl, furanyl, thiophenyl, pyrazolyl, imidazolyl, oxazolyl, thiazolyl, oxadiazolyl, thiadiazolyl, isoxazolyl, isothiazolyl, triazolyl and tetrazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In some embodiments, R is an optionally substituted 6-membered heteroaryl ring having 1-2 nitrogen atoms. In some embodiments, R is an optionally substituted 6-membered heteroaryl ring having 2 nitrogen atoms. In some embodiments, R is an optionally substituted 6-membered heteroaryl ring having 1 nitrogen atom. In some embodiments, R is selected from optionally substituted pyridinyl, pyrimidinyl, pyrazinyl, pyridazinyl, triazinyl and tetrazinyl.

In some embodiments, X is NH. In some embodiments, X is $NCH_3$.

As described generally above, Y is a covalent bond or an optionally substituted bivalent $C_{1-4}$ hydrocarbon chain, wherein one methylene unit of Y is optionally replaced by —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—.

In some embodiments, Y is a covalent bond.

In some embodiments, Y is an optionally substituted bivalent $C_{1-4}$ hydrocarbon chain, wherein one methylene unit of Y is optionally replaced by —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—. In some embodiments, Y is an optionally substituted bivalent $C_{1-3}$ hydrocarbon chain, wherein one methylene unit of Y is optionally replaced by —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—. In some embodiments, Y is an optionally substituted bivalent $C_{1-2}$ hydrocarbon chain, wherein one methylene unit of Y is optionally replaced by —O—, —S—, —N($R^6$)—, —C(O)—, —C(S)—, —C(O)N($R^6$)—, —N($R^6$)C(O)N($R^6$)—, —N(R⁶)C(O)—, —N(R⁶)C(O)O—, —OC(O)N(R⁶)—, —S(O)—, —S(O)₂—, —S(O)₂N(R⁶)—, —N(R⁶)S(O)₂—, —OC(O)— or —C(O)O—.

In some embodiments, Y is —O—. In some embodiments, Y is —S—. In some embodiments, Y is —N(R⁶)—. In some embodiments, Y is —C(O)—. In some embodiments, Y is —C(O)—. In some embodiments, Y is —NH—. In some embodiments, Y is —CH₂O—. In some embodiments, Y is —CH₂S—. In some embodiments, Y is —CH₂N(H)—.

As described generally above, each of $R^1$ and $R^2$ is independently selected from hydrogen or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur.

In some embodiments, $R^1$ and $R^2$ are each hydrogen. In some embodiments, one of $R^1$ and $R^2$ is hydrogen.

In some embodiments, $R^1$ is hydrogen. In some embodiments, $R^1$ is optionally substituted $C_{1-6}$ aliphatic. In some embodiments, $R^1$ is optionally substituted $C_{1-5}$ aliphatic. In some embodiments, $R^1$ is optionally substituted $C_{1-4}$ aliphatic. In some embodiments, $R^1$ is optionally substituted $C_{1-3}$ aliphatic. In some embodiments, $R^1$ is optionally substituted $C_{1-2}$ aliphatic. In some embodiments, $R^1$ is selected from optionally substituted methyl, ethyl, propyl, isopropyl, butyl, isobutyl, tert-butyl, pentyl, neopentyl, isopentyl, hexyl, ethenyl, propenyl, butenyl, pentenyl and hexenyl.

In some embodiments, $R^1$ is an optionally substituted phenyl ring.

In some embodiments, $R^1$ is an optionally substituted 3-8 membered saturated or partially unsaturated monocyclic carbocyclic ring. In some embodiments, $R^1$ is an optionally substituted 3-8 membered saturated monocyclic carbocyclic ring. In some embodiments, $R^1$ is an optionally substituted 3-8 membered partially unsaturated monocyclic carbocyclic ring. In some embodiments, $R^1$ is selected from optionally substituted cyclopropyl, cyclopropenyl, cyclobutyl, cyclobutenyl, cyclopentyl, cyclopentenyl, cyclohexyl, cyclohexenyl, cyclohexadienyl, cycloheptyl, cycloheptenyl, cyclohepadienyl, cyclooctyl, cyclooctenyl and cyclooctadienyl.

In some embodiments, $R^1$ is an optionally substituted 8-10 membered bicyclic aryl ring. In some embodiments, $R^1$ is an optionally substituted naphthyl ring.

In some embodiments, $R^1$ is an optionally substituted 3-8 membered saturated or partially unsaturated monocyclic heterocyclic ring having 1-2 heteroatoms independently selected from nitrogen, oxygen, and sulfur. In some embodiments, $R^1$ is an optionally substituted 3-8 membered saturated monocyclic heterocyclic ring having 1-2 heteroatoms independently selected from nitrogen, oxygen, and sulfur. In some embodiments, $R^1$ is an optionally substituted 3-8 membered saturated monocyclic heterocyclic ring having 2 heteroatoms independently selected from nitrogen, oxygen, and sulfur. In some embodiments, $R^1$ is an optionally substituted 3-8 membered saturated monocyclic heterocyclic ring having 1 heteroatom selected from nitrogen, oxygen, and sulfur. In some embodiments, $R^1$ is an optionally substituted 3-8 membered partially unsaturated monocyclic heterocyclic ring having 1-2 heteroatoms independently selected from nitrogen, oxygen, and sulfur. In some embodiments, $R^1$ is an optionally substituted 3-8 membered partially unsaturated monocyclic heterocyclic ring having 2 heteroatoms independently selected from nitrogen, oxygen, and sulfur. In some embodiments, $R^1$ is an optionally substituted 3-8 membered partially unsaturated monocyclic heterocyclic ring having 1 heteroatom selected from nitrogen, oxygen, and sulfur. In some embodiments, $R^1$ is selected from optionally substituted aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, homopiperazinyl, thiomorpholinyl, dioxanyl, dithianyl, azepanyl, oxepanyl, thiepanyl, azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^1$ is an optionally substituted 5-6 membered monocyclic heteroaryl ring having 1-4 heteroatoms independently selected from nitrogen, oxygen, and sulfur. In some embodiments, $R^1$ is an optionally substituted 5-membered monocyclic heteroaryl ring having 1-4 heteroatoms independently selected from nitrogen, oxygen, and sulfur. In some embodiments, $R^1$ is an optionally substituted 5-membered monocyclic heteroaryl ring having 1-3 heteroatoms independently selected from nitrogen, oxygen, and sulfur. In some embodiments, $R^1$ is an optionally substituted 5-membered monocyclic heteroaryl ring having 1-2 heteroatoms independently selected from nitrogen, oxygen, and sulfur. In some embodiments, $R^1$ is an optionally substituted 5-membered monocyclic heteroaryl ring having 2 heteroatoms independently selected from nitrogen, oxygen, and sulfur. In some embodiments, $R^1$ is an optionally substituted 5-membered monocyclic heteroaryl ring having 1 heteroatom selected from nitrogen, oxygen, and sulfur. In some embodiments, $R^1$ is selected from optionally substituted pyrrolyl, furanyl, thiophenyl, imidazolyl, pyrazolyl, oxazolyl, thiazolyl, isoxazolyl, isothiazolyl, oxadiazolyl, thiadiazolyl, triazolyl and tetrazolyl.

In some embodiments, $R^1$ is an optionally substituted 6-membered monocyclic heteroaryl ring having 1-4 nitrogen atoms. In some embodiments, $R^1$ is an optionally substituted 6-membered monocyclic heteroaryl ring having 1-3 nitrogen atoms. In some embodiments, $R^1$ is an optionally substituted 6-membered monocyclic heteroaryl ring having 1-2 nitrogen atoms. In some embodiments, $R^1$ is an optionally substituted 6-membered monocyclic heteroaryl ring having 2 nitrogen atoms. In some embodiments, $R^1$ is an optionally substituted 6-membered monocyclic heteroaryl ring having 1 nitrogen atom. In some embodiments, $R^1$ is selected from optionally substituted pyridinyl, pyrimidinyl, pyrazinyl, pyridazinyl, triazinyl and tetrazinyl.

In some embodiments, $R^1$ is an optionally substituted 8-10 membered bicyclic heteroaryl ring having 1-4 heteroatoms independently selected from nitrogen, oxygen, and sulfur. In some embodiments, $R^1$ is an optionally substituted 8-10 membered bicyclic heteroaryl ring having 1-3 heteroatoms independently selected from nitrogen, oxygen, and sulfur. In some embodiments, $R^1$ is an optionally substituted 8-10 membered bicyclic heteroaryl ring having 1-2 heteroatoms independently selected from nitrogen, oxygen, and sulfur. In some embodiments, $R^1$ is an optionally substituted 8-10 membered bicyclic heteroaryl ring having 1 heteroatom selected from nitrogen, oxygen, and sulfur. In some embodiments, $R^1$ is selected from optionally substituted indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

In some embodiments, $R^2$ is hydrogen. In some embodiments, $R^2$ is optionally substituted $C_{1-6}$ aliphatic. In some embodiments, $R^2$ is optionally substituted $C_{1-5}$ aliphatic. In some embodiments, $R^2$ is optionally substituted $C_{1-4}$ aliphatic. In some embodiments, $R^2$ is optionally substituted $C_{1-3}$ aliphatic. In some embodiments, $R^2$ is optionally substituted $C_{1-2}$ aliphatic. In some embodiments, $R^2$ is selected from optionally substituted methyl, ethyl, propyl, isopropyl, butyl, isobutyl, tert-butyl, pentyl, neopentyl, isopentyl, hexyl, ethenyl, propenyl, butenyl, pentenyl and hexenyl.

In some embodiments, $R^2$ is an optionally substituted phenyl ring.

In some embodiments, $R^2$ is an optionally substituted 3-8 membered saturated or partially unsaturated monocyclic carbocyclic ring. In some embodiments, $R^2$ is an optionally substituted 3-8 membered saturated monocyclic carbocyclic ring. In some embodiments, $R^2$ is an optionally substituted 3-8 membered partially unsaturated monocyclic carbocyclic ring. In some embodiments, $R^2$ is selected from optionally substituted cyclopropyl, cyclopropenyl, cyclobutyl, cyclobutenyl, cyclopentyl, cyclopentenyl, cyclohexyl, cyclohexenyl, cyclohexadienyl, cycloheptyl, cycloheptenyl, cyclohepadienyl, cyclooctyl, cyclooctenyl and cyclooctadienyl.

In some embodiments, $R^2$ is an optionally substituted 8-10 membered bicyclic aryl ring. In some embodiments, $R^2$ is an optionally substituted naphthyl ring.

In some embodiments, $R^2$ is an optionally substituted 3-8 membered saturated or partially unsaturated monocyclic heterocyclic ring having 1-2 heteroatoms independently selected from nitrogen, oxygen, and sulfur. In some embodiments, $R^2$ is an optionally substituted 3-8 membered saturated monocyclic heterocyclic ring having 1-2 heteroatoms independently selected from nitrogen, oxygen, and sulfur. In some embodiments, $R^2$ is an optionally substituted 3-8 membered saturated monocyclic heterocyclic ring having 2 heteroatoms independently selected from nitrogen, oxygen, and sulfur. In some embodiments, $R^2$ is an optionally substituted 3-8 membered saturated monocyclic heterocyclic ring having 1 heteroatom selected from nitrogen, oxygen, and sulfur. In some embodiments, $R^2$ is an optionally substituted 3-8 membered partially unsaturated monocyclic heterocyclic ring having 1-2 heteroatoms independently selected from nitrogen, oxygen, and sulfur. In some embodiments, $R^2$ is an optionally substituted 3-8 membered partially unsaturated monocyclic heterocyclic ring having 2 heteroatoms independently selected from nitrogen, oxygen, and sulfur. In some embodiments, $R^2$ is an optionally substituted 3-8 membered partially unsaturated monocyclic heterocyclic ring having 1 heteroatom selected from nitrogen, oxygen, and sulfur. In some embodiments, $R^2$ is selected from optionally substituted aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, homopiperazinyl, oxanyl, thianyl, piperazinyl, morpholinyl, thiomorpholinyl, dioxanyl, dithianyl, azepanyl, oxepanyl, thiepanyl, azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^2$ is an optionally substituted 5-6 membered monocyclic heteroaryl ring having 1-4 heteroatoms independently selected from nitrogen, oxygen, and sulfur. In some embodiments, $R^2$ is an optionally substituted 5-membered monocyclic heteroaryl ring having 1-4 heteroatoms independently selected from nitrogen, oxygen, and sulfur. In some embodiments, $R^2$ is an optionally substituted 5-membered monocyclic heteroaryl ring having 1-3 heteroatoms independently selected from nitrogen, oxygen, and sulfur. In some embodiments, $R^2$ is an optionally substituted 5-membered monocyclic heteroaryl ring having 1-2 heteroatoms independently selected from nitrogen, oxygen, and sulfur. In some embodiments, $R^2$ is an optionally substituted 5-membered monocyclic heteroaryl ring having 2 heteroatoms independently selected from nitrogen, oxygen, and sulfur. In some embodiments, $R^2$ is an optionally substituted 5-membered monocyclic heteroaryl ring having 1 heteroatom selected from nitrogen, oxygen, and sulfur. In some embodiments, $R^2$ is selected from optionally substituted pyrrolyl, furanyl, thiophenyl, imidazolyl, pyrazolyl, oxazolyl, thiazolyl, isoxazolyl, isothiazolyl, oxadiazolyl, thiadiazolyl, triazolyl and tetrazolyl.

In some embodiments, $R^2$ is an optionally substituted 6-membered monocyclic heteroaryl ring having 1-4 nitrogen atoms. In some embodiments, $R^2$ is an optionally substituted 6-membered monocyclic heteroaryl ring having 1-3 nitrogen atoms. In some embodiments, $R^2$ is an optionally substituted 6-membered monocyclic heteroaryl ring having 1-2 nitrogen atoms. In some embodiments, $R^2$ is an optionally substituted 6-membered monocyclic heteroaryl ring having 2 nitrogen atoms. In some embodiments, $R^2$ is an optionally substituted 6-membered monocyclic heteroaryl ring having 1 nitrogen atom. In some embodiments, $R^2$ is selected from optionally substituted pyridinyl, pyrimidinyl, pyrazinyl, pyridazinyl, triazinyl and tetrazinyl.

In some embodiments, $R^2$ is an optionally substituted 8-10 membered bicyclic heteroaryl ring having 1-4 heteroatoms independently selected from nitrogen, oxygen, and sulfur. In some embodiments, $R^2$ is an optionally substituted 8-10 membered bicyclic heteroaryl ring having 1-3 heteroatoms independently selected from nitrogen, oxygen, and sulfur. In some embodiments, $R^2$ is an optionally substituted 8-10 membered bicyclic heteroaryl ring having 1-2 heteroatoms independently selected from nitrogen, oxygen, and sulfur. In some embodiments, $R^2$ is an optionally substituted 8-10 membered bicyclic heteroaryl ring having 1 heteroatom selected from nitrogen, oxygen, and sulfur. In some embodiments, $R^2$ is selected from optionally substituted indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

As described generally above, $R^1$ and $R^2$ are taken together with their intervening atoms to form a 4-8 membered saturated, partially unsaturated, or aromatic heterocyclic ring having 1-3 heteroatoms independently selected from nitrogen, oxygen, and sulfur. In some embodiments, $R^1$ and $R^2$ are taken together with their intervening atoms to form a 4-8 membered saturated heterocyclic ring having 1-3 heteroatoms independently selected from nitrogen, oxygen, and sulfur. In some embodiments, $R^1$ and $R^2$ are taken together with their intervening atoms to form a 4-8 membered saturated heterocyclic ring having 1-2 heteroatoms independently selected from nitrogen, oxygen, and sulfur. In some embodiments, $R^1$ and $R^2$ are taken together with their intervening atoms to form a 4-8 membered saturated heterocyclic ring having 2 heteroatoms independently selected from nitrogen, oxygen, and sulfur. In some embodiments, $R^1$ and $R^2$ are taken together with their intervening atoms to form a 4-8 membered saturated heterocyclic ring having 1 nitrogen atom. In some embodiments, $R^1$ and $R^2$ are taken together with their intervening atoms to form a ring selected from azepinyl, azetidinyl, pyrrolidinyl, pyrazolidinyl, oxazolidinyl, thiazolidinyl, piperidinyl, piperazinyl, and morpholinyl.

In some embodiments, the 4-8 membered saturated heterocyclic ring formed by $R^1$, $R^2$ and their intervening atoms is:

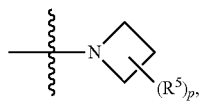

wherein $R^5$ and p are as defined above and described herein.

In some embodiments, the 4-8 membered saturated heterocyclic ring formed by $R^1$, $R^2$ and their intervening atoms is substituted with one or more halogens. In some such embodiments, the 4-8 membered saturated heterocyclic ring formed by $R^1$, $R^2$ and their intervening atoms is:

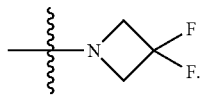 [SMILES: *N1CC(F)(F)C1]

In some embodiments, $R^1$ and $R^2$ are taken together with their intervening atoms to form a 4-8 membered partially unsaturated heterocyclic ring having 1-3 heteroatoms independently selected from nitrogen, oxygen, and sulfur. In some embodiments, $R^1$ and $R^2$ are taken together with their intervening atoms to form a 4-8 membered partially unsaturated heterocyclic ring having 1-2 heteroatoms independently selected from nitrogen, oxygen, and sulfur. In some embodiments, $R^1$ and $R^2$ are taken together with their intervening atoms to form a 4-8 membered partially unsaturated heterocyclic ring having 2 heteroatoms independently selected from nitrogen, oxygen, and sulfur. In some embodiments, $R^1$ and $R^2$ are taken together with their intervening atoms to form a 4-8 membered partially unsaturated heterocyclic ring having 1 nitrogen atom. In some embodiments, $R^1$ and $R^2$ are taken together with their intervening atoms to form a ring selected from azetyl, imidazolidinyl, pyrazolinyl, oxazolinyl, thiazolinyl, oxazinyl, thiazinyl, azepinyl and diazepinyl.

In some embodiments, $R^1$ and $R^2$ are taken together with their intervening atoms to form a 4-8 membered aromatic heterocyclic ring having 1-3 heteroatoms independently selected from nitrogen, oxygen, and sulfur. In some embodiments, $R^1$ and $R^2$ are taken together with their intervening atoms to form a 4-8 membered aromatic heterocyclic ring having 1-2 heteroatoms independently selected from nitrogen, oxygen, and sulfur. In some embodiments, $R^1$ and $R^2$ are taken together with their intervening atoms to form a 4-8 membered aromatic heterocyclic ring having 2 heteroatoms independently selected from nitrogen, oxygen, and sulfur. In some embodiments, $R^1$ and $R^2$ are taken together with their intervening atoms to form a 4-8 membered aromatic heterocyclic ring having 1 nitrogen atom. In some embodiments, $R^1$ and $R^2$ are taken together with their intervening atoms to form a ring selected from pyrrolyl, oxazolyl, thiazolyl, oxadiazolyl, thiadiazolyl, triazolyl and tetrazolyl.

As described generally above, the ring formed by $R^1$ and $R^2$, and their intervening atoms is substituted with $-(R^5)_p$, wherein p is 0-4. As defined above, $R^5$ is halogen, $-NO_2$, $-CN$, $-N_3$, $-L-R^6$, or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or two $R^5$ groups on the ring formed by $R^1$ and $R^2$ are taken together with their intervening atoms to form a fused 4-8 membered saturated, partially unsaturated, or aryl ring having 0-3 heteroatoms independently selected from nitrogen, oxygen, and sulfur.

In some embodiments, $R^5$ is halogen. In some embodiments, $R^5$ is fluorine. In some embodiments, $R^5$ is chlorine. In some embodiments, $R^5$ is bromine. In some embodiments, $R^5$ is $-NO_2$. In some embodiments, $R^5$ is $-CN$. In some embodiments, $R^5$ is $-N_3$. In some embodiments, $R^5$ is $-L-R^6$.

As defined generally above, each $R^6$ is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 4-7-membered saturated or partially unsaturated heterocyclic ring having 1-4 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur.

In some embodiments, $R^6$ is hydrogen. In some embodiments, $R^6$ is optionally substituted phenyl. In some embodiments, $R^6$ is an optionally substituted $C_{1-6}$ aliphatic. In some embodiments, $R^6$ is an optionally substituted $C_{1-5}$ aliphatic. In some embodiments, $R^6$ is an optionally substituted $C_{1-4}$ aliphatic. In some embodiments, $R^6$ is an optionally substituted $C_{1-3}$ aliphatic. In some embodiments, $R^6$ is an optionally substituted $C_{1-2}$ aliphatic.

In some embodiments, $R^6$ is an optionally substituted 3-7 membered saturated or partially unsaturated carbocyclic ring. In some embodiments, $R^6$ is an optionally substituted 3-7 membered saturated carbocyclic ring. In some embodiments, $R^6$ is an optionally substituted 3-7 membered partially unsaturated carbocyclic ring. In some embodiments, $R^6$ is selected from cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl, cyclohexadienyl and cyclooctadienyl.

In some embodiments, $R^6$ is an optionally substituted 8-10 membered bicyclic saturated, partially unsaturated or aryl carbocyclic ring. In some embodiments, $R^6$ is an optionally substituted 8-10 membered bicyclic saturated carbocyclic ring. In some embodiments, $R^6$ is an optionally substituted 8-10 membered bicyclic partially unsaturated carbocyclic ring. In some embodiments, $R^6$ is an optionally substituted 8-10 membered bicyclic aryl carbocyclic ring. In some embodiments, $R^6$ is naphthyl.

In some embodiments, $R^6$ is an optionally substituted 4-7-membered saturated or partially unsaturated heterocyclic ring having 1-4 heteroatoms independently selected from nitrogen, oxygen, and sulfur. In some embodiments, $R^6$ is optionally substituted 4-7-membered saturated heterocyclic ring having 1-4 heteroatoms independently selected from nitrogen, oxygen, and sulfur. In some embodiments, $R^6$ is optionally substituted 4-7-membered saturated heterocyclic ring having 1-3 heteroatoms independently selected from nitrogen, oxygen, and sulfur. In some embodiments, $R^6$ is optionally substituted 4-7-membered saturated heterocyclic ring having 1-2 heteroatoms independently selected from nitrogen, oxygen, and sulfur. In some embodiments, $R^6$ is optionally substituted 4-7-membered saturated heterocyclic ring having 1 heteroatom selected from nitrogen, oxygen, and sulfur. In some embodiments, $R^6$ is selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl and homopiperazinyl.

In some embodiments, $R^6$ is an optionally substituted 4-7-membered partially unsaturated heterocyclic ring having 1-4 heteroatoms independently selected from nitrogen, oxygen, and sulfur. In some embodiments, $R^6$ is optionally substituted 4-7-membered partially unsaturated heterocyclic ring having 1-3 heteroatoms independently selected from nitrogen, oxygen, and sulfur. In some embodiments, $R^6$ is optionally substituted 4-7-membered partially unsaturated heterocyclic ring having 1-2 heteroatoms independently selected from nitrogen, oxygen, and sulfur. In some embodiments, $R^6$ is optionally substituted 4-7-membered partially unsaturated heterocyclic ring having 1 heteroatom selected from nitrogen, oxygen, and sulfur. In some embodiments, $R^6$ is selected from azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^6$ is an optionally substituted 5-6 membered monocyclic heteroaryl ring having 1-4 heteroatoms independently selected from nitrogen, oxygen, and sulfur. In some embodiments, $R^6$ is an optionally substituted 5-membered monocyclic heteroaryl ring having 1-4 heteroatoms independently selected from nitrogen, oxygen, and sulfur. In some embodiments, $R^6$ is an optionally substituted 5-membered monocyclic heteroaryl ring having 1-3 heteroatoms independently selected from nitrogen, oxygen, and sulfur. In some embodiments, $R^6$ is an optionally substituted 5-membered monocyclic heteroaryl ring having 1-2 heteroatoms independently selected from nitrogen, oxygen, and sulfur. In some embodiments, $R^6$ is an optionally substituted 5-membered monocyclic heteroaryl ring having 2 heteroatoms independently selected from nitrogen, oxygen, and sulfur. In some embodiments, $R^6$ is an optionally substituted 5-membered monocyclic heteroaryl ring having 1 heteroatom selected from nitrogen, oxygen, and sulfur. In some embodiments, $R^6$ is selected from pyrrolyl, furanyl, thiophenyl, pyrazolyl, imidazolyl, oxazolyl, isoxazolyl, thiazolyl, isothiazolyl, oxadiazolyl, thiadiazolyl, triazolyl and tetrazolyl.

In some embodiments, $R^6$ is an optionally substituted 6-membered monocyclic heteroaryl ring having 1-4 heteroatoms independently selected from nitrogen, oxygen, and sulfur. In some embodiments, $R^6$ is an optionally substituted 6-membered monocyclic heteroaryl ring having 1-3 heteroatoms independently selected from nitrogen, oxygen, and sulfur. In some embodiments, $R^6$ is an optionally substituted 6-membered monocyclic heteroaryl ring having 1-2 heteroatoms independently selected from nitrogen, oxygen, and sulfur. In some embodiments, $R^6$ is an optionally substituted 6-membered monocyclic heteroaryl ring having 2 heteroatoms independently selected from nitrogen, oxygen, and sulfur. In some embodiments, $R^6$ is an optionally substituted 6-membered monocyclic heteroaryl ring having 1 heteroatom selected from nitrogen, oxygen, and sulfur. In some embodiments, $R^6$ is selected from pyridinyl, pyrazinyl, pyridizinyl, pyrimidinyl, triazinyl and tetrazinyl.

In some embodiments, $R^6$ is an optionally substituted 8-10 membered bicyclic heteroaryl ring having 1-4 heteroatoms independently selected from nitrogen, oxygen, and sulfur. In some embodiments, $R^6$ is an optionally substituted 8-10 membered bicyclic heteroaryl ring having 1-3 heteroatoms independently selected from nitrogen, oxygen, and sulfur. In some embodiments, $R^6$ is an optionally substituted 8-10 membered bicyclic heteroaryl ring having 1-2 heteroatoms independently selected from nitrogen, oxygen, and sulfur. In some embodiments, $R^6$ is an optionally substituted 8-10 membered bicyclic heteroaryl ring having 1 heteroatom selected from nitrogen, oxygen, and sulfur. In some embodiments, $R^6$ is selected from indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

In some embodiments, two $R^6$ on the same nitrogen are taken together with their intervening atoms to form a 4-7 membered saturated, partially unsaturated, or aromatic heterocyclic ring having 1-2 heteroatoms independently selected from nitrogen, oxygen, and sulfur. In some embodiments, two $R^6$ on the same nitrogen are taken together with their intervening atoms to form a saturated heterocyclic ring having 1-2 heteroatoms independently selected from nitrogen, oxygen, and sulfur. In some embodiments, two $R^6$ on the same nitrogen are taken together with their intervening atoms to form a partially unsaturated heterocyclic ring having 1-2 heteroatoms independently selected from nitrogen, oxygen, and sulfur. In some embodiments, two $R^6$ on the same nitrogen are taken together with their intervening atoms to form an aromatic heterocyclic ring having 1-2 heteroatoms independently selected from nitrogen, oxygen, and sulfur. In some embodiments, $R^6$ is selected from diazirinyl, azetyl, oxetyl, thietyl, dioxetyl, dithietyl, imidazolinyl, pyrazolinyl, oxazolinyl, thiazolinyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, pyrrolyl, furanyl, thiophenyl, pyrazolyl, imidazolyl, oxazolyl, isoxazolyl, thiazolyl, isothiazolyl, oxadiazolyl, thiadiazolyl, pyridinyl, pyrazinyl, pyridizinyl and pyrimidinyl.

As defined generally above, each of n, m, and p is independently an integer selected from 0, 1, 2, 3 and 4. In some embodiments, n is 0. In some embodiments, n is 1. In some embodiments, n is 2. In some embodiments, n is 3. In some embodiments, n is 4. In some embodiments, m is 0. In some embodiments, m is 1. In some embodiments, m is 2. In some embodiments, m is 3. In some embodiments, m is 4. In some embodiments, p is 0. In some embodiments, p is 1. In some embodiments, p is 2. In some embodiments, p is 3. In some embodiments, p is 4.

As defined generally above, q is an integer selected from 0, 1 and 2. In some embodiments, q is 0. In some embodiments, q is 1. In some embodiments, q is 2.

As defined generally above, each of $R^3$, $R^4$, and $R^5$ is independently halogen, —$NO_2$, —CN, —$N_3$, -L-$R^6$, or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, and an 8-10 membered bicyclic heteroaryl ring having 1-4 heteroatoms independently selected from nitrogen, oxygen, and sulfur.

In some embodiments, $R^3$ is halogen. In some embodiments, $R^3$ is —$NO_2$. In some embodiments, $R^3$ is —CN. In some embodiments, $R^3$ is —$N_3$.

In some embodiments, $R^3$ is optionally substituted $C_{1-6}$ aliphatic. In some embodiments, $R^3$ is optionally substituted $C_{1-5}$ aliphatic. In some embodiments, $R^3$ is optionally substituted $C_{1-4}$ aliphatic. In some embodiments, $R^3$ is optionally substituted $C_{1-3}$ aliphatic. In some embodiments, $R^3$ is optionally substituted $C_{1-2}$ aliphatic. In some embodiments, $R^3$ is selected from methyl, ethyl, propyl, isopropyl, butyl, sec-butyl, tert-butyl, pentyl, neopentyl, isopentyl and hexyl.

In some embodiments, $R^3$ is -L-$R^6$.

In some embodiments, $R^3$ is an optionally substituted phenyl.

In some embodiments, $R^3$ is an optionally substituted 3-8 membered saturated or partially unsaturated monocyclic carbocyclic ring. In some embodiments, $R^3$ is an optionally substituted 3-8 membered saturated monocyclic carbocyclic ring. In some embodiments, $R^3$ is selected from cyclopropyl, cyclobutyl, cyclopentyl, cyclohexyl, cycloheptyl and cyclooctyl.

In some embodiments, $R^3$ is an optionally substituted 3-8 membered partially unsaturated monocyclic carbocyclic ring. In some embodiments, $R^3$ is selected from cyclopropenyl, cyclobutenyl, cyclopentenyl, cyclohexenyl, cycloheptenyl, cyclooctenyl, cyclopentadienyl, cyclohexadienyl, cycloheptadienyl and cyclooctadienyl.

In some embodiments, $R^3$ is an optionally substituted an 8-10 membered bicyclic aryl ring. In some embodiments, $R^3$ is naphthyl.

In some embodiments, $R^3$ is an optionally substituted 3-8 membered saturated monocyclic heterocyclic ring having 1-2 heteroatoms independently selected from nitrogen, oxygen, and sulfur. In some embodiments, $R^3$ is an optionally substituted 3-8 membered saturated monocyclic heterocyclic ring having 2 heteroatoms independently selected from nitrogen, oxygen, and sulfur. In some embodiments, $R^3$ is an optionally substituted 3-8 membered saturated monocyclic heterocyclic ring having 1 heteroatom selected from nitrogen, oxygen, and sulfur. In some embodiments, $R^3$ is selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, imidazolidinyl, pyrazolidinyl, oxazolidinyl, isoxazolidinyl, dioxolanyl, dithiolanyl, oxolanyl, thiolanyl, piperidinyl, piperazinyl, morpholinyl, oxanyl, thianyl, thiomorpholinyl, dioxanyl, dithianyl, azepanyl, oxepanyl, thiepanyl and homopiperazinyl.

In some embodiments, $R^3$ is an optionally substituted 3-8 membered partially unsaturated monocyclic heterocyclic ring having 1-2 heteroatoms independently selected from nitrogen, oxygen, and sulfur. In some embodiments, $R^3$ is selected from azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^3$ is an optionally substituted 5-6 membered monocyclic heteroaryl ring having 1-4 heteroatoms independently selected from nitrogen, oxygen, and sulfur. In some embodiments, $R^3$ is an optionally substituted 5-membered monocyclic heteroaryl ring having 1-4 heteroatoms independently selected from nitrogen, oxygen, and sulfur. In some embodiments, $R^3$ is an optionally substituted 5-membered monocyclic heteroaryl ring having 1-3 heteroatoms independently selected from nitrogen, oxygen, and sulfur. In some embodiments, $R^3$ is an optionally substituted 5-membered monocyclic heteroaryl ring having 1-2 heteroatoms independently selected from nitrogen, oxygen, and sulfur. In some embodiments, $R^3$ is an optionally substituted 5-membered monocyclic heteroaryl ring having 2 heteroatoms independently selected from nitrogen, oxygen, and sulfur. In some embodiments, $R^3$ is an optionally substituted 5-membered monocyclic heteroaryl ring having 1 heteroatom selected from nitrogen, oxygen, and sulfur. In some embodiments, $R^3$ is selected from pyrrolyl, furanyl, thiophenyl, pyrazolyl, imidazolyl, oxazolyl, isoxazolyl, thiazolyl, isothiazolyl, oxadiazolyl, thiadiazolyl, triazolyl and tetrazolyl.

In some embodiments, $R^3$ is an optionally substituted 6-membered monocyclic heteroaryl ring having 1-4 nitrogen atoms. In some embodiments, $R^3$ is an optionally substituted 6-membered monocyclic heteroaryl ring having 1-3 nitrogen atoms. In some embodiments, $R^3$ is an optionally substituted 6-membered monocyclic heteroaryl ring having 1-2 nitrogen atoms. In some embodiments, $R^3$ is an optionally substituted 6-membered monocyclic heteroaryl ring having 2 nitrogen atoms. In some embodiments, $R^3$ is an optionally substituted 6-membered monocyclic heteroaryl ring having 1 nitrogen atom. In some embodiments, $R^3$ is selected from pyridinyl, pyrazinyl, pyridizinyl, pyrimidinyl, triazinyl and tetrazinyl.

In some embodiments, $R^3$ is an optionally substituted 8-10 membered bicyclic heteroaryl ring having 1-4 heteroatoms independently selected from nitrogen, oxygen, and sulfur. In some embodiments, $R^3$ is an optionally substituted 8-10 membered bicyclic heteroaryl ring having 1-3 heteroatoms independently selected from nitrogen, oxygen, and sulfur. In some embodiments, $R^3$ is an optionally substituted 8-10 membered bicyclic heteroaryl ring having 1-2 heteroatoms independently selected from nitrogen, oxygen, and sulfur. In some embodiments, $R^3$ is an optionally substituted 8-10 membered bicyclic heteroaryl ring having 1 heteroatom selected from nitrogen, oxygen, and sulfur. In some embodiments, $R^3$ is selected from indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

In some embodiments, $R^4$ is halogen. In some embodiments, $R^4$ is —$NO_2$. In some embodiments, $R^4$ is —CN. In some embodiments, $R^4$ is —$N_3$.

In some embodiments, $R^4$ is optionally substituted $C_{1-6}$ aliphatic. In some embodiments, $R^4$ is optionally substituted $C_{1-5}$ aliphatic. In some embodiments, $R^4$ is optionally substituted $C_{1-4}$ aliphatic. In some embodiments, $R^4$ is optionally substituted $C_{1-3}$ aliphatic. In some embodiments, $R^4$ is optionally substituted $C_{1-2}$ aliphatic. In some embodiments, $R^4$ is selected from methyl, ethyl, propyl, isopropyl, butyl, sec-butyl, tert-butyl, pentyl, neopentyl, isopentyl and hexyl.

In some embodiments, $R^4$ is -L-$R^6$.

In some embodiments, $R^4$ is an optionally substituted phenyl.

In some embodiments, $R^4$ is an optionally substituted 3-8 membered saturated or partially unsaturated monocyclic carbocyclic ring. In some embodiments, $R^4$ is an optionally substituted 3-8 membered saturated monocyclic carbocyclic ring. In some embodiments, $R^4$ is selected from cyclopropyl, cyclobutyl, cyclopentyl, cyclohexyl, cycloheptyl and cyclooctyl.

In some embodiments, $R^4$ is an optionally substituted 3-8 membered partially unsaturated monocyclic carbocyclic ring. In some embodiments, $R^4$ is selected from cyclopropenyl, cyclobutenyl, cyclopentenyl, cyclohexenyl, cycloheptenyl, cyclooctenyl, cyclopentadienyl, cyclohexadienyl, cycloheptadienyl and cyclooctadienyl.

In some embodiments, $R^4$ is an optionally substituted an 8-10 membered bicyclic aryl ring. In some embodiments, $R^4$ is naphthyl.

In some embodiments, $R^4$ is an optionally substituted 3-8 membered saturated monocyclic heterocyclic ring having 1-2 heteroatoms independently selected from nitrogen, oxygen, and sulfur. In some embodiments, $R^4$ is an optionally substituted 3-8 membered saturated monocyclic heterocyclic ring having 2 heteroatoms independently selected from nitrogen, oxygen, and sulfur. In some embodiments, $R^4$ is an optionally substituted 3-8 membered saturated monocyclic heterocyclic ring having 1 heteroatom selected from nitrogen, oxygen, and sulfur. In some embodiments, $R^4$ is selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, imidazolidinyl, pyrazolidinyl, oxazolidinyl, isoxazolidinyl, dioxolanyl, dithiolanyl, oxolanyl, thiolanyl, piperidinyl, piperazinyl, morpholinyl, oxanyl, thianyl, thiomorpholinyl, dioxanyl, dithianyl, azepanyl, oxepanyl, thiepanyl and homopiperazinyl.

In some embodiments, $R^4$ is an optionally substituted 3-8 membered partially unsaturated monocyclic heterocyclic ring having 1-2 heteroatoms independently selected from nitrogen, oxygen, and sulfur. In some embodiments, $R^4$ is selected from azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^4$ is an optionally substituted 5-6 membered monocyclic heteroaryl ring having 1-4 heteroatoms independently selected from nitrogen, oxygen, and sulfur. In some embodiments, $R^4$ is an optionally substituted 5-membered monocyclic heteroaryl ring having 1-4 heteroatoms independently selected from nitrogen, oxygen, and sulfur. In some embodiments, $R^4$ is an optionally substituted 5-membered monocyclic heteroaryl ring having 1-3 heteroatoms independently selected from nitrogen, oxygen, and sulfur. In some embodiments, $R^4$ is an optionally substituted 5-membered monocyclic heteroaryl ring having 1-2 heteroatoms independently selected from nitrogen, oxygen, and sulfur. In some embodiments, $R^4$ is an optionally substituted 5-membered monocyclic heteroaryl ring having 2 heteroatoms independently selected from nitrogen, oxygen, and sulfur. In some embodiments, $R^4$ is an optionally substituted 5-membered monocyclic heteroaryl ring having 1 heteroatom selected from nitrogen, oxygen, and sulfur. In some embodiments, $R^4$ is selected from pyrrolyl, furanyl, thiophenyl, pyrazolyl, imidazolyl, oxazolyl, isoxazolyl, thiazolyl, isothiazolyl, oxadiazolyl, thiadiazolyl, triazolyl and tetrazolyl.

In some embodiments, $R^4$ is an optionally substituted 6-membered monocyclic heteroaryl ring having 1-4 nitrogen atoms. In some embodiments, $R^4$ is an optionally substituted 6-membered monocyclic heteroaryl ring having 1-3 nitrogen atoms. In some embodiments, $R^4$ is an optionally substituted 6-membered monocyclic heteroaryl ring having 1-2 nitrogen atoms. In some embodiments, $R^4$ is an optionally substituted 6-membered monocyclic heteroaryl ring having 2 nitrogen atoms. In some embodiments, $R^4$ is an optionally substituted 6-membered monocyclic heteroaryl ring having 1 nitrogen atom. In some embodiments, $R^4$ is selected from pyridinyl, pyrazinyl, pyridizinyl, pyrimidinyl, triazinyl and tetrazinyl.

In some embodiments, $R^4$ is an optionally substituted 8-10 membered bicyclic heteroaryl ring having 1-4 heteroatoms independently selected from nitrogen, oxygen, and sulfur. In some embodiments, $R^4$ is an optionally substituted 8-10 membered bicyclic heteroaryl ring having 1-3 heteroatoms independently selected from nitrogen, oxygen, and sulfur. In some embodiments, $R^4$ is an optionally substituted 8-10 membered bicyclic heteroaryl ring having 1-2 heteroatoms independently selected from nitrogen, oxygen, and sulfur. In some embodiments, $R^4$ is an optionally substituted 8-10 membered bicyclic heteroaryl ring having 1 heteroatom selected from nitrogen, oxygen, and sulfur. In some embodiments, $R^4$ is selected from indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

In some embodiments, $R^5$ is halogen. In some embodiments, $R^5$ is $-NO_2$. In some embodiments, $R^5$ is $-CN$. In some embodiments, $R^5$ is $-N_3$.

In some embodiments, $R^5$ is optionally substituted $C_{1-6}$ aliphatic. In some embodiments, $R^5$ is optionally substituted $C_{1-5}$ aliphatic. In some embodiments, $R^5$ is optionally substituted $C_{1-4}$ aliphatic. In some embodiments, $R^5$ is optionally substituted $C_{1-3}$ aliphatic. In some embodiments, $R^5$ is optionally substituted $C_{1-2}$ aliphatic. In some embodiments, $R^5$ is selected from methyl, ethyl, propyl, isopropyl, butyl, sec-butyl, tert-butyl, pentyl, neopentyl, isopentyl and hexyl.

In some embodiments, $R^5$ is -L-$R^6$.

In some embodiments, $R^5$ is an optionally substituted phenyl.

In some embodiments, $R^5$ is an optionally substituted 3-8 membered saturated or partially unsaturated monocyclic carbocyclic ring. In some embodiments, $R^5$ is an optionally substituted 3-8 membered saturated monocyclic carbocyclic ring. In some embodiments, $R^5$ is selected from cyclopropyl, cyclobutyl, cyclopentyl, cyclohexyl, cycloheptyl and cyclooctyl.

In some embodiments, $R^5$ is an optionally substituted 3-8 membered partially unsaturated monocyclic carbocyclic ring. In some embodiments, $R^5$ is selected from cyclopropenyl, cyclobutenyl, cyclopentenyl, cyclohexenyl, cycloheptenyl, cyclooctenyl, cyclopentadienyl, cyclohexadienyl, cycloheptadienyl and cyclooctadienyl.

In some embodiments, $R^5$ is an optionally substituted an 8-10 membered bicyclic aryl ring. In some embodiments, $R^5$ is naphthyl.

In some embodiments, $R^5$ is an optionally substituted 3-8 membered saturated monocyclic heterocyclic ring having 1-2 heteroatoms independently selected from nitrogen, oxygen, and sulfur. In some embodiments, $R^5$ is an optionally substituted 3-8 membered saturated monocyclic heterocyclic ring having 2 heteroatoms independently selected from nitrogen, oxygen, and sulfur. In some embodiments, $R^5$ is an optionally substituted 3-8 membered saturated monocyclic heterocyclic ring having 1 heteroatom selected from nitrogen, oxygen, and sulfur. In some embodiments, $R^5$ is selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, imidazolidinyl, pyrazolidinyl, oxazolidinyl, isoxazolidinyl, dioxolanyl, dithiolanyl, oxolanyl, thiolanyl, piperidinyl, piperazinyl, morpholinyl, oxanyl, thianyl, thiomorpholinyl, dioxanyl, dithianyl, azepanyl, oxepanyl, thiepanyl and homopiperazinyl.

In some embodiments, $R^5$ is an optionally substituted 3-8 membered partially unsaturated monocyclic heterocyclic ring having 1-2 heteroatoms independently selected from nitrogen, oxygen, and sulfur. In some embodiments, $R^5$ is selected from azirinyl, oxirenyl, thiirenyl, diazirinyl, azetyl, oxetyl, thietyl, dioxetyl, dithietyl, imidazolinyl, pyrazolinyl, oxazolinyl and thiazolinyl.

In some embodiments, $R^5$ is an optionally substituted 5-6 membered monocyclic heteroaryl ring having 1-4 heteroatoms independently selected from nitrogen, oxygen, and sulfur. In some embodiments, $R^5$ is an optionally substituted 5-membered monocyclic heteroaryl ring having 1-4 heteroatoms independently selected from nitrogen, oxygen, and sulfur. In some embodiments, $R^5$ is an optionally substituted 5-membered monocyclic heteroaryl ring having 1-3 heteroatoms independently selected from nitrogen, oxygen, and sulfur. In some embodiments, $R^5$ is an optionally substituted 5-membered monocyclic heteroaryl ring having 1-2 heteroatoms independently selected from nitrogen, oxygen, and sulfur. In some embodiments, $R^5$ is an optionally substituted 5-membered monocyclic heteroaryl ring having 2 heteroatoms independently selected from nitrogen, oxygen, and sulfur. In some embodiments, $R^5$ is an optionally substituted 5-membered monocyclic heteroaryl ring having 1 heteroatom selected from nitrogen, oxygen, and sulfur. In some embodiments, $R^5$ is selected from pyrrolyl, furanyl, thiophenyl, pyrazolyl, imidazolyl, oxazolyl, isoxazolyl, thiazolyl, isothiazolyl, oxadiazolyl, thiadiazolyl, triazolyl and tetrazolyl.

In some embodiments, $R^5$ is an optionally substituted 6-membered monocyclic heteroaryl ring having 1-4 nitrogen atoms. In some embodiments, $R^5$ is an optionally substituted 6-membered monocyclic heteroaryl ring having 1-3 nitrogen atoms. In some embodiments, $R^5$ is an optionally substituted 6-membered monocyclic heteroaryl ring having 1-2 nitrogen atoms. In some embodiments, $R^5$ is an optionally substituted 6-membered monocyclic heteroaryl ring having 2 nitrogen atoms. In some embodiments, $R^5$ is an optionally substituted 6-membered monocyclic heteroaryl ring having 1 nitrogen atom. In some embodiments, $R^5$ is selected from pyridinyl, pyrazinyl, pyridizinyl, pyrimidinyl, triazinyl and tetrazinyl.

In some embodiments, $R^5$ is an optionally substituted 8-10 membered bicyclic heteroaryl ring having 1-4 heteroatoms independently selected from nitrogen, oxygen, and sulfur. In some embodiments, $R^5$ is an optionally substituted 8-10 membered bicyclic heteroaryl ring having 1-3 heteroatoms independently selected from nitrogen, oxygen, and sulfur. In some embodiments, $R^5$ is an optionally substituted 8-10 membered bicyclic heteroaryl ring having 1-2 heteroatoms independently selected from nitrogen, oxygen, and sulfur. In some embodiments, $R^5$ is an optionally substituted 8-10 membered bicyclic heteroaryl ring having 1 heteroatom selected from nitrogen, oxygen, and sulfur. In some embodiments, $R^5$ is selected from indolyl, indazolyl, benzofuranyl, benzothiophenyl, benzothiazolyl, benzoxazolyl, benzisoxazolyl, benzimidazolyl, benzotriazolyl, azaindolyl, quinolinyl, isoquinolinyl, quinazolinyl, quinoxalinyl and cinnolinyl.

In some embodiments, two $R^3$ groups on Ring B are taken together with their intervening atoms to form a fused 4-8 membered saturated, partially unsaturated, or aryl ring having 0-3 heteroatoms independently selected from nitrogen, oxygen, and sulfur. In some embodiments, two $R^3$ groups on Ring B are taken together with their intervening atoms to form a fused 4-8 membered saturated, partially unsaturated, or aryl ring having 1-3 heteroatoms independently selected from nitrogen, oxygen, and sulfur. In some embodiments, two $R^3$ groups on Ring B are taken together with their intervening atoms to form a fused 4-8 membered saturated, partially unsaturated, or aryl ring having 1 heteroatom selected from nitrogen, oxygen, and sulfur. In some embodiments, two $R^3$ groups on Ring B are taken together with their intervening atoms to form a fused 4-8 membered saturated, partially unsaturated, or aryl ring having 2-3 heteroatoms independently selected from nitrogen, oxygen, and sulfur. In some embodiments, two $R^3$ groups on Ring B are taken together with their intervening atoms to form a fused 4-8 membered saturated, partially unsaturated, or aryl ring having 2 heteroatoms independently selected from nitrogen, oxygen, and sulfur. In some embodiments, two $R^3$ groups on Ring B are taken together with their intervening atoms to form a phenyl ring. In some embodiments, two $R^3$ groups on Ring B are taken together with their intervening atoms to form a ring selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl, homopiperazinyl, azirinyl, oxirenyl, thiirenyl, diazirinyl, azetyl, oxetyl, thietyl, dioxetyl, dithietyl, imidazolinyl, pyrazolinyl, oxazolinyl, thiazolinyl, cyclobutyl, cyclopentyl, cyclohexyl, cycloheptyl, cyclooctyl, pyrrolyl, furanyl, thiophenyl, pyrazolyl, imidazolyl, oxazolyl, isoxazolyl, thiazolyl, isothiazolyl, oxadiazolyl, thiadiazolyl, triazolyl, tetrazolyl, pyridinyl, pyrazinyl, pyridizinyl, pyrimidinyl, triazinyl and tetrazinyl.

In some embodiments, two $R^4$ groups on Ring A are taken together with their intervening atoms to form a fused 4-8 membered saturated, partially unsaturated, or aryl ring having 0-3 heteroatoms independently selected from nitrogen, oxygen, and sulfur. In some embodiments, two $R^4$ groups on Ring B are taken together with their intervening atoms to form a fused 4-8 membered saturated, partially unsaturated, or aryl ring having 1-3 heteroatoms independently selected from nitrogen, oxygen, and sulfur. In some embodiments, two $R^4$ groups on Ring B are taken together with their intervening atoms to form a fused 4-8 membered saturated, partially unsaturated, or aryl ring having 1 heteroatom selected from nitrogen, oxygen, and sulfur. In some embodiments, two $R^4$ groups on Ring B are taken together with their intervening atoms to form a fused 4-8 membered saturated, partially unsaturated, or aryl ring having 2-3 heteroatoms independently selected from nitrogen, oxygen, and sulfur. In some embodiments, two $R^4$ groups on Ring B are taken together with their intervening atoms to form a fused 4-8 membered saturated, partially unsaturated, or aryl ring having 2 heteroatoms independently selected from nitrogen, oxygen, and sulfur. In some embodiments, two $R^4$ groups on Ring B are taken together with their intervening atoms to form a phenyl ring. In some embodiments, two $R^4$ groups on Ring B are taken together with their intervening atoms to form a ring selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl, homopiperazinyl, azirinyl, oxirenyl, thiirenyl, diazirinyl, azetyl, oxetyl, thietyl, dioxetyl, dithietyl, imidazolinyl, pyrazolinyl, oxazolinyl, thiazolinyl, cyclobutyl, cyclopentyl, cyclohexyl, cycloheptyl, cyclooctyl, pyrrolyl, furanyl, thiophenyl, pyrazolyl, imidazolyl, oxazolyl, isoxazolyl, thiazolyl, isothiazolyl, oxadiazolyl, thiadiazolyl, triazolyl, tetrazolyl, pyridinyl, pyrazinyl, pyridizinyl, pyrimidinyl, triazinyl and tetrazinyl.

In some embodiments, two $R^5$ groups on the ring formed by $R^1$ and $R^2$ are taken together with their intervening atoms to form a fused 4-8 membered saturated, partially unsaturated, or aryl ring having 0-3 heteroatoms independently selected from nitrogen, oxygen, and sulfur. In some embodiments, two $R^5$ groups on Ring B are taken together with their intervening atoms to form a fused 4-8 membered saturated, partially unsaturated, or aryl ring having 1-3 heteroatoms independently selected from nitrogen, oxygen, and sulfur. In some embodiments, two $R^5$ groups on Ring B are taken together with their intervening atoms to form a fused 4-8 membered saturated, partially unsaturated, or aryl ring having 1 heteroatom selected from nitrogen, oxygen, and sulfur. In some embodiments, two $R^5$ groups on Ring B are taken together with their intervening atoms to form a fused 4-8 membered saturated, partially unsaturated, or aryl ring having 2-3 heteroatoms independently selected from nitrogen, oxygen, and sulfur. In some embodiments, two $R^5$ groups on Ring B are taken together with their intervening atoms to form a fused 4-8 membered saturated, partially unsaturated, or aryl ring having 2 heteroatoms independently selected from nitrogen, oxygen, and sulfur. In some embodiments, two $R^5$ groups on Ring B are taken together with their intervening atoms to form a phenyl ring. In some embodiments, two $R^5$ groups on Ring B are taken together with their intervening atoms to form a ring selected from aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, oxolanyl, thiolanyl, imidazolidinyl, pyrazolidinyl, oxazolidinyl, isoxazolidinyl, thiazolidinyl, isothiazolidinyl, dioxolanyl, dithiolanyl, piperidinyl, oxanyl, thianyl, piperazinyl, morpholinyl, thiomorpholinyl, dioxanyl, dithianyl, azepanyl, oxepanyl, thiepanyl, homopiperazinyl, azirinyl, oxirenyl, thiirenyl, diazirinyl, azetyl, oxetyl, thietyl, dioxetyl, dithietyl, imidazolinyl, pyrazolinyl, oxazolinyl, thiazolinyl, cyclobutyl, cyclopentyl, cyclohexyl, cycloheptyl, cyclooctyl, pyrrolyl, furanyl, thiophenyl, pyrazolyl, imidazolyl, oxazolyl, isoxazolyl, thiazolyl, isothiazolyl, oxadiazolyl, thiadiazolyl, triazolyl, tetrazolyl, pyridinyl, pyrazinyl, pyridizinyl, pyrimidinyl, triazinyl and tetrazinyl.

As defined generally above, L is a covalent bond or an optionally substituted bivalent $C_{1-6}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is a covalent bond. In some embodiments, L is an optionally substituted bivalent $C_{1-6}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is an optionally substituted bivalent $C_{1-5}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is an optionally substituted bivalent $C_{1-4}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is an optionally substituted bivalent $C_{1-3}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is an optionally substituted bivalent $C_{1-2}$ hydrocarbon chain, wherein one or two methylene units of L is optionally and independently replaced by -Cy-, —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—. In some embodiments, L is -Cy-. In some embodiments, L is —O—. In some embodiments, L is –5-. In some embodiments, L is —N(R$^6$)—. In some embodiments, L is —C(O)—. In some embodiments, L is —C(S)—. In some embodiments, L is —C(O)N(R$^6$)—. In some embodiments, L is —N(R$^6$)C(O)N(R$^6$)—. In some embodiments, L is —N(R$^6$)C(O)—. In some embodiments, L is —N(R$^6$)C(O)O—. In some embodiments, L is —OC(O)N(R$^6$)—. In some embodiments, L is —S(O)—. In some embodiments, L is —S(O)$_2$—. In some embodiments, L is —S(O)$_2$N(R$^6$)—. In some embodiments, L is —N(R$^6$)S(O)$_2$—. In some embodiments, L is —OC(O)—. In some embodiments, L is —C(O)O—.

In some embodiments, L is —CH$_2$-Cy-. In some embodiments, L is —CH$_2$—O—. In some embodiments, L is —CH$_2$—S—. In some embodiments, L is —CH$_2$—N(R$^6$)—. In some embodiments, L is —CH$_2$—C(O)—. In some embodiments, L is —CH$_2$—C(S)—. In some embodiments, L is —CH$_2$—C(O)N(R$^6$)—. In some embodiments, L is —CH$_2$—N(R$^6$)C(O)N(R$^6$)—. In some embodiments, L is —CH$_2$—N(R$^6$)C(O)—. In some embodiments, L is —CH$_2$—N(R$^6$)C(O)O—. In some embodiments, L is —CH$_2$—OC(O)N(R$^6$)—. In some embodiments, L is —CH$_2$—S(O)—. In some embodiments, L is —CH$_2$—S(O)$_2$—. In some embodiments, L is —CH$_2$—S(O)$_2$N(R$^6$)—. In some embodiments, L is —CH$_2$—N(R$^6$)S(O)$_2$—. In some embodiments, L is —CH$_2$—OC(O)—. In some embodiments, L is —CH$_2$—C(O)O—.

In some embodiments, L is -Cy-CH$_2$—. In some embodiments, L is —O—CH$_2$—. In some embodiments, L is —S—CH$_2$—. In some embodiments, L is —N(R$^6$)—CH$_2$—. In some embodiments, L is —C(O)—CH$_2$—. In some embodiments, L is —C(S)—CH$_2$—. In some embodiments, L is —C(O)N(R$^6$)—CH$_2$—. In some embodiments, L is —N(R$^6$)C(O)N(R$^6$)—CH$_2$—. In some embodiments, L is —N(R$^6$)C(O)—CH$_2$—. In some embodiments, L is N(R$^6$)C(O)O—CH$_2$—. In some embodiments, L is —OC(O)N(R$^6$)—CH$_2$—. In some embodiments, L is —S(O)—CH$_2$—. In some embodiments, L is —S(O)$_2$—CH$_2$—. In some embodiments, L is —S(O)$_2$N(R$^6$)—CH$_2$—. In some embodiments, L is —N(R$^6$)S(O)$_2$—CH$_2$—. In some embodiments, L is —OC(O)—CH$_2$—. In some embodiments, L is —C(O)O—CH$_2$—.

As defined generally above, -Cy- is an optionally substituted bivalent ring selected from a 3-7 membered saturated or partially unsaturated cycloalkylenylene ring, a 4-7-membered saturated or partially unsaturated heterocycloalkylene ring having 1-4 heteroatoms independently selected from nitrogen, oxygen, and sulfur, phenylene, a 5-6 membered monocyclic heteroarylene having 1-4 heteroatoms independently selected from nitrogen, oxygen, and sulfur, an 8-10 membered bicyclic arylene, or an 8-10 membered bicyclic heteroarylene having 1-4 heteroatoms independently selected from nitrogen, oxygen, and sulfur.

In some embodiments, the present invention provides a compound of formula I-a or I-b:

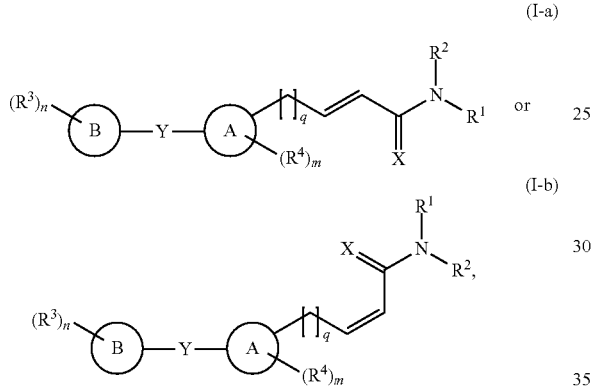

or a pharmaceutically acceptable salt thereof, wherein each of Ring A, Ring B, X, Y, R$^1$, R$^2$, R$^3$, R$^4$, m, n and q is as defined above and described herein.

In some embodiments of formulae I-a and I-b, q is 0. Thus, in some embodiments, the present invention provides a compound of formula II-a or II-b:

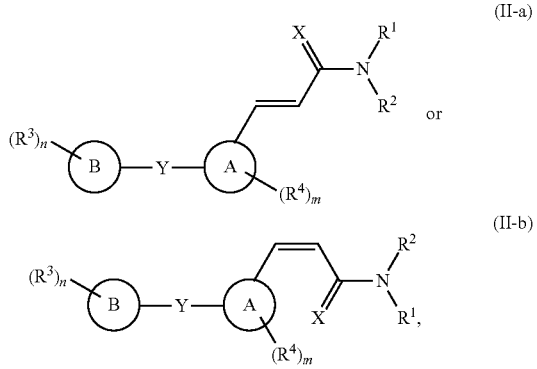

or a pharmaceutically acceptable salt thereof, wherein each of Ring A, Ring B, X, Y, R$^1$, R$^2$, R$^3$, R$^4$, m and n is as defined above and described herein.

In some embodiments of formulae II-a and II-b, Y is a covalent bond. Thus, in some embodiments, the present invention provides a compound of formula III-a or III-b:

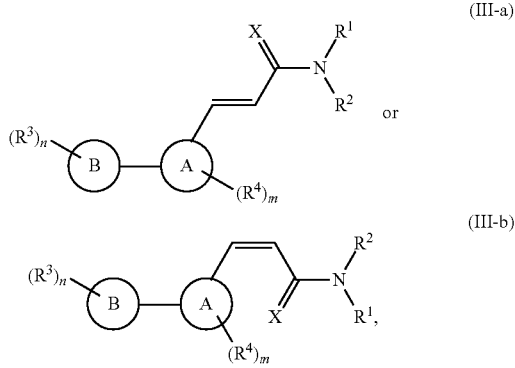

or a pharmaceutically acceptable salt thereof, wherein each of Ring A, Ring B, X, R$^1$, R$^2$, R$^3$, R$^4$, m and n is as defined above and described herein.

In some embodiments of formulae III-a and III-b, X is O. Accordingly, in some embodiments, the present invention provides a compound of formula IV-a or IV-b:

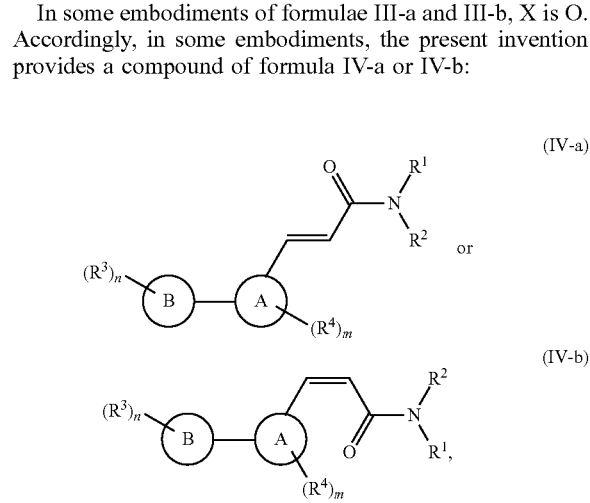

or a pharmaceutically acceptable salt thereof, wherein each of Ring A, Ring B, R$^1$, R$^2$, R$^3$, R$^4$, m and n is as defined above and described herein.

In some embodiments of formulae IV-a and IV-b, Ring A is a 5-membered monocyclic heteroaryl ring having 1-4 heteroatoms independently selected from nitrogen, oxygen, and sulfur. In some embodiments of formulae IV-a and IV-b, Ring A is a 5-membered monocyclic heteroaryl ring having 1-3 heteroatoms independently selected from nitrogen, oxygen, and sulfur. In some embodiments of formulae IV-a and IV-b, Ring A is a 5-membered monocyclic heteroaryl ring having 1-2 heteroatoms independently selected from nitrogen, oxygen, and sulfur. In some embodiments of formulae IV-a and IV-b, Ring A is a 5-membered monocyclic heteroaryl ring having 2 heteroatoms independently selected from nitrogen, oxygen, and sulfur. In some embodiments of formulae IV-a and IV-b, Ring A is a 5-membered monocyclic heteroaryl ring having 1 heteroatom selected from nitrogen, oxygen, and sulfur. In some embodiments of formulae IV-a and IV-b, Ring A is selected from pyrrolyl, furanyl, thiophenyl, pyrazolyl, imidazolyl, oxazolyl, isoxazolyl, thiazolyl, isothiazolyl, oxadiazolyl, thiadiazolyl, triazolyl and tetrazolyl.

In some embodiments of formulae IV-a and IV-b, Ring A is triazolyl. Accordingly, the present invention provides compounds of formulae V-a, V-b, V-c and V-d:

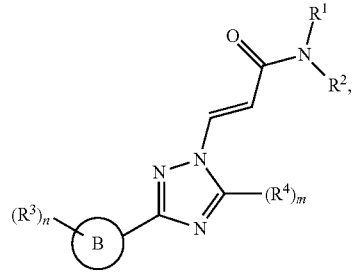
(V-a)

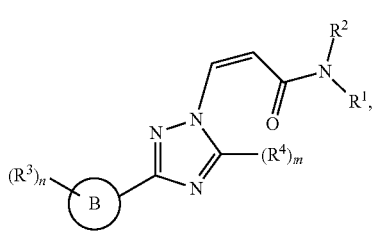
(V-b)

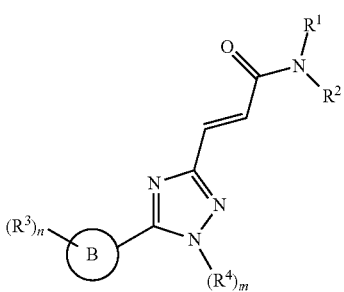
(V-c)

and

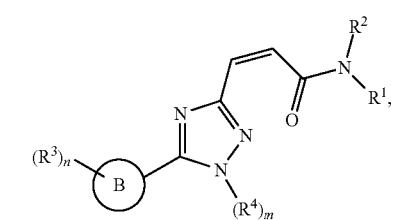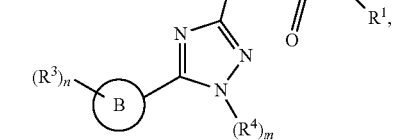
(V-d)

or a pharmaceutically acceptable salt thereof, wherein each of Ring B, R$^1$, R$^2$, R$^3$, R$^4$ and n is as defined above and described herein and m is 0 or 1.

In some embodiments of formulae IV-a and IV-b, Ring A is imidazolyl. Accordingly, in some embodiments, the present invention provides compounds of formulae V-e, V-f, V-g, V-h, V-i and V-i:

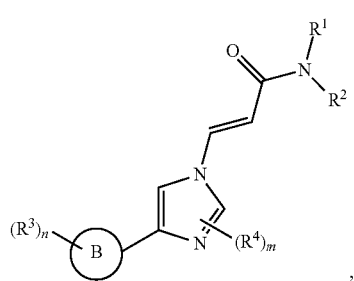
(V-e)

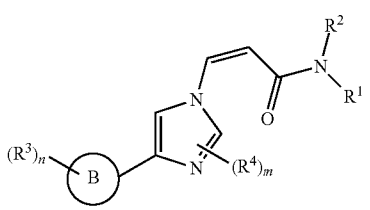
(V-f)

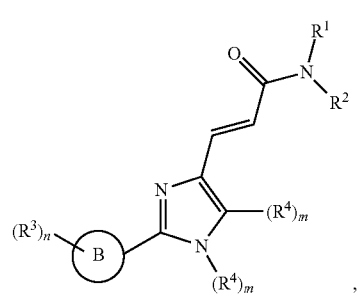
(V-g)

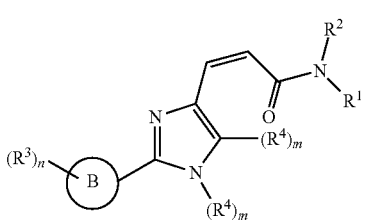
(V-h)

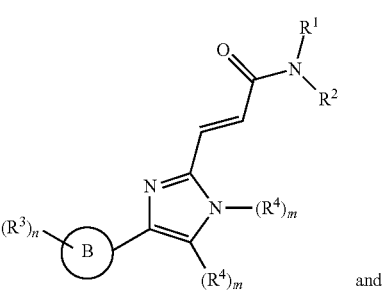
(V-i)

and

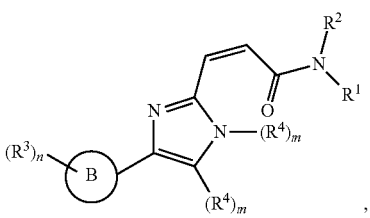
(V-j)

or a pharmaceutically acceptable salt thereof, wherein each of Ring B, R$^1$, R$^2$, R$^3$, R$^4$, m and n is as defined above and described herein.

In some embodiments of formulae IV-a and IV-b, Ring A is pyrazolyl. Accordingly, in some embodiments, the present invention provides compounds of formulae V-k, V-l, V-m, V-n, V-o, V-p, V-q, V-r, V-s and V-t:

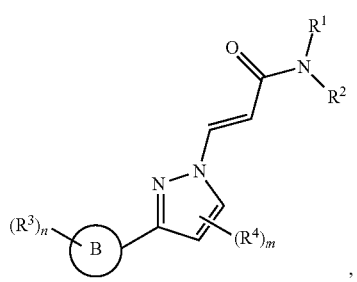 (V-k)
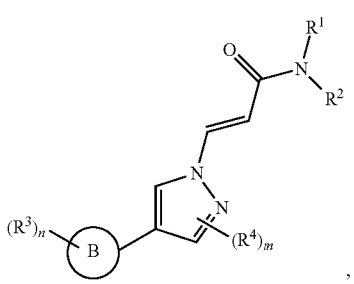 (V-l)
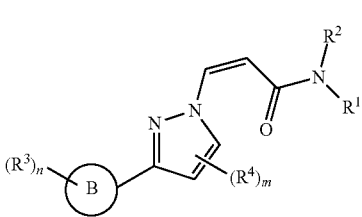 (V-m)
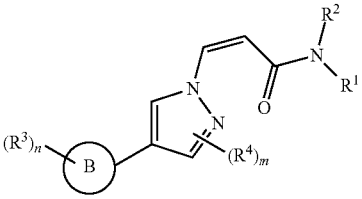 (V-n)
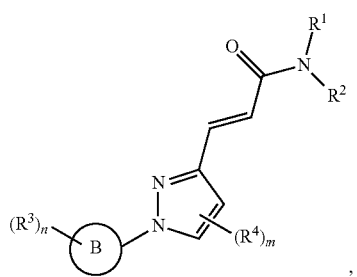 (V-o)
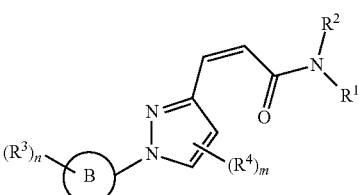 (V-p)
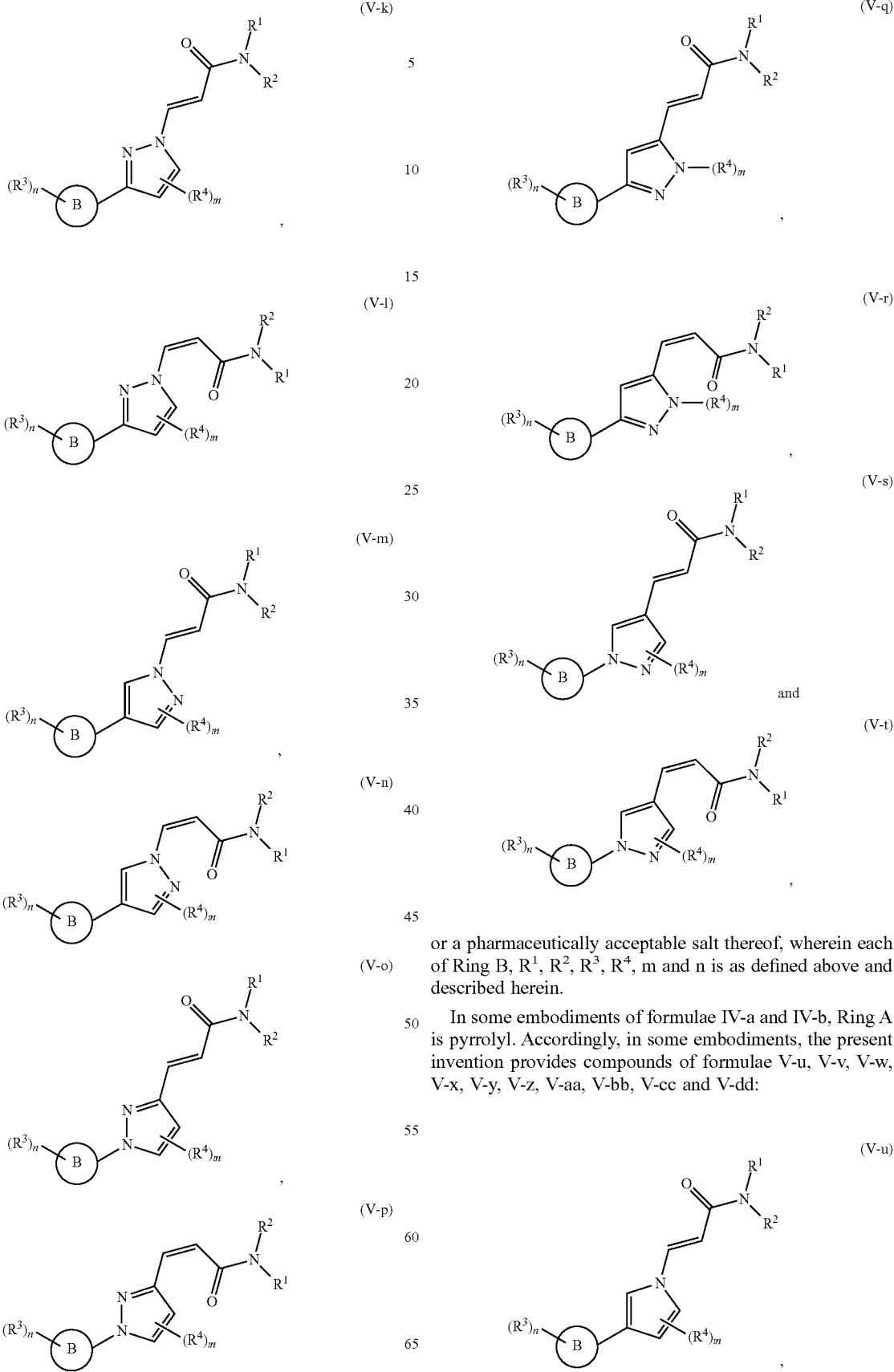 (V-q)
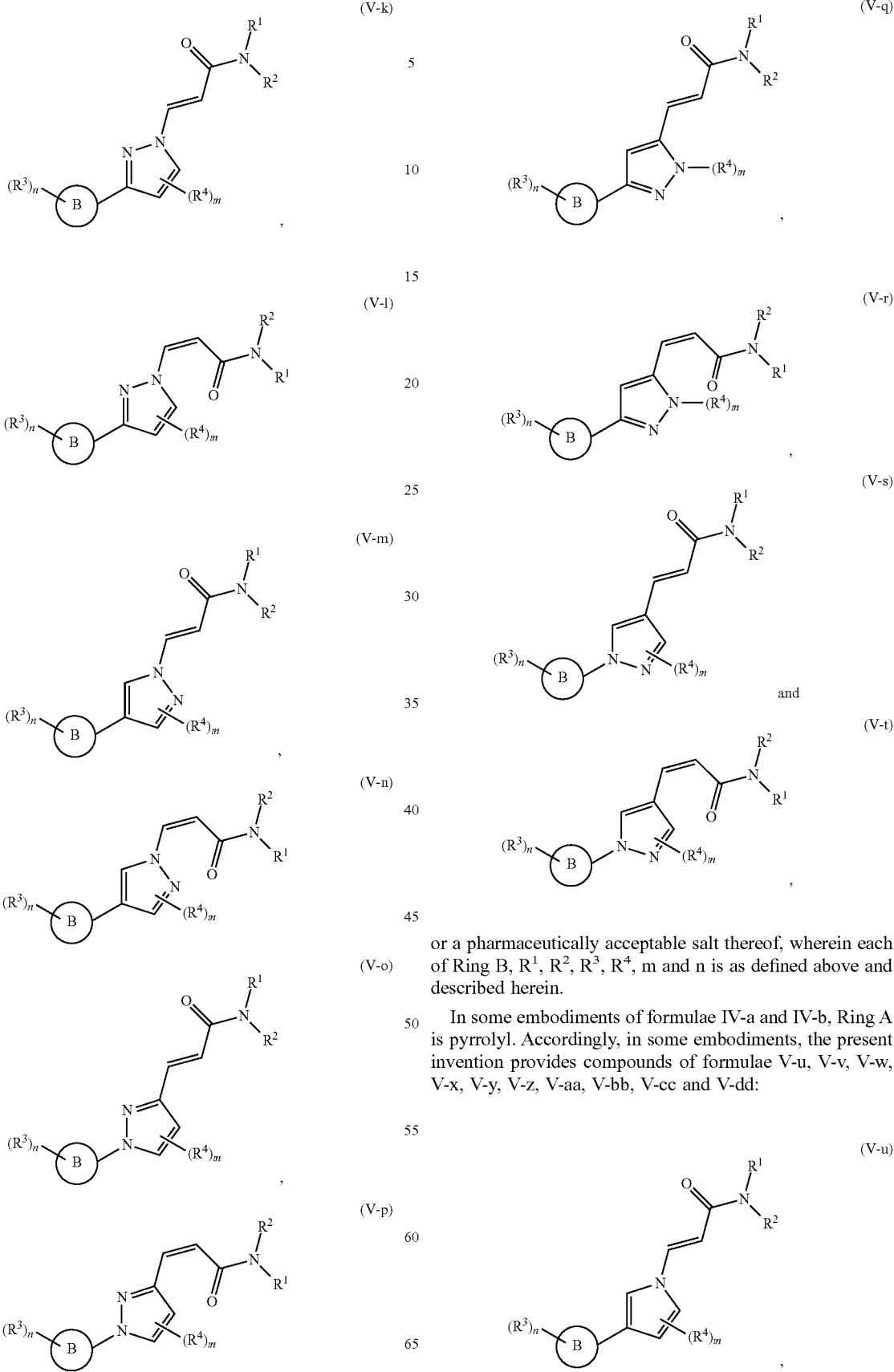 (V-r)
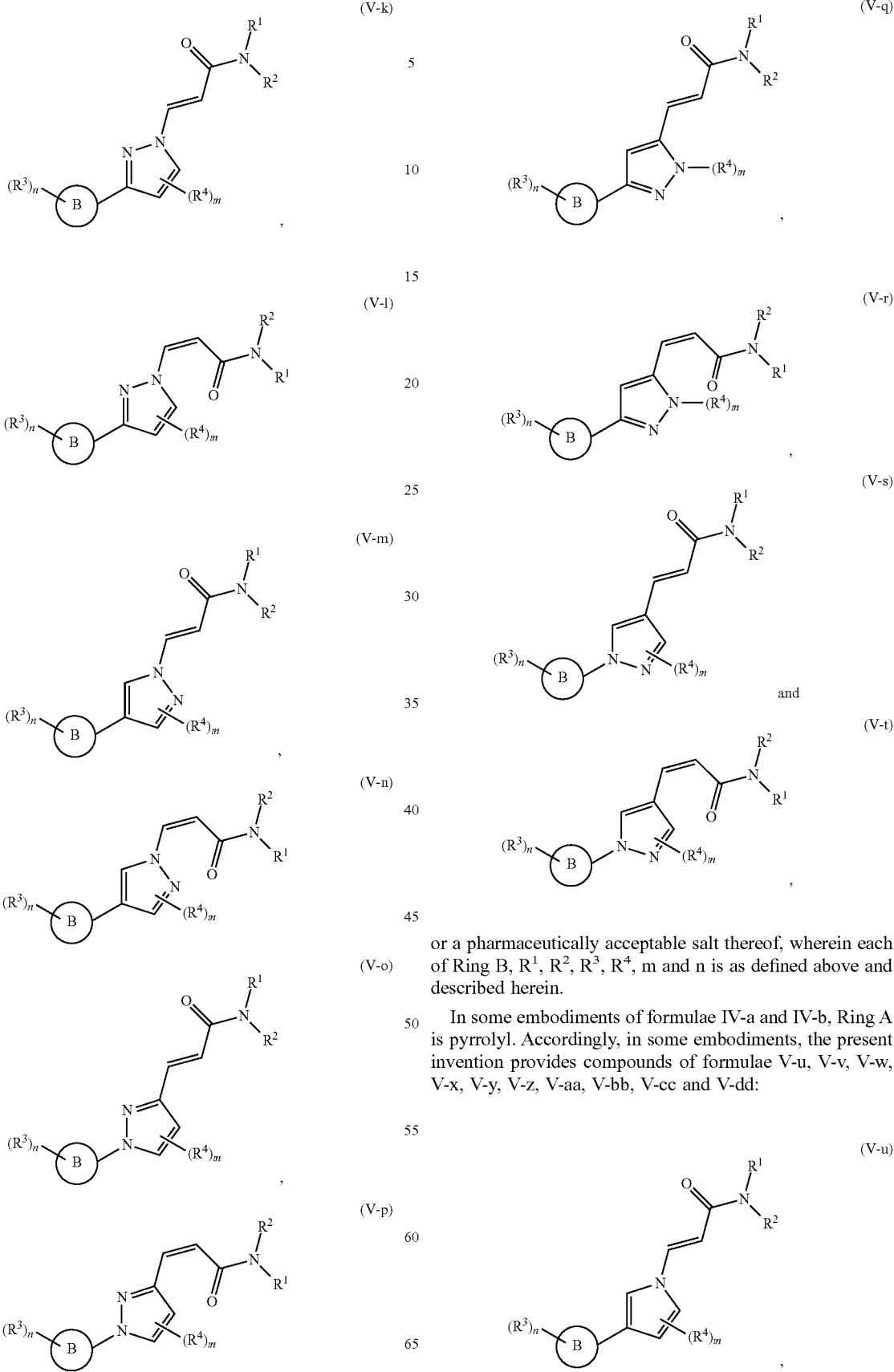 (V-s)
and
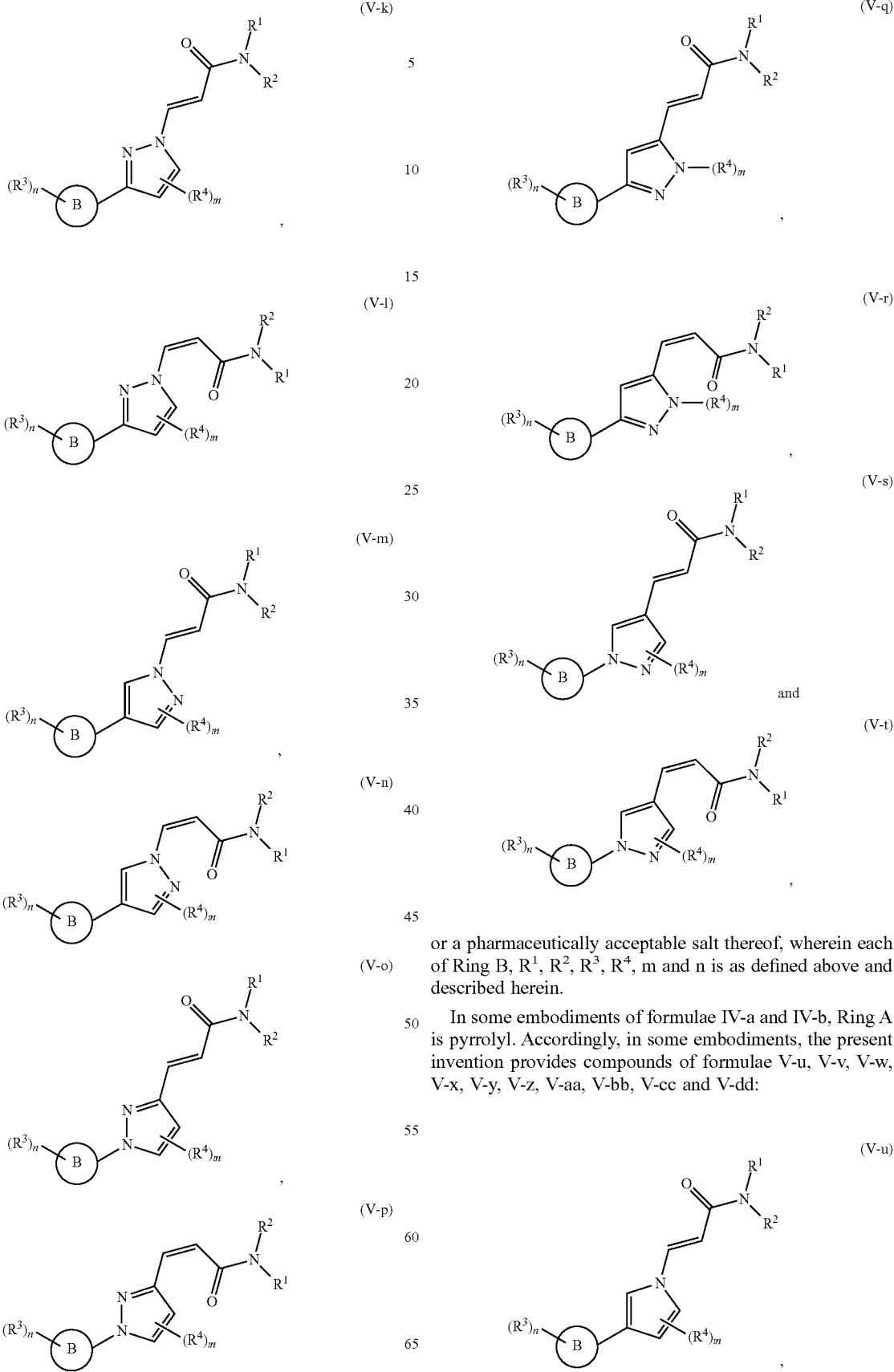 (V-t)
or a pharmaceutically acceptable salt thereof, wherein each of Ring B, $R^1$, $R^2$, $R^3$, $R^4$, m and n is as defined above and described herein.
In some embodiments of formulae IV-a and IV-b, Ring A is pyrrolyl. Accordingly, in some embodiments, the present invention provides compounds of formulae V-u, V-v, V-w, V-x, V-y, V-z, V-aa, V-bb, V-cc and V-dd:
(V-u)

(V-v) 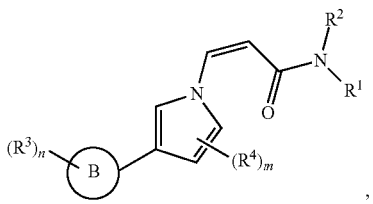

(V-w) 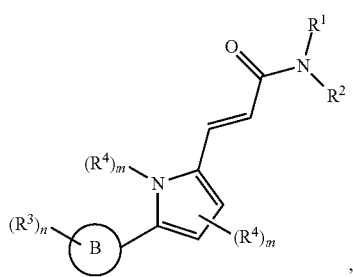

(V-x) 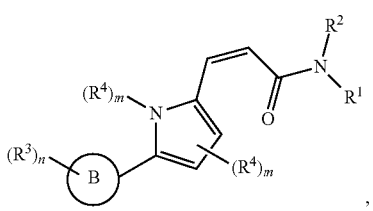

(V-y) 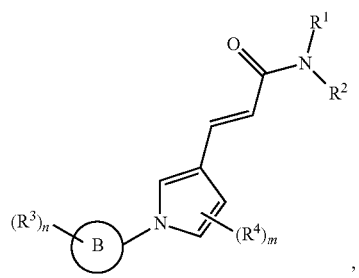

(V-z) 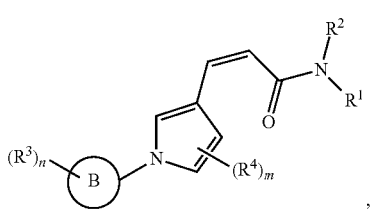

(V-aa) 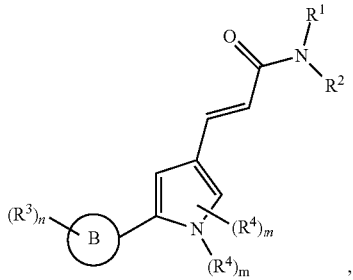

(V-bb) 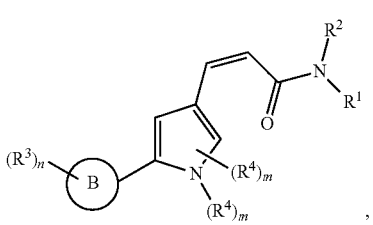

(V-cc) 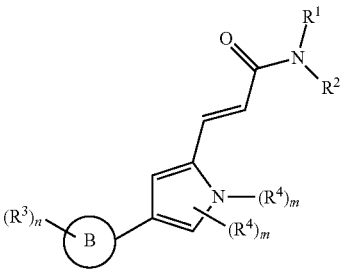

and (V-dd) 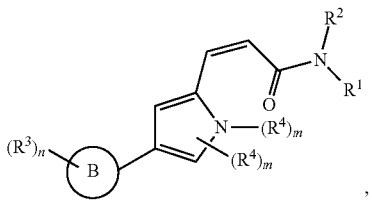

or a pharmaceutically acceptable salt thereof, wherein each of Ring B, $R^1$, $R^2$, $R^3$, $R^4$, m and n is as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is optionally substituted phenyl. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more optionally substituted methyl groups. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one optionally substituted methyl group. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two optionally substituted methyl groups.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with at least one halogen. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with at least two halogens. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with three halogens.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more —CF$_3$ groups. In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two —CF$_3$ groups.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is:

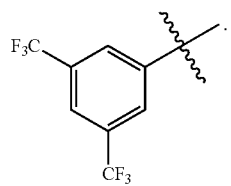

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, R$^1$ and R$^2$ are taken together with their intervening atoms to form a 4-8 membered saturated, partially unsaturated, or aromatic heterocyclic ring having 1-3 heteroatoms independently selected from nitrogen, oxygen, and sulfur, wherein the ring formed thereby is substituted with —(R$^5$)$_p$.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, the 4-8 membered saturated heterocyclic ring formed by R$^1$, R$^2$ and their intervening atoms is:

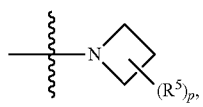

wherein R$^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, the 4-8 membered saturated heterocyclic ring formed by R$^1$, R$^2$ and their intervening atoms is substituted with one or more halogens. In some such embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, the 4-8 membered saturated heterocyclic ring formed by R$^1$, R$^2$ and their intervening atoms is:

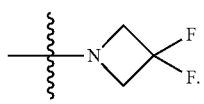 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is optionally substituted phenyl and the 4-8 membered saturated heterocyclic ring formed by R$^1$, R$^2$ and their intervening atoms is:

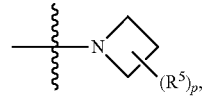

wherein R$^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more optionally substituted methyl groups and the 4-8 membered saturated heterocyclic ring formed by R$^1$, R$^2$ and their intervening atoms is:

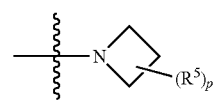

wherein R$^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two optionally substituted methyl groups and the 4-8 membered saturated heterocyclic ring formed by R$^1$, R$^2$ and their intervening atoms is:

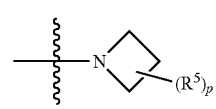

wherein R$^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with at least one halogen and the 4-8 membered saturated heterocyclic ring formed by R$^1$, R$^2$ and their intervening atoms is:

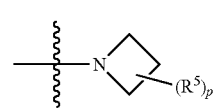

wherein R$^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with three halogens and the 4-8 membered saturated heterocyclic ring formed by R$^1$, R$^2$ and their intervening atoms is:

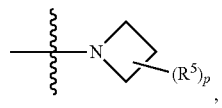

wherein $R^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more —$CF_3$ groups and the 4-8 membered saturated heterocyclic ring formed by $R^1$, $R^2$ and their intervening atoms is:

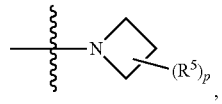

wherein $R^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two —$CF_3$ groups and the 4-8 membered saturated heterocyclic ring formed by $R^1$, $R^2$ and their intervening atoms is:

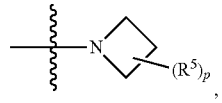

wherein $R^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is:

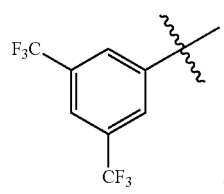

and the 4-8 membered saturated heterocyclic ring formed by $R^1$, $R^2$ and their intervening atoms is:

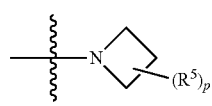

wherein $R^5$ and p are as defined above and described herein.

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is optionally substituted phenyl and the 4-8 membered saturated heterocyclic ring formed by $R^1$, $R^2$ and their intervening atoms is:

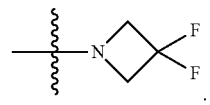

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more optionally substituted methyl groups and the 4-8 membered saturated heterocyclic ring formed by $R^1$, $R^2$ and their intervening atoms is:

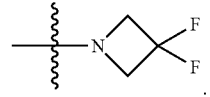 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two optionally substituted methyl groups and the 4-8 membered saturated heterocyclic ring formed by $R^1$, $R^2$ and their intervening atoms is:

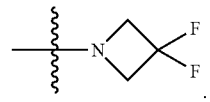

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with at least one halogen and the 4-8 membered saturated heterocyclic ring formed by $R^1$, $R^2$ and their intervening atoms is:

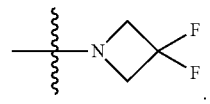 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more methyl groups substituted with three halogens and the 4-8 membered saturated heterocyclic ring formed by $R^1$, $R^2$ and their intervening atoms is:

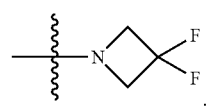 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with one or more —CF$_3$ groups and the 4-8 membered saturated heterocyclic ring formed by R$^1$, R$^2$ and their intervening atoms is:

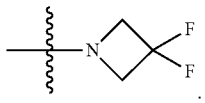 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is phenyl substituted with two —CF$_3$ groups and the 4-8 membered saturated heterocyclic ring formed by R$^1$, R$^2$ and their intervening atoms is:

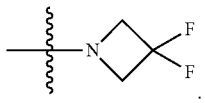 [SMILES: *N1CC(F)(F)C1]

In some embodiments of formula V-a, V-b, V-c, V-d, V-e, V-f, V-g, V-h, V-i, V-j, V-k, V-l, V-m, V-n, V-o, V-p, V-q, V-r, V-s, V-t, V-u, V-v, V-w, V-x, V-y, V-z, V-aa, V-bb, V-cc or V-dd, Ring B is:

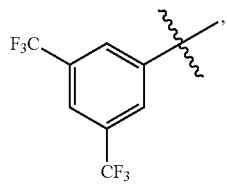

and the 4-8 membered saturated heterocyclic ring formed by R$^1$, R$^2$ and their intervening atoms is:

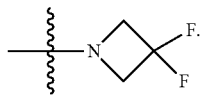 [SMILES: *N1CC(F)(F)C1]

One embodiment of the invention is a compound of formula I, or a pharmaceutically acceptable salt thereof, wherein:

Ring A is an optionally substituted ring selected from phenyl, an 8-10 membered bicyclic aryl ring, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur;

Ring B is an optionally substituted ring selected from a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur;

X is selected from O, S, N—CN, and NR;

R is hydrogen or an optionally substituted group selected from C$_{1-6}$ aliphatic, 3-8 membered saturated or partially unsaturated heterocyclic ring having 1-2 heteroatoms independently selected from nitrogen, oxygen, and sulfur, phenyl, and a 5-6 membered heteroaryl ring having 1-4 heteroatoms independently selected from nitrogen, oxygen, and sulfur;

Y is a covalent bond or an optionally substituted bivalent C$_{1-4}$ hydrocarbon group, wherein one methylene unit of Y is optionally replaced by —O—, —S—, —N(R$^6$)—, —C(O)—, —C(S)—, —C(O)N(R$^6$)—, —N(R$^6$)C(O)N(R$^6$)—, —N(R$^6$)C(O)—, —N(R$^6$)C(O)O—, —OC(O)N(R$^6$)—, —S(O)—, —S(O)$_2$—, —S(O)$_2$N(R$^6$)—, —N(R$^6$)S(O)$_2$—, —OC(O)— or —C(O)O—;

each of R$^1$ and R$^2$ is independently hydrogen or an optionally substituted group selected from C$_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or:

R$^1$ and R$^2$ are taken together with their intervening atoms to form a 4-8 membered saturated, partially unsaturated, or aromatic heterocyclic ring having 1-3 heteroatoms independently selected from nitrogen, oxygen, and sulfur, wherein the ring formed thereby is substituted with —(R$^5$)$_p$;

each of n, m, and p is independently an integer selected from 0, 1, 2, 3 and 4;

q is an integer selected from 0, 1 and 2;

each of R$^3$, R$^4$, and R$^5$ is independently halogen, —NO$_2$, —CN, —N$_3$, -L-R$^6$, or an optionally substituted group selected from C$_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or:

two R$^3$ groups on Ring B are taken together with their intervening atoms to form a fused 4-8 membered saturated, partially unsaturated, or aryl ring having 0-3 heteroatoms independently selected from nitrogen, oxygen, and sulfur; or:

two R$^4$ groups on Ring A are taken together with their intervening atoms to form a fused 4-8 membered saturated, partially unsaturated, or aryl ring having 0-3 heteroatoms independently selected from nitrogen, oxygen, and sulfur; or:

two R$^5$ groups on the ring formed by R$^1$ and R$^2$ are taken together with their intervening atoms to form a fused 4-8 membered saturated, partially unsaturated, or aryl ring having 0-3 heteroatoms independently selected from nitrogen, oxygen, and sulfur;

L is a covalent bond or an optionally substituted bivalent $C_{1-6}$ hydrocarbon group, wherein one or two methylene units of L is optionally and independently replaced by -Cy-, —O—, —S—, —N($R^6$)—, —C(O)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—;

-Cy- is an optionally substituted bivalent ring selected from a 3-7 membered saturated or partially unsaturated cycloalkylenylene ring, a 4-7-membered saturated or partially unsaturated heterocycloalkylene ring having 1-4 heteroatoms independently selected from nitrogen, oxygen, and sulfur, phenylene, a 5-6 membered monocyclic heteroarylene having 1-4 heteroatoms independently selected from nitrogen, oxygen, and sulfur, an 8-10 membered bicyclic arylene, and an 8-10 membered bicyclic heteroarylene having 1-4 heteroatoms independently selected from nitrogen, oxygen, and sulfur; and each $R^6$ is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 4-7-membered saturated or partially unsaturated heterocyclic ring having 1-4 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur; or:

two $R^6$ on the same nitrogen are taken together with their intervening atoms to form a 4-7 membered saturated, partially unsaturated, or aromatic heterocyclic ring having 1-2 heteroatoms independently selected from nitrogen, oxygen, and sulfur.

In one specific embodiment of a compound of formula I, the compound is not a compound listed in Table 1A.

TABLE 1A

| Compound Structure | Compound Name |
| --- | --- |
| 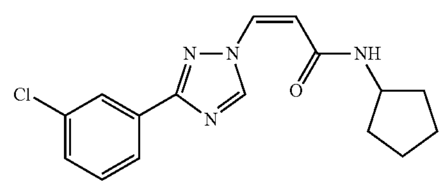 [SMILES: O=C(/C=C\n1cnc(-c2cccc(Cl)c2)n1)NC1CCCC1] | (Z)-3-(3-(3-chlorophenyl)-1H-1,2,4-triazol-1-yl)-N-cyclopentylacrylamide |
| 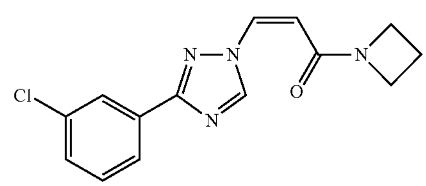 [SMILES: O=C(/C=C\n1cnc(-c2cccc(Cl)c2)n1)N1CCC1] | (Z)-1-(azetidin-1-yl)-3-(3-(3-chlorophenyl)-1H-1,2,4-triazol-1-yl)prop-2-en-1-one |
| 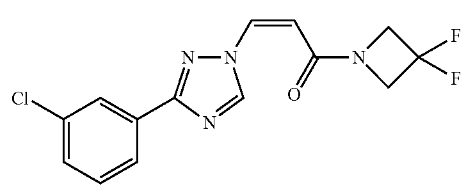 [SMILES: O=C(/C=C\n1cnc(-c2cccc(Cl)c2)n1)N1CC(F)(F)C1] | (Z)-3-(3-(3-chlorophenyl)-1H-1,2,4-triazol-1-yl)-1-(3,3-difluoroazetidin-1-yl)prop-2-en-1-one |
| 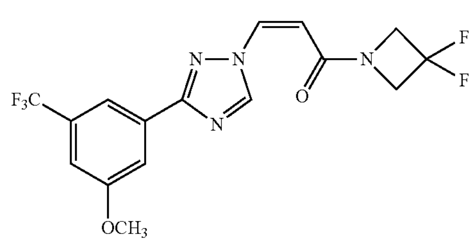 [SMILES: COc1cc(-c2ncn(/C=C\C(=O)N3CC(F)(F)C3)n2)cc(C(F)(F)F)c1] | (Z)-1-(3,3-difluoroazetidin-1-yl)-3-(3-(3-methoxy-5-(trifluoromethyl)phenyl)-1H-1,2,4-triazol-1-yl)prop-2-en-1-one |

TABLE 1A-continued

| Compound Structure | Compound Name |
| --- | --- |
| 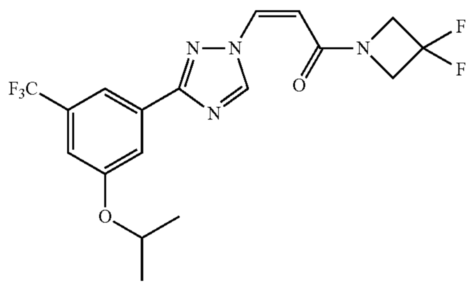 [SMILES: CC(C)Oc1cc(-c2ncn(/C=C\C(=O)N3CC(F)(F)C3)n2)cc(C(F)(F)F)c1] | (Z)-1-(3,3-difluoroazetidin-1-yl)-3-(3-(3-isopropoxy-5-(trifluoromethyl)phenyl)-1H-1,2,4-triazol-1-yl)prop-2-en-1-one |
| 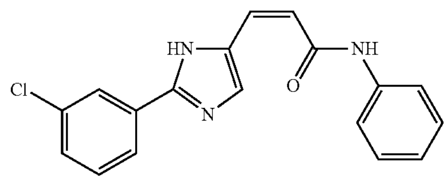 [SMILES: O=C(/C=C\c1cnc(-c2cccc(Cl)c2)[nH]1)Nc1ccccc1] | (Z)-3-(5-(3-chlorophenyl)-4H-1,2,4-triazol-3-yl)-N-phenylacrylamide |
| 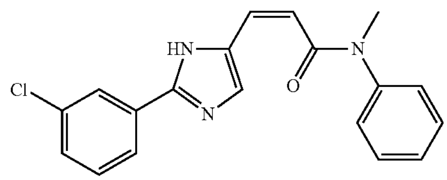 [SMILES: CN(C(=O)/C=C\c1cnc(-c2cccc(Cl)c2)[nH]1)c1ccccc1] | (Z)-3-(5-(3-chlorophenyl)-4H-1,2,4-triazol-3-yl)-N-methyl-N-phenylacrylamide |
| 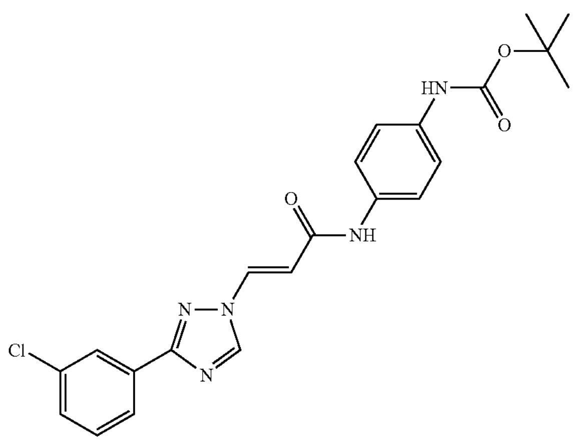 [SMILES: CC(C)(C)OC(=O)Nc1ccc(NC(=O)/C=C/n2cnc(-c3cccc(Cl)c3)n2)cc1] | (E)-tert-butyl (4-(3-(3-(3-chlorophenyl)-1H-1,2,4-triazol-1-yl)acrylamido)phenyl)carbamate |
| 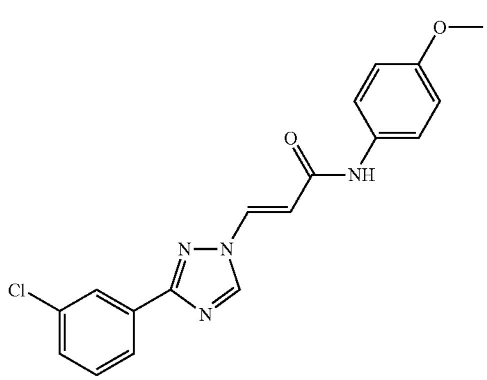 [SMILES: COc1ccc(NC(=O)/C=C/n2cnc(-c3cccc(Cl)c3)n2)cc1] | (E)-3-(3-(3-chlorophenyl)-1H-1,2,4-triazol-1-yl)-N-(4-methoxyphenyl)acrylamide |

TABLE 1A-continued

| Compound Structure | Compound Name |
|---|---|
| 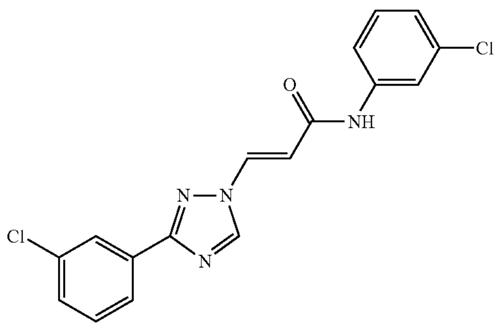 [SMILES: O=C(/C=C/n1cnc(-c2cccc(Cl)c2)n1)Nc1cccc(Cl)c1] | (E)-N-(3-chlorophenyl)-3-(3-(3-chlorophenyl)-1H-1,2,4-triazol-1-yl)acrylamide |
| 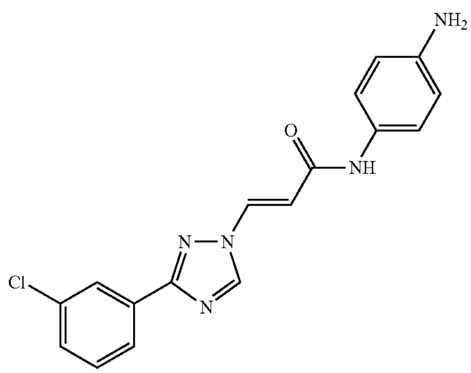 [SMILES: Nc1ccc(NC(=O)/C=C/n2cnc(-c3cccc(Cl)c3)n2)cc1] | (E)-N-(4-aminophenyl)-3-(3-(3-chlorophenyl)-1H-1,2,4-triazol-1-yl)acrylamide |
| 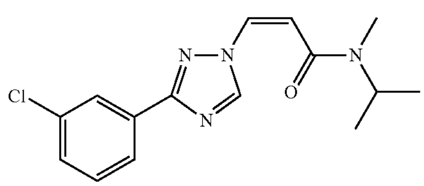 [SMILES: CC(C)N(C)C(=O)/C=C\n1cnc(-c2cccc(Cl)c2)n1] | (Z)-3-(3-(3-chlorophenyl)-1H-1,2,4-triazol-1-yl)-N-isopropyl-N-methylacrylamide |
| 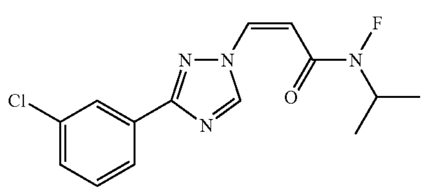 [SMILES: CC(C)N(F)C(=O)/C=C\n1cnc(-c2cccc(Cl)c2)n1] | (Z)-3-(3-(3-chlorophenyl)-1H-1,2,4-triazol-1-yl)-N-fluoro-N-isopropylacrylamide |

In another specific embodiment of a compound of formula I, the compound is not a compound listed in Table 1B.

TABLE 1B

| Compound Structure | Compound Name |
|---|---|
| 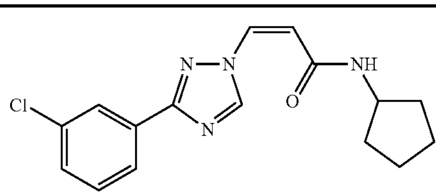 | (Z)-3-(3-(3-chlorophenyl)-1H-1,2,4-triazol-1-yl)-N-cyclopentylacrylamide |

TABLE 1B-continued

| Compound Structure | Compound Name |
|---|---|
| 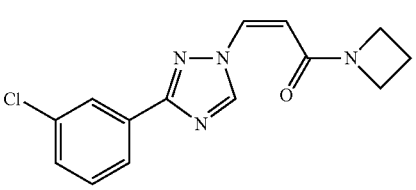 [SMILES: O=C(/C=C\n1cnc(-c2cccc(Cl)c2)n1)N1CCC1] | (Z)-1-(azetidin-1-yl)-3-(3-(3-chlorophenyl)-1H-1,2,4-triazol-1-yl)prop-2-en-1-one |
| 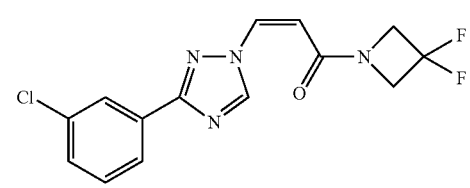 [SMILES: O=C(/C=C\n1cnc(-c2cccc(Cl)c2)n1)N1CC(F)(F)C1] | (Z)-3-(3-(3-chlorophenyl)-1H-1,2,4-triazol-1-yl)-1-(3,3-difluoroazetidin-1-yl)prop-2-en-1-one |
| 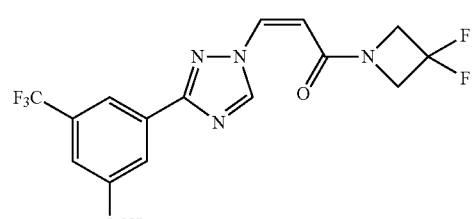 | (Z)-1-(3,3-difluoroazetidin-1-yl)-3-(3-(3-methoxy-5-(trifluoromethyl)phenyl)-1H-1,2,4-triazol-1-yl)prop-2-en-1-one |
| 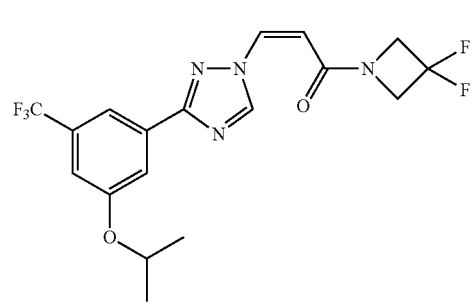 [SMILES: CC(C)Oc1cc(-c2ncn(/C=C\C(=O)N3CC(F)(F)C3)n2)cc(C(F)(F)F)c1] | (Z)-1-(3,3-difluoroazetidin-1-yl)-3-(3-(3-isopropoxy-5-(trifluoromethyl)phenyl)-1H-1,2,4-triazol-1-yl)prop-2-en-1-one |
| 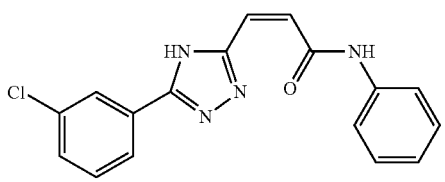 | (Z)-3-(5-(3-chlorophenyl)-4H-1,2,4-triazol-3-yl)-N-phenylacrylamide |
| 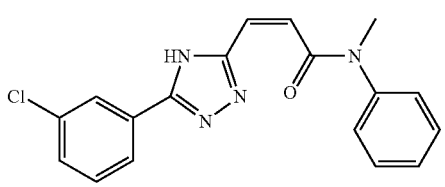 | (Z)-3-(5-(3-chlorophenyl)-4H-1,2,4-triazol-3-yl)-N-methyl-N-phenylacrylamide |

TABLE 1B-continued

| Compound Structure | Compound Name |
|---|---|
| 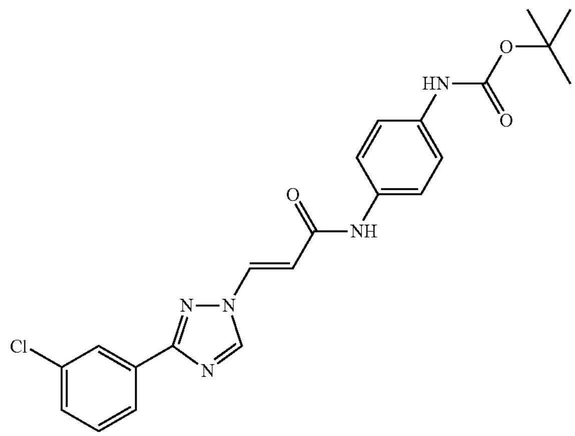 [SMILES: CC(C)(C)OC(=O)Nc1ccc(NC(=O)/C=C/n2cnc(-c3cccc(Cl)c3)n2)cc1] | (E)-tert-butyl (4-(3-(3-(3-chlorophenyl)-1H-1,2,4-triazol-2-yl)acrylamido)phenyl)carbamate |
| 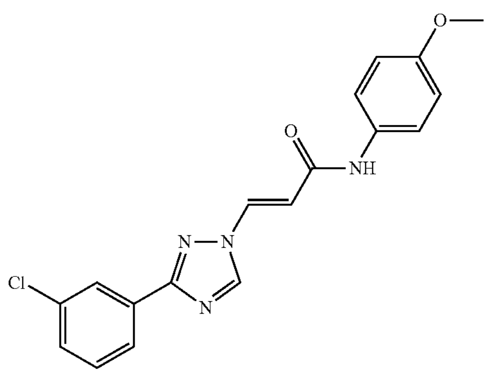 [SMILES: COc1ccc(NC(=O)/C=C/n2cnc(-c3cccc(Cl)c3)n2)cc1] | (E)-3-(3-(3-chlorophenyl)-1H-1,2,4-triazol-1-yl)-N-(4-methoxyphenyl)acrylamide |
| 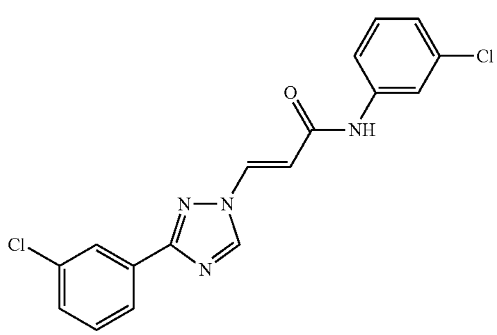 [SMILES: O=C(/C=C/n1cnc(-c2cccc(Cl)c2)n1)Nc1cccc(Cl)c1] | (E)-N-(3-chlorophenyl)-3-(3-(3-chlorophenyl)-1H-1,2,4-triazol-1-yl)acrylamide |
| 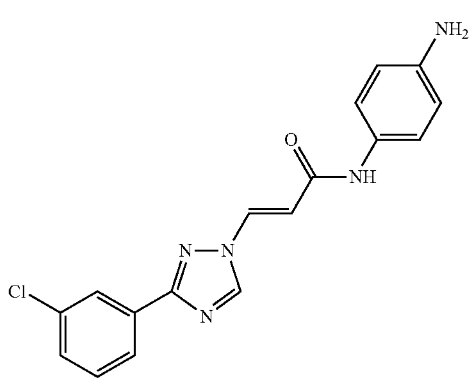 [SMILES: Nc1ccc(NC(=O)/C=C/n2cnc(-c3cccc(Cl)c3)n2)cc1] | (E)-N-(4-aminophenyl)-3-(3-(3-chlorophenyl)-1H-1,2,4-triazol-1-yl)acrylamide |

TABLE 1B-continued

| Compound Structure | Compound Name |
|---|---|
| 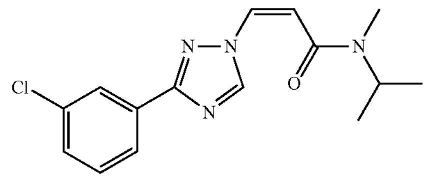 [SMILES: CC(C)N(C)C(=O)/C=C\n1cnc(-c2cccc(Cl)c2)n1] | (Z)-3-(3-(3-chlorophenyl)-1H-1,2,4-triazol-1-yl)-N-isopropyl-N-methylacrylamide |
| 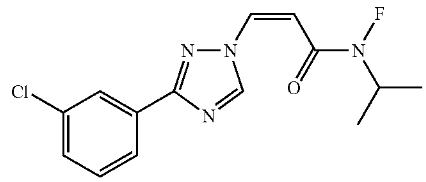 [SMILES: CC(C)N(F)C(=O)/C=C\n1cnc(-c2cccc(Cl)c2)n1] | (Z)-3-(3-(3-chlorophenyl)-1H-1,2,4-triazol-1-yl)-N-fluoro-N-isopropylacrylamide |
| 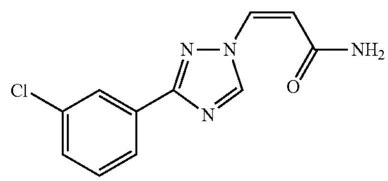 [SMILES: NC(=O)/C=C\n1cnc(-c2cccc(Cl)c2)n1] | (Z)-3-(3-(3-chlorophenyl)-1H-1,2,4-triazol-1-yl)acrylamide |
| 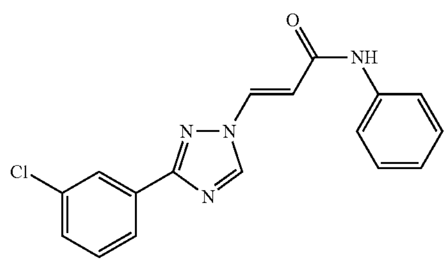 [SMILES: O=C(/C=C/n1cnc(-c2cccc(Cl)c2)n1)Nc1ccccc1] | (E)-3-(3-(3-chlorophenyl)-1H-1,2,4-triazol-1-yl)-N-phenylacrylamide |
| 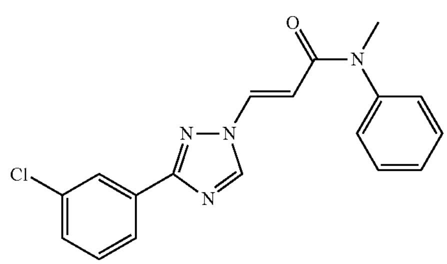 [SMILES: CN(C(=O)/C=C/n1cnc(-c2cccc(Cl)c2)n1)c1ccccc1] | (E)-3-(3-(3-chlorophenyl)-1H-1,2,4-triazol-1-yl)-N-methyl-N-phenylacrylamide |
| 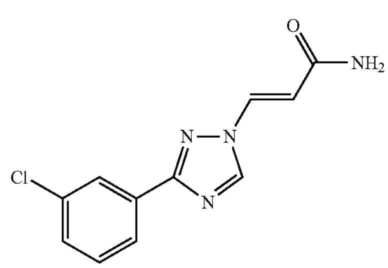 [SMILES: NC(=O)/C=C/n1cnc(-c2cccc(Cl)c2)n1] | (E)-3-(3-(3-chlorophenyl)-1H-1,2,4-triazol-1-yl)acrylamide |

TABLE 1B-continued

| Compound Structure | Compound Name |
|---|---|
| 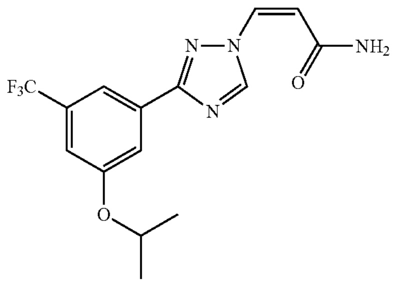 [SMILES: CC(C)Oc1cc(-c2ncn(/C=C\C(N)=O)n2)cc(C(F)(F)F)c1] | (Z)-3-(3-(3-isopropoxy-5-(trifluoromethyl)phenyl)-1H-1,2,4-triazol-1-yl)acrylamide |

In another specific embodiment of a compound of formula I, the compound is not a compound listed in Table 1C.

TABLE 1C

| Compound Structure | Compound Name |
|---|---|
| 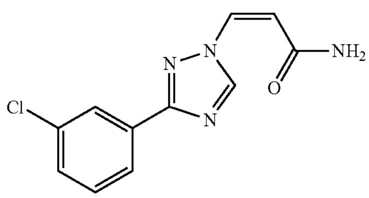 [SMILES: NC(=O)/C=C\n1cnc(-c2cccc(Cl)c2)n1] | (Z)-3-(3-(3-chlorophenyl)-1H-1,2,4-triazol-1-yl)acrylamide |
| 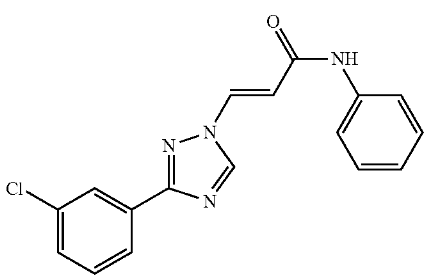 [SMILES: O=C(/C=C/n1cnc(-c2cccc(Cl)c2)n1)Nc1ccccc1] | (E)-3-(3-(3-chlorophenyl)-1H-1,2,4-triazol-1-yl)-N-phenylacrylamide |
| 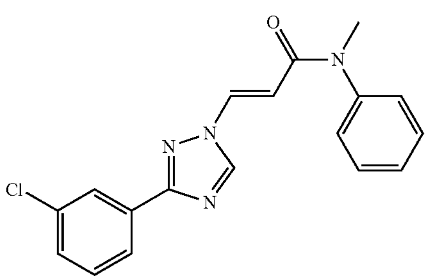 [SMILES: CN(C(=O)/C=C/n1cnc(-c2cccc(Cl)c2)n1)c1ccccc1] | (E)-3-(3-(3-chlorophenyl)-1H-1,2,4-triazol-1-yl)-N-methyl-N-phenylacrylamide |
| 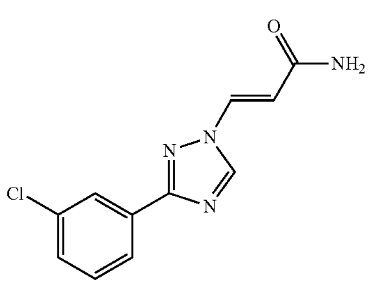 [SMILES: NC(=O)/C=C/n1cnc(-c2cccc(Cl)c2)n1] | (E)-3-(3-(3-chlorophenyl)-1H-1,2,4-triazol-1-yl)acrylamide |

TABLE 1C-continued

| Compound Structure | Compound Name |
|---|---|
| (structure) | (Z)-3-(3-(3-isopropoxy-5-(trifluoromethyl)phenyl)-1H-1,2,4-triazol-1-yl)acrylamide |

Exemplary compounds of the invention are set forth in Table 2.

TABLE 2

Exemplary compounds of the invention.

| Compound | Structure | Name |
|---|---|---|
| 1 | (structure) | (Z)-3-(3-(3,5-bis(trifluoromethyl)phenyl)-1H-1,2,4-triazol-1-yl)-1-(3,3-difluoroazetidin-1-yl)prop-2-en-1-one |
| 2 | (structure) | (Z)-1-(3,3-difluoroazetidin-1-yl)-3-(3-(3-fluoro-5-(trifluoromethyl)phenyl)-1H-1,2,4-triazol-1-yl)prop-2-en-1-one |
| 3 | (structure) | (Z)-1-(3,3-difluoroazetidin-1-yl)-3-(3-(3-hydroxy-5-(trifluoromethyl)phenyl)-1H-1,2,4-triazol-1-yl)prop-2-en-1-one |

TABLE 2-continued

Exemplary compounds of the invention.

| Compound | Structure | Name |
|---|---|---|
| 4 | 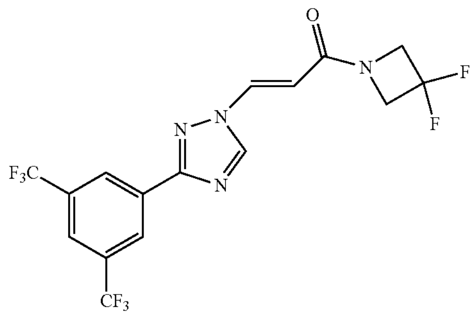 [SMILES: O=C(/C=C/n1cnc(-c2cc(C(F)(F)F)cc(C(F)(F)F)c2)n1)N1CC(F)(F)C1] | (E)-3-(3-(3,5-bis(trifluoromethyl)phenyl)-1H-1,2,4-triazol-1-yl)-1-(3,3-difluoroazetidin-1-yl)prop-2-en-1-one |
| 5 | 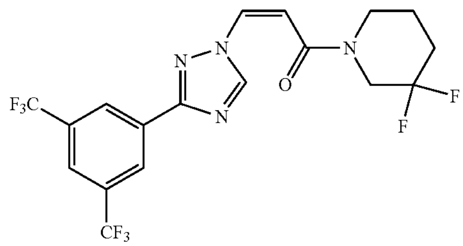 [SMILES: O=C(/C=C\n1cnc(-c2cc(C(F)(F)F)cc(C(F)(F)F)c2)n1)N1CCCC(F)(F)C1] | (Z)-3-(3-(3,5-bis(trifluoromethyl)phenyl)-1H-1,2,4-triazol-1-yl)-1-(3,3-difluoropiperidin-1-yl)prop-2-en-1-one |
| 6 | 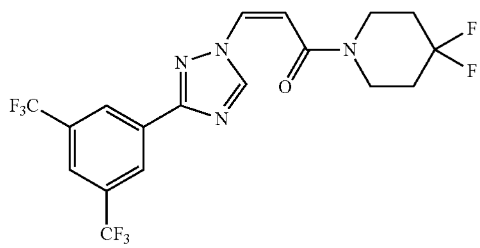 [SMILES: O=C(/C=C\n1cnc(-c2cc(C(F)(F)F)cc(C(F)(F)F)c2)n1)N1CCC(F)(F)CC1] | (Z)-3-(3-(3,5-bis(trifluoromethyl)phenyl)-1H-1,2,4-triazol-1-yl)-1-(4,4-difluoropiperidin-1-yl)prop-2-en-1-one |
| 7 | 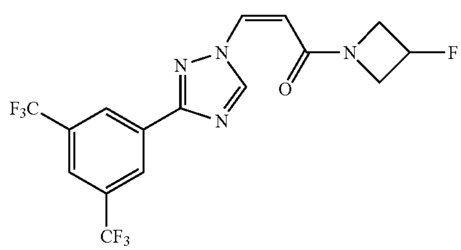 [SMILES: O=C(/C=C\n1cnc(-c2cc(C(F)(F)F)cc(C(F)(F)F)c2)n1)N1CC(F)C1] | (Z)-3-(3-(3,5-bis(trifluoromethyl)phenyl)-1H-1,2,4-triazol-1-yl)-1-(3-fluoroazetidin-1-yl)prop-2-en-1-one |
| 8 | 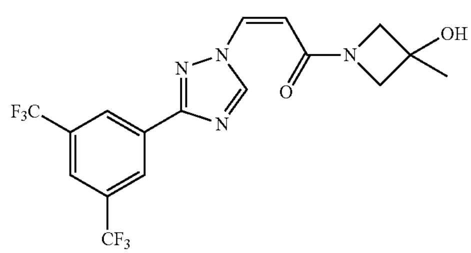 | (Z)-3-(3-(3,5-bis(trifluoromethyl)phenyl)-1H-1,2,4-triazol-1-yl)-1-(3-hydroxy-3-methylazetidin-1-yl)prop-2-en-1-one |
| 9 | 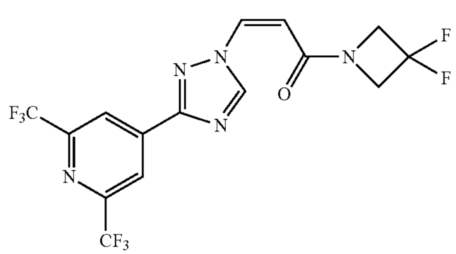 | (Z)-3-(3-(2,6-bis(trifluoromethyl)pyridin-4-yl)-1H-1,2,4-triazol-1-yl)-1-(3,3-difluoroazetidin-1-yl)prop-2-en-1-one |

TABLE 2-continued

Exemplary compounds of the invention.

| Compound | Structure | Name |
| --- | --- | --- |
| 10 | 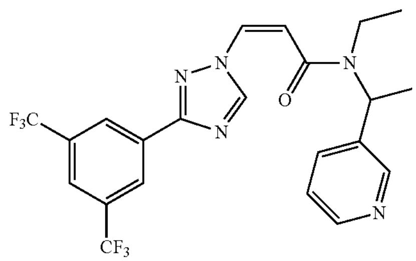 [SMILES: CCN(C(=O)/C=C\n1cnc(-c2cc(C(F)(F)F)cc(C(F)(F)F)c2)n1)C(C)c1cccnc1] | (Z)-3-(3-(3,5-bis(trifluoromethyl)phenyl)-1H-1,2,4-triazol-1-yl)-N-ethyl-N-(1-(pyridin-3-yl)ethyl)acrylamide |
| 11 | 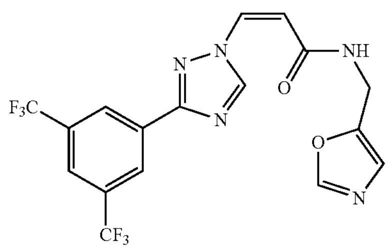 | (Z)-3-(3-(3,5-bis(trifluoromethyl)phenyl)-1H-1,2,4-triazol-1-yl)-N-(oxazol-5-ylmethyl)acrylamide |
| 12 | 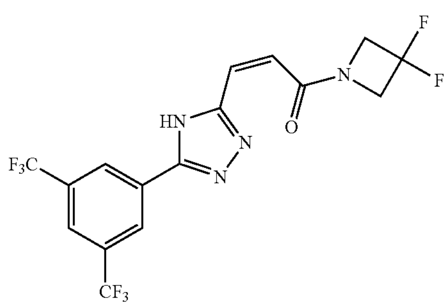 [SMILES: O=C(/C=C\c1nnc(-c2cc(C(F)(F)F)cc(C(F)(F)F)c2)[nH]1)N1CC(F)(F)C1] | (Z)-3-(5-(3,5-bis(trifluoromethyl)phenyl)-4H-1,2,4-triazol-3-yl)-1-(3,3-difluoroazetidin-1-yl)prop-2-en-1-one |
| 13 | 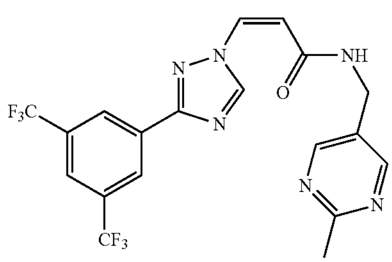 [SMILES: Cc1ncc(CNC(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-((2-methylpyrimidin-5-yl)methyl)acrylamide |
| 14 | 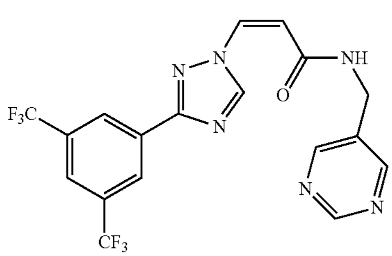 [SMILES: O=C(/C=C\n1cnc(-c2cc(C(F)(F)F)cc(C(F)(F)F)c2)n1)NCc1cncnc1] | (Z)-3-(3-(3,5-bis(trifluoromethyl)phenyl)-1H-1,2,4-triazol-1-yl)-N-(pyrimidin-5-ylmethyl)acrylamide |

TABLE 2-continued

Exemplary compounds of the invention.

| Compound | Structure | Name |
| --- | --- | --- |
| 15 | 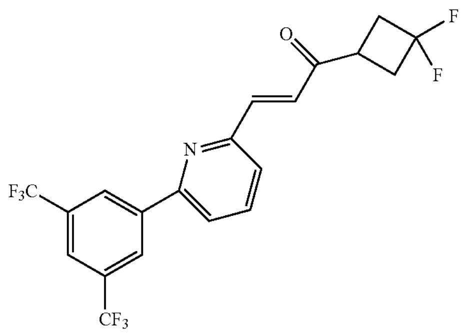 [SMILES: O=C(/C=C/c1cccc(-c2cc(C(F)(F)F)cc(C(F)(F)F)c2)n1)C1CC(F)(F)C1] | (E)-3-(6-(3,5-bis(trifluoromethyl)phenyl)pyridin-2-yl)-1-(3,3-difluorocyclobutyl)prop-2-en-1-one |
| 16 | 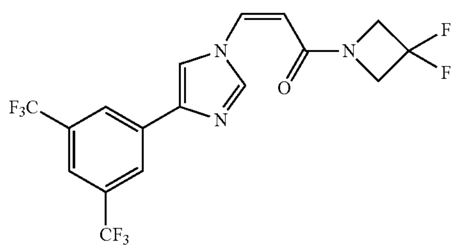 | (Z)-3-(4-(3,5-bis(trifluoromethyl)phenyl)-1H-imidazol-1-yl)-1-(3,3-difluoroazetidin-1-yl)prop-2-en-1-one |
| 17 | 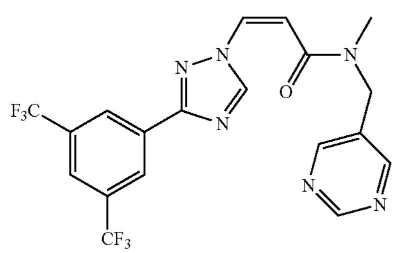 | (Z)-3-(3-(3,5-bis(trifluoromethyl)phenyl)-1H-1,2,4-triazol-1-yl)-N-methyl-N-(pyrimidin-5-ylmethyl)acrylamide |
| 18 | 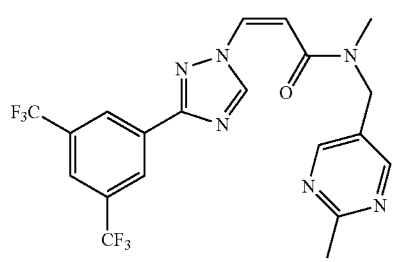 [SMILES: Cc1ncc(CN(C)C(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-methyl-N-((2-methylpyrimidin-5-yl)methyl)acrylamide |
| 19 | 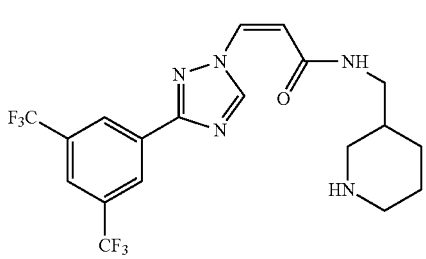 [SMILES: O=C(/C=C\n1cnc(-c2cc(C(F)(F)F)cc(C(F)(F)F)c2)n1)NCC1CCCNC1] | (Z)-3-(3-(3,5-bis(trifluoromethyl)phenyl)-1H-1,2,4-triazol-1-yl)-N-(piperidin-3-ylmethyl)acrylamide |

TABLE 2-continued

Exemplary compounds of the invention.

| Compound | Structure | Name |
|---|---|---|
| 20 | 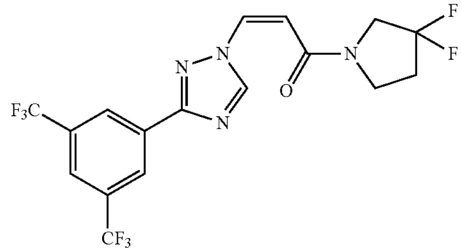 [SMILES: O=C(/C=C\n1cnc(-c2cc(C(F)(F)F)cc(C(F)(F)F)c2)n1)N1CCC(F)(F)C1] | (Z)-3-(3-(3,5-bis(trifluoromethyl)phenyl)-1H-1,2,4-triazol-1-yl)-1-(3,3-difluoropyrrolidin-1-yl)prop-2-en-1-one |
| 21 | 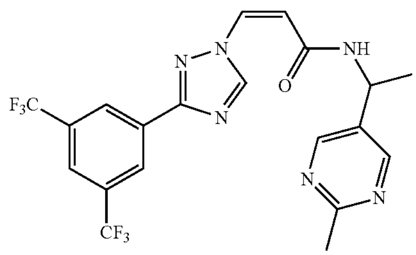 [SMILES: Cc1ncc(C(C)NC(=O)/C=C\n2cnc(-c3cc(C(F)(F)F)cc(C(F)(F)F)c3)n2)cn1] | (Z)-3-(3-(3,5-bis(trifluoromethyl)phenyl)-1H-1,2,4-triazol-1-yl)-N-(1-(2-methylpyrimidin-5-yl)ethyl)acrylamide |
| 22 | 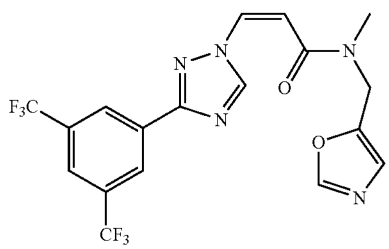 [SMILES: CN(Cc1cnco1)C(=O)/C=C\n1cnc(-c2cc(C(F)(F)F)cc(C(F)(F)F)c2)n1] | (Z)-3-(3-(3,5-bis(trifluoromethyl)phenyl)-1H-1,2,4-triazol-1-yl)-N-methyl-N-(oxazol-5-ylmethyl)acrylamide |
| 23 | 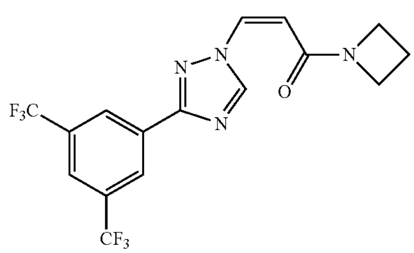 [SMILES: O=C(/C=C\n1cnc(-c2cc(C(F)(F)F)cc(C(F)(F)F)c2)n1)N1CCC1] | (Z)-1-(azetidin-1-yl)-3-(3-(3,5-bis(trifluoromethyl)phenyl)-1H-1,2,4-triazol-1-yl)prop-2-en-1-one |
| 24 | 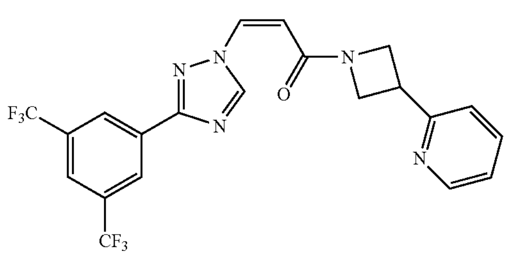 [SMILES: O=C(/C=C\n1cnc(-c2cc(C(F)(F)F)cc(C(F)(F)F)c2)n1)N1CC(c2ccccn2)C1] | (Z)-3-(3-(3,5-bis(trifluoromethyl)phenyl)-1H-1,2,4-triazol-1-yl)-1-(3-(pyridin-2-yl)azetidin-1-yl)prop-2-en-1-one |
| 25 | 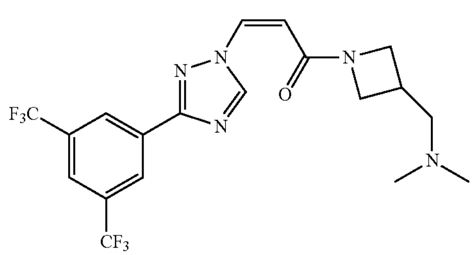 [SMILES: CN(C)CC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)azetidin-1-yl)prop-2-en-1-one |

TABLE 2-continued

Exemplary compounds of the invention.

| Compound | Structure | Name |
|---|---|---|
| 26 | 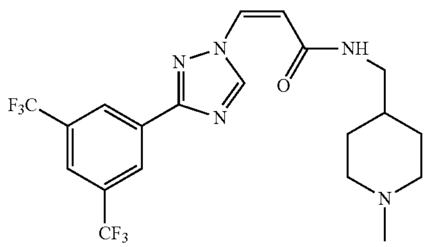 [SMILES: CN1CCC(CNC(=O)/C=C\n2cnc(-c3cc(C(F)(F)F)cc(C(F)(F)F)c3)n2)CC1] | (Z)-3-(3-(3,5-bis(trifluoromethyl)phenyl)-1H-1,2,4-triazol-1-yl)-N-((1-methylpiperidin-4-yl)methyl)acrylamide |
| 27 | 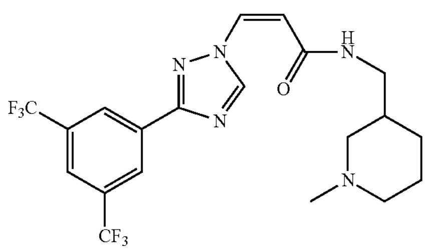 [SMILES: CN1CCCC(CNC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-((1-methylpiperidin-3-yl)methyl)acrylamide |
| 28 | 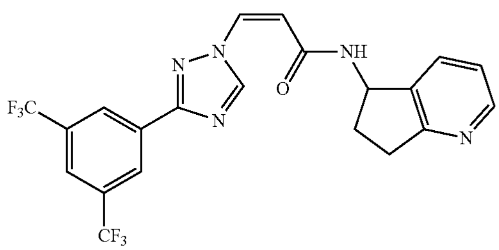 [SMILES: O=C(/C=C\n1cnc(-c2cc(C(F)(F)F)cc(C(F)(F)F)c2)n1)NC1CCc2ncccc21] | (Z)-3-(3-(3,5-bis(trifluoromethyl)phenyl)-1H-1,2,4-triazol-1-yl)-N-(6,7-dihydro-5H-cyclopenta[b]pyridin-5-yl)acrylamide |
| 29 | 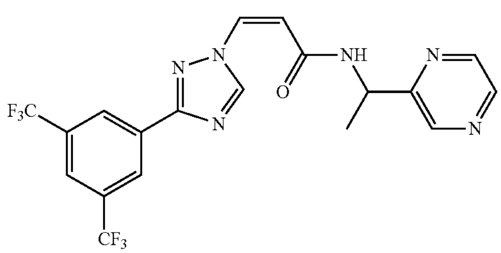 [SMILES: CC(NC(=O)/C=C\n1cnc(-c2cc(C(F)(F)F)cc(C(F)(F)F)c2)n1)c1cnccn1] | (Z)-3-(3-(3,5-bis(trifluoromethyl)phenyl)-1H-1,2,4-triazol-1-yl)-N-(1-(pyrazin-2-yl)ethyl)acrylamide |
| 30 | 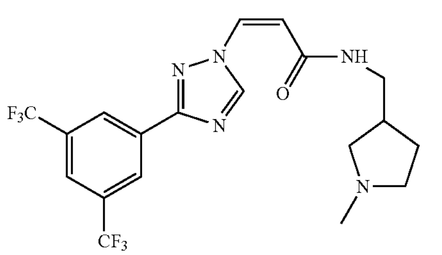 [SMILES: CN1CCC(CNC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-((1-methylpyrrolidin-3-yl)methyl)acrylamide |
| 31 | 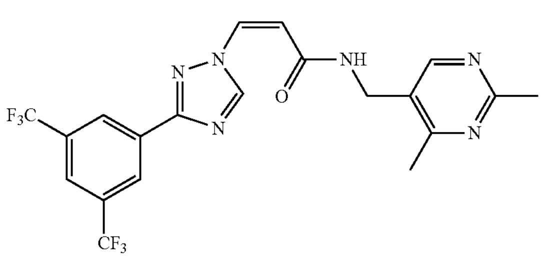 [SMILES: Cc1ncc(CNC(=O)/C=C\n2cnc(-c3cc(C(F)(F)F)cc(C(F)(F)F)c3)n2)c(C)n1] | (Z)-3-(3-(3,5-bis(trifluoromethyl)phenyl)-1H-1,2,4-triazol-1-yl)-N-((2,4-dimethylpyrimidin-5-yl)methyl)acrylamide |

TABLE 2-continued

Exemplary compounds of the invention.

| Compound | Structure | Name |
|---|---|---|
| 32 | 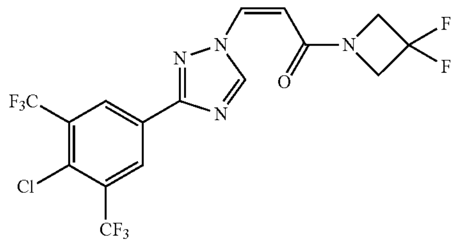 [SMILES: O=C(/C=C\n1cnc(-c2cc(C(F)(F)F)c(Cl)c(C(F)(F)F)c2)n1)N1CC(F)(F)C1] | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| 33 | 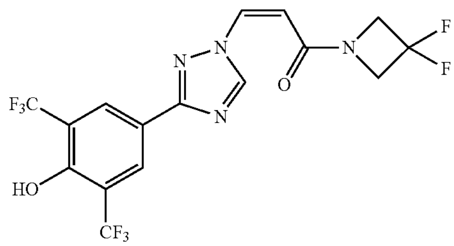 [SMILES: O=C(/C=C\n1cnc(-c2cc(C(F)(F)F)c(O)c(C(F)(F)F)c2)n1)N1CC(F)(F)C1] | (Z)-1-(3,3-difluoroazetidin-1-yl)-3-(3-(4-hydroxy-3,5-bis(trifluoromethyl)phenyl)-1H-1,2,4-triazol-1-yl)prop-2-en-1-one |
| 34 | 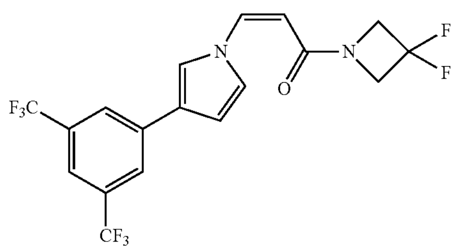 [SMILES: O=C(/C=C\n1ccc(-c2cc(C(F)(F)F)cc(C(F)(F)F)c2)c1)N1CC(F)(F)C1] | (Z)-3-(3-(3,5-bis(trifluoromethyl)phenyl)-1H-pyrrol-1-yl)-1-(3,3-difluoroazetidin-1-yl)prop-2-en-1-one |
| 35 | 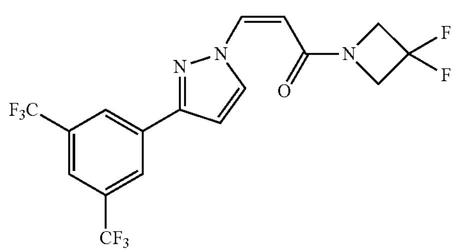 [SMILES: O=C(/C=C\n1ccc(-c2cc(C(F)(F)F)cc(C(F)(F)F)c2)n1)N1CC(F)(F)C1] | (Z)-3-(3-(3,5-bis(trifluoromethyl)phenyl)-1H-pyrazol-1-yl)-1-(3,3-difluoroazetidin-1-yl)prop-2-en-1-one |
| 36 | 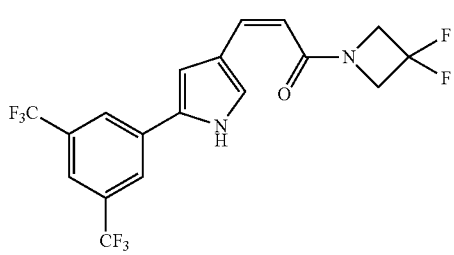 [SMILES: O=C(/C=C\c1c[nH]c(-c2cc(C(F)(F)F)cc(C(F)(F)F)c2)c1)N1CC(F)(F)C1] | (Z)-3-(5-(3,5-bis(trifluoromethyl)phenyl)-1H-pyrrol-3-yl)-1-(3,3-difluoroazetidin-1-yl)prop-2-en-1-one |
| 37 | 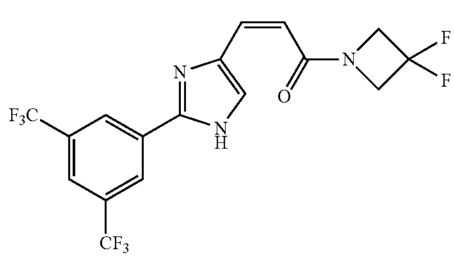 [SMILES: O=C(/C=C\c1c[nH]c(-c2cc(C(F)(F)F)cc(C(F)(F)F)c2)n1)N1CC(F)(F)C1] | (Z)-3-(2-(3,5-bis(trifluoromethyl)phenyl)-1H-imidazol-4-yl)-1-(3,3-difluoroazetidin-1-yl)prop-2-en-1-one |

TABLE 2-continued

Exemplary compounds of the invention.

| Compound | Structure | Name |
|---|---|---|
| 38 | 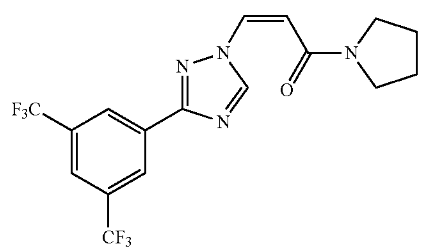 [SMILES: O=C(/C=C\n1cnc(-c2cc(C(F)(F)F)cc(C(F)(F)F)c2)n1)N1CCCC1] | (Z)-3-(3-(3,5-bis(trifluoromethyl)phenyl)-1H-1,2,4-triazol-1-yl)-1-(pyrrolidin-1-yl)prop-2-en-1-one |
| 39 | 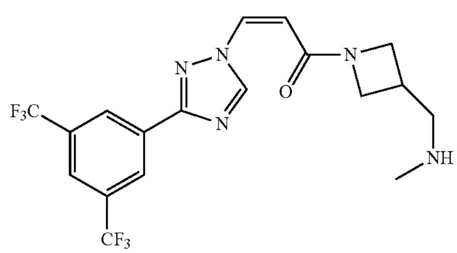 [SMILES: CNCC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((methylamino)methyl)azetidin-1-yl)prop-2-en-1-one |
| 40 | 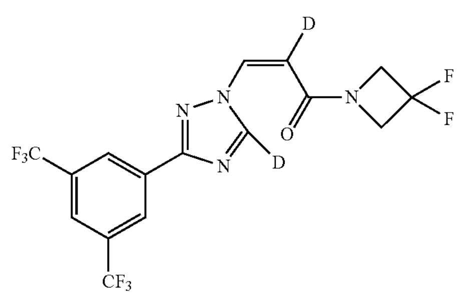 [SMILES: [2H]/C(=C/n1nc(-c2cc(C(F)(F)F)cc(C(F)(F)F)c2)nc1[2H])C(=O)N1CC(F)(F)C1] | D2-(Z)-3-(3-(3,5-bis(trifluoromethyl)phenyl)-1H-1,2,4-triazol-1-yl)-1-(3,3-difluoroazetidin-1-yl)prop-2-en-1-one |
| 41 | 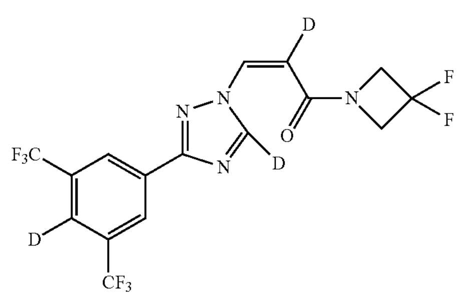 [SMILES: [2H]/C(=C/n1nc(-c2cc(C(F)(F)F)c([2H])c(C(F)(F)F)c2)nc1[2H])C(=O)N1CC(F)(F)C1] | D3-(Z)-3-(3-(3,5-bis(trifluoromethyl)phenyl)-1H-1,2,4-triazol-1-yl)-1-(3,3-difluoroazetidin-1-yl)prop-2-en-1-one |
| 42 | 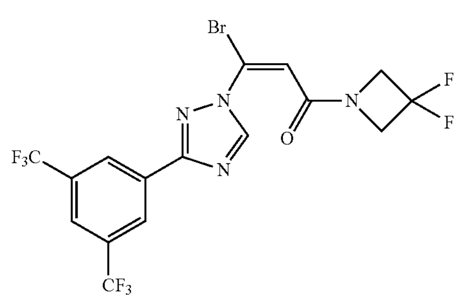 [SMILES: O=C(/C=C(/Br)n1cnc(-c2cc(C(F)(F)F)cc(C(F)(F)F)c2)n1)N1CC(F)(F)C1] | (E)-3-(3-(3,5-bis(trifluoromethyl)phenyl)-1H-1,2,4-triazol-1-yl)-3-bromo-1-(3,3-difluoroazetidin-1-yl)prop-2-en-1-one |

TABLE 2-continued

Exemplary compounds of the invention.

| Compound | Structure | Name |
|---|---|---|
| 43 | 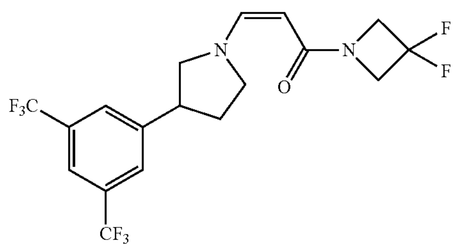 [SMILES: O=C(/C=C\N1CCC(c2cc(C(F)(F)F)cc(C(F)(F)F)c2)C1)N1CC(F)(F)C1] | 3-(3-(3,5-bis(trifluoromethyl)phenyl)pyrrolidin-1-yl)-1-(3,3-difluoroazetidin-1-yl)propan-1-one |
| 44 | 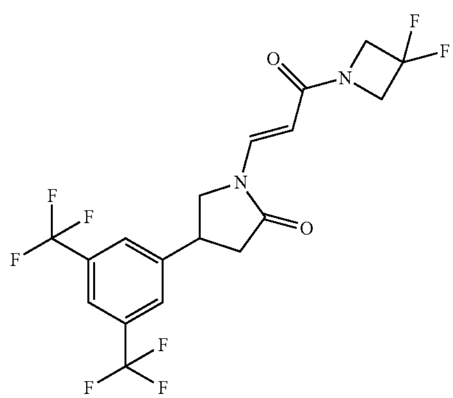 [SMILES: O=C1CC(c2cc(C(F)(F)F)cc(C(F)(F)F)c2)CN1/C=C/C(=O)N1CC(F)(F)C1] | (E)-4-(3,5-bis(trifluoromethyl)phenyl)-1-(3-(3,3-difluoroazetidin-1-yl)-3-oxoprop-1-en-1-yl)pyrrolidin-2-one |
| 45 | 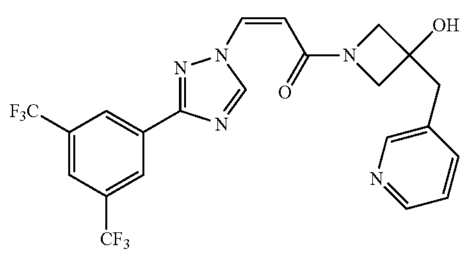 [SMILES: O=C(/C=C\n1cnc(-c2cc(C(F)(F)F)cc(C(F)(F)F)c2)n1)N1CC(O)(Cc2cccnc2)C1] | (Z)-3-(3-(3,5-bis(trifluoromethyl)phenyl)-1H-1,2,4-triazol-1-yl)-1-(3-hydroxy-3-(pyridin-3-ylmethyl)azetidin-1-yl)prop-2-en-1-one |
| 46 | 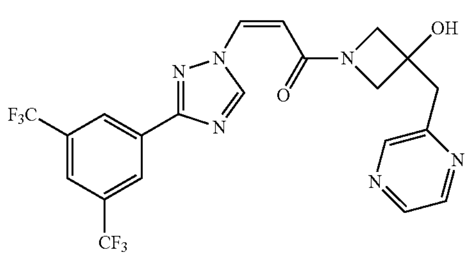 [SMILES: O=C(/C=C\n1cnc(-c2cc(C(F)(F)F)cc(C(F)(F)F)c2)n1)N1CC(O)(Cc2cnccn2)C1] | (Z)-3-(3-(3,5-bis(trifluoromethyl)phenyl)-1H-1,2,4-triazol-1-yl)-1-(3-hydroxy-3-(pyrazin-2-ylmethyl)azetidin-1-yl)prop-2-en-1-one |
| 47 | 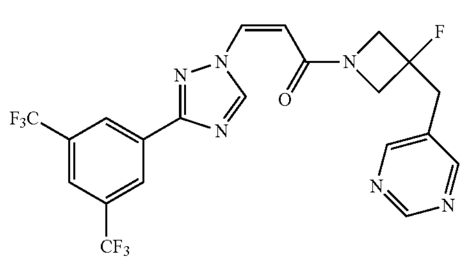 [SMILES: O=C(/C=C\n1cnc(-c2cc(C(F)(F)F)cc(C(F)(F)F)c2)n1)N1CC(F)(Cc2cncnc2)C1] | (Z)-3-(3-(3,5-bis(trifluoromethyl)phenyl)-1H-1,2,4-triazol-1-yl)-1-(3-fluoro-3-(pyrimidin-5-ylmethyl)azetidin-1-yl)prop-2-en-1-one |

TABLE 2-continued

Exemplary compounds of the invention.

| Compound | Structure | Name |
|---|---|---|
| 48 | 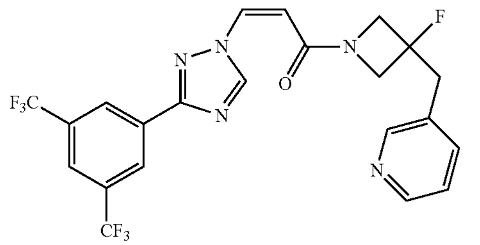 [SMILES: O=C(/C=C\n1cnc(-c2cc(C(F)(F)F)cc(C(F)(F)F)c2)n1)N1CC(F)(Cc2cccnc2)C1] | (Z)-3-(3-(3,5-bis(trifluoromethyl)phenyl)-1H-1,2,4-triazol-1-yl)-1-(3-fluoro-3-(pyridin-3-ylmethyl)azetidin-1-yl)prop-2-en-1-one |
| 49 | 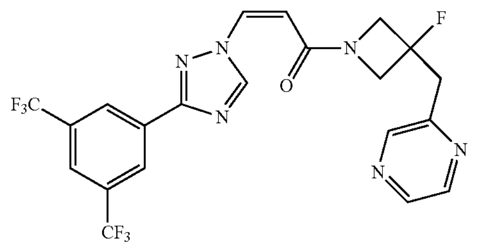 [SMILES: O=C(/C=C\n1cnc(-c2cc(C(F)(F)F)cc(C(F)(F)F)c2)n1)N1CC(F)(Cc2cnccn2)C1] | (Z)-3-(3-(3,5-bis(trifluoromethyl)phenyl)-1H-1,2,4-triazol-1-yl)-1-(3-fluoro-3-(pyrazin-2-ylmethyl)azetidin-1-yl)prop-2-en-1-one |
| 50 | 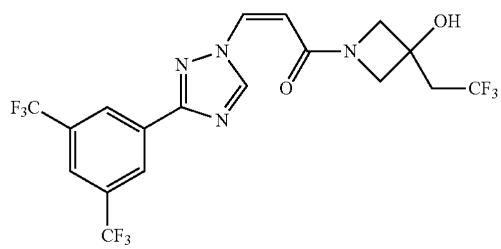 [SMILES: O=C(/C=C\n1cnc(-c2cc(C(F)(F)F)cc(C(F)(F)F)c2)n1)N1CC(O)(CC(F)(F)F)C1] | (Z)-3-(3-(3,5-bis(trifluoromethyl)phenyl)-1H-1,2,4-triazol-1-yl)-1-(3-hydroxy-3-(2,2,2-trifluoroethyl)azetidin-1-yl)prop-2-en-1-one |
| 51 | 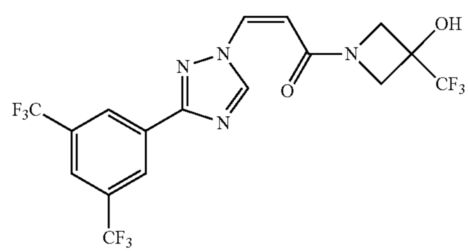 [SMILES: O=C(/C=C\n1cnc(-c2cc(C(F)(F)F)cc(C(F)(F)F)c2)n1)N1CC(O)(C(F)(F)F)C1] | (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one |
| 52 | 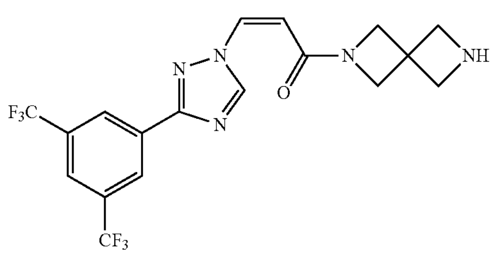 [SMILES: O=C(/C=C\n1cnc(-c2cc(C(F)(F)F)cc(C(F)(F)F)c2)n1)N1CC2(CNC2)C1] | (Z)-3-(3-(3,5-bis(trifluoromethyl)phenyl)-1H-1,2,4-triazol-1-yl)-1-(2,6-diazaspiro[3.3]heptan-2-yl)prop-2-en-1-one |
| 53 | 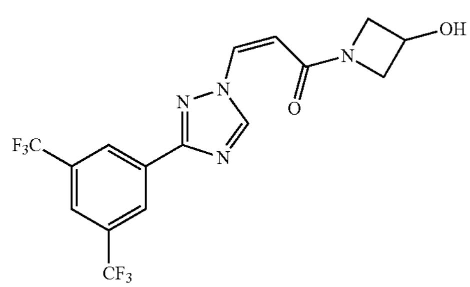 | (Z)-1-(3-(3-(3,5-bis(trifluoromethyl)phenyl)-1H-1,2,4-triazol-1-yl)acryloyl)azetidine-3-carbonitrile |

TABLE 2-continued

Exemplary compounds of the invention.

| Compound | Structure | Name |
|---|---|---|
| 54 | 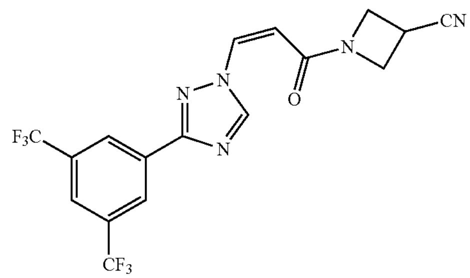 [SMILES: N#CC1CN(C(=O)/C=C\n2cnc(-c3cc(C(F)(F)F)cc(C(F)(F)F)c3)n2)C1] | (Z)-1-(3-(3-(3,5-bis(trifluoromethyl)phenyl)-1H-1,2,4-triazol-1-yl)acryloyl)azetidine-3-carbonitrile |
| 55 | 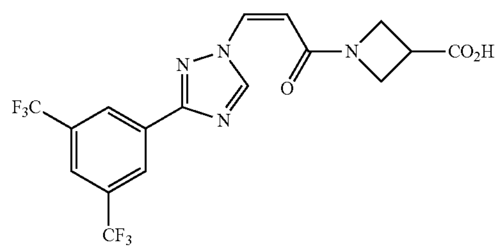 [SMILES: O=C(O)C1CN(C(=O)/C=C\n2cnc(-c3cc(C(F)(F)F)cc(C(F)(F)F)c3)n2)C1] | (Z)-1-(3-(3-(3,5-bis(trifluoromethyl)phenyl)-1H-1,2,4-triazol-1-yl)acryloyl)azetidine-3-carboxylic acid |
| 56 | 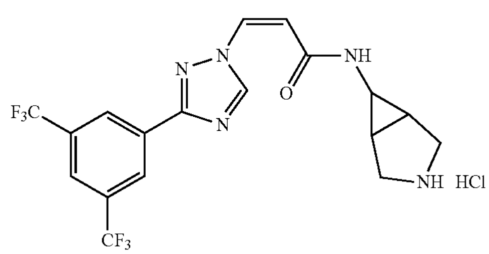 [SMILES: O=C(/C=C\n1cnc(-c2cc(C(F)(F)F)cc(C(F)(F)F)c2)n1)NC1C2CNCC21 ; Cl] | (Z)-N-(3-azabicyclo[3.1.0]hexan-6-yl)-3-(3-(3,5-bis(trifluoromethyl)phenyl)-1H-1,2,4-triazol-1-yl)acrylamide |
| 57 | 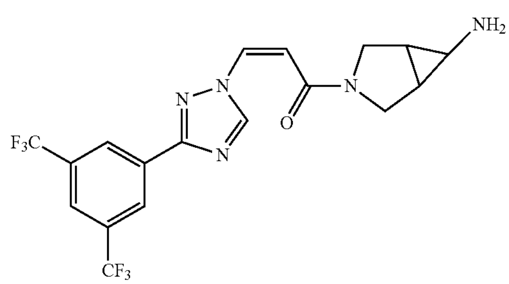 [SMILES: NC1C2CN(C(=O)/C=C\n3cnc(-c4cc(C(F)(F)F)cc(C(F)(F)F)c4)n3)CC12] | (Z)-N-(3-aminobicyclo[3.1.0]hexan-6-yl)-3-(3-(3,5-bis(trifluoromethyl)phenyl)-1H-1,2,4-triazol-1-yl)acrylamide |
| 58 | 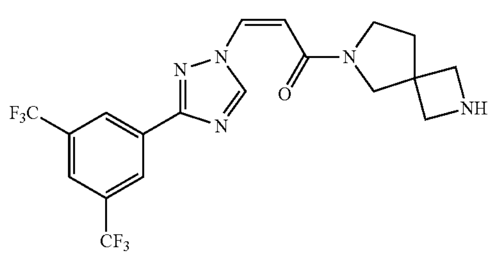 [SMILES: O=C(/C=C\n1cnc(-c2cc(C(F)(F)F)cc(C(F)(F)F)c2)n1)N1CCC2(CNC2)C1] | (Z)-N-(2,6-diazaspiro[3.4]octan-6-ylmethyl)-3-(3-(3,5-bis(trifluoromethyl)phenyl)-1H-1,2,4-triazol-1-yl)acrylamide |
| 59 | 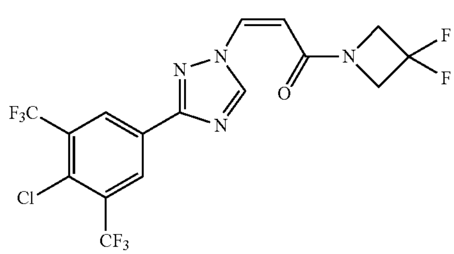 | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |

TABLE 2-continued

Exemplary compounds of the invention.

| Compound | Structure | Name |
|---|---|---|
| 60 | 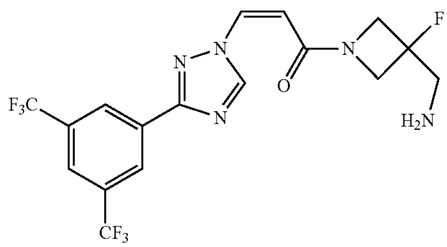 [SMILES: NCC1(F)CN(C(=O)/C=C\n2cnc(-c3cc(C(F)(F)F)cc(C(F)(F)F)c3)n2)C1] | (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one |
| 61 | 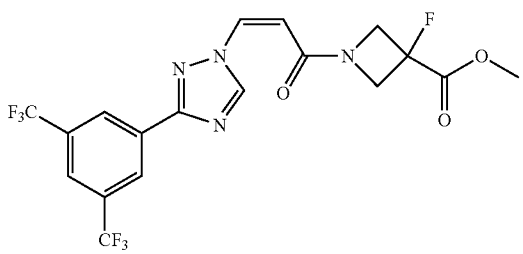 [SMILES: COC(=O)C1(F)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-fluoro-3-(2-methoxyacetyl)azetidin-1-yl)prop-2-en-1-one |
| 62 | 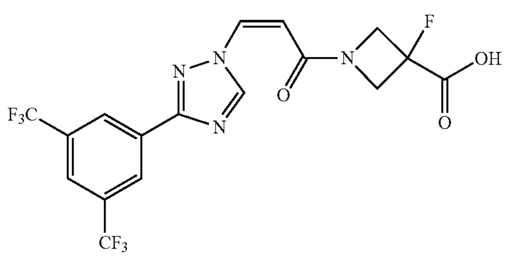 [SMILES: O=C(/C=C\n1cnc(-c2cc(C(F)(F)F)cc(C(F)(F)F)c2)n1)N1CC(F)(C(=O)O)C1] | (Z)-3-(3-(3,5-bis(trifluoromethyl)phenyl)-1H-1,2,4-triazol-1-yl)-1-(3-fluoro-3-(2-hydroxyacetyl)azetidin-1-yl)prop-2-en-1-one |
| 63 | 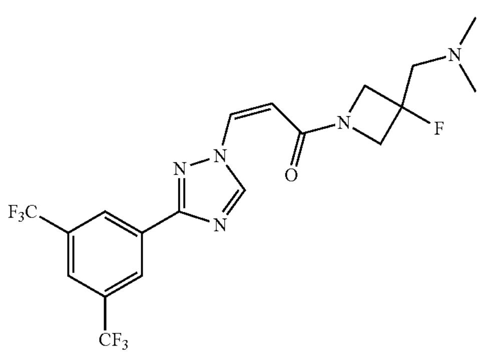 [SMILES: CN(C)CC1(F)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one |
| 64 | 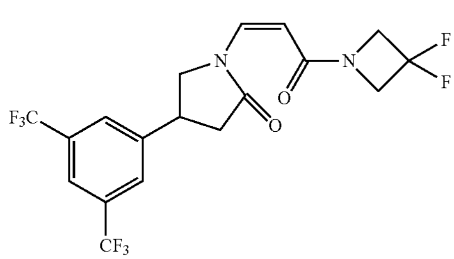 [SMILES: O=C1CC(c2cc(C(F)(F)F)cc(C(F)(F)F)c2)CN1/C=C\C(=O)N1CC(F)(F)C1] | (Z)-4-(3,5-bis(trifluoromethyl)phenyl)-1-(3-(3,3-difluoroazetidin-1-yl)-3-oxoprop-1-en-1-yl)pyrrolidin-2-one |
| 65 | 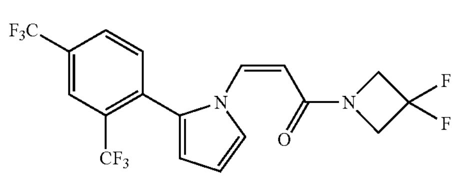 [SMILES: O=C(/C=C\n1cccc1-c1ccc(C(F)(F)F)cc1C(F)(F)F)N1CC(F)(F)C1] | (Z)-3-(2-(2,4-bis(trifluoromethyl)phenyl)-1H-pyrrol-1-yl)-1-(3,3-difluoroazetidin-1-yl)prop-2-en-1-one |

TABLE 2-continued

Exemplary compounds of the invention.

| Compound | Structure | Name |
|---|---|---|
| 66 | 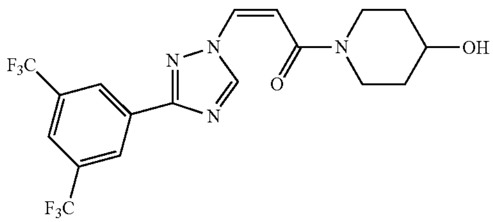 [SMILES: O=C(/C=C\n1cnc(-c2cc(C(F)(F)F)cc(C(F)(F)F)c2)n1)N1CCC(O)CC1] | (Z)-3-(3-(3,5-bis(trifluoromethyl)phenyl)-1H-1,2,4-triazol-1-yl)-1-(4-hydroxypiperidin-1-yl)prop-2-en-1-one |
| 67 | 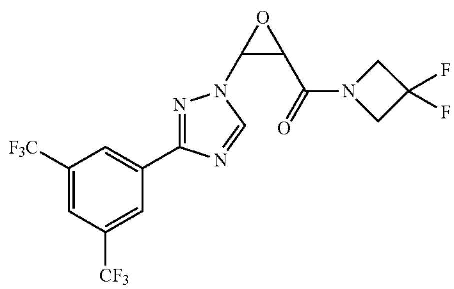 [SMILES: O=C(C1OC1n1cnc(-c2cc(C(F)(F)F)cc(C(F)(F)F)c2)n1)N1CC(F)(F)C1] | (3-(3-(3,5-bis(trifluoromethyl)phenyl)-1H-1,2,4-triazol-1-yl)oxiran-2-yl)(3,3-difluoroazetidin-1-yl)methanone |
| 68 | 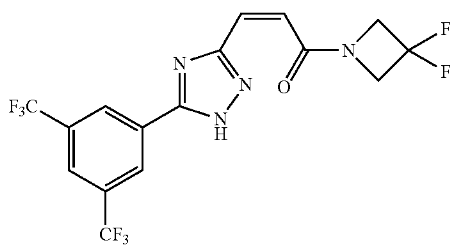 [SMILES: O=C(/C=C\c1n[nH]c(-c2cc(C(F)(F)F)cc(C(F)(F)F)c2)n1)N1CC(F)(F)C1] | (Z)-3-(5-(3,5-bis(trifluoromethyl)phenyl)-1H-1,2,4-triazol-3-yl)-1-(3,3-difluoroazetidin-1-yl)prop-2-en-1-one |
| 69 | 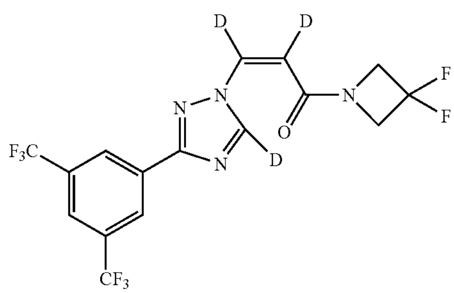 [SMILES: [2H]/C(C(=O)N1CC(F)(F)C1)=C(\[2H])n1nc(-c2cc(C(F)(F)F)cc(C(F)(F)F)c2)nc1[2H]] | D3-(Z)-3-(3-(3,5-bis(trifluoromethyl)phenyl)-1H-1,2,4-triazol-1-yl)-1-(3,3-difluoroazetidin-1-yl)prop-2-en-1-one |

Another embodiment of the invention is a compound represented by structural formula (VI):

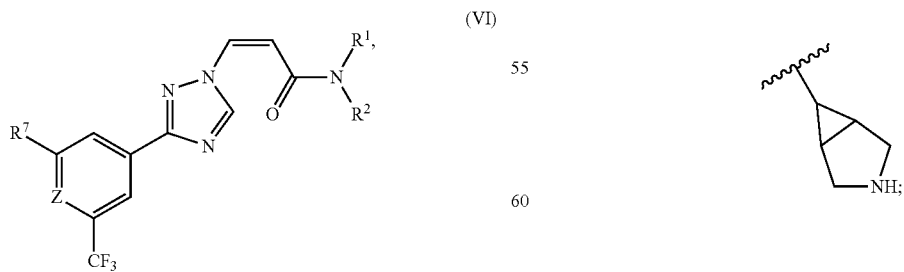

(VI)

or a pharmaceutically acceptable salt thereof, wherein:
Z is selected from N, CH and C(Cl);
$R^1$ is hydrogen; and
$R^2$ is selected from —$CH_2$-oxazol-5-yl, —$CH_2$-pyrimidin-5-yl, —$CH_2$-(1-methylpyrrolidin-3-yl), or

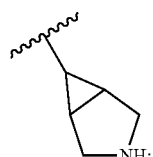

or:
$R^1$ and $R^2$ are taken together with the nitrogen atom to which they are bound to form

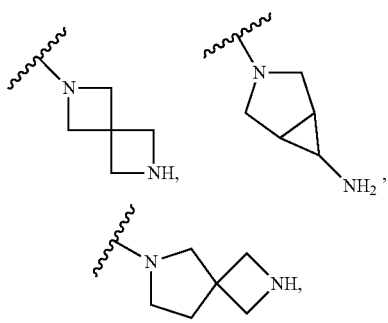

4-hydroxypiperidin-1-yl, pyrrolidiny-1-yl, or azetidin-1-yl, wherein the pyrrolidiny-1-yl and azetidin-1-yl are each optionally and independently substituted at the 3-position with up to two substituents independently selected from fluoro, —CF$_3$, —CH$_3$, —OH, pyridin-2-yl, —CH$_2$—N(CH$_3$)$_2$, —CH$_2$—NH—CH$_3$, —CH$_2$—NH$_2$, —CN, —C(O)—O—CH$_3$; and R$^7$ is selected from fluoro, —OH and —CF$_3$.

Representative compounds of structural formula VI include:

| Compound | Structure | Name |
|---|---|---|
| 1 | 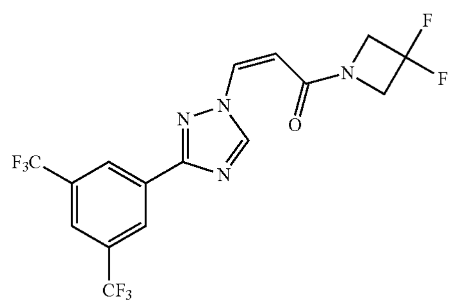 [SMILES: O=C(/C=C\n1cnc(-c2cc(C(F)(F)F)cc(C(F)(F)F)c2)n1)N1CC(F)(F)C1] | (Z)-3-(3-(3,5-bis(trifluoromethyl)phenyl)-1H-1,2,4-triazol-1-yl)-1-(3,3-difluoroazetidin-1-yl)prop-2-en-1-one |
| 2 | 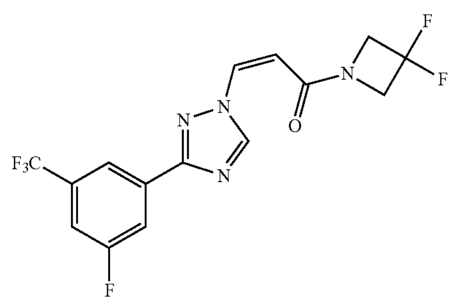 [SMILES: O=C(/C=C\n1cnc(-c2cc(F)cc(C(F)(F)F)c2)n1)N1CC(F)(F)C1] | (Z)-1-(3,3-difluoroazetidin-1-yl)-3-(3-(3-fluoro-5-(trifluoromethyl)phenyl)-1H-1,2,4-triazol-1-yl)prop-2-en-1-one |
| 3 | 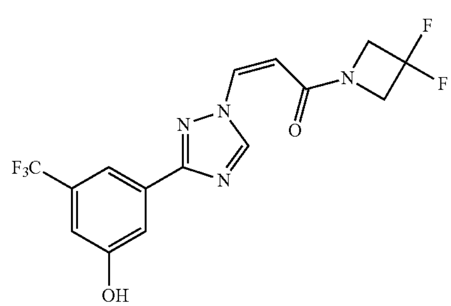 [SMILES: O=C(/C=C\n1cnc(-c2cc(O)cc(C(F)(F)F)c2)n1)N1CC(F)(F)C1] | (Z)-1-(3,3-difluoroazetidin-1-yl)-3-(3-(3-hydroxy-5-(trifluoromethyl)phenyl)-1H-1,2,4-triazol-1-yl)prop-2-en-1-one |
| 7 | 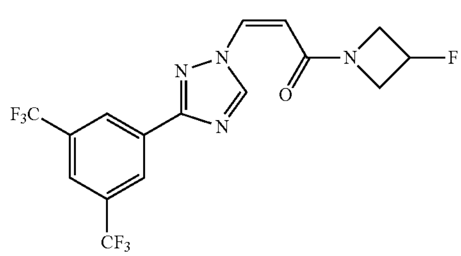 [SMILES: O=C(/C=C\n1cnc(-c2cc(C(F)(F)F)cc(C(F)(F)F)c2)n1)N1CC(F)C1] | (Z)-3-(3-(3,5-bis(trifluoromethyl)phenyl)-1H-1,2,4-triazol-1-yl)-1-(3-fluoroazetidin-1-yl)prop-2-en-1-one |

-continued

| Compound | Structure | Name |
|---|---|---|
| 8 | 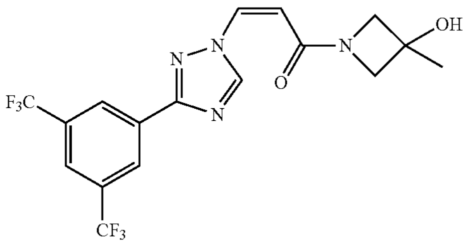 [SMILES: CC1(O)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-hydroxy-3-methylazetidin-1-yl)prop-2-en-1-one |
| 9 | 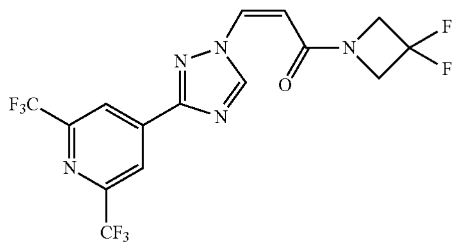 | (Z)-3-(3-(2,6-bis(trifluoromethyl)pyridin-4-yl)-1H-1,2,4-triazol-1-yl)-1-(3,3-difluoroazetidin-1-yl)prop-2-en-1-one |
| 11 | 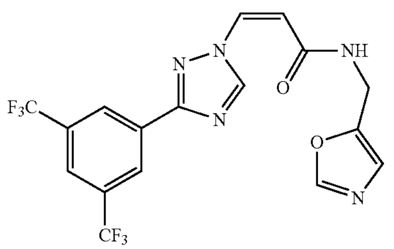 [SMILES: O=C(/C=C\n1cnc(-c2cc(C(F)(F)F)cc(C(F)(F)F)c2)n1)NCc1cnco1] | (Z)-3-(3-(3,5-bis(trifluoromethyl)phenyl)-1H-1,2,4-triazol-1-yl)-N-(oxazol-5-ylmethyl)acrylamide |
| 14 | 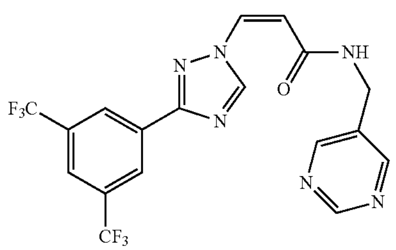 [SMILES: O=C(/C=C\n1cnc(-c2cc(C(F)(F)F)cc(C(F)(F)F)c2)n1)NCc1cncnc1] | (Z)-3-(3-(3,5-bis(trifluoromethyl)phenyl)-1H-1,2,4-triazol-1-yl)-N-(pyrimidin-5-ylmethyl)acrylamide |
| 20 | 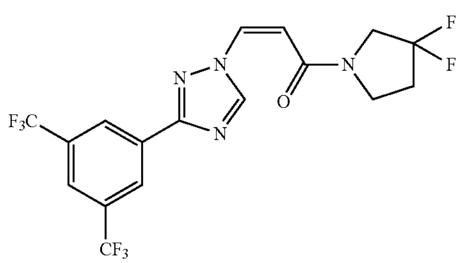 [SMILES: O=C(/C=C\n1cnc(-c2cc(C(F)(F)F)cc(C(F)(F)F)c2)n1)N1CCC(F)(F)C1] | (Z)-3-(3-(3,5-bis(trifluoromethyl)phenyl)-1H-1,2,4-triazol-1-yl)-1-(3,3-difluoropyrrolidin-1-yl)prop-2-en-1-one |
| 23 | 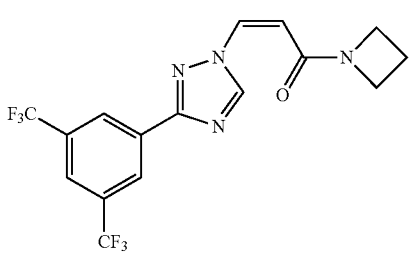 [SMILES: O=C(/C=C\n1cnc(-c2cc(C(F)(F)F)cc(C(F)(F)F)c2)n1)N1CCC1] | (Z)-1-(azetidin-1-yl)-3-(3-(3,5-bis(trifluoromethyl)phenyl)-1H-1,2,4-triazol-1-yl)prop-2-en-1-one |

| Compound | Structure | Name |
|---|---|---|
| 24 | 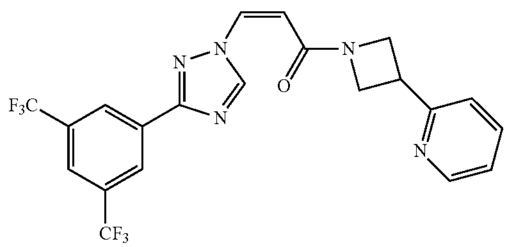 [SMILES: O=C(/C=C\n1cnc(-c2cc(C(F)(F)F)cc(C(F)(F)F)c2)n1)N1CC(c2ccccn2)C1] | (Z)-3-(3-(3,5-bis(trifluoromethyl)phenyl)-1H-1,2,4-triazol-1-yl)-1-(3-(pyridin-2-yl)azetidin-1-yl)prop-2-en-1-one |
| 25 | 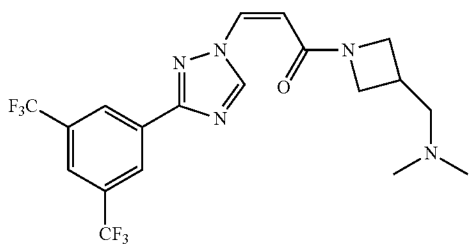 [SMILES: CN(C)CC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)azetidin-1-yl)prop-2-en-1-one |
| 30 | 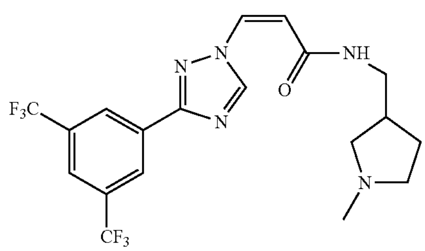 [SMILES: CN1CCC(CNC(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-N-((1-methylpyrrolidin-3-yl)methyl)acrylamide |
| 32 | 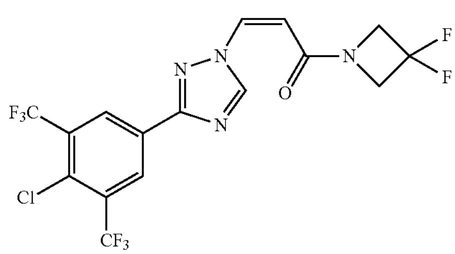 | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| 38 | 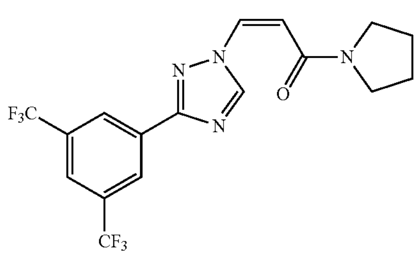 [SMILES: O=C(/C=C\n1cnc(-c2cc(C(F)(F)F)cc(C(F)(F)F)c2)n1)N1CCCC1] | (Z)-3-(3-(3,5-bis(trifluoromethyl)phenyl)-1H-1,2,4-triazol-1-yl)-1-(pyrrolidin-1-yl)prop-2-en-1-one |
| 39 | 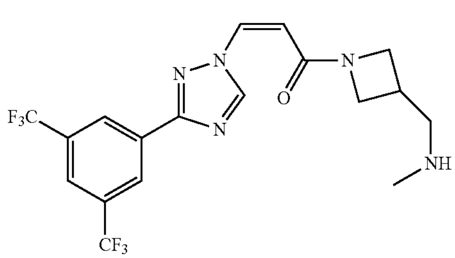 [SMILES: CNCC1CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((methylamino)methyl)azetidin-1-yl)prop-2-en-1-one |

-continued

| Compound | Structure | Name |
|---|---|---|
| 40 | 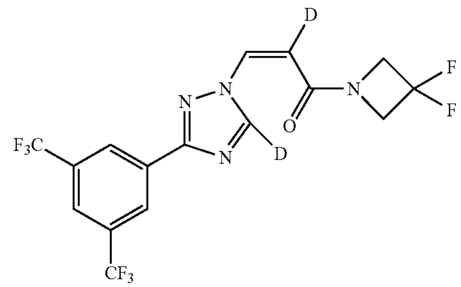 [SMILES: [2H]/C(=C/n1nc(-c2cc(C(F)(F)F)cc(C(F)(F)F)c2)nc1[2H])C(=O)N1CC(F)(F)C1] | D2-(Z)-3-(3-(3,5-bis(trifluoromethyl)phenyl)-1H-1,2,4-triazol-1-yl)-1-(3,3-difluoroazetidin-1-yl)prop-2-en-1-one |
| 41 | 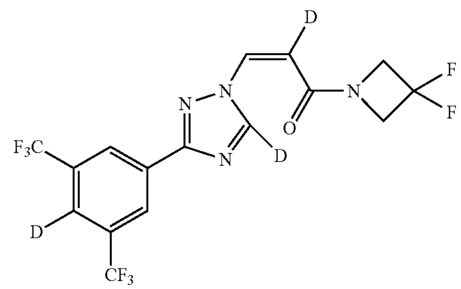 [SMILES: [2H]/C(=C/n1nc(-c2cc(C(F)(F)F)c([2H])c(C(F)(F)F)c2)nc1[2H])C(=O)N1CC(F)(F)C1] | D3-(Z)-3-(3-(3,5-bis(trifluoromethyl)phenyl)-1H-1,2,4-triazol-1-yl)-1-(3,3-difluoroazetidin-1-yl)prop-2-en-1-one |
| 51 | 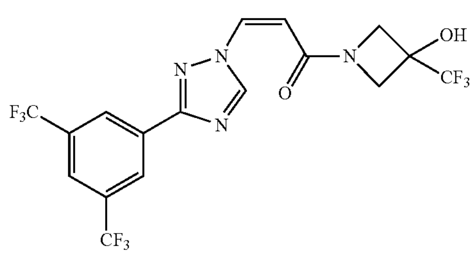 [SMILES: O=C(/C=C\n1cnc(-c2cc(C(F)(F)F)cc(C(F)(F)F)c2)n1)N1CC(O)(C(F)(F)F)C1] | (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one |
| 52 | 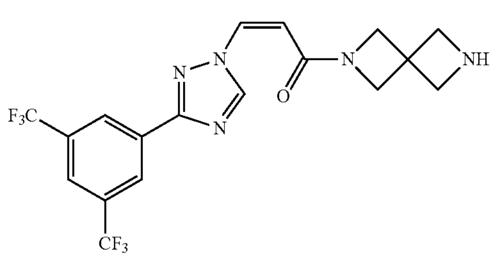 [SMILES: O=C(/C=C\n1cnc(-c2cc(C(F)(F)F)cc(C(F)(F)F)c2)n1)N1CC2(CNC2)C1] | (Z)-3-(3-(3,5-bis(trifluoromethyl)phenyl)-1H-1,2,4-triazol-1-yl)-1-(2,6-diazaspiro[3.3]heptan-2-yl)prop-2-en-1-one |
| 53 | 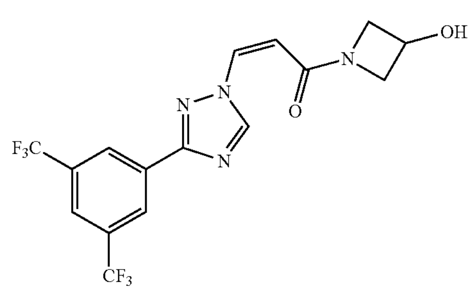 | (Z)-1-(3-(3-(3,5-bis(trifluoromethyl)phenyl)-1H-1,2,4-triazol-1-yl)acryloyl)azetidine-3-carbonitrile |

| Compound | Structure | Name |
|---|---|---|
| 54 | 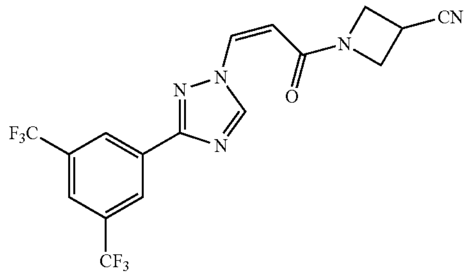 | (Z)-1-(3-(3-(3,5-bis(trifluoromethyl)phenyl)-1H-1,2,4-triazol-1-yl)acryloyl)azetidine-3-carbonitrile |
| 56 | 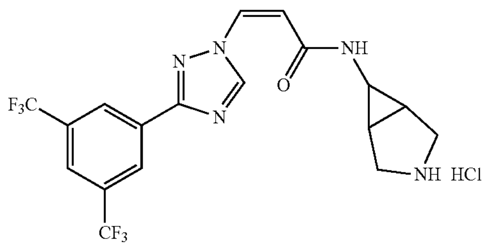 [SMILES: O=C(/C=C\n1cnc(-c2cc(C(F)(F)F)cc(C(F)(F)F)c2)n1)NC1C2CNCC21 ; Cl] | (Z)-N-(3-azabicyclo[3.1.0]hexan-6-yl)-3-(3-(3,5-bis(trifluoromethyl)phenyl)-1H-1,2,4-triazol-1-yl)acrylamide |
| 57 | 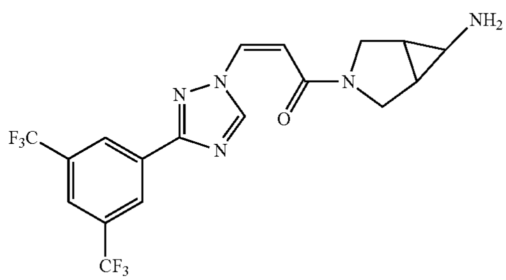 [SMILES: NC1C2CN(C(=O)/C=C\n3cnc(-c4cc(C(F)(F)F)cc(C(F)(F)F)c4)n3)CC12] | (Z)-N-(3-aminobicyclo[3.1.0]hexan-6-yl)-3-(3-(3,5-bis(trifluoromethyl)phenyl)-1H-1,2,4-triazol-1-yl)acrylamide |
| 58 | 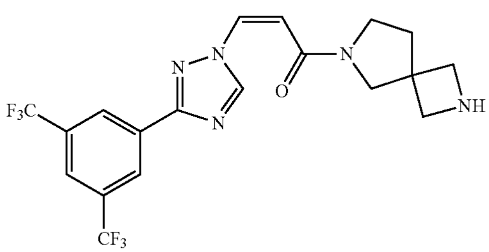 [SMILES: O=C(/C=C\n1cnc(-c2cc(C(F)(F)F)cc(C(F)(F)F)c2)n1)N1CCC2(CNC2)C1] | (Z)-N-(2,6-diazaspiro[3.4]octan-6-ylmethyl)-3-(3-(3,5-bis(trifluoromethyl)phenyl)-1H-1,2,4-triazol-1-yl)acrylamide |
| 59 | 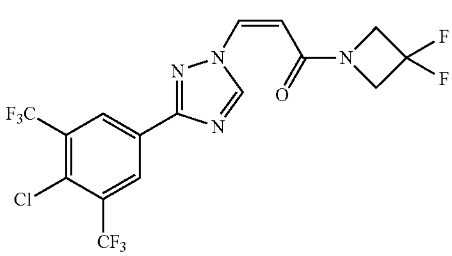 | (Z)-3-(3-(4-chloro-3,5-bis(trifluoromethyl)phenyl)-1H-1,2,4-triazol-1-yl)-1-(3,3-difluoroazetidin-1-yl)prop-2-en-1-one |
| 60 | 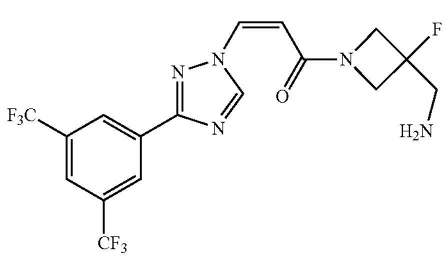 [SMILES: NCC1(F)CN(C(=O)/C=C\n2cnc(-c3cc(C(F)(F)F)cc(C(F)(F)F)c3)n2)C1] | (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one |

| Compound | Structure | Name |
|---|---|---|
| 61 | 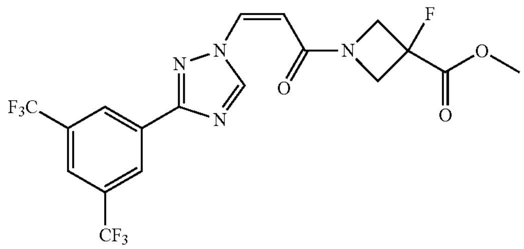 | (Z)-3-(3-(3,5-bis(trifluoromethyl)phenyl)-1H-1,2,4-triazol-1-yl)-1-(3-fluoro-3-(2-methoxyacetyl)azetidin-1-yl)prop-2-en-1-one |
| 63 | 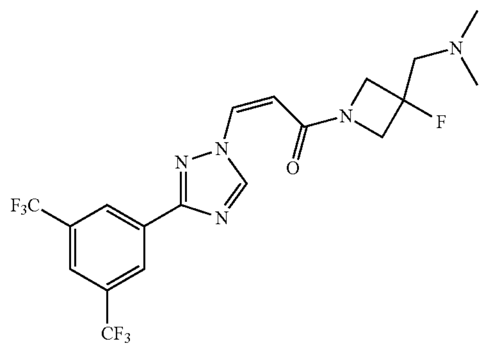 [SMILES: CN(C)CC1(F)CN(C(=O)/C=C\n2cnc(-c3cc(C(F)(F)F)cc(C(F)(F)F)c3)n2)C1] | (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one |
| 66 | 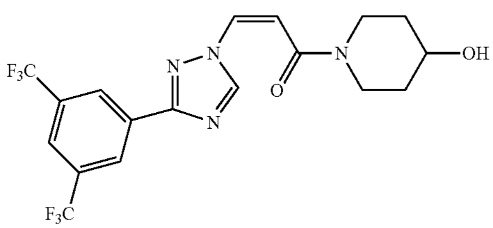 [SMILES: O=C(/C=C\n1cnc(-c2cc(C(F)(F)F)cc(C(F)(F)F)c2)n1)N1CCC(O)CC1] | (Z)-3-(3-(3,5-bis(trifluoromethyl)phenyl)-1H-1,2,4-triazol-1-yl)-1-(4-hydroxypiperidin-1-yl)prop-2-en-1-one |
| 69 | 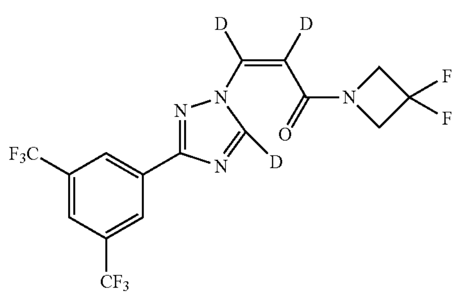 [SMILES: [2H]/C(C(=O)N1CC(F)(F)C1)=C(\[2H])n1nc(-c2cc(C(F)(F)F)cc(C(F)(F)F)c2)nc1[2H]] | D3-(Z)-3-(3-(3,5-bis(trifluoromethyl)phenyl)-1H-1,2,4-triazol-1-yl)-1-(3,3-difluoroazetidin-1-yl)prop-2-en-1-one |

Another embodiment of the invention is a compound represented by any of the following structural formulas, or a pharmaceutically acceptable salt thereof:

| Compound | Structure | Name |
|---|---|---|
| 28 | 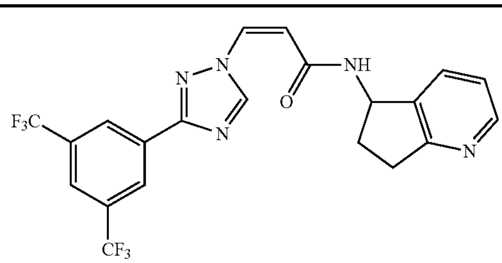 | (Z)-3-(3-(3,5-bis(trifluoromethyl)phenyl)-1H-1,2,4-triazol-1-yl)-N-(6,7-dihydro-5H-cyclopenta[b]pyridin-5-yl)acrylamide |

-continued

| Compound | Structure | Name |
|---|---|---|
| 42 | 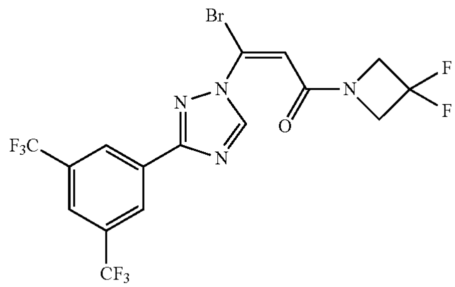 [SMILES: O=C(/C=C(/Br)n1cnc(-c2cc(C(F)(F)F)cc(C(F)(F)F)c2)n1)N1CC(F)(F)C1] | (E)-3-(3-(3,5-bis(trifluoromethyl)phenyl)-1H-1,2,4-triazol-1-yl)-3-bromo-1-(3,3-difluoroazetidin-1-yl)prop-2-en-1-one |
| 43 | 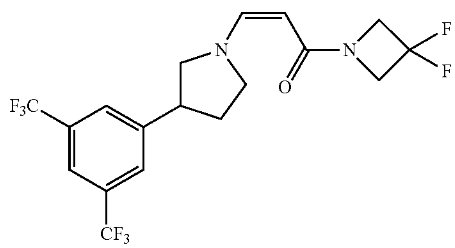 [SMILES: O=C(/C=C\N1CCC(c2cc(C(F)(F)F)cc(C(F)(F)F)c2)C1)N1CC(F)(F)C1] | 3-(3-(3,5-bis(trifluoromethyl)phenyl)pyrrolidin-1-yl)-1-(3,3-difluoroazetidin-1-yl)propan-1-one |
| 44 | 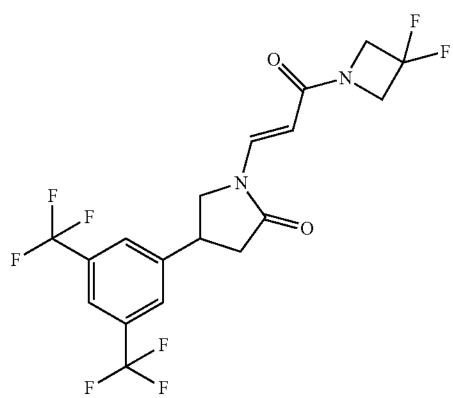 [SMILES: O=C1CC(c2cc(C(F)(F)F)cc(C(F)(F)F)c2)CN1/C=C/C(=O)N1CC(F)(F)C1] | (E)-4-(3,5-bis(trifluoromethyl)phenyl)-1-(3-(3,3-difluoroazetidin-1-yl)-3-oxoprop-1-en-1-yl)pyrrolidin-2-one |
| 64 | 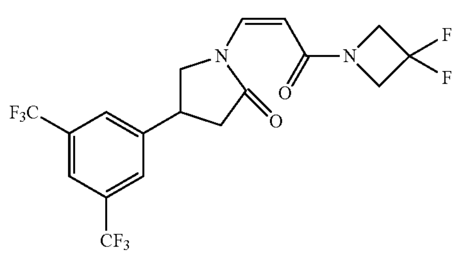 [SMILES: O=C1CC(c2cc(C(F)(F)F)cc(C(F)(F)F)c2)CN1/C=C\C(=O)N1CC(F)(F)C1] | (Z)-4-(3,5-bis(trifluoromethyl)phenyl)-1-(3-(3,3-difluoroazetidin-1-yl)-3-oxoprop-1-en-1-yl)pyrrolidin-2-one |
| 67 | 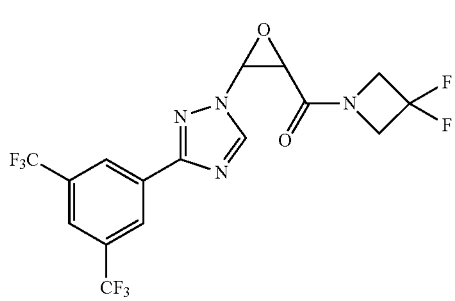 [SMILES: O=C(C1OC1n1cnc(-c2cc(C(F)(F)F)cc(C(F)(F)F)c2)n1)N1CC(F)(F)C1] | (3-(3-(3,5-bis(trifluoromethyl)phenyl)-1H-1,2,4-triazol-1-yl)oxiran-2-yl)(3,3-difluoroazetidin-1-yl)methanone |

Formulation and Administration

Another embodiment of the invention is a composition comprising a compound of the invention, or a pharmaceutically acceptable salt thereof, and a pharmaceutically acceptable carrier, adjuvant, or vehicle. The amount of compound in a composition of the invention is an amount that is effective to measurably inhibit CRM1 in a biological sample or in a patient. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

The term "patient," as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

"Pharmaceutically or pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the invention can also be in microencapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound of the invention can be provided in an extended (or "delayed" or "sustained") release composition. This delayed-release composition comprises a compound of the invention in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

In some embodiments, pharmaceutically acceptable compositions of this invention are formulated for topical administration.

The amount of compounds of the present invention that can be combined with the carrier materials to produce a composition in a single dosage form will vary depending upon the host treated, the particular mode of administration and the activity of the compound employed. Preferably, compositions should be formulated so that a dosage of between 0.01-100 mg/kg body weight/day of the inhibitor can be administered to a patient receiving the composition.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

The pharmaceutical compositions of this invention are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agent(s) can be administered separately, as part of a multiple dose regimen, from the compounds of this invention. Alternatively, the additional agent(s) can be part of a single dosage form, mixed together with the compound of this invention in a single composition.

The compounds described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 to about 100 mg/kg of body weight or, alternatively, in a dosage ranging from about 1 mg to about 1000 mg/dose, every 4 to 120 hours, or according to the requirements of the particular drug. The methods herein contemplate administration of an effective amount of a compound of the invention, or a composition thereof, to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

Uses of Compounds and Pharmaceutically Acceptable Compositions

Compounds and compositions described herein are generally useful for the inhibition of CRM1 and are, therefore, useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable salt or composition thereof. The compounds and compositions described herein can also be administered to cells in culture, e.g., in vitro or ex vivo, or to a subject, e.g., in vivo, to treat, prevent, and/or diagnose a variety of disorders, including those described herein below.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Exemplification.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject or a cell, in curing, alleviating, relieving or improving one or more symptoms of a disorder.

As used herein, an amount of a compound effective to prevent a disorder, or a "prophylactically effective amount" of the compound refers to an amount effective, upon single- or multiple-dose administration to the subject, in preventing or delaying the onset or recurrence of a disorder or one or more symptoms of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.).

As used herein, the term "CRM1-mediated disorder or condition" or "disorder or condition associated with CRM1 activity" means any disease or other deleterious condition in which CRM1 plays a role. Accordingly, another embodiment of the present invention relates to treating or lessening the severity of one or more diseases in which CRM1 plays a role. Specifically, the present invention relates to a method of treating or lessening the severity of a proliferative disorder, the method comprising administering to a patient in need thereof a compound of the invention, or a pharmaceutically acceptable salt or composition thereof. Other disorders are set forth in detail below.

In some embodiments, the present invention provides methods of treating a disease associated with expression or activity of p53, p73, p21, pRB, p2'7, IκB, NFκB, c-Abl, FOXO proteins, COX-2 in a patient, comprising administering to the patient a therapeutically effective amount of a compound described herein, or a pharmaceutically acceptable salt or composition thereof. For example, provided herein are methods of treating various cancers in mammals (including humans and non-humans), comprising administering to a patient in need thereof a compound of the invention, or a pharmaceutically acceptable salt thereof. Such cancers include hematologic malignancies (leukemias, lymphomas, myelomas, myelodysplastic and myeloproliferative syndromes) and solid tumors (carcinomas such as prostate, breast, lung, colon, pancreatic, renal, ovarian as well as soft tissue and osteo-sarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple.

In some embodiments, the present invention provides a method of treating inflammatory disorders in a patient, comprising administering to the patient a compound of the invention, or a pharmaceutically acceptable salt thereof. Such inflammatory disorders include rheumatoid arthritis, systemic lupus, systemic sclerosis, vasculitis syndromes (small, medium and large vessel), atherosclerosis, psoriasis and other dermatological inflammatory disorders (such as pemphigous, pemphigoid, allergic dermatitis), and urticarial syndromes.

In some embodiments, the disorder or condition associated with CRM1 activity is muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodonitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

In other embodiments, the disorder or condition associated with CRM1 activity is head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum, acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/ urushiol oil-induced inflammation, chemical irritant-induced inflammation, bee sting-induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a compound of the invention, of a pharmaceutically acceptable salt thereof, for the manufacture of a medicament for the treatment of a disease associated with expression or activity of p53, p73, p21, pRB, p27, IκB, NFκB, c-Abl, FOXO proteins or COX-2. In some embodiments, the present invention provides a use of a compound of the invention in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases or ophthalmologic disorders.

In some embodiments, the present invention provides a method for inhibiting CRM1 in a biological sample or in a patient, comprising contacting the biological sample with, or administering to the patient, a pharmaceutically acceptable salt of a compound of the invention, or a pharmaceutically acceptable salt or composition thereof.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia;

and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example, chemotherapy, targeted therapies such as antibody therapies, kinase inhibitors, immunotherapy, and hormonal therapy, and anti-angiogenic therapies. Examples of each of these treatments are provided below.

As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within a cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and tositumomab typically used in a variety of B-cell malignancies. Other exemplary antibodies include cetuximab, panitumumab, trastuzumab, alemtuzumab, bevacizumab, edrecolomab, and gemtuzumab. Exemplary fusion proteins include aflibercept and denileukin diftitox. In some embodiments, targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding a tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one.

Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including 06-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucloetides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Inflammation and Autoimmune Disease

The compounds and methods described herein may be used to treat or prevent a disease or disorder associated with inflammation, particularly in humans and other mammals. A compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis. In a specific aspect, the compound used to treat multiple sclerosis is Compound 1: (Z)-3-(3-(3,5-bis(trifluoromethyl)phenyl)-1H-1,2,4-triazol-1-yl)-1-(3,3-difluoroazetidin-1-yl)prop-2-en-1-one).

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lomoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papavereturn, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection, particularly in humans and other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

Ophthalmology

Compounds and methods described herein may be used to treat or prevent an ophthalmology disorder. Exemplary ophthalmology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations
atm Atmosphere
aq. Aqueous
BINAP 2,2'-bis(diphenylphosphino)-1,1'-binaphthyl
Boc tert-butoxycarbonyl CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EA Ethyl acetate
EDCI N-[3-(dimethylamino)propyl]-N'-ethylcarbodiimide hydrochloride
EDC 1-Ethyl-3-(3-dimethylaminopropyl)carbodiimide
$Et_2O$ Diethylether
EtOAc Ethyl acetate
EtOH Ethanol
EtI Iodoethane
Et Ethyl
Fmoc 9-fluorenylmethyloxycarbonyl
h hour(s)
HetAr Heteroaryl
HOBt N-Hydroxybenzotriazole
HBTU O-(Benzotriazol-1-yl)-N,N,N',N-tetramethyluronium hexafluorophosphate
HPLC High performance liquid chromatography
LAH Lithium aluminium hydride
LCMS HPLC mass spec
MCPBA m-Chlorbenzoic acid
MeCN Acetonitrile
MeOH Methanol
min Minutes
MeI Iodomethane
MeMgCl Methyl magnesium chloride
Me Methyl
n-BuLi 1-Butyllithium
NaOAc Sodium acetate
NMR Nuclear magnetic resonance
NMP N-Methyl pyrrolidinone
nBuLi 1-Butyl lithium
o.n. Over night
RBF Round-bottomed flask
RT, rt, r.t. Room temperature
T3P Propylphosphonic anhydride (available from Archimica)
TEA Triethylamine
THF Tetrahydrofurane
nBu normal Butyl
OMs Mesylate or methane sulfonate ester
OTs Tosylate, toluene sulfonate or 4-methylbenzene sulfonate ester
PCC Pyridinium chlorochromate
PPTS Pyridinium p-toluenesulfonate
TBAF Tetrabutylammonium fluoride
pTsOH p-Toluenesulfonic acid
SPE Solid phase extraction (usually containing silica gel for mini-chromatography)
sat. Saturated
GP Protecting group
mins minutes Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

Synthesis of Common Intermediate 4

Synthesis of 3,5-bis(trifluoromethyl)benzothioamide (1)

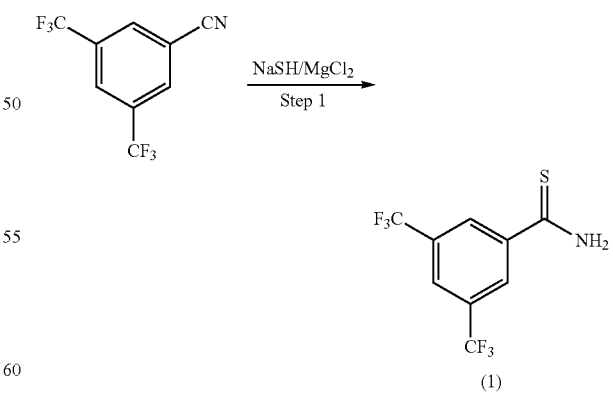

A 3-neck round-bottom flask was charged with a solution 3,5-bis(trifluoromethyl)benzonitrile (200 g, 1.0 eq) in DMF (1 L), to which was added NaSH (123.7 g, 2.0 eq.) and $MgCl_2$ (186.7 g, 1 eq.). The reaction mixture was stirred at ambien temperature for 2-3 h before being poured in to ice water slurry (10 L) and extracted with EtOAc (3×1 L). The combined organic layers were washed with brine (3×100 mL), dried over anhydrous Na₂SO₄, filtered, and concentrated under reduced pressure to afford 205 g (90% yield) of crude desired thioamide (1), used as such in the subsequent step.

Synthesis of 3-(3,5-bis(trifluoromethyl)phenyl)-1H-1,2,4-triazole (2)

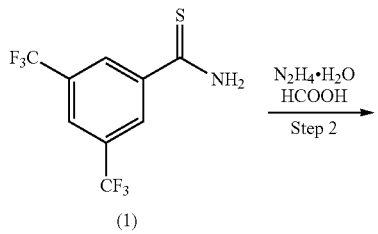

A solution of 3,5-bis(trifluoromethyl)benzothioamide (1) (205.65 g) in DMF (1.03 L) was treated with hydrazine hydrate (73.16 mL, 2.0 eq). The reaction mixture was stirred at ambient temperature for 1 h. before being treated with formic acid (1.03 L). The reaction mixture was refluxed at 90° C. for 2-3 h then allowed to cool down to ambient temperature, poured into saturated aqueous sodium bicarbonate (7 L) and extracted with EtOAc (3×1 L), The combined organic layers were washed with brine (3×500 mL), dried over anhydrous Na₂SO₄, filtered, and concentrated under reduced pressure to afford 180 g of crude compound. This crude material was washed with petroleum ether (3×500 mL), filtered and dried well to afford 160 grams (75% yield) of triazole (2) obtained as a pale yellow solid.

Synthesis of (Z)-isopropyl 3-(3-(3,5-bis(trifluoromethyl)phenyl)-1H-1,2,4-triazol-1-yl)acrylate (3)

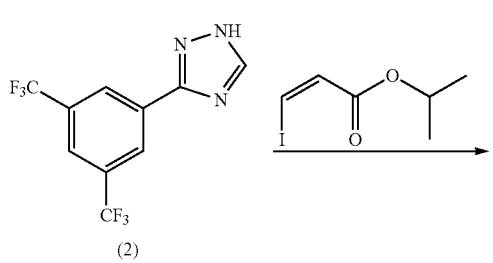

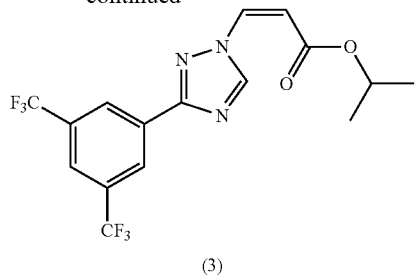

A 3-neck round-bottom flask was charged with a solution of 3-(3,5-bis(trifluoromethyl)phenyl)-1H-1,2,4-triazole (2) (160 g, 1.0 eq.) in DMF (960 mL). The solution was treated DABCO (127.74 g, 2 eq.) and stirred for 30 min before being treated with (Z)-isopropyl 3-iodoacrylate (150.32 g, 1.1 eq.). After 1 hm the reaction mixture was poured into ice water slurry (5 L) and extracted with EtOAc (3×1 L). The combined organic layers were washed with brine (3×100 mL), dried over anhydrous Na₂SO₄, filtered, and concentrated under reduced pressure to afford 250 g of crude compound. Purification by column chromatography (silica gel, eluting with EtOAc/hexane) afforded 138 g (61% yield) of pure isopropyl ester (3).

Synthesis of (Z)-3-(3-(3,5-bis(trifluoromethyl)phenyl)-1H-1,2,4-triazol-1-yl)acrylic acid (4)

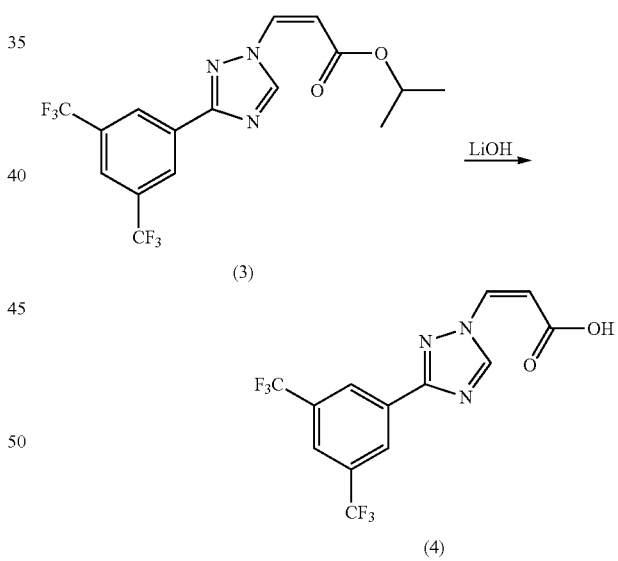

A 3-neck round-bottom flask was charged with a solution of (Z)-isopropyl 3-(3-(3,5-bis(trifluoromethyl)phenyl)-1H-1,2,4-triazol-1-yl)acrylate (3) (130 g, 1.0 eq.) in THF (1.3 L) and treated with a solution of LiOH (69.3 g, 5 eq) in water (1.3 L). The reaction mixture was stirred at ambient temperature for 3-4 h before being diluted with 400 mL water, acidified (pH=2-3) with dilute aqueous HCl and extracted with EtOAc (3×1 L). The combined organic layers were washed with brine, dried over anhydrous Na₂SO₄ and concentrated under reduced pressure to afford 110 g (94% yield) of desired compound (4); Z/E ratio=90.0/8.2 by LCMS.

Synthesis of (Z)-3-iodoacrylic acid (1a)

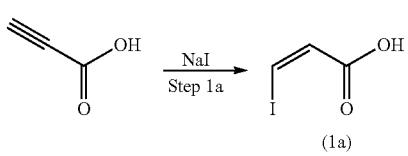

A solution of propiolic acid (50.0 g, 1.0 eq) in acetic acid (500 mL), was treated with sodium iodide (213.97 g, 2.0 eq). The reaction mixture was refluxed at 100° C. for 2-3 h then cooled down to ambient temperature, poured into ice water (5.0 L), neutralized with saturated aqueous sodium bicarbonate and extracted with EtOAc (3×1 L). The combined organic layers were washed with brine (3×1 L), dried over $MgSO_4$, filtered, and concentrated under reduced pressure to afford 90.0 g of crude compound which was purified by column chromatography (silica gel, elution with MeOH: $CH_2Cl_2$) affording 56.0 g (39.7% yield) of pure carboxylic acid (1a).

Example 1

Synthesis of (Z)-1-(3,3-difluoroazetidin-1-yl)-3-iodoprop-2-en-1-one (2a)

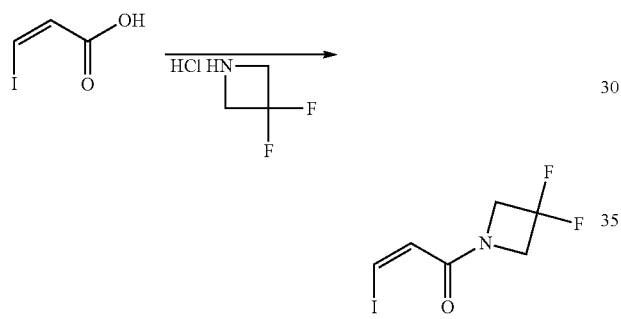

A solution of (Z)-3-iodoacrylic acid (1a) (2.75 g, 1.0 eq.) in $CH_2Cl_2$ (25.0 mL) was cooled to 0° C. and sequentially treated with DIPEA (1.96 g, 1.1 eq), HATU (5.78 g, 1.1 eq) and 3,3-difluoroazetidine hydrochloride (1.98 g, 1.1 eq). The reaction mixture was stirred at 0° C. for 2-3 hr before being filtered, and concentrated under reduced pressure affording 3.5 g of crude compound. Purification by column chromatography (silica gel, elution with EtOAc/hexane) afforded 1.89 g of pure desired compound. Yield (49.87%). Mass: (ES+) 273.8 (M+1).

Synthesis of (Z)-3-(3-(3,5-bis(trifluoromethyl)phenyl)-1H-1,2,4-triazol-1-yl)-1-(3,3-difluoroazetidin-1-yl)prop-2-en-1-one

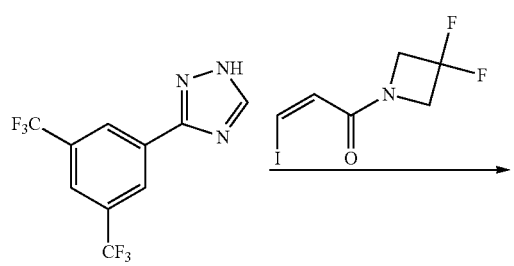

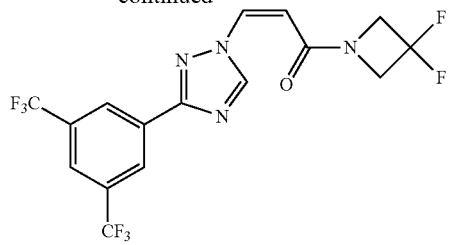

A solution of 3-(3-(difluoromethyl)-5-(trifluoromethyl)phenyl)-1H-1,2,4-triazole (2) (1.5 g, 1.0 eq.) in DMF (9.0 mL) was treated with DABCO (1.19 g, 2.0 eq) and stirred for 30 mins before being treated (Z)-1-(3,3-difluoroazetidin-1-yl)-3-iodoprop-2-en-1-one (2a) (1.60 g, 1.1 eq). The reaction mixture was stirred at ambient temperature for 2-3 hr then poured in to ice water (90 mL) and extracted with EtOAc (3×50 mL). The combined organic layers were washed with brine (3×50 mL), dried over $MgSO_4$, filtered, and concentrated under reduced pressure to afford 2.0 g of crude amide. (cis isomer: 71.1%, trans isomer: 15.87%). Purification by column chromatography (silica gel, eluting with EtOAC/hexane) afforded 500 mg of pure desired amide (22.0% yield):

$^1$H NMR (CDCl$_3$): δ 9.63 (s, 1H), 7.95-7.65 (m, 3H), 7.24-7.27 (d, J=10.8 Hz, 1H), 5.66-5.69 (d, J=10.8 Hz, 1H), 4.46-4.59 (m, 4H). LCMS for $C_{16}H_{10}F_8N_4O$: [M+H]$^+$=427.27. found 427.29, RT: 3.03 min (98.17%).

(E)-3-(3-(3,5-bis(trifluoromethyl)phenyl)-1H-1,2,4-triazol-1-yl)-4-(3,3-difluoroazetidin-1-yl)prop-2-en-1-one $^1$H NMR (CDCl$_3$): δ 9.18 (s, 1H), 8.59 (s, 2H), 8.32 (s, 1H), 8.24-8.27 (d, J=13.6 Hz, 1H), 6.80-6.84 (d, J=13.6 Hz, 1H), 4.83-4.88 (m, 2H), 4.40-4.46 (m, 2H). LCMS for $C_{16}H_{10}F_8N_4O$: [M+H]$^+$=427.27. found 427.34, RT: 3.13 min (100%).

Alternative synthesis of (Z)-3-(3-(3,5-bis(trifluoromethyl)phenyl)-1H-1,2,4-triazol-1-yl)-1-(3,3-difluoroazetidin-1-yl)prop-2-en-1-one

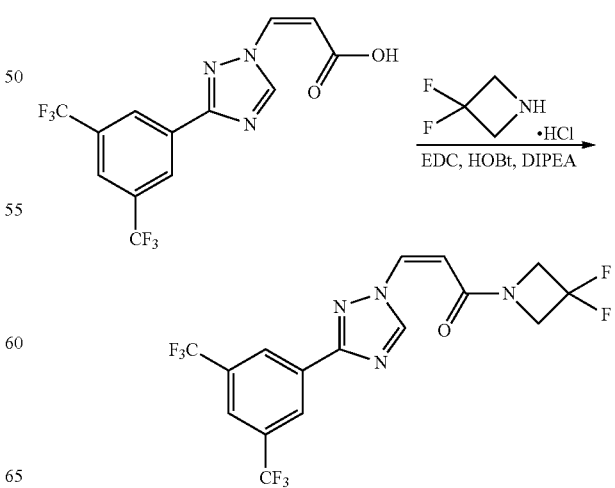

A solution of (Z)-3-(3-(3,5-bis(trifluoromethyl)phenyl)-1H-1,2,4-triazol-1-yl)acrylic acid (33.0 g, 1.0 eq.) in CH₂Cl₂ (660 mL) was cooled to 0° C. and then treated sequentially with HOBT (17.27 g, 1.2 eq), EDC.HCl (27.029 g, 1.5 eq.),3,3-difluoroazetidine hydrochloride (14.61 g, 1.2 eq.) and DIPEA (24.31 mL, 1.5 eq). The reaction mixture was stirred at 0° C. for 1.15 hr before being quenched with 1 L water and extracted with EtOAc (3×500 mL). The combined organic layers were washed with brine, dried over anhydrous NaSO₄ and concentrated under reduced pressure to afford 35 g of crude compound. Purification by column chromatography (silica gel, eluting with MeOH:CH₂Cl₂) afforded pure desired amide (15 g, 37% yield):

(Z)-3-(3-(3,5-(trifluoromethyl)-1H-1,2,4-triazol-1-yl)-1-(3,3-difluoroazetidin-1-yl)prop-2-en-1-one ¹H NMR (CDCl₃): δ 9.63 (s, 1H), 7.95-7.65 (m, 3H), 7.24-7.27 (d, J=10.8 Hz, 1H), 5.66-5.69 (d, J=10.8 Hz, 1H), 4.46-4.59 (m, 4H). LCMS for C₁₆H₁₀F₈N₄O: [M+H]⁺ 427.27. found 427.29, RT: 3.027 (98.17%).

Example 2

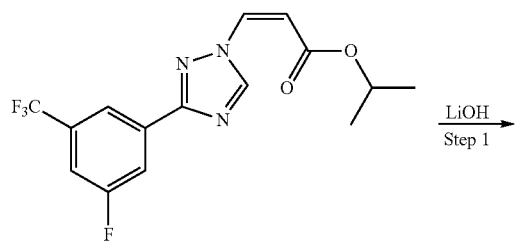

Synthesis of (Z)-3-(3-(3-fluoro-5-(trifluoromethyl)phenyl)-1H-1,2,4-triazol-1-yl)acrylic acid (1)

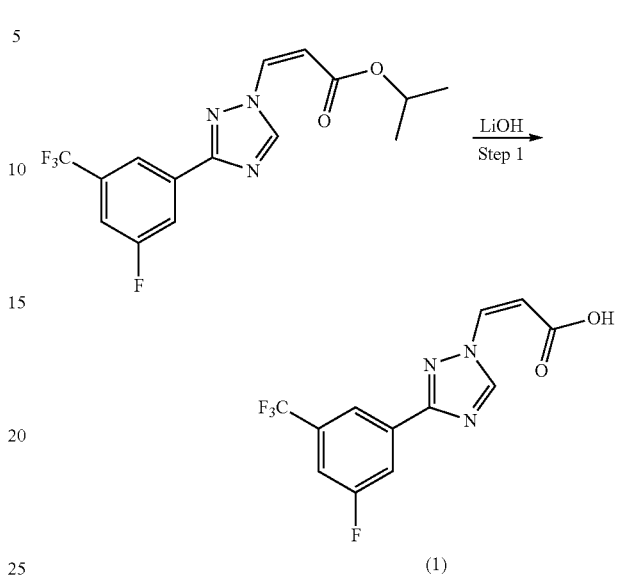

A solution of (Z)-isopropyl 3-(3-(3-fluoro-5-(trifluoromethyl)phenyl)-1H-1,2,4-triazol-1-yl)acrylate (0.400 g, 1.0 eq.) in THF (5 mL) and water (5 mL) was treated with LiOH (0.097 g, 2.0 eq.). The reaction mixture was stirred at RT for 2-3 hrs, quenched with ice cold water (10 mL), acidified to pH 1-2 with dilute aqueous HCl and extracted with EtOAc (3×25 mL). The combined organic layers were dried over anhydrous Na₂SO₄ and concentrated under reduced pressure to afford 150 mg (42% yield) desired carboxylic acid, used in the subsequent step. Mass: (ES+) 302.19 (M+1).

Synthesis of (Z)-1-(3,3-difluoroazetidin-1-yl)-3-(3-(3-fluoro-5-(trifluoromethyl)phenyl)-1H-1,2,4-triazol-1-yl)prop-2-en-1-one

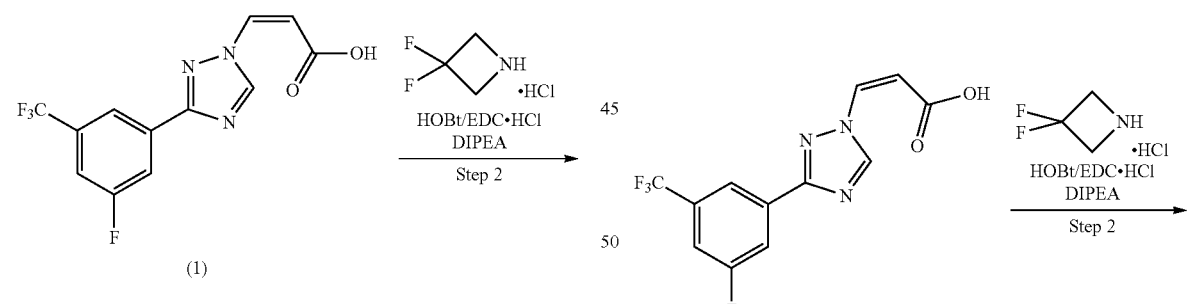

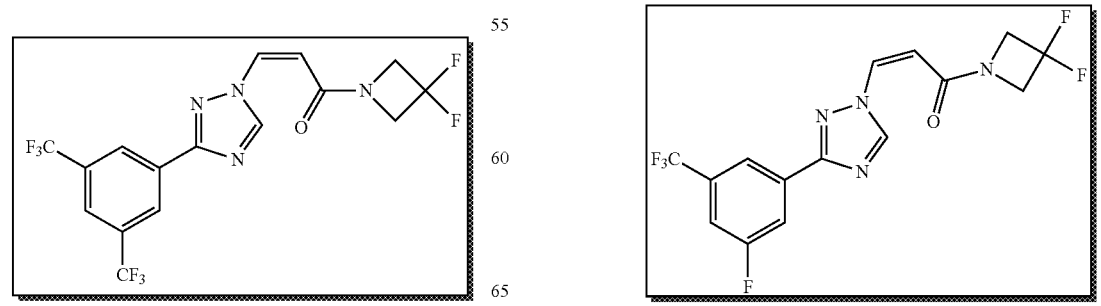

A 25-mL flask was charged with (Z)-3-(3-(3-fluoro-5-(trifluoromethyl)phenyl)-1H-1,2,4-triazol-1-yl)acrylic acid (1) (0.150 g, 1.0 eq) followed by dichloromethane (3 mL) before being treated sequentially with DIPEA (0.102 mL, 1.2 eq), EDC.HCl (0.143 g, 1.5 eq), 3,3-difluoroazetidine hydrochloride (0.077 g, 1.2 eq) and HOBT (0.091 g, 1.2 eq) at 0° C. The reaction mixture was stirred at 0° C. for 1 hr., diluted with water (5 mL) and extracted with dichloromethane (3×5 mL). Drying over Na$_2$SO$_4$ and concentration under reduced pressure afforded 0.150 g of crude compound. (Cis 49%: Trans 42%). Purification by column chromatography (silica gel, eluting with MeOH/CH$_2$Cl$_2$) afforded pure desired amide (0.025 g; 13% yield):

(Z)-1-(3,3-difluoroazetidin-1-yl)-3-(3-(3-fluoro-5-(trifluoromethyl)phenyl)-1H-1,2,4-triazol-1-yl)prop-2-en-1-one $^1$H NMR (400 MHz, CDCl$_3$) δ 9.6 (s, 1H), 7.40-8.37 (m, 3H), 7.22-7.25 (d, J=10.8 Hz, 1H), 5.64-5.67 (d, J=10.8 Hz, 1H), 4.46-4.59 (m, 4H). LCMS for C$_{15}$H$_{10}$F$_6$N$_4$O [M+H]$^+$ 377.26 found 377.24 at RT 2.79 min purity (92.79%). Mass: (ES+) 377.2 (M+1).

Example 3

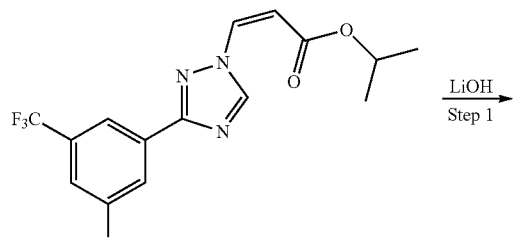

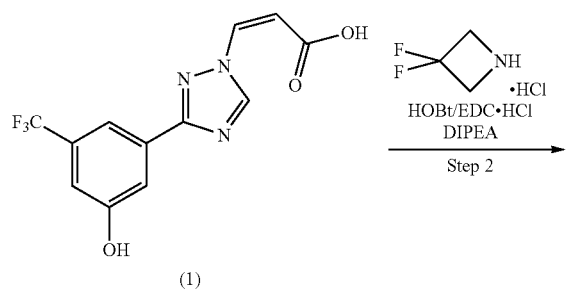

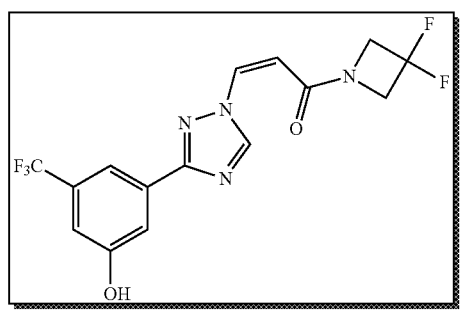

Synthesis of (Z)-3-(3-(3-hydroxy-5-(trifluoromethyl)phenyl)-1H-1,2,4-triazol-1-yl)acrylic acid (1)

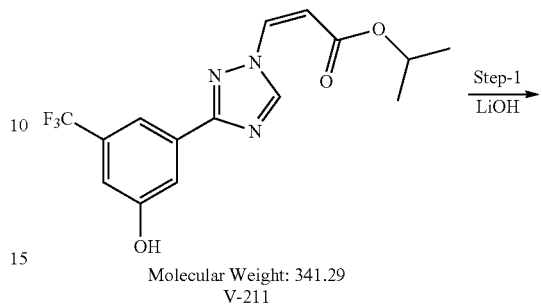

Molecular Weight: 341.29
V-211

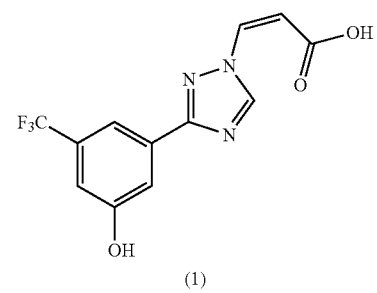

(1)

Molecular Weight: 299.21

A solution of (Z)-isopropyl 3-(3-(3-hydroxy-5-(trifluoromethyl)phenyl)-1H-1,2,4-triazol-1-yl)acrylate (4 g, 1.0 eq.) in THF (40 mL) and water (40 mL) was treated with LiOH (1.92 g, 4 eq.). The reaction mixture was stirred at RT for 2-3 hrs then quenched with acidic ice-water slurry (300 mL) and extracted with EtOAc (3×250 mL). The combined organic layers were washed with dil HCl solution (50 mL), dried over anhydrous Na$_2$SO$_4$ and concentrated under reduced pressure to afford 3 g of crude compound. The resulting crude off-white compound was used as such in the following step. Yield: 85.5%. Mass: (ES+) 299.92 (M+1).

Synthesis of (Z)-1-(3,3-difluoroazetidin-1-yl)-3-(3-(3-hydroxy-5-(trifluoromethyl)phenyl)-1H-1,2,4-triazol-1-yl)prop-2-en-1-one (2)

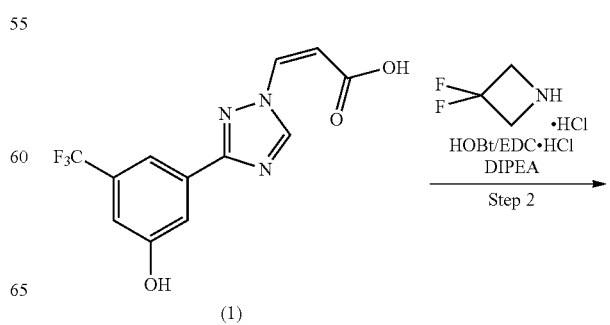

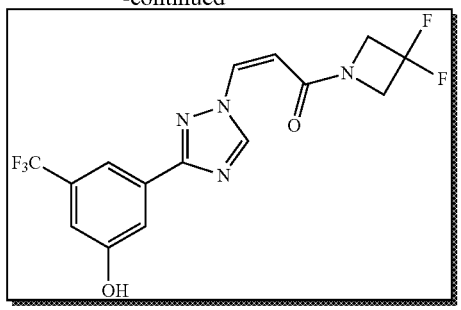

A cold (0° C.) solution of (Z)-3-(3-(3-hydroxy-5-(trifluoromethyl)phenyl)-1H-1,2,4-triazol-1-yl)acrylic acid (1) (1.5 g, 1.0 eq) in 30 ml of $CH_2Cl_2$ was treated sequentially with DIPEA (0.78 g, 1.2 eq), EDC.HCl (01.15 g, 1.2 eq), 3,3-difluoroazetidine hydrochloride (0.78 g, 1.2 eq) and HOBt (0.92 g, 1.2 eq). The reaction mixture was stirred at 0° C. for 3-4 hrs before being concentrated under reduced pressure to afford 0.5 g of crude compound. (trans isomer was not observed during reaction). The crude reaction mixture was purified by column chromatography affording pure desired amide (0.5 g). Yield: 26.7%:

(Z)-1-(3,3-difluoroazetidin-1-yl)-3-(3-(3-hydroxy-5-(trifluoromethyl)phenyl)-1H-1,2,4-triazol-1-yl)prop-2-en-1-one $^1$H NMR (400 MHz, $CDCl_3$) δ 10.53 (1H, $D_2O$ exchangeable), 9.17 (s, 1H), 7.14-7.71 (m, 3H), 7.41-7.43 (d, J=10.4 Hz, 1H), 5.92-5.95 (d, J=10.4 Hz, 1H), 4.41-4.49 (m, 4H). LCMS for $C_{15}H_{11}F_5N_4O_2$ [M+H]$^+$ 375.27. found 375.24 at RT 2.44 min, purity (97.03%). Mass: (ES+) 375.2 (M+1).

Example 5

Synthesis of (Z)-3-(3-(3,5-bis(trifluoromethyl)phenyl)-1H-1,2,4-triazol-1-yl)-1-(3,3-difluoropiperidin-1-yl)prop-2-en-1-one

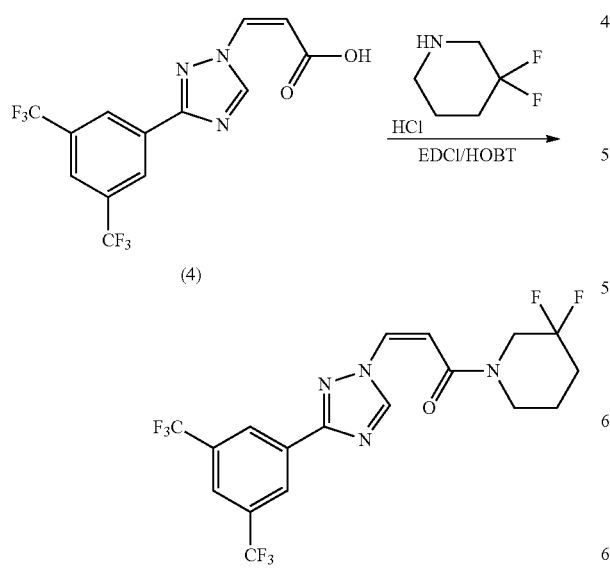

A cold (0° C.) solution of (Z)-3-(3-(3,5-bis(trifluoromethyl)phenyl)-1H-1,2,4-triazol-1-yl)acrylic acid (4) (1.0 g, 1.0 eq.) in $CH_2Cl_2$ (20 mL) was treated sequentially with EDC HCl (0.656 g, 1.2 eq.), 3,3-difluoropiperidine hydrochloride (0.540 g, 1.2), DIPEA (435 mg, 1.2 eq) and HOBT (25.92 g, 1.2 eq.). The clear reaction mixture was stirred at 0° C. for 1.5-2 h then quenched with 50 mL ice-water slurry and extracted with $CH_2Cl_2$ (2×25 mL). The combined organic layers were washed with brine, dried over anhydrous $Na_2SO_4$ and concentrated under reduced pressure to afford 0.70 g of crude compound. No trans compound was formed as confirmed by LCMS and $^1$H NMR. Purification by column chromatography afforded 0.20 g of material that was further recrystallized/triturated using ether: petroleum ether to remove aliphatic impurity affording 0.180 g (14.1% yield) of desired pure compound.

(Z)-3-(3-(3,5-bis(trifluoromethyl)phenyl)-1H-1,2,4-triazol-1-yl)-1-(3,3-difluoropiperidin-1-yl)prop-2-en-1-one $^1$H NMR (400 MHz, $CDCl_3$) δ 8.739 (s, 1H), 7.94-8.59 (m, 3H), 7.13-7.15 (d, J=10.4 Hz, 1H), 5.99-6.016 (d, J=10.4 Hz, 1H), 3.95-4.01 (t, 1H), 3.68-3.77 (m, 2H), 3.56-3.53 (t, 1H), 2.11-2.05 (m, 2H), 1.77-1.89 (m, 2H). LCMS for $C_{18}H_{14}F_8N_4O$ [M+H]$^+$ 455.33. found 455.07 at RT 3.82 min, purity (98.64%).

Example 6

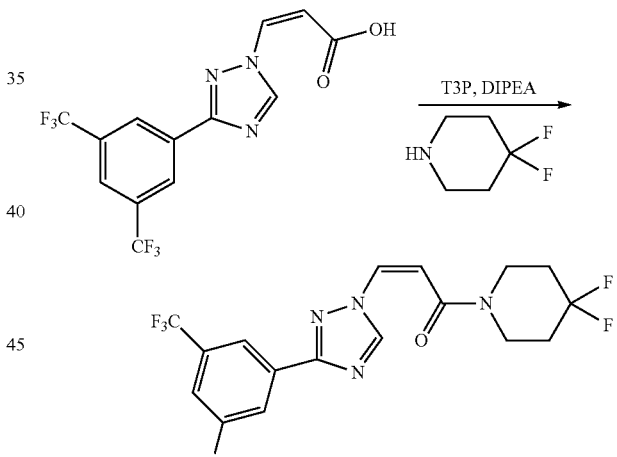

Synthesis of (Z)-3-(3-(3,5-bis(trifluoromethyl)phenyl)-1H-1,2,4-triazol-1-yl)-1-(4,4-difluoropiperidin-1-yl)prop-2-en-1-one A cold (0° C.) solution of (Z)-3-(3-(3,5-bis(trifluoromethyl)phenyl)-1H-1,2,4-triazol-1-yl)acrylic acid (4) (0.500 g, 1.0 eq.) in $CH_2Cl_2$ (20 mL) was treated sequentially with EDC HCl (0.409 g, 1.5 eq.), 4,4-difluoropiperidine hydrochloride (0.269 g, 1.2), DIPEA (0.220 g, 1.2 eq) and HOBT (0.261 g, 1.2 eq.). The clear reaction mixture was stirred at 0° C. for 1.5-2 h then quenched with 50 mL ice-water slurry. The aqueous layer was extracted with $CH_2Cl_2$ (2×25 mL) and the combined organic layers were washed with brine, dried over anhydrous $Na_2SO_4$ and concentrated under reduced pressure to afford 0.60 g of crude compound.

Purification by preparative TLC (eluting with MeOH/CH$_2$Cl$_2$) afforded 0.090 g compound which was further triturated using ether: petroleum ether to remove aliphatic impurity affording 0.06 g pure compound. Yield: 9.28%.

(Z)-3-(3-(3,5-bis(trifluoromethyl)phenyl)-1H-1,2,4-triazol-1-yl)-1-(4,4-difluoropiperidin-1-yl)prop-2-en-1-one $^1$H NMR (400 MHz, CDCl$_3$) δ 8.705 (s, 1H), 8.557 (s, 2H), 7.950 (s, 1H), 7.111-7.136 (d, J=10.0 Hz, 1H), 5.998-6.024 (d, J=10.8 Hz, 1H), 3.886-3.916 (t, 2H), 3.654-3.683 (t, 2H), 2.055-2.152 (m, 2H), 1.940-2.035 (m, 2H). LCMS for C$_{18}$H$_{15}$F$_8$N$_4$O [M+H]$^+$ 455.33. found 455.38 at RT 3.057 min purity (99.77%).

Example 7

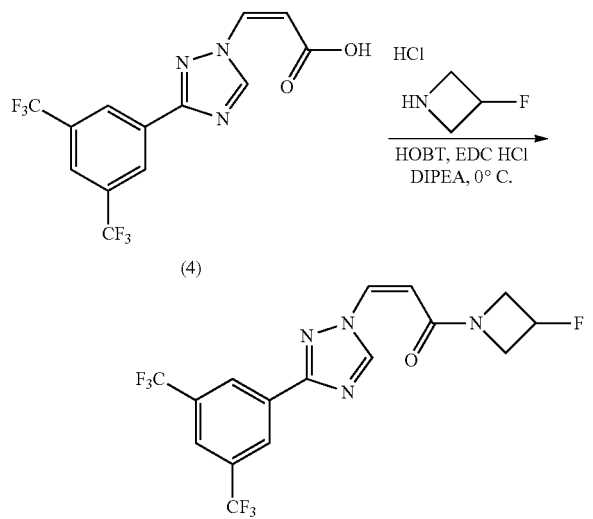

Synthesis of (Z)-3-(3-(3,5-bis(trifluoromethyl)phenyl)-1H-1,2,4-triazol-1-yl)-1-(3-fluoroazetidin-1-yl)prop-2-en-1-one To a stirred solution of (Z)-3-(3-(3,5-bis(trifluoromethyl)phenyl)-1H-1,2,4-triazol-1-yl)acrylic acid (4) (0.500 g, 1 eq.) dichloromethane (10 mL, 20 V) in 3 necked 100 mL round-bottomed flask equipped with nitrogen bubbler HOBT (0.19 g, 1.2 eq.), EDC.HCl (0.41 g, 1.5 eq.) and DIPEA (0.27 g, 1.5 eq.) were added at 0° C. After 1 hr, the reaction mixture was quenched with water (50 ml) and extracted with dichloromethane (3×30 mL) The combined organic layers were washed with brine (50 mL), dried over anhydrous Na$_2$SO$_4$ and concentrated under reduced pressure affording 0.25 g crude titled compound. Purification by flash chromatography (eluting with EtOAc/hexane) afforded 0.03 g of pure titled compound.

(Z)-3-(3-(3,5-bis(trifluoromethyl)phenyl)-1H-1,2,4-triazol-1-yl)-1-(3-fluoroazetidin-1-yl)prop-2-en-1-one $^1$H NMR (400 MHz, CDCl$_3$) δ 9.76 (s, 1H), 8.62 (s, 2H), 7.94 (s, 1H), 7.21-7.24 (d, J=10.8 Hz, 1H), 5.65-5.68 (d, J=10.8 Hz, 1H), 5.45-5.48 (m, 1H), 5.31-5.34 (m, 1H), 4.44-4.56 (m, 4H), 4.23-4.43 (m, 2H). LCMS for C$_{16}$H$_{11}$F$_7$N$_4$O [M+H]$^+$ 409.28. found 409.38 at RT 2.963 min purity (96.03%).

Example 8

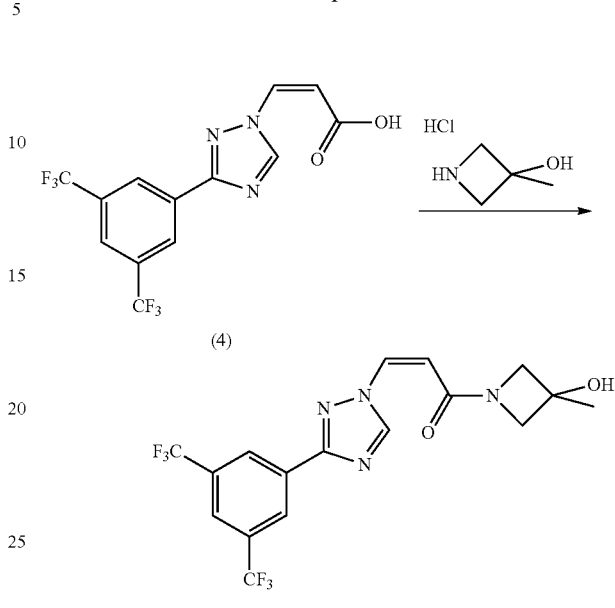

Synthesis of (Z)-3-(3-(3,5-bis(trifluoromethyl)phenyl)-1H-1,2,4-triazol-1-yl)-1-(3-hydroxy-3-methyl-azetidin-1-yl)prop-2-en-1-one In a 25 mL 3N round-bottomed flask equipped with nitrogen inlet, (Z)-3-(3-(3,5-bis(trifluoromethyl)phenyl)-1H-1,2,4-triazol-1-yl)acrylic acid (4) (0.250 g, 1.0 eq.) was charged along with dichloromethane (5.0 mL, 20 V). The reaction mixture was cooled to 0° C. and then added HOBT (0.119 g, 1.1 eq.) followed by EDC HCl (0.149 g, 1.1 eq.) and 3-methyl azetidin-3-ol HCl (0.096 g g, 1.1 eq.). DIPEA (0.101 g, 1.1 eq) was added to this reaction mixture drop-wise at the same temperature. The clear reaction mixture was stirred at 0° C. for 1.5 h. The progress of the reaction was followed by TLC analysis on silica gel with 10% methanol in dichloromethane as mobile phase and visualization with UV. Reaction mixture was quenched in 20 mL ice-water slurry. Organic layer was separated and aqueous layer was extracted with dichloromethane (2×10 mL) to ensure complete extraction. The organic layer was washed with brine solution and dried over anhydrous Na$_2$SO$_4$ and concentrated by rotary evaporation under reduced pressure (35° C., 20 mm Hg) to afford 0.280 g of crude compound. (cis: 61.9%, trans: 16.46%)

The crude reaction mixture was purified by column chromatography using 60/120 mesh silica and methanol: dichloromethane as mobile phase. The column was packed in dichloromethane and started eluting in MeOH in gradient manner starting with fraction collection (500 mL fractions). The compound started eluting from 0.2-2.0% methanol in dichloromethane. Fractions containing such TLC profile were collected together to obtain pure compound 90 mg. Yield: 30.1%.

(Z)-3-(3-(3,5-bis(trifluoromethyl)phenyl)$_4$H-1,2,4-triazol-1-yl)-1-(3-hydroxy-3-methylazetidin-1-yl)prop-2-en-one $^1$H NMR (400 MHz, DMSO) δ 9.39 (s, 1H), 8.55 (s, 2H), 8.301 (s, 1H), 7.37-7.40 (d, J=10.4 Hz, 1H), 5.95-5.98 (d, J=10.0 Hz, 1H), 5.69 (s, 1H), 3.90 (s, 2H), 3.78-3.85 (m, 2H), 1.32 (s, 3H). LCMS for $C_{17}H_{14}F_6N_4O_2$ [M+H]$^+$: 420.31. found 421.4 at RT 2.665 min purity (99.54%).

Example 9 washed with brine solution (3×50 mL). The organic layer was dried using anhydrous sodium sulfate, filtered, and concentrated under reduced pressure to provide the 0.40 g crude titled compound. This crude material was directly used for next step without purification.

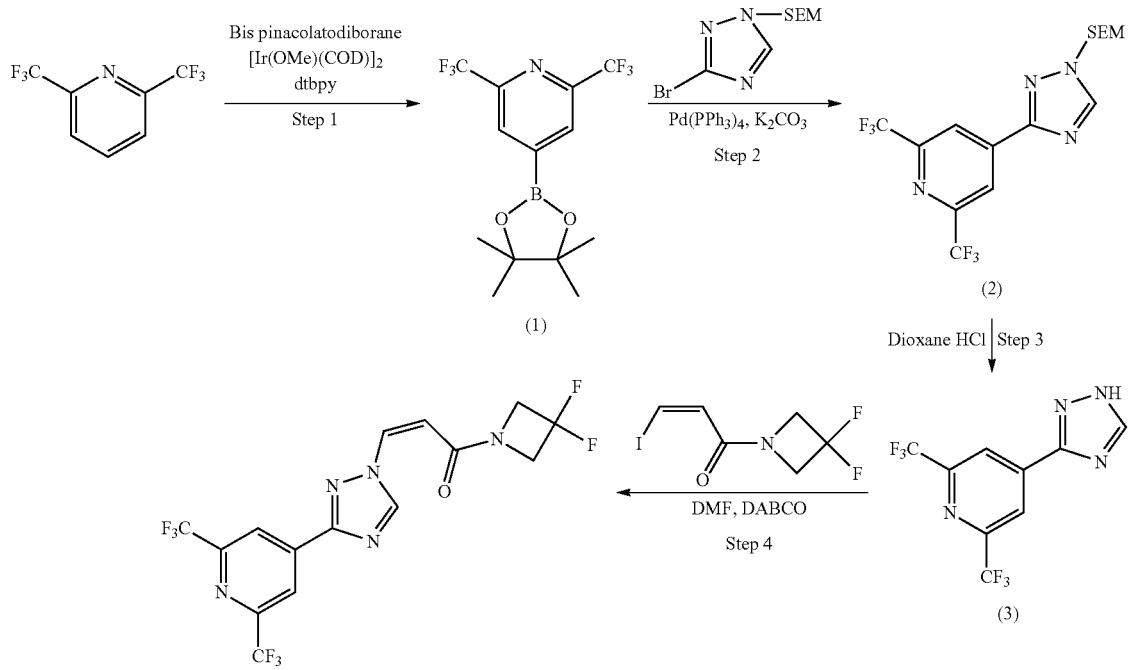

Synthesis of 4-(4,4,5,5-tetramethyl-1,3,2-dioxaborolan-2-yl)-2,6-bis(trifluoromethyl)pyridine (1)

Synthesis of 2,6-bis(trifluoromethyl)-4-(1-((2-(trimethylsilyl)ethoxy)methyl)-1H-1,2,4-triazol-3-yl)pyridine (2)

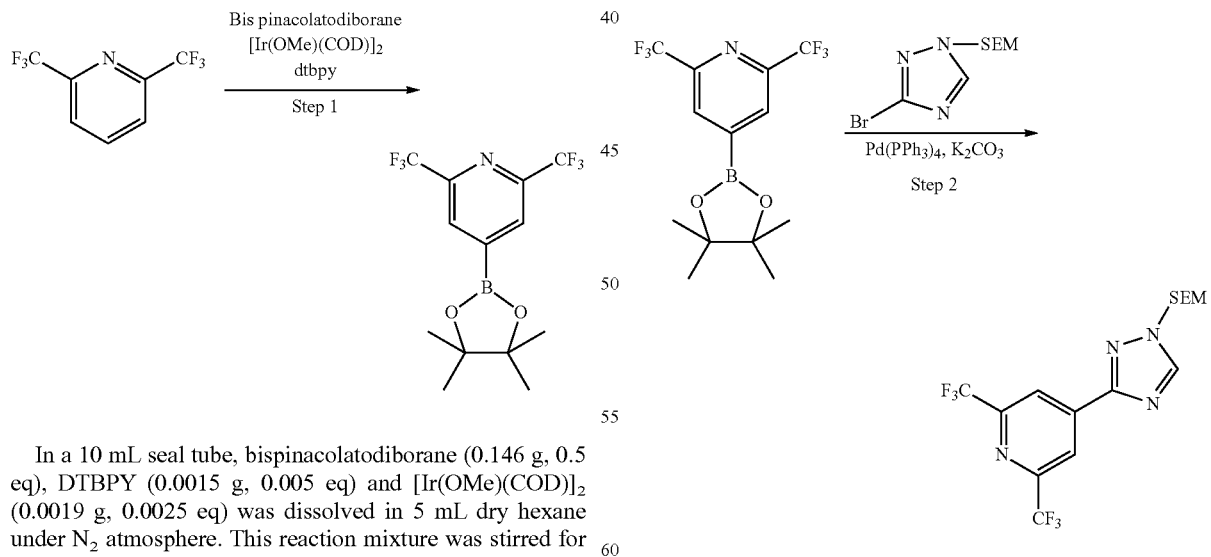

In a 10 mL seal tube, bispinacolatodiborane (0.146 g, 0.5 eq), DTBPY (0.0015 g, 0.005 eq) and [Ir(OMe)(COD)]$_2$ (0.0019 g, 0.0025 eq) was dissolved in 5 mL dry hexane under N$_2$ atmosphere. This reaction mixture was stirred for 10 min at RT to give dark red solution. 3,5-bis(trifluoromethyl)pyridine (0.250 g, 1 eq.) was charged in seal tube. Seal tube was closed and heated at 50° C. for 6 h. Reaction completion was monitored on TLC using ethyl acetate: hexane(1:9) as mobile phase. The reaction mixture was quenched into the ice-water slurry (50 mL) and was extracted with ethyl acetate (3×50 mL). Organic layer was In a 10 mL seal tube, 4-(4,4,5,5-tetramethyl-1,3,2-dioxaborolan-2-yl)-2,6-bis(trifluoromethyl)pyridine(1) (0.395 g, 1 eq.) was dissolved in DME (5 mL), then 3-bromo-1-((2-(trimethylsilyl)ethoxy)methyl)-1H-1,2,4-triazole (0.323 g, 1 eq.) and K$_2$CO$_3$ (0.480 g, 3 eq.) in water (1 mL) was added. Mixture was degassed by purging nitrogen for 1 h. Tetrakis (0.067 g, 0.05 eq.) was added in the reaction mixture and seal tube was heated at 90° C. for 18 h. Reaction completion was monitored on TLC using ethyl acetate:hexane (2:8) as mobile phase The reaction mixture was quenched into the ice-water solution (50 mL) and was extracted with ethyl acetate (3×50 mL). Organic layer was washed with brine solution (3×50 mL). The organic layer was dried using anhydrous sodium sulfate, filtered, and concentrated under reduced pressure to provide the 0.30 g crude compound. The compound was purified by column chromatography using ethyl acetate/n-hexane as mobile phase. Compound was eluted out at 8% ethylacetate in hexane to afford (intermediate-2) 0.150 g. Yield: 31.0%.

Synthesis of 4-(1H-1,2,4-triazol-3-yl)-2,6-bis(trifluoromethyl)pyridine (3)

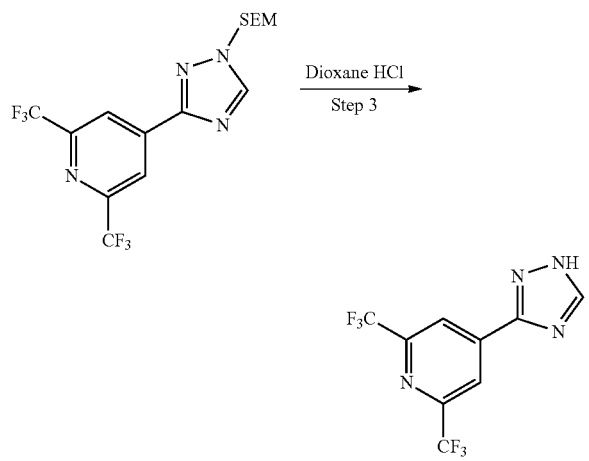

In a 10 mL seal tube, 2,6-bis(trifluoromethyl)-4-(1-((2-(trimethylsilyl)ethoxy)methyl)-1H-1,2,4-triazol-3-yl)pyridine (2) (0.15 g, 1 eq.) was dissolved in dioxane HCl (5 mL) and seal tube was heated to 60° C. for 6 h. Reaction completion was monitored on TLC using ethyl acetate: hexane (5:5) as mobile phase. The reaction mixture was quenched into the ice-water NaHCO₃ solution (50 mL) and was extracted with ethyl acetate (3×50 mL). Organic layer was washed with brine solution (3×50 mL). The organic layer was dried using anhydrous sodium sulfate, filtered, and concentrated under reduced pressure to provide the 0.3 g of crude compound. The compound was purified by column chromatography using ethyl acetate/hexane as mobile phase. Compound was eluted out at 30% ethyl acetate in hexane to afford 4-(1H-1,2,4-triazol-3-yl)-2,6-bis(trifluoromethyl) pyridine (3) 0.060 g. Yield: 58.4%.

Synthesis of (Z)-3-(3-(2,6-bis(trifluoromethyl)pyridin-4-yl)-1H-1,2,4-triazol-1-yl)-1-(3,3-difluoroazetidin-1-yl)prop-2-en-1-one

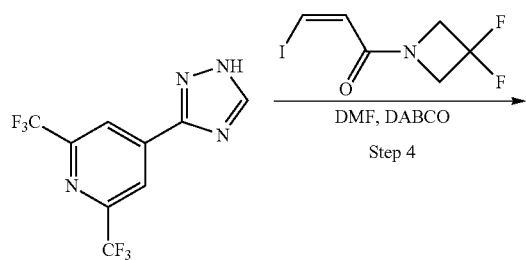

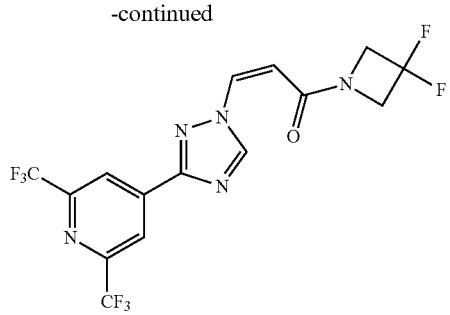

In a 3-neck 50 mL round-bottomed flask, 4-(1H-1,2,4-triazol-3-yl)-2,6-bis(trifluoromethyl)pyridine (3) (0.060 g, 1 eq.) and (Z)-1-(3,3-difluoroazetidin-1-yl)-3-iodoprop-2-en-1-one (0.064 g, 1.1 eq) was dissolved in DMF (2 mL). DABCO (0.047 g, 2 eq.) was added at RT. Reaction mixture was stirred for 1 h at RT. Reaction completion was monitored on TLC using MeOH:dichloromethane (0.25:9.75) as mobile phase. The reaction mixture was quenched into the ice-water slurry (50 mL) and was extracted with ethyl acetate (3×25 mL). Organic layer was washed with brine solution (3×25 mL). The organic layer was dried using anhydrous sodium sulfate, filtered, and concentrated under reduced pressure to provide the 0.70 g crude compound which was purified by preparative TLC using 2.5% methanol in dichloromethane as mobile phase to afford 0.011 g (12%) title compound.

(Z)-3-(3-(2,6-bis(trifluoromethyl)pyridin-4-yl)-1H-1,2,4-triazol-1-yl)-1-(3,3-difluoroazetidin-1-yl)prop-2-en-1-one ¹H NMR (400 MHz, DMSO) δ 9.768 (s, 1H), 8.590 (s, 2H), 7.268-7.295 (d, J=10.8, 1H), 5.732-5.759 (d, J=10.8 Hz, 1H), 4.56-4.62 (t, 2H), 4.46-4.52 (t, 2H). LCMS for $C_{15}H_9F_8N_5O$ [M+H]⁺ 427.25 found 428.5 at 2.901 min purity (95.46%).

Example 10

Synthesis of (Z)-3-(3-(3,5-bis(trifluoromethyl)phenyl)-1H-1,2,4-triazol-1-yl)-N-ethyl-N-(1-(pyridin-3-yl)ethyl)acrylamide

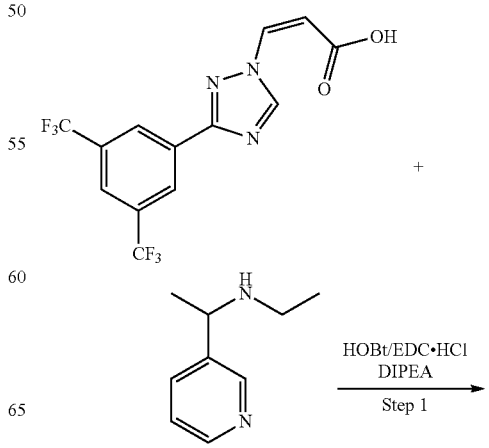

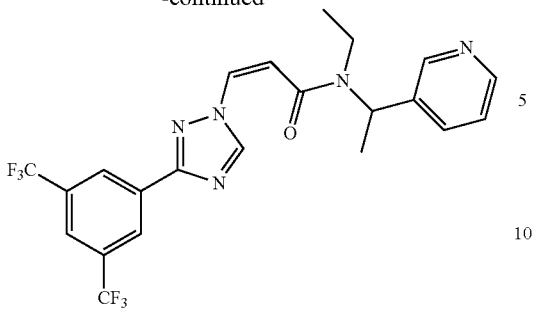

In a 3-neck 50 mL round-bottomed flask, (Z)-3-(3-(3,5-bis(trifluoromethyl)phenyl)-1H-1,2,4-triazol-1-yl)acrylic acid (0.2 g, 1.0 eq.) was dissolved in dichloromethane (15 mL) at 0° C. under $N_2$ atmosphere. To this reaction DIPEA (0.088 g, 1.2 eq.), EDC.HCl (0.131 g, 1.2 eq.) and N-ethyl-1-(pyridin-3-yl)ethanamine (0.102 g, 1.2 eq.) was added followed by HOBt (0.104 g, 1.2 eq.). Reaction mixture was stirred at 20° C. for 1 h. The progress of the reaction was followed by TLC analysis on silica gel with 10% methanol:dichloromethane as mobile phase and visualization with UV, SM $R_f$=0.15 and Product $R_f$=0.40. Reaction was stirred for 3-4 h and yellow reaction mixture was evaporated on rotary evaporator under reduced pressure to afford 0.4 g of crude compound.

The crude reaction mixture was purified by column chromatography using silica 60/120 using methanol: dichloromethane as mobile phase. The column (2×10 cm) was packed in dichloromethane and started eluting in Methanol in gradient manner starting with fraction collection (25 mL fractions) from 1.5% to 2.5% methanol in dichloromethane. Compound started eluting with 1.5% methanol in dichloromethane Fraction containing such TLC profile was collected together to obtain pure compound (0.006 g). Yield: 3%.

(Z)-3-(3-(3,5-bis(trifluoromethyl)phenyl)-1H-1,2,4-triazol-1-yl)-N-ethyl-N-(1-(pyridin-3-yl)ethyl)acrylamide $^1$H NMR (400 MHz, DMSO) δ 9.04 (s, 1H), 7.38-8.73 (m, 7H), 8.19-8.22 (d, J=12.4, 1H), 6.01-6.04 (d, J=12.8 Hz, 1H), 4.77-4.79 (d, 1H), 3.29-3.46 (m, 2H), 1.79-1.81 (d, 3H), 1.24-1.27 (t, 3H). LCMS for $C_{22}H_{19}F_6N_5O$ [M+H]$^+$ 483.4 found 484.55 at 3.283 min purity (91.38%).

Example 11

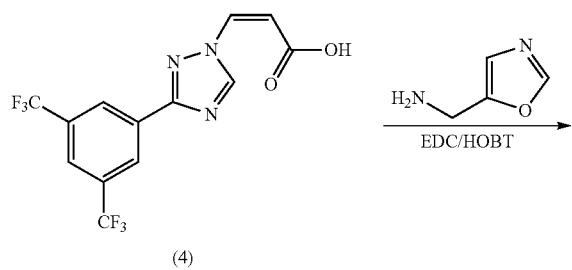

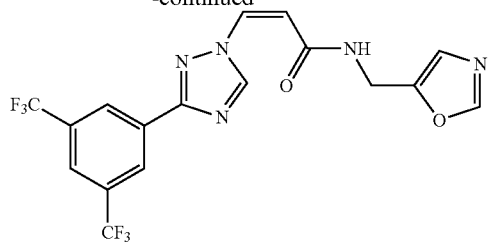

Synthesis of (Z)-3-(3-(3,5-bis(trifluoromethyl)phenyl)-1H-1,2,4-triazol-1-yl)-N-(oxazol-5-ylmethyl)acrylamide In a 25 mL 3N round-bottomed flask equipped with nitrogen inlet, (Z)-3-(3-(3,5-bis(trifluoromethyl)phenyl)-1H-1,2,4-triazol-1-yl)acrylic acid (4) (0.250 g, 1.0 eq.) was dissolved in dichloromethane (5.0 mL, 20 V). The reaction mixture was cooled to 0° C. and then added HOBT (0.119 g, 1.1 eq.) followed by EDC HCl (0.150 g, 1.1 eq.) and oxazol-5-ylmethanamine HCl (0.143 g, 1.1 eq.). DIPEA (0.101 g, 1.1 eq) was added to this reaction mixture dropwise at the same temperature. The clear reaction mixture was stirred at 0° C. for 1.5 h. The progress of the reaction was followed by TLC analysis on silica gel with 5% methanol in dichloromethane as mobile phase and visualization with UV.

Reaction mixture was quenched in ice-water slurry (20 mL) Organic layer was separated and aqueous layer was extracted with dichloromethane (2×10 mL) to ensure complete extraction. The organic layer was washed with brine solution and dried over anhydrous $Na_2SO_4$ and concentrated by rotary evaporation under reduced pressure (35° C., 20 mm Hg) to afford 0.280 g of crude compound (cis: 30.71%; trans: 28.02%).

The crude reaction mixture was purified by column chromatography using 60/120 mesh silica and Methanol: dichloromethane as mobile phase. The column was packed in dichloromethane and started eluting in MeOH in gradient manner starting with fraction collection (500 mL fractions). The compound started eluting from 0.2-2.0% Methanol in dichloromethane. Fractions containing such TLC profile were collected together to obtain 90 mg of compound cis and trans mixture. (cis: 57.86%; trans: 52.49%).

The mixture was purified by Prep TLC using 5% methanol: dichloromethane as mobile phase. Fractions containing such TLC profile were collected together to obtain 15 mg of compound pure compound. (4.88% Yield).

(Z)-3-(3(3,5-bis(trifluoromethyl)phenyl)-1H-1,2,4-triazol-1-yl)-N-(oxazol-5-ylmethyl)acrylamide $^1$H NMR (400 MHz, DMSO) δ 9.62 (s, 1H), 9.05 (s, 1H), 8.53 (s, 2H), 8.30 (s, 2H), 7.41-7.44 (d, J=10.4 Hz, 1H), 7.07 (s, 1H), 5.95-5.98 (d, J=10.8 Hz, 1H), 4.47-4.48 (d, 2H). LCMS for $C_{17}H_{11}F_6N_5O_2$ [M+H]$^+$: 431.28 found 432.39 at RT 2.822 min purity (95.52%).

Example 12

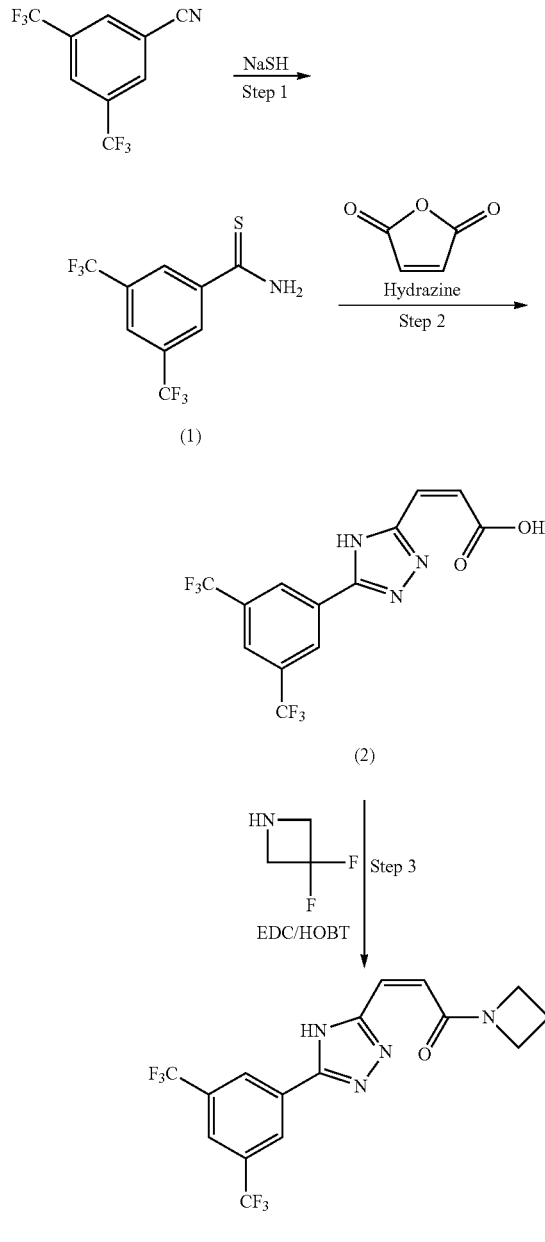

Synthesis of (Z)-3-(5-(3,5-bis(trifluoromethyl)phenyl)-4H-1,2,4-triazol-3-yl)acrylic acid (2)

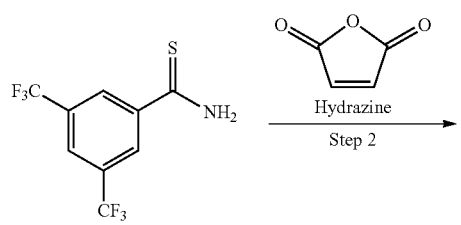

In a 3-neck 100 mL round-bottomed flask, 3,5-bis(trifluoromethyl)benzothioamide (0.564 g, 1 eq.) was dissolved in DMF (5 mL, 10 Vol), then hydrazine hydrate (0.123 g, 1.2 eq.) was added at 0° C. The reaction mixture was stirred at RT till all SM consumed and converted in to polar hydrazine adduct. Preserve sample from this reaction mass for TLC. At last Maleic anhydride (0.242 g mL, 1.2 eq.) was added at 0° C. Then reaction mixture was stirred at RT till all hydrazine adduct consumed and converted in to uncyclised intermediate. Again preserve this uncyclised intermediate sample for TLC. Reaction mixture was heated at 80° C. for 6 h. Reaction completion was monitored on TLC using MeOH: dichloromethane (2:8) as mobile phase and uncyclised intermediate as a SM. The reaction mixture was quenched into the ice-water solution (100 mL) and was extracted with ethyl acetate (3×50 mL). Organic layer was washed with brine solution (3×50 mL). The organic layer was dried using anhydrous sodium sulfate, filtered, and concentrated under reduced pressure to provide the 0.51 g crude compound. This crude compound was dissolved in minimum amount of diethyl ether. This solution was stirred at −5° C. and precipitated compound filtered and washed with chilled diethylether to give 0.150 g (20%) pure (Z)-3-(5-(3,5-bis(trifluoromethyephenyl)-4H-1,2,4-triazol-3-yl)acrylic acid.

Synthesis of (Z)-3-(5-(3,5-bis(trifluoromethyl)phenyl)-4H-1,2,4-triazol-3-yl)-1-(3,3-difluoroazetidin-1-yl)prop-2-en-1-one

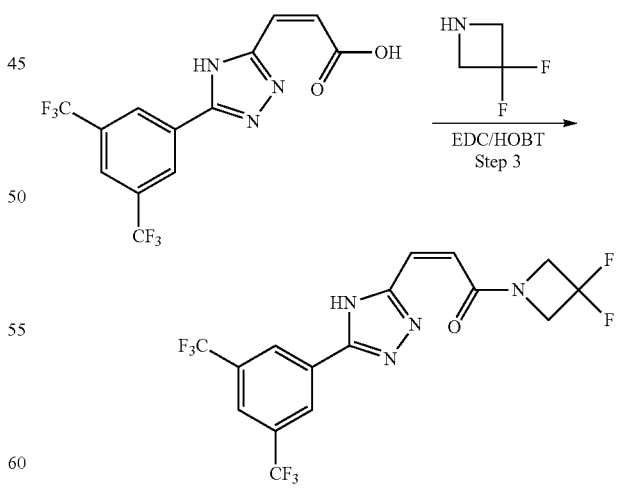

In a 3-neck 50 mL round-bottomed flask, (Z)-3-(5-(3,5-bis(trifluoromethyl)phenyl)-4H-1,2,4-triazol-3-yl)acrylic acid (2) (0.065 g, 1 eq.), 3,3-difluoroazetidine HCl (0.028 g, 1.2 eq.) and EDC. HCl (0.042 g, 1.2 eq.) was dissolved in dichloromethane (5 mL). DIPEA (0.028 g, 1.2 eq.) was added at −5° C. followed by HOBt (0.033 g, 1.2 eq.) added at same temperature. Reaction was maintained at this temp for 1 h. Reaction completion was monitored on TLC using MeOH: dichloromethane (0.5:9.5) as mobile phase. The reaction mixture was quenched into the ice-water slurry (50 mL) and was extracted with ethyl acetate (3×20 mL). Organic layer was washed with brine solution (3×25 mL). The organic layer was dried using anhydrous sodium sulfate, filtered, and concentrated under reduced pressure to provide the 0.80 g crude compound which was purified by column chromatography using ethylacetate and hexane as mobile phase. Product was eluted in 35% ethylacetate in hexane to afford 0.055 g (78%) title compound.

(Z)-3-(5-(3,5-bis(trifluoromethyl)phenyl)-4H-1,2,4-triazol-3-yl)-1-(3,3-difluoroazetidin-1-yl)prop-2-en-1-one $^1$H NMR (400 MHz, DMSO) δ 14.826 (s, 1H, D$_2$O exchangeable), 8.557 (s, 2H), 8.259 (s, 1H), 6.847-6.877 (d, J=12, 1H), 6.445-6.476 (d, J=12.4 Hz, 1H), 4.611 (m, 2H), 4.480 (m, 2H). LCMS for C$_{16}$H$_{10}$F$_8$N$_4$O [M+H]$^+$ 426.26 found 427.3 at 3.303 min purity (99.83%).

Example 13

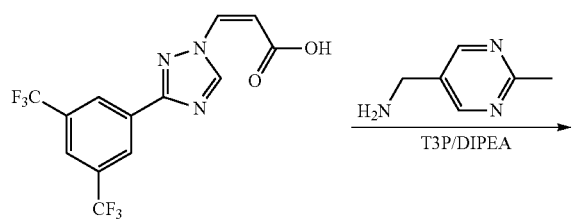

(4)

Synthesis of (Z)-3-(3-(3,5-bis(trifluoromethyl)phenyl)-1H-1,2,4-triazol-1-yl)-N-((2-methylpyrimidin-5-yl)methyl)acrylamide In a 25 mL 3N round-bottomed flask equipped with nitrogen inlet, (Z)-3-(3-(3,5-bis(trifluoromethyl)phenyl)-1H-1,2,4-triazol-1-yl)acrylic acid (4) (0.1 g, 1.0 eq.) was charged along with dichloromethane (5.0 mL, 50 V) and ethyl acetate (5.0 mL, 50 V). The reaction mixture was cooled to 0° C. and then added T3P (50% in ethyl acetate) (0.214 g, 1.2 eq.) followed by DIPEA (0.073 g, 2.0 eq.) and (2-methylpyrimidin-5-yl)methanamine (0.038 g, 1.1 eq.). The clear reaction mixture was stirred at 0° C. for 30 min. The progress of the reaction was followed by TLC analysis on silica gel with 10% Methanol in dichloromethane as mobile phase and visualization with UV. Reaction mixture was quenched in 30 mL ice-water slurry. Organic layer was separated and aqueous layer was extracted with dichloromethane (2×20 mL) to ensure complete extraction. The organic layer was washed with brine solution and dried over anhydrous Na$_2$SO$_4$ and concentrated by rotary evaporation under reduced pressure (35° C., 20 mm Hg) to afford 0.129 g of crude compound. (cis: 81.98%; trans: not detected; unreacted SM: 13.95%).

The crude reaction mixture was purified by column chromatography using 60/120 mesh silica and methanol: dichloromethane as mobile phase. The column was packed in dichloromethane and started eluting in MeOH in gradient manner starting with fraction collection (500 mL fractions). The compound started eluting from 0.2% to 4.0% methanol in dichloromethane. Fractions containing such TLC profile were collected together to obtain 65 mg of pure compound. Yield: 50.38%.

(Z)-3-(3-(3,5-bis(trifluoromethyl)-1H-1,2,4-triazol-1-yl)-N-(2-methylpyrimidin-5-yl)acrylamide $^1$H NMR (400 MHz, DMSO) δ 9.57 (s, 1H), 9.12 (s, 1H), 8.62 (s, 2H), 8.55 (s, 2H), 7.41-7.43 (d, J=10.4 Hz, 1H), 5.98-6.01 (d, J=10.4 Hz, 1H), 4.38-4.39 (d, 2H). LCMS for C$_{19}$H$_{14}$F$_6$N$_6$O [M+H]$^+$: 456.34 found 457.39 at RT 2.725 min purity (99.81%).

Example 14

Synthesis of (Z)-3-(3-(3,5-bis(trifluoromethyl)phenyl)-1H-1,2,4-triazol-1-yl)-N-(pyrimidin-5-ylmethyl)acrylamide

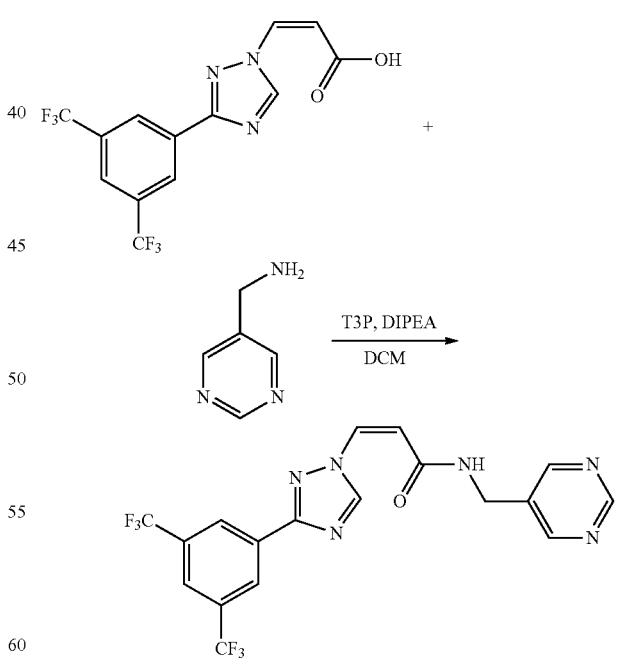

In a 50 mL, 3N round-bottomed flask equipped with nitrogen inlet, (Z)-3-(3-(3,5-bis(trifluoromethyl)phenyl)-1H-1,2,4-triazol-1-yl)acrylic acid (0.2 g, 1.0 eq.) was charged along with dichloromethane (5 mL, 10V). The reaction mixture was cooled to −20° C. and then added pyrimidine-5-ylmethanamine (0.075 g, 1.2 eq), T3P (50% in EtOAc) (0.4 mL, 1.2 eq) followed by DIPEA (0.2 ml, 2 eq) dropwise into the reaction mixture. The reaction mixture was stirred at −20° C. for another 30 min. The progress of the reaction was followed by TLC analysis on silica gel with 5% Methanol in dichloromethane as mobile phase and visualization with UV. Reaction mixture was concentrated by rotary evaporation (25° C., 20 mm Hg) to afford crude compound. The crude reaction mixture was purified by column chromatography using 60/120 mesh silica and methanol: dichloromethane as mobile phase. The column was packed in dichloromethane and started eluting in MeOH in gradient manner starting with fraction collections (500 mL fractions). The compound started eluting from 4% methanol in dichloromethane. Fractions containing such TLC profile were collected together to obtain pure compound 0.2 g. Yield: 80%.

(Z)-3-(3-(3,5-bis(trifluoromethyl)phenyl)-1H-1,2,4-triazole-1-yl)-N-(pyrimidine-5-yl)methyl)acrylamide $^1$H NMR (400 MHz, DMSO) δ=9.58 (s, 1H), 9.07 (s, 2H), 8.76 (s, 2H), 8.50 (s, 2H), 8.28 (s, 1H), 7.44-7.41 (d, J=10.4 Hz, 1H), 6.02-5.99 (d, J=10.4 Hz, 1H), 4.45-4.43 (d, J=5.6 Hz, 2H). LCMS (%): 100%.

Example 15

Synthesis of 6-bromopicolinaldehyde (1a)

A three necked 100 mL round-bottomed flask with magnetic stirring, an immersion thermometer, and an addition funnel was charged with THF (30 mL) and cooled to −78° C. n-butyllithium (1.35 g, 21.10 mmol) was carefully added to the reaction maintaining an internal temperature of −70° C. After the addition of 2,6-dibromopyridine (5.0 g, 21.10 mmol), the resulting dark green solution was stirred for 15 min, then neat DMF (2.31 g, 31.66 mmol) was added over a period of 30 seconds. The reaction mass was stirred for 15 min at −70° C. The progress of the reaction was monitored by TLC analysis on silica gel with ethyl acetate:hexane (3:7) as mobile phase. Reaction mixture was poured into saturated NH$_4$Cl (50 mL) and extracted with EtOAc (3×50 mL). The combined organic layers were washed with brine solution (3×50 mL), dried over MgSO$_4$, filtered, and concentrated by rotary evaporation to afford 5.0 g of crude compound which

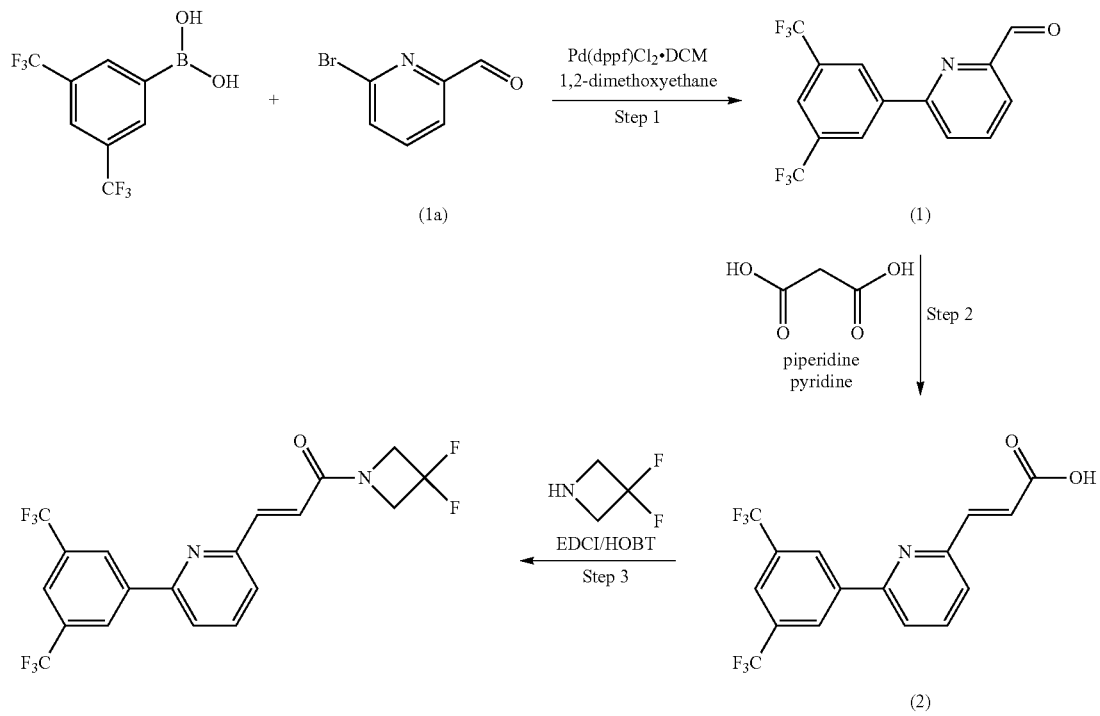

was purified by chromatography. Product elute at 3% ethyl acetate in hexane to give 1.5 g of pure product (Yield 38.4%).

Synthesis of 6-(3,5-bis(trifluoromethyl)phenyl)picolinaldehyde

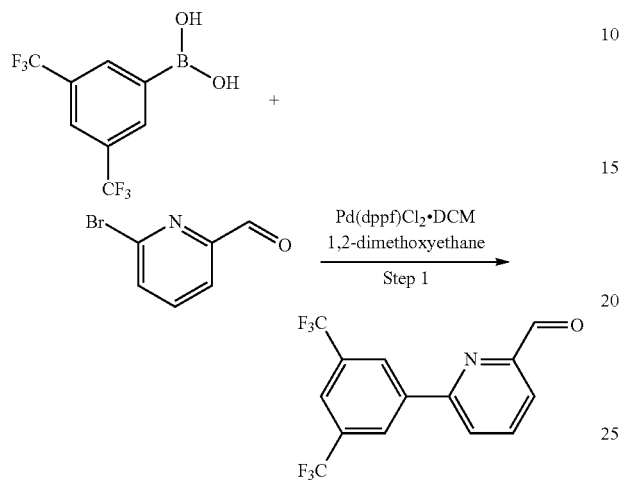

In a 35 mL, microwave vial, 3,5-bis(trifluoromethyl) phenylboronic acid (2.0 g, 7.7 mmol) and 6-bromopicolinaldehyde (1a) (1.44 g, 7.7 mmol) dissolved in 1,2-dimethoxyethane (20 mL) was treated with a solution of $K_2CO_3$ (3.22 g, 23.3 mmol) in water at room temperature. Pd(dppf)Cl$_2$.dichloromethane was added to reaction mass and charged in microwave for 30 min at 90° C. The progress of the reaction was monitored by TLC analysis on silica gel with ethyl acetate:hexane (3:7) as mobile phase. Reaction mixture was poured into water (50 mL) and extracted with EtOAc (3×20 mL). The combined organic layers were washed with brine solution (3×50 mL), dried over MgSO$_4$, filtered, and concentrated by rotary evaporation to afford 2.5 g of Crude compound which was purified by chromatography. Product elute at 4% ethyl acetate in hexane to give 1.2 g of pure product. (Yield 48.38%).

Synthesis of (E)-3-(6-(3,5-bis(trifluoromethyl)phenyl)pyridin-2-yl)acrylic acid

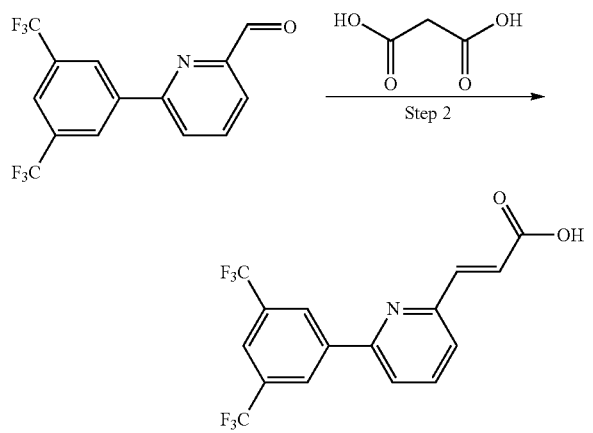

In a 35 mL, microwave vial, 6-(3,5-bis(trifluoromethyl) phenyl)picolinaldehyde (1) (0.3 g, 0.93 mmol) and malonic acid (0.097 g, 0.93 mmol) was dissolved in ethanol. Piperidine (2-3 drops) was added in reaction in microwave for 20 min at 90° C. The progress of the reaction was followed by TLC analysis on silica gel with 10% MeOH-dichloromethane as mobile phase. Reaction mixture was poured into water (15 mL) and extracted with EtOAc (3×20 mL). The combined organic layers were washed with brine solution (3×50 mL), dried over MgSO$_4$, filtered, and concentrated by rotary evaporation to afford 0.4 g of crude compound which was used for next step without further purification.

Synthesis of (E)-3-(6-(3,5-bis(trifluoromethyl)phenyl)pyridin-2-yl)-1-(3,3-difluoroazetidin-1-yl)prop-2-en-1-one

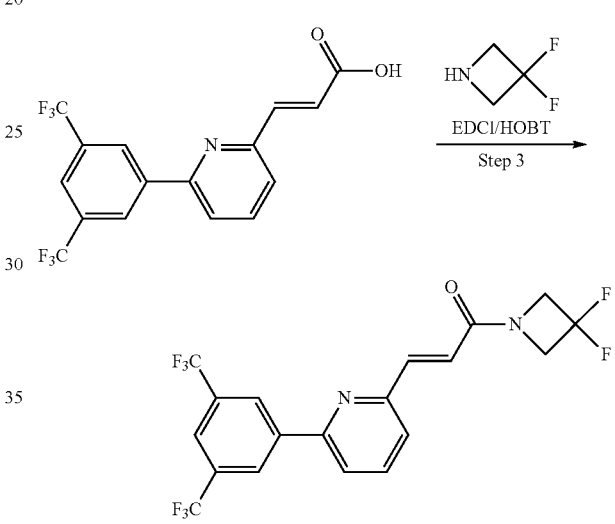

In a 50-mL round-bottomed flask Intermediate 2 (0.4 g, 1.1 mmol) and 3,3-difluoroazetidine hydrochloride (0.17 g, 1.3 mmol) was dissolved in dichloromethane (20 mL). Propylphosphonic anhydride (0.42 g, 1.3 mmol), DIPEA (0.28 g, 2.2 mmol) was added at room temperature and stirred reaction mixture for 30 min. The progress of the reaction was followed by TLC analysis on silica gel with 0.5% Methanol:dichloromethane as mobile phase and visualization with U.V light, reaction mixture was quenched into ice water slurry, filter it, compound was extracted in dichloromethane, dried over Na$_2$SO$_4$, filtered, and concentrated by rotary evaporation (28° C., 20 mmHg) to afford 0.5 g of a solid crude, The purification done by Flash chromatography and product elute at neat dichloromethane to afford pure compound 0.030 g yield (6.2%).

(E)-3-(6-(3,5-bis(trifluoromethyl)phenyl)pyridin-2-yl)-1-(3,3-difluoroazetidin-1-yl)prop-2-en-1-one $^1$H NMR (400 MHz, CDCl$_3$) δ 8.55 (S, 2H), 7.97 (s, 1H), 7.89-7.93 (t, 1H), 7.81-7.83 (d, 2H), 7.75-7.79 (d, J=15.2, 1H), 7.45-7.47 (d, 1H), 7.18-7.22 (d, J=15.2, 1H), 4.68-4.70 (t, 2H), 4.50-4.53 (t, 2H) LCMS for C$_{19}$H$_{12}$F$_8$N$_2$O [M+H]$^+$ 436.3 found 437.39 at RT 3.34 min purity (93.47%).

Example 16

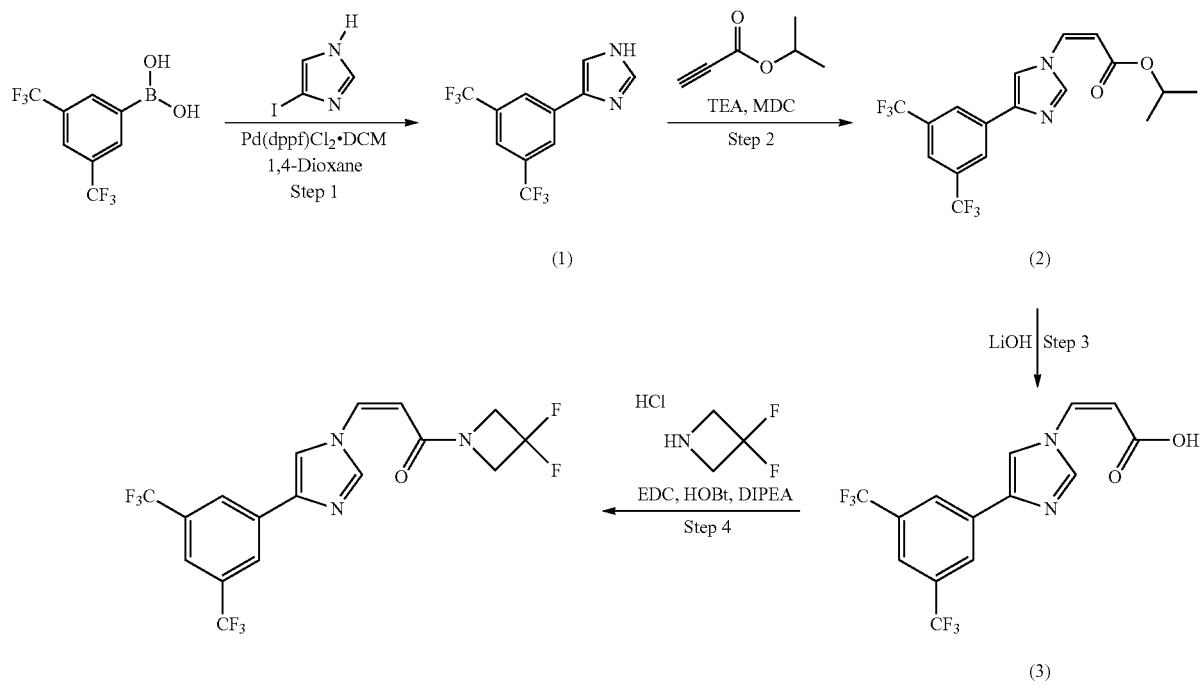

Synthesis of 4-(3,5-bis(trifluoromethyl)phenyl)-1H-imidazole (1)

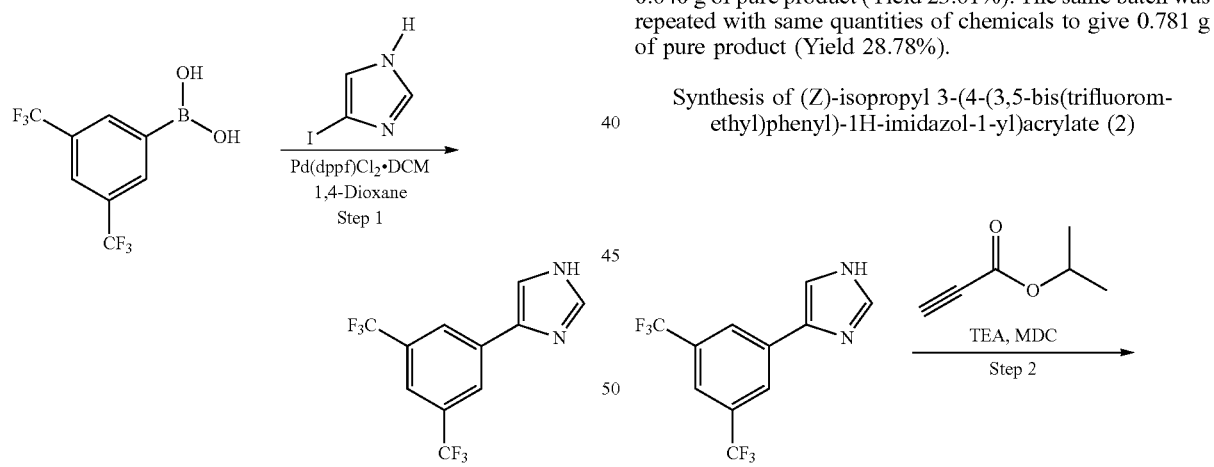

In a 35 mL, microwave vial, 3,5-bis(trifluoromethyl) phenylboronic acid (2.5 g, 9.69 mmol) and 4-Iodo-1H-imidazole (2.068 g, 10.66 mmol) was dissolved in 1,4-dioxane (18 mL). To this reaction mixture aq. solution of NaHCO₃ (1.628 g, 19.38 mmol) was added at room temperature. The reaction mixture was degassed for 30 min and Pd(dppf)Cl₂.dichloromethane (0.791 g 0.1 eq.) was charged in microwave for 16 h at 90° C. The progress of the reaction was monitored by TLC using methanol: dichloromethane (0.5:9.5) as mobile phase. Reaction mixture was poured into water (50 mL) and filtered through celite bed. The filtrate was extracted with EtOAc (3×20 mL). The combined organic layers was washed with brine solution (3×50 mL), dried over MgSO₄, filtered, and concentrated under reduced pressure using rotary evaporator to afford 2.5 g of crude compound which was purified by column chromatography. Compound was eluted at 40% ethylacetate in hexane to give 0.640 g of pure product (Yield 23.61%). The same batch was repeated with same quantities of chemicals to give 0.781 g of pure product (Yield 28.78%).

Synthesis of (Z)-isopropyl 3-(4-(3,5-bis(trifluoromethyl)phenyl)-1H-imidazol-1-yl)acrylate (2)

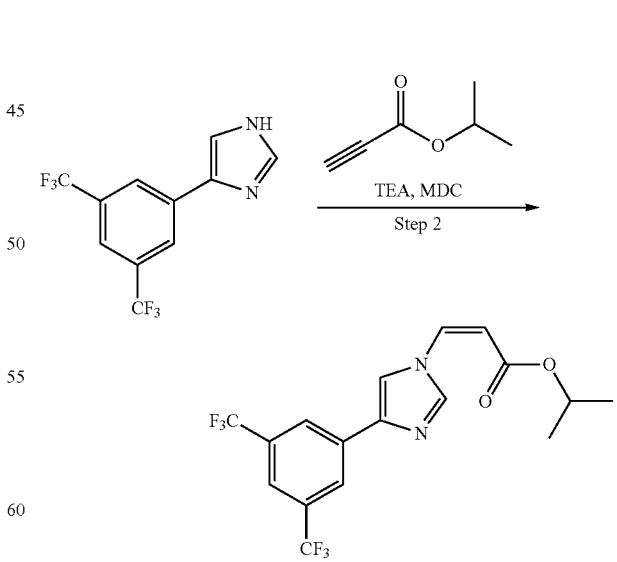

In a 100 mL, 3N round-bottomed flask equipped with nitrogen inlet, thermometer pocket and stopper, 4-(3,5-bis(trifluoromethyl)phenyl)-1H-imidazole (1) (1.1 g, 1.0 eq.) was dissolved in dichloromethane (20 mL, 19V) the reaction mixture was cooled to 0° C. To this reaction mixture TEA (0.709 mL, 1.3 eq.) followed by Isopropyl acrylate (0.571 g, 1.3 eq.) was added at 0° C. and reaction mixture was stirred for 30 min. The progress of the reaction was followed by TLC analysis on silica gel with 20% Ethyl acetate-n-Hexane as mobile phase. Reaction mixture was poured into water (50 mL). The filtrate was extracted with EtOAc (3×20 mL). The combined organic layers were washed with brine solution (3×50 mL), dried over MgSO$_4$, filtered, and concentrated by rotary evaporation to afford 1.2 g of Crude compound which was purified by column chromatography. Product elute at 4% ethyl acetate in hexane to give 1.0 g of crude product (Cis 39%+Trans 56%) (Yield 65.35%).

Synthesis of (Z)-3-(4-(3,5-bis(trifluoromethyl)phenyl)-1H-imidazol-1-yl)acrylic acid (3)

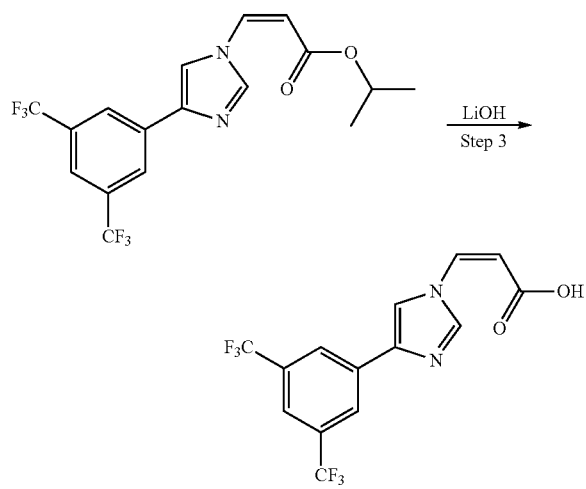

In a 50 mL, 3N round-bottomed flask equipped with nitrogen inlet, thermometer pocket and stopper, (Z)-isopropyl 3-(4-(3,5-bis(trifluoromethyl)phenyl)-1H-imidazol-1-yl)acrylate (2) (1.0 g, 1.0 eq.) was dissolved in THF: H$_2$O (20 mL, 1:1, 20V). To this reaction mixture LiOH.H2O (0.535 g, 5.0 eq.) was added at 0° C. This reaction mixture was stirred for 3-4 h and progress of the reaction was followed by TLC using 20% ethyl acetate/n-hexane as mobile phase. Reaction mixture was acidified using dilute HCl. The reaction mixture was extracted with EtOAc (3×20 mL). The combined organic layers was washed with brine solution (3×50 mL), dried over MgSO$_4$, filtered, and concentrated under reduced pressure by rotary evaporation to afford 0.4 g of crude compound which was used for next step without purification.

Synthesis of (Z)-3-(4-(3,5-bis(trifluoromethyl)phenyl)-1H-imidazol-1-yl)-1-(3,3-difluoroazetidin-1-yl)prop-2-en-1-one

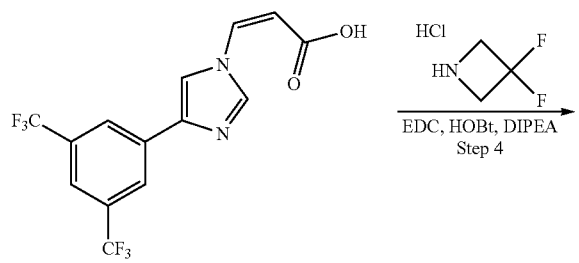

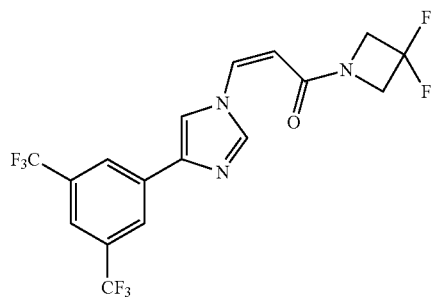

In a 50 mL, 3N round-bottomed flask equipped with nitrogen inlet, thermometer pocket, stopper, (Z)-3-(4-(3,5-bis(trifluoromethyl)phenyl)-1H-imidazol-1-yl)acrylic acid (3) (0.4 g, 1.0 eq.) was dissolved in dichloromethane (8 mL, 20V) and reaction mixture was cooled to 0° C. To this reaction mixture HOBT (0.209 g, 1.2 eq.), Difluoroazitidine HCl (0.177 g, 1.2 eq.) and EDC.HCl (0.328 g, 1.5 eq.) was added at 0° C. To this reaction mixture DIPEA (0.177 g, 1.2 eq.) was added dropwise at 0° C. The progress of the reaction was followed by TLC using 5% Methanol-dichloromethane as mobile phase. Reaction mixture was poured into water (50 mL) and compound was extracted with EtOAc (3×20 mL). The combined organic layer was washed with brine solution (3×50 mL), dried over MgSO$_4$, filtered, and concentrated by rotary evaporation to afford 0.420 g of Crude compound was purified by column chromatography. Compound was eluted at 0.5-0.6% methanol in dichloromethane to give 0.05 g of pure product (Yield 10.41%).

(Z)-3-(4-(3,5-bis(trifluoromethyl)phenyl)-1H-imidazol-1-yl)-1-(3,3-difluoroazetidin-1-yl)prop-2-en-1-one $^1$H NMR (400 MHz, CDCl$_3$) δ 8.57 (s, 1H), 8.27 (s, 2H), 8.06 (s, 1H), 7.78 (s, 1H), 6.94-6.91 (d, J=12, 1H), 5.47-5.45 (d, J=8, 1H), 4.58-4.45 (m, 4H). LCMS for C$_{17}$H$_{11}$F$_8$N$_3$O [M+H]$^+$ found 281.34 at RT 2.54 min purity (99.13%).

Example 17

Synthesis of (Z)-3-(3-(3,5-bis(trifluoromethyl)phenyl)-1H-1,2,4-triazol-1-yl)-N-methyl-N-(pyrimidin-5-ylmethyl)acrylamide

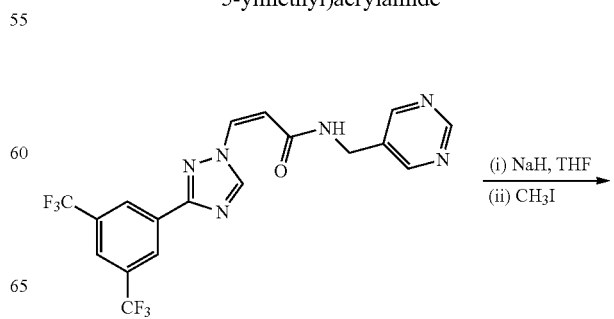

-continued

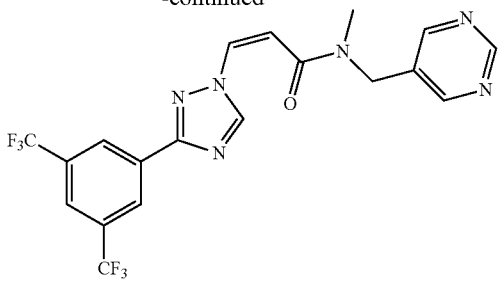

In a 50 mL, 3N round-bottomed flask equipped with nitrogen inlet, (Z)-3-(3-(3,5-bis(trifluoromethyl)phenyl)-1H-1,2,4-triazol-1-yl)-N-(pyrimidin-5-ylmethyl)acrylamide (0.05 g, 1.0 eq.) was charged along with THF (5 mL, 5V). The reaction mixture was cooled to −20° C. and sodium hydride (60% in mineral oil) was added (0.051 g, 1.1 eq.). Reaction mixture was allowed to stir for 1 h. Methyl Iodide (0.018 g, 1.1) was added into the reaction mixture and stirred at −20° C. for 1 h. The progress of the reaction was followed by TLC analysis on silica gel with 5% Methanol in dichloromethane as mobile phase and visualization with UV. Reaction mixture was quenched in water (50 mL) and extracted with EtOAc (50×2). The organic layer was washed with brine solution, dried over $Na_2SO_4$ and concentrated by rotary evaporation (25° C., 20 mm Hg) to afford 0.060 g of Crude compound. The crude reaction mixture was purified by column chromatography using 60/120 mesh silica and Methanol: dichloromethane as mobile phase. The column was packed in dichloromethane and started eluting in MeOH in gradient manner starting with fraction collection (500 mL fractions). The compound started eluting from 4% Methanol in dichloromethane. Fractions containing such TLC profile were collected together to obtain pure compound 0.015 g Yield (30%).

(Z)-3-(3-(3,5-bis(trifluoromethyl)phenyl)-1H-1,2,4-triazole-1-yl)-N-methyl-N-(pyrimidine-5-ylmethyl)acrylamide $^1$H NMR (400 MHz, DMSO) δ=9.04-8.99 (d, J=21.6 Hz, 2H), 8.77-8.71 (d, J=24 Hz, 2H), 8.46 (s, 1H), 8.39 (s, 1H), 8.29 (s, 1H), 7.42-7.38 (m, 1H), 6.37-6.35, 6.31-6.28 (d, J=10 Hz, J=10.4 Hz, 1H), 4.68-4.61 (d, J=28 Hz, 2H), 2.99-2.96 (d, J=14 Hz, 3H). LCMS for $C_{19}H_{14}F_6N_6O$ [M+H]$^+$ 456.3 found 457.44 at RT 2.59 min purity (94.12%). Compound was observed as rotamers as confirmed by NMR.

Example 18

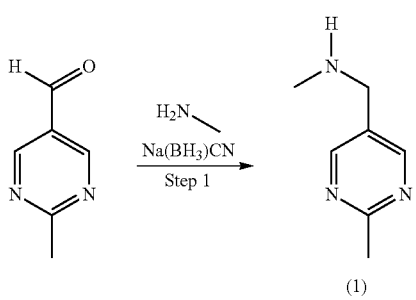

-continued

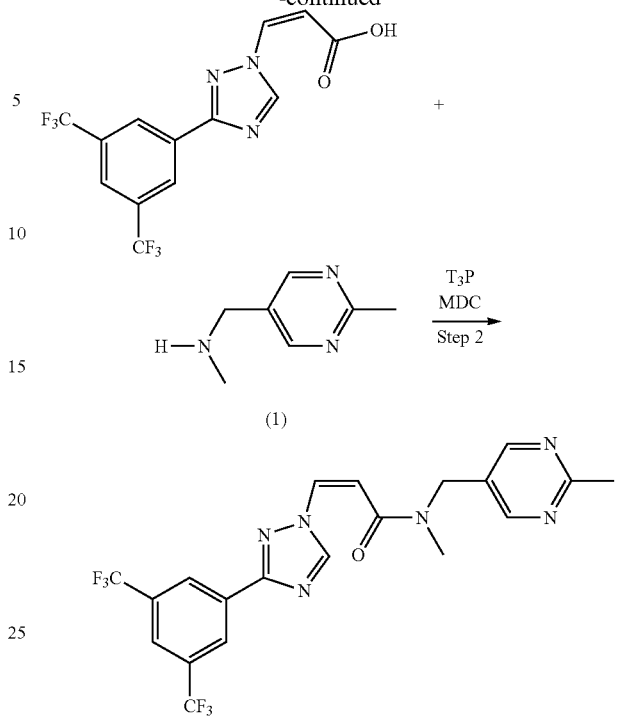

Synthesis of N-methyl-1-(2-methylpyrimidin-5-yl)methanamine (1)

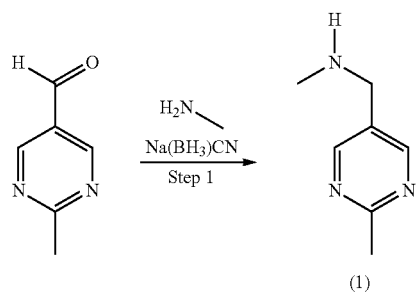

In a three necked 100 mL round-bottomed flask equipped with magnetic stirring, an immersion thermometer, and nitrogen bubbler was charged 5-pyrimidine carboxaldehyde-2-methyl (1 g, 0.0082 mol.) in methanol (10 mL) and cooled to 0° C. Methyl amine (20.5 mL, 0.0409 mol.) and acetic acid (2.4 mL, 0.0409 mol.) was added to the reaction maintaining an 0° C. The resulting dark yellow solution was stirred for 2 h. Sodium cyanoborohydride (2.05 g, 0.0328 mol.) was added over a period of 10 min. The reaction mass was stirred for 2-3 h at RT. The progress of the reaction was monitored by TLC analysis on silica gel with methanol: dichloromethane (0.5:9.5) with TEA (1%) as mobile phase. Which shows that starting material was consumed after 3 hr. stirring at RT. Solvent was remove under reduce pressure, residue quenched by water and extracted with EtOAc (3×50 mL). The combined organic layers were washed with brine solution (3×15 mL), dried over Sodium sulfate, filtered, and concentrated by rotary evaporation to afford 0.5 g of crude compound. The crude material was subjected to column purification using Silica 60/120 as a stationary phase and dichloromethane: methanol as mobile phase. The column was packed in dichloromethane and started eluting in methanol in gradient manner starting with fraction collection from 0.5.0% to 3.0% methanol in dichloromethane with 1% TEA. Compound started eluting with 2.5% methanol in dichloromethane with 1% TEA. Fraction containing such TLC profile was collected together to obtain compound 200 mg of pure product. (Yield 17.78%).

Synthesis of (Z)-3-(3-(3,5-bis(trifluoromethyl)phenyl)-1H-1,2,4-triazol-1-yl)-N-methyl-N-((2-methylpyrimidin-5-yl)methyl)acrylamide

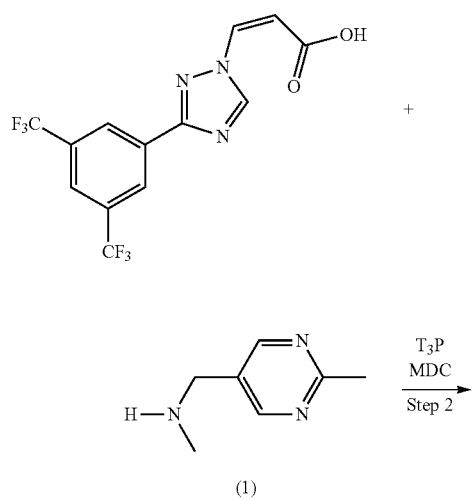

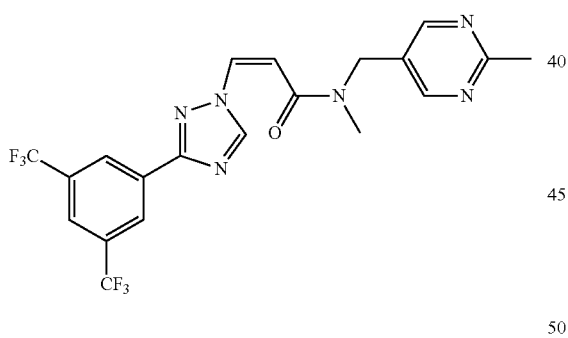

In a 25 mL, 3N round-bottomed flask equipped with nitrogen inlet, N-methyl-1-(2-methylpyrimidin-5-yl)methanamine (1) (0.1 g, 1.0 eq.) and (Z)-3-(3-(3,5-bis(trifluoromethyl)phenyl)-1H-1,2,4-triazol-1-yl)acrylic acid (0.178 g, 0.7 eq.) was charged along with dichloromethane (2 mL, 10 V). The reaction mixture was cooled to −20° C. and then added T3P (50% in EtOAc) (0.550 mL, 1.2 eq.) followed by DIPEA (0.250 mL, 2 eq.) was added to reaction mixture. The clear reaction mixture was stirred at −20° C. for 30 min. The progress of the reaction was followed by TLC analysis on silica gel with 5% Methanol in dichloromethane as mobile phase and visualization with UV, which shows that starting material was consumed after 30 min stirring at −30° C. Reaction mixture was diluted by dichloromethane wash with water (2×10 mL), organic layer dried over sodium sulfate and concentrated by rotary evaporation (25° C., 20 mm Hg) to afford crude compound (0.2 g). The crude reaction mixture was purified by column chromatography using 60/120 mesh silica and methanol: dichloromethane as mobile phase. The column was packed in dichloromethane and started eluting in MeOH in gradient manner starting with fraction collection (500 mL fractions). The compound started eluting from 2% methanol in dichloromethane. Fractions containing such TLC profile were collected together to obtain pure compound 0.01 g Yield (4.19%).

(Z)-3-(3-(3,5-bis(trifluoromethyl)phenyl)-1H-1,2,4-triazol-1-yl)-N-methyl-N-((2-methylpyrimidin-5-yl)methyl)acrylamide $^1$H NMR (400 MHz, CDCl$_3$) δ 9.02 (s, 1H), 8.65 (s, 2H), 8.52-8.59 (m, 3H), 7.15-7.17 (d, J=10.8 Hz, 1H), 6.02-6.04 (d, J=10.4 Hz, 1H), 4.69 (s, 2H), 3.07 (s, 3H), 2.75 (s, 3H). LCMS for C$_{20}$H$_{16}$F$_6$N$_6$O [M+H]$^+$ 470.4 found 471.20 at RT 4.215 min purity (91.16%).

Example 19

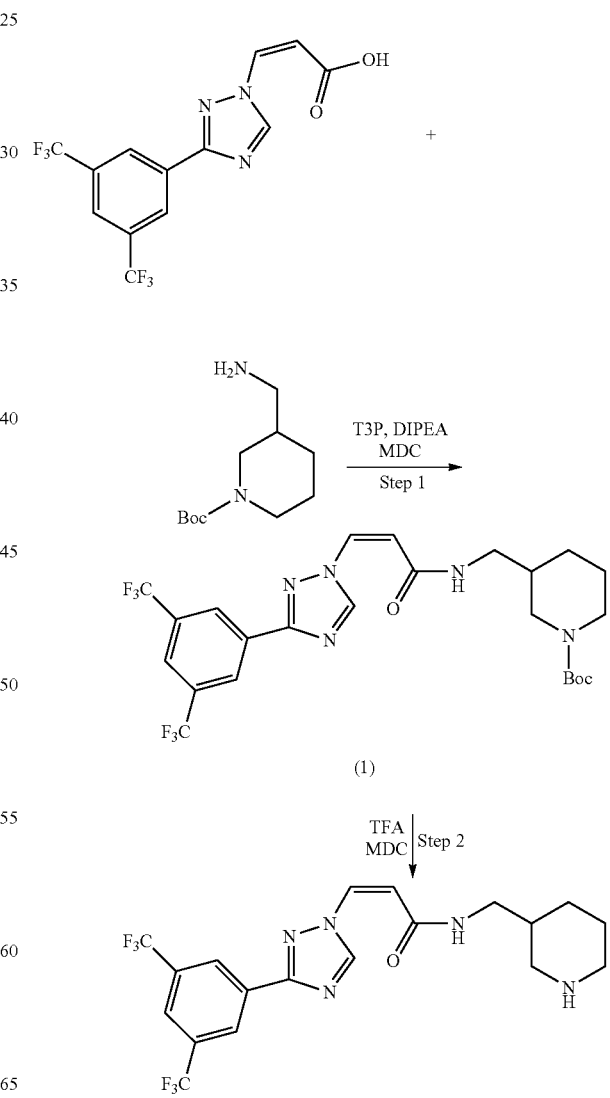

Synthesis of (Z)-tert-butyl 3-(3-(3-(3,5-bis(trifluoromethyl)phenyl)-1H-1,2,4-triazol-1-yl)acrylamido)methyl)piperidine-1-carboxylate (1)

Synthesis of (Z)-3-(3-(3,5-bis(trifluoromethyl)phenyl)-1H-1,2,4-triazol-1-yl)-N-(piperidin-3-ylmethyl)acrylamide

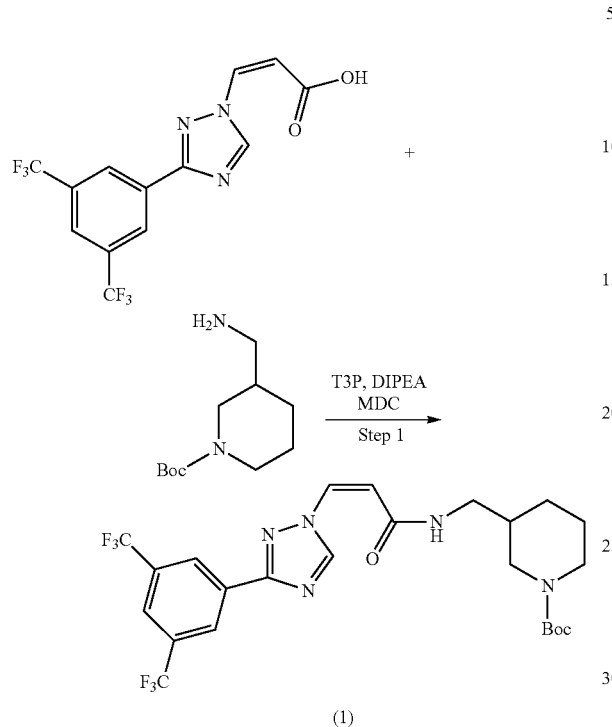

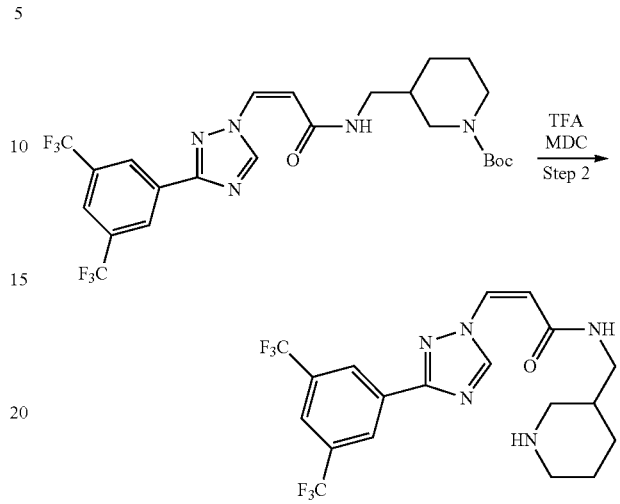

In a 50 mL, 3N round-bottomed flask (Z)-3-(3-(3,5-bis(trifluoromethyl)phenyl)-1H-1,2,4-triazol-1-yl)acrylic acid (0.2 g, 1.0 eq.) and tert-butyl-3-(aminomethyl)piperidine-1-carboxylate (0.134 g) was dissolved in dichloromethane (5.0 mL) and T3P (50%)(0.453 g) was added. DIPEA (0.147 g) was added under nitrogen atmosphere. The progress of the reaction was followed by TLC analysis on TLC with 5% methanol: dichloromethane as mobile phase and visualization with U.V light. Reaction mixture was concentrated by rotary evaporation (40° C., 20 mmHg) to afford 0.35 g of a white solid. The resulting crude compound was purified by column chromatography using silica 60/120 and methanol:dichloromethane as mobile phase. The column was packed in dichloromethane and started eluting in methanol in gradient manner starting with fraction collection from 2-4% methanol in dichloromethane. Compound started eluting with 3% methanol in dichloromethane. Fraction containing such TLC profile was collected together to obtain compound (230 mg) yield 80%.

(Z)-tert-butyl-3-(3-(3-(3,5-bis(trifluoromethyl)phenyl)-1H-1,2,4-triazol-1-yl)acrylamido)methyl)piperidine-1-carboxylate $^1$H NMR (400 MHz, DMSO) δ: 9.61 (s, 1H), 8.52-8.57 (q, 3H), 8.28 (s, 1H), 7.37-7.39 (d, J=10.4 Hz, 1H), 5.95-5.97 (d, J=10.4 Hz, 1H), 3.74-3.87 (br. s, 2H), 3.06 (s, 2H), 2.67-2.77 (m, 1H), 1.46 (brs, 2H), 1.31 (s, 9H). LCMS for C$_{24}$H$_{27}$F$_6$N$_5$O$_3$ [M+H]$^+$547.49 found 548.6 at RT 3.51 min purity (96.47%).

In a 25 mL single neck round-bottomed flask (Z)-tert-butyl 3-((3-(3-(3,5-bis(trifluoromethyl)phenyl)-1H-1,2,4-triazol-1-yl)acrylamido)methyl)piperidine-1-carboxylate (1) (0.1 g) was dissolved in dichloromethane (5 mL) and TFA (1.0 mL) dissolved in dichloromethane added dropwise. The progress of the reaction was followed by TLC on silica gel in 10% methanol in dichloromethane as a mobile phase in UV visualization. Reaction mixture was concentrated by rotary evaporation (40° C., 20 mmHg) to afford 0.12 g of compound. The resulting crude compound was purified by 'SAEx' column chromatography. Fraction collected together to obtain compound (40 mg) yield 49%.

(Z)-3-(3-(3,5-bis(trifluoromethyl)phenyl)-1H-1,2,4-triazol-1-yl)-N-(piperidin-3-ylmethyl)acrylamide $^1$H NMR (400 MHz, DMSO) δ: 9.69 (s, 1H), 8.61 (s, 2H), 7.94 (s, 1H), 7.13-7.16 (d, J=10.8 Hz, 1H), 6.55 (s 1H), 5.66-5.68 (d, J=10.8 Hz, 1H), 3.23-3.37 (m, 2H), 2.98-3.10 (m, 2H), 2.58-2.65 (t, 1H), 2.40-2.45 (t, 1H), 1.68-1.80 (m, 2H), 1.43-1.54 (m, 1H), 1.15-1.29 (m, 1H). LCMS for C$_{19}$H$_{19}$F$_6$N$_5$O [M+H]$^+$ 447.38 found 448.44 at RT 3.13 min purity (99.12%).

Example 20

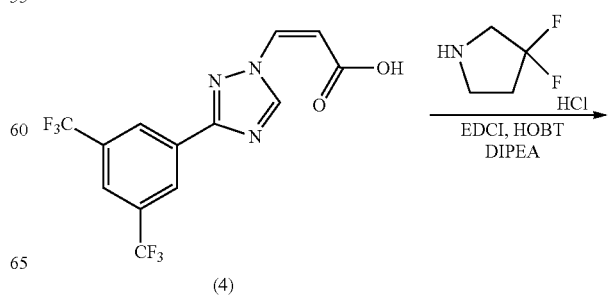

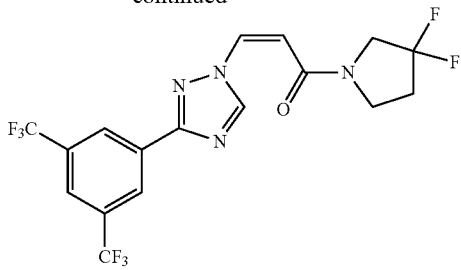

Synthesis of (Z)-3-(3-(3,5-bis(trifluoromethyl)phenyl)-1H-1,2,4-triazol-1-yl)-1-(3,3-difluoropyrrolidin-1-yl)prop-2-en-1-one In a 100 mL, 3N round-bottomed flask equipped with nitrogen inlet, (Z)-3-(3-(3,5-bis(trifluoromethyl)phenyl)-1H-1,2,4-triazol-1-yl)acrylic acid (4) (1 g, 1.0 eq.) was charged in dichloromethane (20 mL, 20 V). The reaction mixture was cooled to 0° C. HOBT (0.461 g, 1.2 eq.), EDC.HCl (0.819 g, 1.5 eq.), 3,3-Difluoropyrrolidine hydrochloride (0.490 g, 1.2) and DIPEA (0.731 mL, 1.5 eq.) was added to the reaction mixture. The clear reaction mixture was stirred at 0° C. for 1.5 h. The progress of the reaction was followed by TLC using 5% methanol in dichloromethane as mobile phase and visualization with UV. Reaction mixture was quenched in water (50 mL). Organic layer was separated and aqueous layer was extracted with dichloromethane (20×2). The combined organic layer was washed with brine solution, dried over $Na_2SO_4$ and concentrated by rotary evaporation (25° C., 20 mm Hg) to afford 0.67 g of crude compound. The crude compound was purified by column chromatography using 60/120 mesh silica and methanol: dichloromethane as mobile phase. The column was packed in dichloromethane and started eluting in MeOH in gradient manner starting with fraction collection (25 mL fractions). The compound started eluting from 0.9% to 1.0% methanol in dichloromethane. Fractions containing such TLC profile were collected together to obtain pure compound 0.115 g Yield (9.2%).

(Z)-3-(3-(3,5-bis(trifluoromethyl)phenyl)-4H-1,2,4-triazol-1-yl)-1-(3,3-difluoropyrrolidin-1-yl)prop-2-en-1-one $^1$H NMR (400 MHz, $CDCl_3$) δ 9.25-9.30 (d, 1H), 8.59 (s, 2H), 7.94 (s, 1H), 7.17-7.28 (m, J=10.8 Hz, 1H), 5.82-5.91 (m, J=10.8 Hz, 1H), 3.78-4.00 (m, 4H), 2.41-2.54 (m, 2H); LCMS for $C_{17}H_{12}F_8N_4O$ [M+H]$^+$ 440.29 found 441.39 at RT 2.982 min purity (99.75%).

Example 21

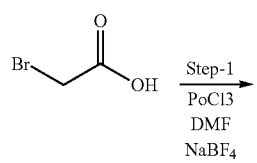

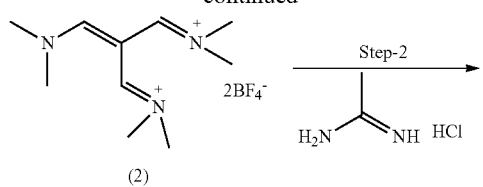

Synthesis of Intermediate-2

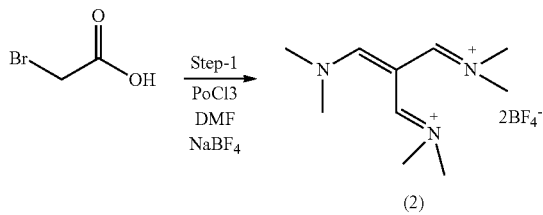

In a 250-mL, 3N round-bottomed flask equipped with thermometer pocket fitted with nitrogen inlet and a rubber septum, DMF (40 mL, 14.67 eq.) was cool to −10° C. and POCl$_3$ (10.58 mL, 3.21 eq.) was added. The reaction mixture was stirred at 0° C. for 3 h. To this reaction mixture bromo acetic acid (5 g, 1 eq.) was added at 0° C. Resulting reaction mixture was stirred for 6 h at 85-90° C. After completion of 6 h stirring, DMF was removed by high vacuum distillation. Dark red residue was observed, residue was cool down to room temperature and sodium tetrafluoro borate was added in to the residue and exotherm was observed. Reaction mass was cooled using ice bath. The solid residue (6.5 g) was observed which was filtered and used for next step directly.

Synthesis of Intermediate-3

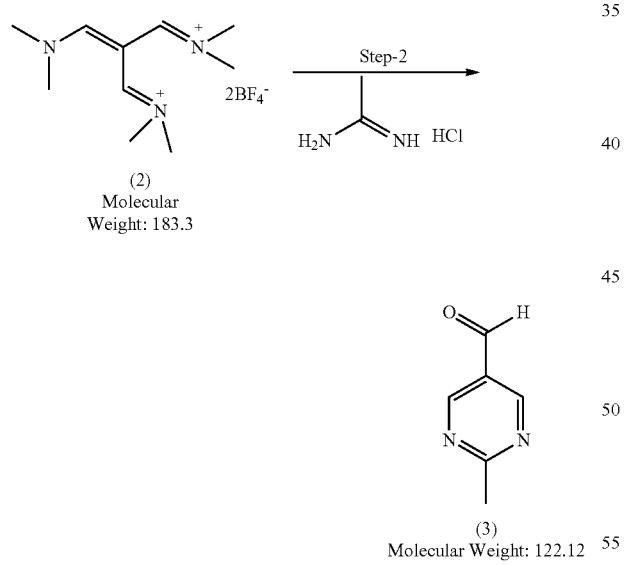

In a 100-mL, 3N round-bottomed flask equipped with thermometer pocket fitted with water condenser, nitrogen inlet and a rubber septum, vinamidium salt (5.65 g, 0.5 eq.) and acetamidine HCl (3 g, 1 eq) was dissolved in ethanol (30 mL) and sodium ethoxide was added, resulting reaction mixture was stirred at reflux for 2-3 h, The progress of the reaction was followed by TLC analysis on silica gel with 70% ethyl acetate-Hexane as mobile phase which shows that starting material was consumed after 3 h. Solvent was removed under reduce pressure to give crude mass which was dissolved in water, and compound was extracted by ethyl acetate. Combined organic layer were dried over sodium sulfate and distilled under reduce pressure to obtain crude material. The crude material was subjected to column purification using Silica 60/120 as a stationary phase and hexane:ethyl acetate as mobile phase. The column was packed in hexane and started eluting in Ethylacetate in gradient manner starting with fraction collection from 20-24% ethyl acetate in hexane. Compound started eluting with 22% ethyl acetate in hexane. Fraction containing such TLC profile was collected together to obtain compound 700 mg.

Synthesis of Intermediate-4

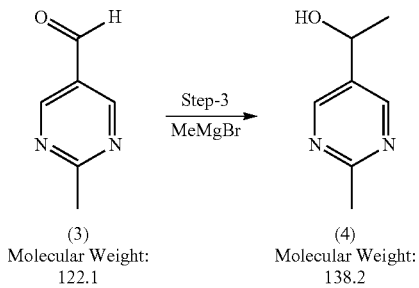

In a 50 mL, 3N round-bottomed flask equipped with thermometer pocket fitted with nitrogen inlet and a rubber septum, Intermediate-3 (1.0 g, 1.0 eq.) was added methyl magnesium bromide (2.47 mL, 1.0 eq.) at −30° C. Resulting reaction mixture was stirred at −30° C. The progress of the reaction was followed by TLC analysis on silica gel with 70% EtOAc-hexane as mobile phase which shows that little starting material was observed after 30 min stirring, reaction was stirred again for 1 h at 0° C. temperature. Reaction was quenched by cold water, extracted by ethyl acetate, dried over sodium sulfate and distilled under reduce pressure to obtain crude material. The crude material was subjected to column purification by using silica (60-120 mesh size) as stationary phase and Ethyl acetate:Hexane as mobile phase. Required compound eluted at 25% ethyl acetate:hexane. Fraction containing such TLC profile was collected together to obtain compound 1.5 g yield (82.41%); LCMS (%): Retention Time: 4.532 min. (84.82%) (M+H)$^+$ 139.

Synthesis of Intermediate-5

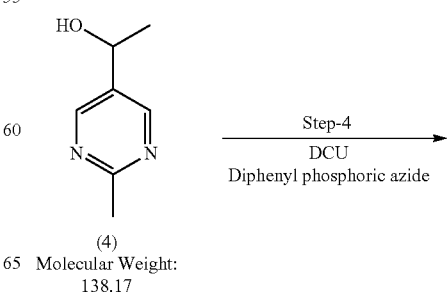

-continued

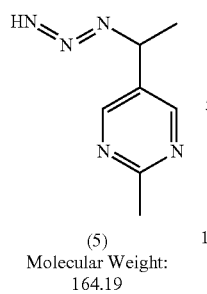

(5)
Molecular Weight:
164.19

In a 25 mL, 3N round-bottomed flask equipped with thermometer pocket fitted with nitrogen inlet and a rubber septum, Intermediate-4 (0.25 g, 1.0 eq.) was dissolved in toluene (5 mL). To this reaction mixture diphenyl phosphoryl azide (0.87 mL, 2.4 eq.) and DBU (0.65 mL, 2.4 eq.) was added at 0° C. temperature. Resulting reaction mixture was stirred at 0° C. for 30 min at RT for 3-4 h. The progress of the reaction was followed by TLC analysis on silica gel with 70% EtOAc-hexane as mobile phase which shows that starting material was consumed after 4 h. Reaction was quenched into ice cold water, extracted by ethyl acetate (50×3 mL). Combined organic layer was dried over sodium sulfate and concentrated under reduce pressure to give crude compound. Crude compound was subjected to column chromatography using ethyl acetate:hexane as mobile phase. Compound was eluted in 30% ethyl acetate in hexane. Fractions containing such TLC profile was collected together to obtain compound 0.14 g yield (29.7%); LCMS (%): Retention Time: 2.454 min (14.35%), (M+H)$^+$ 164.

Synthesis of Intermediate-6

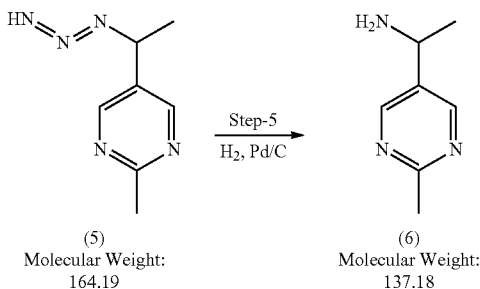

(5)                (6)
Molecular Weight:   Molecular Weight:
164.19              137.18

In a 25 mL, single neck round-bottomed flask equipped with rubber septum, Intermediate-5 (0140 g), palladium carbon (0.07 g) was suspended in methanol (2 mL) and H$_2$ was purged into it. Resulting reaction mixture was stirred at RT. The progress of the reaction was followed by TLC analysis on silica gel with 5% Methanol-dichloromethane and ammonia atmosphere as mobile phase which shows that starting material was consumed after 15 h. Reaction was Filter through Celite Bed, filtrate was concentrated under reduce pressure to give crude (0.19 g). The crude material was subjected to column purification using silica as stationary phase and MeOH: dichloromethane with 1% of TEA as mobile phase. Required compound eluted in 2% MeOH: dichloromethane with 1% TEA as mobile phase. Fraction containing such TLC profile was collected together to obtain compound 0.09 g yield (76.9%). $^1$H NMR (400 MHz, DMSO): δ=8.73 (s, 2H), 5.72 (Broad singlet, 2H D2O exchangeable), 4.187-4.23 (quartet, 2H), 2.6 (s, 3H), 1.38-1.4 (d, 3H); LCMS (%): LC-MS Retention time: 5.457 min (1.2%) (M+H)$^+$ 138.

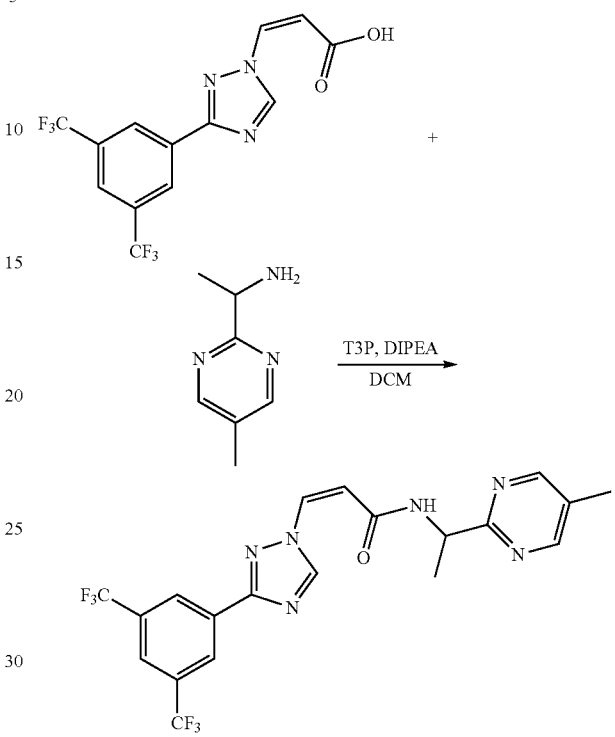

In a 250 mL, 3N round-bottomed flask equipped with nitrogen inlet, Intermediate 1 (0.19 g, 1.0 eq.) was charged along with dichloromethane (5 mL, 10 V). The reaction mixture was cooled to −20° C. and then added 1-(5-methylpyrimidine-2-yl)ethanamine (0.09 g, 1.2 eq.), T3P(50% in EtOAc) (0.2 mL, 1.2 eq.) followed by DIPEA (0.18 mL, 2 eq.) was added into the reaction mixture. The clear reaction mixture was stirred at −20° C. for 30 min. The progress of the reaction was followed by TLC analysis on silica gel with 5% Methanol in dichloromethane as mobile phase and visualization with UV. Reaction mixture was concentrated by rotary evaporation (25° C., 20 mm Hg) to afford Crude compound. The crude reaction mixture was purified by column chromatography using 60/120 mesh silica and methanol: dichloromethane as mobile phase. The column was packed in dichloromethane and started eluting in MeOH in gradient manner starting with fraction collection (500 mL fractions). The compound started eluting from 5% Methanol in dichloromethane. Fractions containing such TLC profile were collected together to obtain pure compound 0.5 gm Yield (20%).

(Z)-3-(3-(3,5-bis(trifluoromethyl)phenyl)-1H-1,2,4-triazole-1-yl)-N-(1-(5-methylpyrimidine-2-yl)ethyl) acrylamide $^1$H NMR (400 MHz, DMSO) δ=9.48 (s, 1H), 9.01-8.99 (d, J=8 Hz, 1H), 8.64 (s, 2H), 8.47 (s, 2H), 8.28 (s, 1H), 7.42-7.39 (d, J=10.4 Hz, 1H), 6.01-5.99 (d, J=10.4 Hz, 1H), 5.058 (m, 1H), 2.53 (s, 3H), 1.44-1.42 (d, J=7.2 Hz, 3H) LCMS for $C_{20}H_{16}N_6F_6O$ [M+H]$^+$ 470.35 found 471.49 at RT 2.775 min purity 97.38%.

Example 22

Synthesis of (Z)-3-(3-(3,5-bis(trifluoromethyl)phenyl)-1H-1,2,4-triazol-1-yl)-N-methyl-N-(oxazol-5-ylmethyl)acrylamide

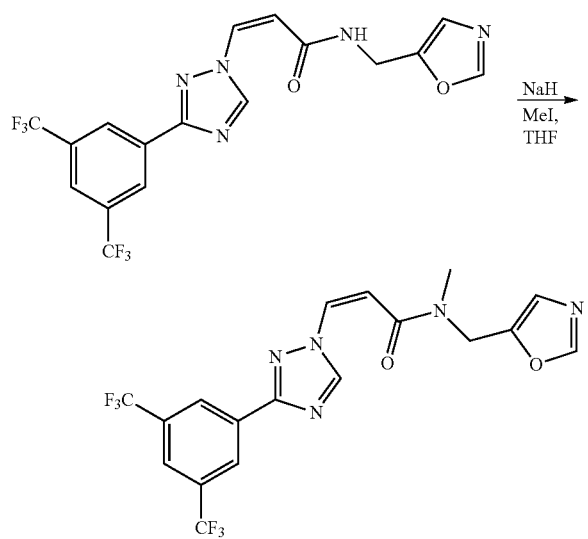

(Z)-3-(3-(3,5-Bis(trifluoromethyl)phenyl)-1H-1,2,4-triazol-1-yl)-N-methyl-N-(oxazol-5-yl methyl)acrylamide (0.15 g, 0.34 mmol) was dissolved in THF (30 mL). The reaction mixture was cooled to 0° C.; NaH (0.012 g, 0.52 mmol) was added and the reaction mixture was stirred for 0.5 h. Methyl iodide (1.5 mL) was added dropwise at the same temperature. The clear reaction mixture was further stirred at 0° C. for 1.5 h. Reaction mixture was partitioned in 20 mL ice-water and extracted with DCM (3×50 mL). The combined organic layers were washed with saturated brine and dried over anhydrous $Na_2SO_4$ and concentrated under reduced pressure to afford 0.180 g of crude product, which was purified by column chromatography (0-2% methanol: DCM) to give 15 mg of (Z)-3-(3-(3,5-bis(trifluoromethyl)phenyl)-1H-1,2,4-triazol-1-yl)-N-methyl-N-(oxazol-5-ylmethyl)acrylamide (Yield: 9.6%). $^1$H NMR (400 MHz, DMSO-$d_6$) δ=9.01 (s, 1H); 8.61 (s, 1H); 8.48 (s, 1H); 8.39 (s, 1H); 8.30 (s, 1H); 8.07 (s, 1H); 7.38-7.41 (d, J=10 Hz, 1H); 6.99 (s, 1H); 6.23-6.26 (d, J=10 Hz, 1H); 4.72 (s, 1H); 4.62 (s, 1H); 3.02 (s, 3H) LCMS for $C_{18}H_{14}F_6N_5O_2$ [M+H]$^+$: 446.32 found 446.03 (retention time: 3.432 min).

Example 23

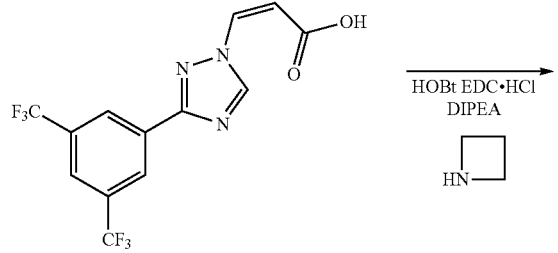

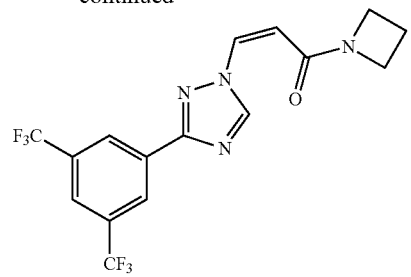

In a 100 mL, 3N round-bottomed flask equipped with nitrogen inlet, Intermediate-4 (1 g, 1.0 eq.) was dissolved in dichloromethane (20 mL, 20 V). The reaction mixture was cooled to 0° C. HOBT (0.461 g, 1.2 eq.), EDC.HCl (0.819 g, 1.5 eq.), azetidine (0.195 g, 1.2 eq.) and DIPEA (0.731 mL, 1.5 eq.) was added to the reaction mixture, and the clear reaction mixture was stirred at 0° C. for 1.5 h. The progress of reaction was monitored by TLC using 5% methanol in dichloromethane as mobile phase and visualization with UV. The reaction mixture was quenched in 50 mL water, the dichloromethane layer separated, and aqueous layer extracted with dichloromethane (20×2). The combined organic layer was washed with brine solution, dried over $Na_2SO_4$ and concentrated under reduced pressure by rotary evaporation (25° C., 20 mmHg) to afford 0.980 g of crude compound. The crude compound was purified by column chromatography using 60/120 mesh silica and methanol: dichloromethane as the mobile phase. The column was packed in dichloromethane and eluted with MeOH in a gradient manner. The compound started eluting from 0.9-1.0% methanol in dichloromethane Fractions containing the required TLC profile were collected together to obtain pure compound 0.225 gm Yield (20.25%).

(Z)-1-(azetidin-1-yl)-3-(3-(3,5-bis(trifluoromethyl) phenyl)-1H-1,2,4-triazol-1-yl) prop-2-en-1-one $^1$H NMR (400 MHz, CDCl$_3$) δ 9.87 (s, 1H), 8.62 (s, 2H), 7.93 (s, 1H), 7.18-7.20 (d, J=10.8 Hz, 1H), 5.65-5.68 (d, J=10.8 Hz, 1H), 4.26-4.30 (t, 2H), 4.16-4.20 (t, 2H), 2.34-2.42 (m, 2H); LCMS for $C_{16}H_{12}F_6N_4O$ [M+H]$^+$ 390.28 found 391.39 at RT 2.935 min purity (100%).

Example 24

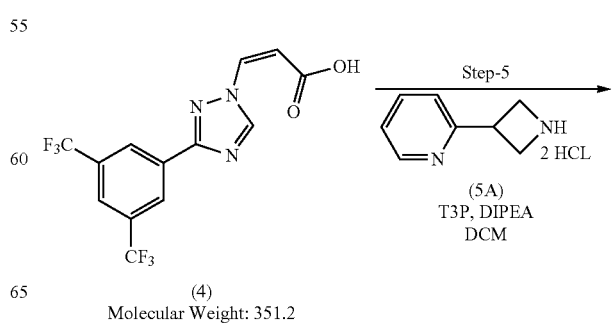

(4)
Molecular Weight: 351.2

-continued

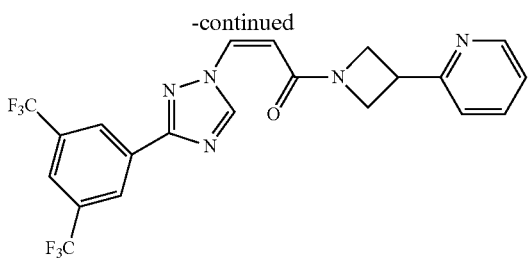

V-324
Molecular Weight: 467.4

In a 50-mL, 3N round-bottomed flask equipped with a nitrogen inlet and a rubber septum, Intermediate-4 (acid) was suspended in dichloromethane (5 mL). Intermediate-5a & DIPEA and T3P (50% in ethyl acetate) was added at −20° C., and the reaction stirred at the same temperature for 50-60 min. Progress of the reaction was followed by TLC using 30% acetone-hexane as mobile phase. The reaction mixture was then concentrated under vacuum at 30° C. at 20 mbar, and the resulting crude compound purified by flash chromatography using hexane & Acetone as mobile phase. The crude compound mixture was eluted out at 15-20% acetone-hexane to afford a semi-pure compound with purity 55.91% (Yield: 200 mg); LCMS: m/z 468.03 (M+1). This semi-pure compound was further purified by flash chromatography using same solvent ratio to afford 100 mg, which was further purified by preparative TLC using 30% Acetone-hexane as mobile phase affording 14 mg of product (Yield 15%). $^1$H NMR (400 MHz, DMSO-$d_6$, ppm) δ=9.63 (s, 1H); 8.63-8.60 (t, 1H); 8.53 (s, 2H); 8.29 (s, 1H); 7.39-7.37 (d, J=10.4 Hz, 1H); 6.01-5.99 (d, J=10.4 Hz, 1H); 5.46-5.44 (d, J=5.5 Hz, 1H); 3.82-3.77 (m, 2H) 3.63-3.59 (m, 2H): LCMS calcd for $C_{21}H_{16}F_6N_5O$ [M+H]$^+$ 468.13. found: 468.3 (retention time 3.719 min).

Example 25

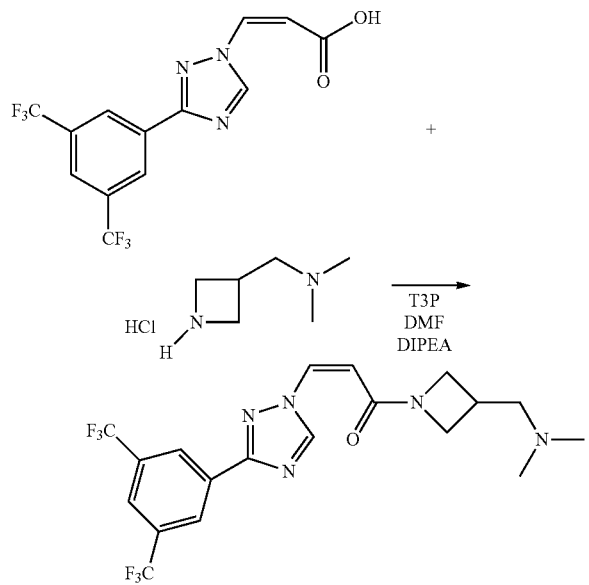

In a 50-mL 3-neck round-bottomed flask under nitrogen atmosphere (Z)-3-(3-(3,5-bis(trifluoromethyl)phenyl)-1H-1,2,4-triazol-1-yl)acrylic acid (0.529 g, 0.91 eq.) & 1-(azetidin-3-yl)-N,N-dimethyl methanamine hydrochloride (0.250 g, 1.0 eq) were dissolved in DMF(10 mL, 15 Vol). Then T3P (1.055 g, 1.0 eq.) followed by DIPEA (0.748 g, 3.5 eq.) were added slowly and the reaction mixture stirred at 0° C. for 30-45 min. The Completion of the reaction was confirmed by TLC using 5% Methanol in dichloromethane with ammonia atmosphere as mobile phase. The reaction mixture was quenched into ice water slurry extracted with ethylacetate and the aqueous layer washed with ethylacetate (100 mL×2). The combined organic extracts were dried over Na$_2$SO$_4$, filtered and concentrated by rotary evaporation (40° C., 20 mmHg) to afford an off-white semisolid (0.490 g). The product was purified by Prep.TLC using 4% methanol and dichloromethane with ammonia atmosphere to afford 30 mg compound (4.0%).

(Z)-3-(3-(3,5-bis(trifluoromethyl)phenyl)-1H-1,2,4-triazol-1-yl)-1-(3-((dimethylamino)methyl)azetidin-1-yl)prop-2-en-1-one $^1$H NMR (400 MHz DMSO) δ 9.80-9.84 (d, J=17.6 Hz, 1H), 8.62 (s, 2H), 7.93 (s, 1H), 7.19-7.22 (d, J=10.4, 1H), 5.63-5.67 (d, J=10.8, 1H), 4.30-4.35 (t, 1H), 4.21-4.26 (t, 1H), 3.89-3.93 (q, 1H), 3.76-3.80 (q, 1H), 2.84-2.87 (q, 1H), 2.50-2.61 (m, 2H), 2.24 (s, 6H); LCMS for $C_{19}H_{19}F_6N_5O$ [M+H]$^+$ 447.38 found 448.05 at RT 3.77 min purity (84.74%).

Example 26

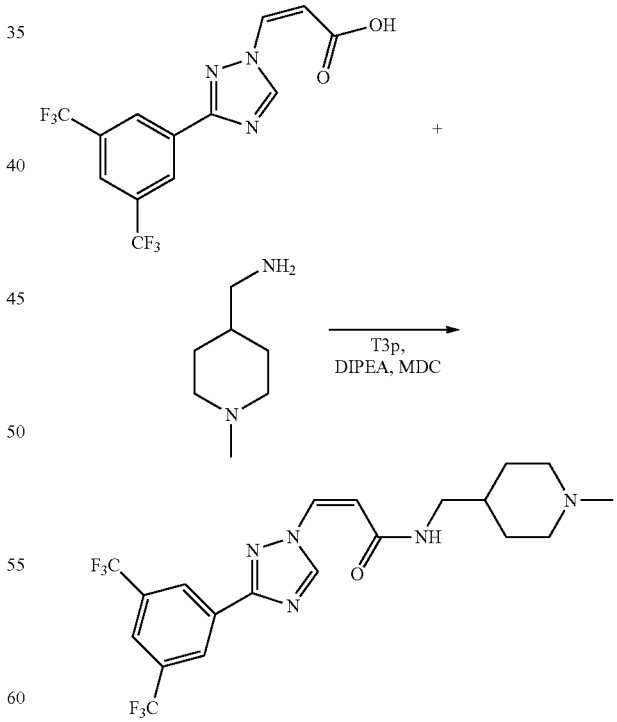

In a 50 mL, 3N round-bottomed flask under a nitrogen atmosphere, (Z)-3-(3-(3,5-bis(trifluoromethyl)phenyl)-1H-1,2,4-triazol-1-yl)acrylic acid (Intermediate-4) (0.200 g, 1.0 eq.) and (1-methylpiperidin-4-yl)methanamine (0.073 g, 1 eq.) were suspended in dichloromethane (10.0 mL) and T3P(50%)(0.432 g, 1.2 eq.) added maintaining the temp at −40° C., followed by DIPEA (0.147 g, 2.0 eq.). The progress of the reaction was followed by TLC analysis on TLC with 5% Methanol: dichloromethane with ammonia atmosphere as mobile phase and visualization with UV light. The reaction mixture was concentrated by rotary evaporation (35° C., 20 mmHg) to afford 0.250 g of an oil. The resulting crude compound was purified by Preparative TLC using Methanol: dichloromethane (5:5) as mobile phase with ammonia atmosphere, affording 40 mg (yield-15%) pure compound; (Z)-3-(3-(3,5-bis(trifluoromethyl)phenyl)-1H-1,2,4-triazol-1-yl)-N-((1-methylpiperidin-4-yl)methyl)acrylamide: $^1$H NMR (400 MHz, DMSO) δ, 9.59 (s, 1H), 8.52 (s, 2H), 8.46-8.49 (t, 1H), 8.29 (s, 1H), 7.35-7.37 (d, J=10.4 Hz, 1H), 5.95-5.98 (d, J=10.4 Hz, 1H), 3.03-3.06 (m, 2H), 2.67-2.70 (m, 2H), 2.09 (s, 3H), 1.69-1.74 (m, 2H), 1.56-1.59 (m, 2H), 1.07-1.17 (m, 2H); LCMS for $C_{20}H_{21}F_6N_5O$ [M+H]$^+$461.4 found 462.5 at RT 3.69 min purity (94.31%).

Example 27

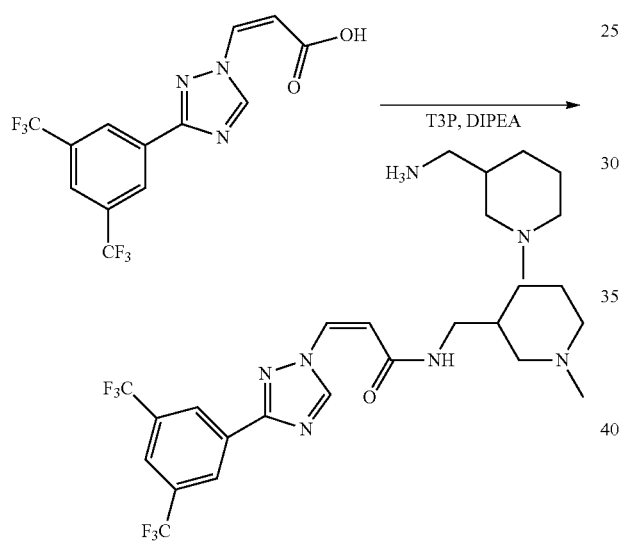

In a 50 mL, 3N round-bottomed flask under nitrogen atmosphere, intermediate 4 (acid) (0.100 g, 1.0 eq.) and (1-methylpiperidin-3-yl)methanamine (0.036 g, 1.0 eq.) were suspended in dichloromethane (10.0 mL) then T3P (50%)(0.216 g, 1.2 eq.) and DIPEA (0.073 g, 2.0 eq.) were added at −40° C. The progress of the reaction was followed by TLC analysis on TLC with 5% Methanol: dichloromethane with ammonia atmosphere as mobile phase and visualization with UV light. The reaction mixture was concentrated by rotary evaporation (35° C., 20 mmHg) to afford 0.120 g of an oil. The resulting crude compound was purified by Preparative TLC using Methanol: dichloromethane (5:5) as mobile phase with ammonia atmosphere, affording 11 mg (yield-15%) pure compound; (Z)-3-(3-(3,5-bis(trifluoromethyl)phenyl)-1H-1,2,4-triazol-1-yl)-N-((1-methylpiperidin-3-yl)methyl)acrylamide: $^1$H NMR (400 MHz, DMSO) δ, 9.72 (s, 1H), 8.61 (s, 2H), 7.94 (s, 1H), 7.14-7.16 (d, J=10.8 Hz, 1H), 5.66-5.68 (d, J=10.8 Hz, 1H), 3.71-3.76 (m, 2H), 3.31 (m, 2H), 2.73-2.79 (m, 2H), 2.26 (s, 3H) 2.02 (m, 1H), 1.87 (m, 2H), 1.73 (m, 2H) LCMS for $C_{20}H_{21}F_6N_5O$ [M+H]$^+$ 461.4 found 462.5 at RT 3.81 min purity (88.64%).

Example 28

Synthesis of (Z)-6,7-dihydro-5H-cyclopenta[b]pyridin-5-one oxime

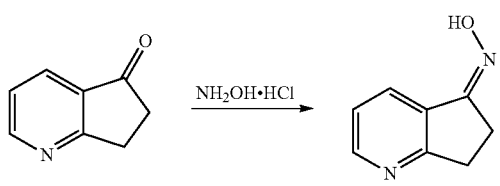

In a 100-mL, 3N round-bottomed flask 6,7-dihydro-5H-cyclopenta[b]pyridin-5-one (2.0 g, 1.0 eq.) was dissolved in EtOH (24.0 mL) and H2O (6.0 mL) at RT. Then Sodium acetate trihydrate (8.175 g, 4.0 eq.) and Hydroxylamine hydrochloride (4.174 g, 4.0 eq.) were added at the same temperature. The progress of the reaction was followed by TLC analysis on TLC with 5% Methanol: dichloromethane with ammonia atmosphere as mobile phase and visualization with U.V light. The reaction mixture was quenched in 50 mL water and extracted by dichloromethane. Organic layer was concentrated by rotary evaporation (35° C., 20 mmHg) to afford 2.10 g of crude compound which was used in the next step without purification.

Synthesis of 6,7-dihydro-5H-cyclopenta[b]pyridin-5-amine

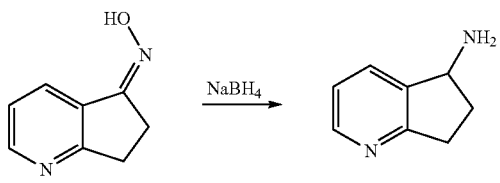 [SMILES: O/N=C1/CCc2ncccc21 ; "NaBH4" ; NC1CCc2ncccc21]

In a 50 mL, 3N round-bottomed flask Intermediate Step (1) (1.0 g, 1.0 eq.) was dissolved in MeOH (15.0 mL, 15 V) at RT. Nickel Chloride Hexahydrate (0.010 g) was added at same temperature to this reaction mixture. The reaction mixture was cooled to −40° C. and NaBH4 (2.5 g, 10.0 eq.) was added at the same temperature in portions over 30 min. The progress of the reaction was followed by TLC analysis on TLC with 5% Methanol: dichloromethane with ammonia atmosphere as mobile phase and visualization with U.V light. The reaction mixture was quenched in 50 mL water and extracted by Ethyl acetate. The organic phase was concentrated by rotary evaporation (35° C., 20 mmHg) to afford 0.64 g of crude compound which was used in the next step without purification.

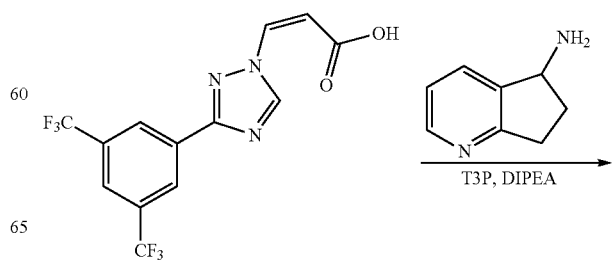

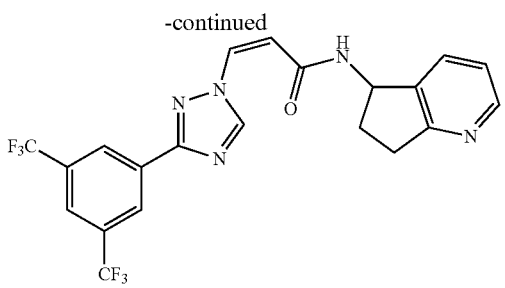

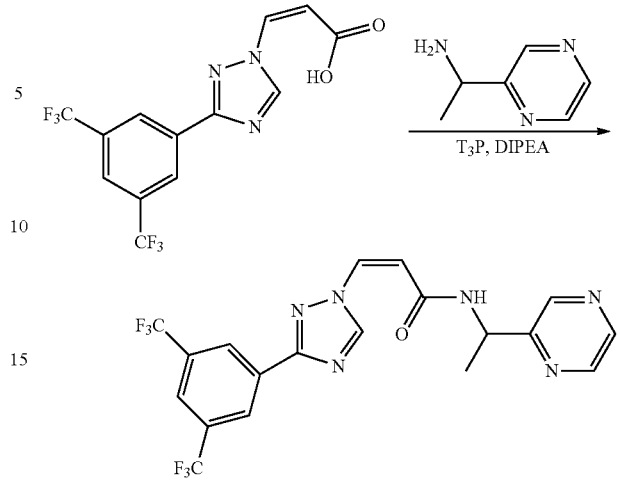

In a 100 mL, 3N round-bottomed flask equipped with nitrogen inlet, the acid (0.327 g, 1.0 eq.) was dissolved in dichloromethane (20 mL). To this reaction mixture (1a) (0.150 g, 1.2 eq.) was added and the reaction mixture cooled to −70° C. T3P (Propyl phosphonic anhydride) (0.665 mL, 1.2 eq.) was added dropwise followed by DIPEA (0.318 mL, 2.0). The progress of the reaction was followed by TLC analysis on silica gel with 5% Methanol: dichloromethane with ammonia atmosphere as mobile phase and visualization with UV light. The reaction mixture was quenched in 50 mL water and extracted by dichloromethane. The organic layer was concentrated by rotary evaporation (35° C., 20 mmHg) to afford 0.369 g of crude compound which was purified by column chromatography. The product eluted at 0.6% Methanol in dichloromethane to give 0.017 g of pure product. (Yield 3.90%); (Z)-3-(3-(3,5-bis(trifluoromethyl)phenyl)-1H-1,2,4-triazol-1-yl)-N-(6,7-dihydro-5H-cyclopenta[b]pyridin-5-yl)acrylamide: $^1$H NMR (400 MHz, DMSO) δ 9.61 (s, 1H), 9.03-9.01 (d, 1H), 8.54 (s, 2H), 8.49-8.47 (d, 1H), 8.307 (s, 1H), 8.02-8.00 (d, 1H), 8.19-8.18 (m, 1H), 7.45-7.42 (d, J=10.4 Hz, 1H), 5.97-5.45 (d, J=10.4 Hz, 1H), 5.53-5.47 (m, 1H), 3.12-3.03 (m, 1H), 2.50-2.28 (m, 2H), 2.03-2.02 (m, 1H). LCMS for $C_{21}H_{15}F_6N_5O$ [M+H]$^+$ found 480.44 at RT 3.21 min purity (95.48%).

Example 29

Synthesis of 1-(pyrazin-2-yl)ethanamine

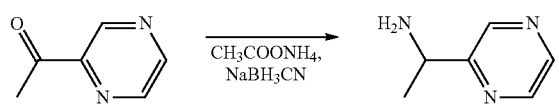

To a 3-necked 100 mL round-bottomed flask equipped with a magnetic stirrer, and immersion thermometer, 1-(pyrazin-2-yl)ethanone (1.0 g, 1.0 eq.), and MeOH (30 mL), was added ammonium acetate (6.31 g, 10 eq.) at room temperature. To this reaction mixture sodium cyanoborohydride (0.360 g, 0.7 eq.) was added, and the reaction mass stirred overnight at room temperature. The progress of the reaction was monitored by TLC analysis on silica gel with MeOH:dichloromethane (2.5%) as mobile phase and visualization with UV, SM Rf=0.70 and product Rf=0.20. The reaction mixture was concentrated and poured into water (100 mL) and basifed (PH=13) using aqueous NaOH solution. The resulting mixture was extracted with dichloromethane (2×100 mL) and the combined organic layers were washed with brine solution (2×50 mL), dried over MgSO$_4$, filtered, and concentrated by rotary evaporation to afford 0.3 g of desired amine Yield: 30%.

In a 100 mL 3-neck round bottom flask equipped with septum, nitrogen bubbler and thermometer pocket, intermediate-1A (0.300 g, 1.0 eq.) was dissolved in dichloromethane (20 mL). A second portion of Intermediate-1A (0.126 g, 1.2 eq.) was added and the reaction mixture cooled to −60° C. To this reaction mixture T$_3$P (Propyl Phosphonic anhydride) (0.60 mL, 1.2 eq.) and DIPEA (0.29 mL, 2.0 eq.) were added at the same temperature, and the mixture stirred for 30 min. The progress of the reaction was followed by TLC analysis on silica gel with 5% MeOH: dichloromethane as mobile phase and visualization with UV, SM Rf=0.20 and product Rf=0.50. The reaction mixture was then poured into water (100 mL) and extracted with dichloromethane (2×100 mL). The combined organic layers were washed with brine solution (2×50 mL), dried over anhydrous MgSO$_4$, filtered, and concentrated by rotary evaporation (25° C., 20 mmHg) to afford the crude compound which was purified by column chromatography (diameter: 2.5 cm) using silica 60/120 and MeOH: dichloromethane as mobile phase. Column purification was started with 0.5% MeOH in dichloromethane up to 2.0% MeOH in dichloromethane. The desired product started eluting in 1.5% methanol. Fractions containing the compound were distilled using rotary evaporation at 40° C./250 mm Hg to obtain 0.2 g of pure compound. Yield: 51.4%; (Z)-3-(3-(3,5-bis(trifluoromethyl)phenyl)-1H-1,2,4-triazol-1-yl)-N-(1-(pyrazin-2-yl)ethyl)acrylamide: $^1$H NMR (400 MHz, DMSO) δ, 9.52 (s, 1H), 8.28-9.13 (m, 6H), 7.40-7.42 (d, J=10.4 Hz, 1H), 6.04-6.07 (d, J=10.4 Hz, 1H), 5.12-5.19 (m, 1H), 1.46-1.47 (d, 3H); LCMS for $C_{19}H_{14}F_6N_6O$ [M+H]$^+$456.3 found 457.44 at RT 2.894 min purity (99.91%).

Example 30

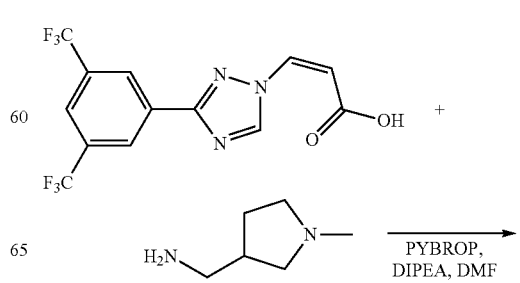

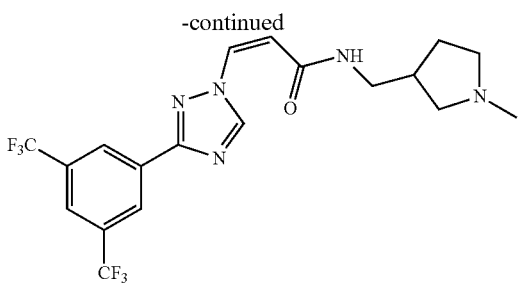

Synthesis of (Z)-3-(3-(3,5-bis(trifluoromethyl)phenyl)-1H-1,2,4-triazol-1-yl)-N-((1-methylpyrrolidin-3-yl)methyl)acrylamide In a 50 mL 3N round-bottomed flask, (Z)-3-(3-(3,5-bis(trifluoromethyl)phenyl)-1H-1,2,4-triazol-1-yl)acrylic acid (0.100 g, 1.0 eq) and (1-methylpyrrolidin-3-yl)methanamine (0.035 g, 1.1 eq) was dissolved in DMF (10 mL) and PYBROP (0.140 g, 1.1 eq.) with DIPEA (0.073 mg, 2.0 eq.) was added under nitrogen atmosphere. The progress of the reaction was followed by TLC analysis on silica gel with 0.5% Methanol:dichloromethane with ammonia atmosphere as mobile phase and visualization with UV light. The reaction mixture was quenched into ice water and compound was extracted by Ethylacetate (25×3 mL), dried over anhydrous $Na_2SO_4$, filtered, and concentrated by rotary evaporation (25° C., 20 mmHg) to afford 0.232 g of solid crude. Purification was achieved via column chromatography in dichloromethane and Methanol. Compound started eluting at 10% methanol in dichloromethane with ammonia. Fractions containing compound was distilled out using rotary evaporation at 25° C., 20 mmHg to afford 98.0 mg of pure compound. Yield 77%; (Z)-3-(3-(3,5-bis(trifluoromethyl)phenyl)-1H-1,2,4-triazol-1-yl)-N-((1-methylpyrrolidin-3-yl)methyl)acrylamide: $^1$H NMR (400 MHz, DMSO) δ 9.83 (s, 1H), 8.61-8.65 (d, J=12.4 Hz, 2H), 7.93 (s, 1H), 7.31-7.15 (d, J=10.8 Hz, 1H), 5.69-5.71 (d, J=10.8 Hz, 1H), 3.34-3.43 (m, 2H), 2.87-2.91 (m, 1H), 2.63-2.65 (d, J=9.2 Hz, 1H), 2.41-2.54 (m, 2H), 2.73 (s, 3H), 2.05-2.11 (m, 2H), 1.71 (s, 1H), LCMS for $C_{19}H_{19}F_6N_5O$ $[M+H]^+$ 447.24 found 448.26 at RT 6.50 min purity (89.08%).

Example 31

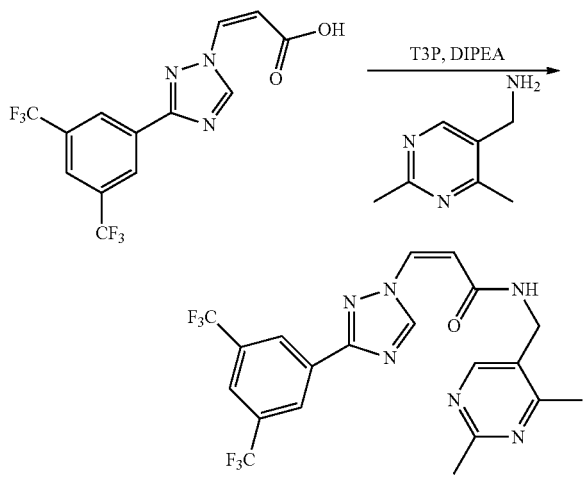

In a 50 mL, 3N round-bottomed flask, Intermediate 4 (0.2 g, 1.0 eq.) was added to dichloromethane:ethylacetate (25.0 mL, 1:1). (2,4-dimethylpyrimidin-5-yl)methanamine (0.078 g, 1 eq.) was then added at −40° C. T3P (50% ethyl acetate) (0.432 g, 1.2 eq.) and DIPEA (0.147 g, 2.0 eq.) were added simultaneously at the same temperature, and the reaction mixture stirred for 30 min at −40° C. The progress of the reaction was monitored by TLC using 5% methanol: dichloromethane with ammonia atmosphere as mobile phase and visualization with U.V light. The reaction mixture was concentrated by rotary evaporation (35° C., 20 mmHg) to afford 0.270 g of an oil. The resulting crude mixture was purified by column chromatography using dichloromethane:methanol as a mobile phase, the compound eluted at 4% methanol in dichloromethane. The compound containing fractions were concentrated under reduced pressure to obtain 80 mg (yield-29.85%) of pure compound.

(Z)-3-(3-(3,5-bis(trifluoromethyl)phenyl)-1H-1,2,4-triazol-1-yl)-N-((2,4-dimethylpyrimidin-5-yl)methyl)acrylamide $^1$H NMR (400 MHz, DMSO) δ, 9.57 (s, 1H), 8.91-8.94 (t, 1H), 8.51 (s, 2H), 8.43 (s, 1H), 8.29 (s, 1H), 7.40-7.42 (d, J=10.4 Hz, 1H), 5.98-6.01 (d, J=10.4, 1H), 4.37-4.38 (d, J=5.6 Hz, 2H), 3.35 (s, 3H), 2.50 (s, 3H); LCMS for $C_{20}H_{16}F_6N_6O$ $[M+H]^+$ 470.37 found 471.25 at RT 2.69 min purity (99.89%).

Example 32

Synthesis of (Z)-3-(3-(4-chloro-3,5-bis(trifluoromethyl)phenyl)-1H-1,2,4-triazol-1-yl)-1-(3,3-difluoroazetidin-1-yl)prop-2-en-1-one

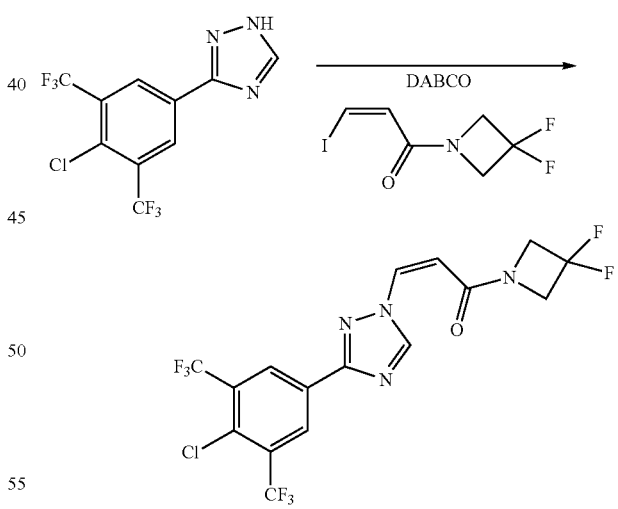

In a 50 mL, 3N round-bottomed flask equipped with nitrogen inlet, Intermediate-3 (0.1 g, 1.0 eq.) was dissolved in DMF (5 mL). To this reaction mixture DABCO (0.071 g, 2 eq.) was added and stirred for 30 min. Then (Z)-1-(3,3-difluoroazetidin-1-yl)-3-iodoprop-2-en-1-one (0.095 g, 1.1 eq.) was added, and the reaction mixture stirred at room temperature for 5 h. The progress of the reaction was followed by TLC using dichloromethane: methanol (9.5:0.5) mobile phase and visualization with UV. The reaction mixture was poured into ice water (50 mL), then extracted with EtOAc (3×15 mL). The combined organic layers were washed with brine solution, (20 mL), dried over $Na_2SO_4$, filtered, and concentrated by rotary evaporation (25° C., 20 mmHg) to afford 0.150 g of crude compound which was purified by preparative TLC obtain pure compound 0.004 g yield (3%).

(Z)-3-(3-(4-chloro-3,5-bis(trifluoromethyl)phenyl)-1H-1,2,4-triazol-1-yl)-1-(3,3-difluoroazetidin-1-yl)prop-2-en-1-one $^1$H NMR (400 MHz, DMSO) δ=9.32 (s, 1H), 8.46 (s, 1H), 8.32 (s, 1H), 7.47-7.49 (d, J=10.4 Hz, 1H), 6.00-5.04 (d, J=10.4 Hz, 1H), 4.55-4.58 (m, 2H), 4.33-4.36 (m, 2H) LCMS for $C_{16}H_9ClF_8N_4O$ [M+H]$^+$: 460.7. Found: 461.14, Purity 98.77% at 2.99 min retention time Example 35

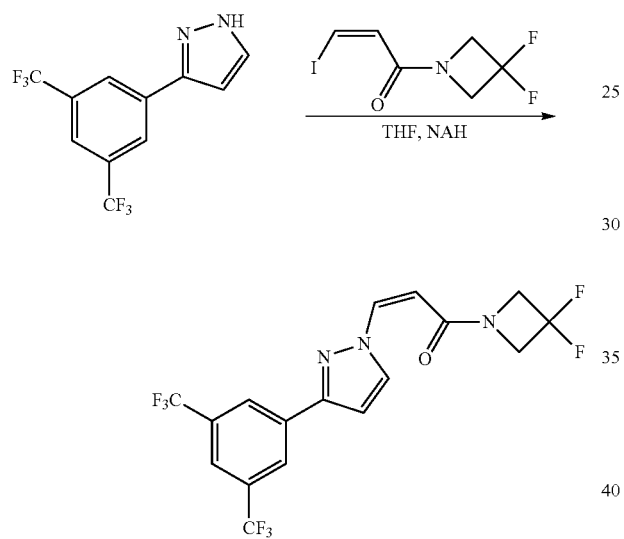

In a 25 ml sealed tube NaH (0.064 g, 1.5 eq.) was suspended in THF (10 mL) and then cooled to 0° C. To this mixture, a solution of intermediate 3 (0.3 g, 1.0 eq.) in THF was added dropwise at 0° C. and then the mixture was heated under reflux at 80° C. for 2 h. The progress of the reaction was followed by TLC analysis using 10% ethyl acetate in hexane as mobile phase. The reaction mixture was then concentrated and resulted mass extracted with ethyl acetate (2×150 mL). The combined organic layers were washed with brine solution (2×100 mL), dried over anhydrous $Na_2SO_4$, filtered, and concentrated by rotary evaporation (40° C., 20 mmHg) to afford 0.43 g of crude mixture. The mixture was purified by column chromatography using ethyl acetate in hexane. The compound eluted in 25% ethyl acetate hexane., and the cis product was isolated via preparative TLC using a mobile phase consisting of 10% acetone in hexane. The pure product obtained was 0.016 g; (Z)-3-(3-(3,5-bis(trifluoromethyl)phenyl)-1H-pyrazol-1-yl)-1-(3,3-difluoro azetidin-1-yl)prop-2-en-1-one: $^1$H NMR (400 MHz, CDCl$_3$) δ, 8.78-8.79 (d, J=2.4, 1H), 8.28 (s, 2H), 7.19-7.22 (d, J=10.8 Hz, 1H), 6.81-6.82 (d, J=2.4, 1H), 5.44-5.47 (d, J=10.8 Hz, 1H), 4.44-4.51 (m, 4H); LCMS for $C_{17}H_{11}F_8N_3O$ [M+1]$^+$ 425.28 found 426.09 at RT 3.202 min. purity (22.42%).

Example 40

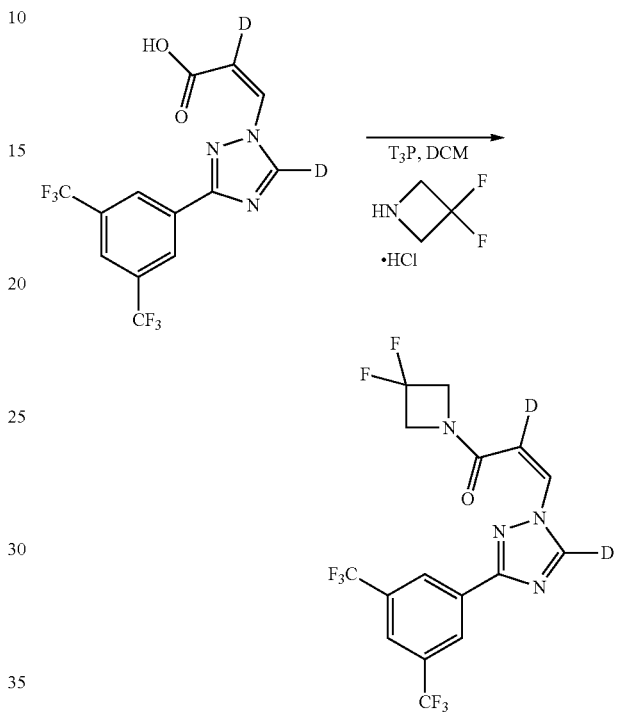

In a 25 mL 3-neck round bottom flask equipped with septum, Nitrogen bubbler and thermometer pocket, intermediate-1 (acid) (0.080 g, 1.0 eq.) and dichloromethane (6.0 mL) were added. Then 3,3-difluoroazetidine.HCl (0.0.035 g, 1.2 eq.) was added and the reaction mixture cooled to −60° C. To this mixture, T$_3$P (Propyl Phosphonic anhydride) (0.161 ml, 1.2 eq.), and DIPEA (0.077 ml, 2.0 eq.) were added at the same temperature, and the resulting mixture stirred for 1 h. The progress of the reaction was followed by TLC analysis using 5% MeOH: dichloromethane as mobile phase and visualization with UV, SM Rf=0.20 and product Rf=0.70. The reaction mixture was then poured into D$_2$O (10 mL) and extracted with dichloromethane (2×20 ml). The combined organic layers were dried over anhydrous MgSO$_4$, filtered and concentrated by rotary evaporation (25° C., 20 mmHg) to afford a crude compound which was purified by column chromatography using silica 60/120 and MeOH: dichloromethane as mobile phase. Column purification was started with 1.5% MeOH in dichloromethane up to 2.0% MeOH in dichloromethane. The desired product started eluting in 1.5% methanol and the fractions containing compound were distilled using a rotary evaporation at 40° C./250 mm Hg to obtain 0.020 g of pure compound. Yield: 20%. $^1$H NMR (400 MHz, CDCl$_3$) δ 9.63-9.66 (d, J=10.8 Hz, 1H), 8.61 (s, 2H), 7.95 (s, 1H), 7.24-7.27 (t, J=4.4 Hz, 1H), 5.67-5.69 (d, J=10.8 Hz, 1H), 4.46-4.60 (m, 4H); LCMS for Chemical Formula: $C_{16}H_8D_2F_8N_4O$ [M+H]$^+$ 428.28 found 429.14 at RT 2.992 min purity (98.62%).

Example 43

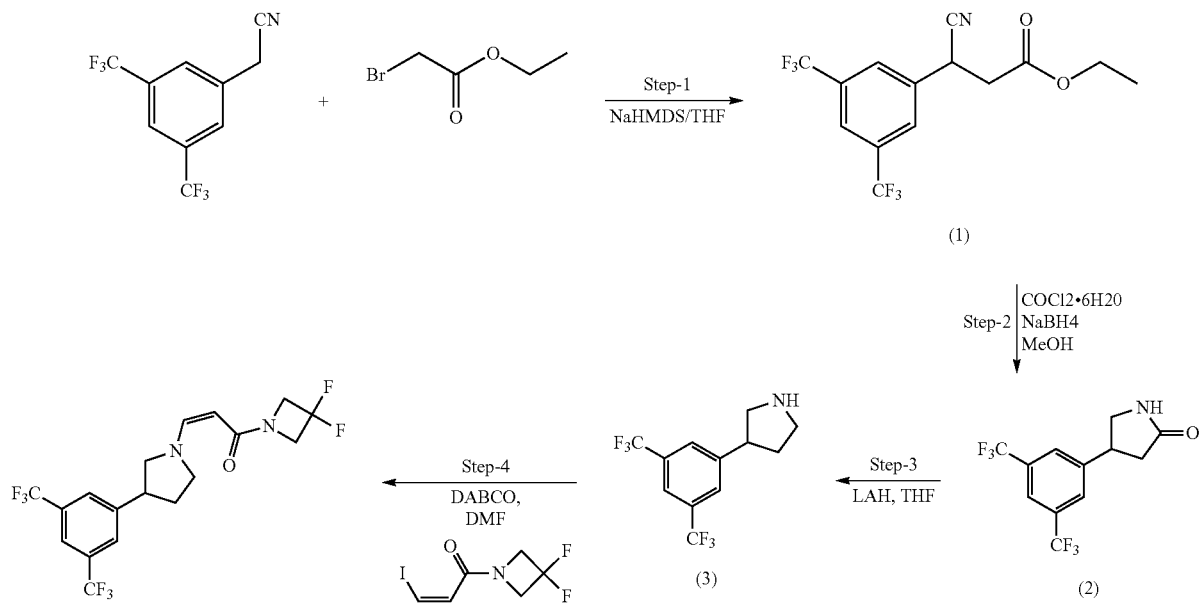

Synthesis of Intermediate (1)

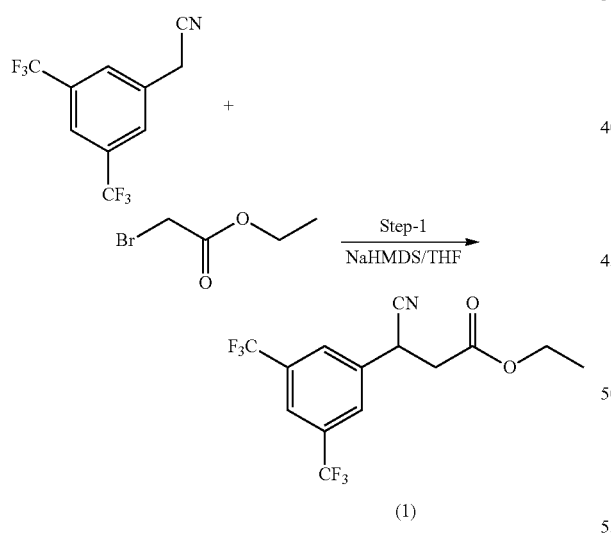

In a 100-mL, 3N RBF equipped with nitrogen inlet, a Thermometer pocket and stopper, 3,5-bis(trifluoromethyl)-phenylacetonitrile (1.4 mL, 1.0 eq.) was dissolved in THF (20 mL, 10V). The reaction mixture was cooled to −78° C. NaHMDS (35% in THF) (4.34 mL, 1.05 eq.) was added dropwise in this reaction mixture. After completion of addition reaction mixture was brought to 10° C. and stirred for 15 min. Again this reaction mixture was cooled to −78° C. and ethyl bromoacetate (0.87 mL, 1.0 eq.) was added. Reaction mixture was brought to room temperature. This reaction mixture was stirred at room temperature for 16 hrs.

The progress of the reaction was monitored by TLC analysis using 20% Ethyl acetate-Hexane as mobile phase. Reaction mixture was poured into water (50 mL) and extracted with EtOAc (3×20 mL). The combined organic layer was washed with brine solution (50 mL), dried over $Na_2SO_4$, filtered, and concentrated by rotary evaporation to afford 3.5 g of Crude compound. The crude compound was purified by column chromatography using 60/120 mesh silica and ethyl acetate: hexane as mobile phase. The column was packed in hexane and started eluting in ethyl acetate in gradient manner starting with fraction collection (25-mL fractions). The compound started eluting from 4% to 6% ethyl acetate in hexane. Fractions containing such TLC profile were collected together to obtain pure compound 1.2 gm Yield (44.94%).

Synthesis of Intermediate (2)

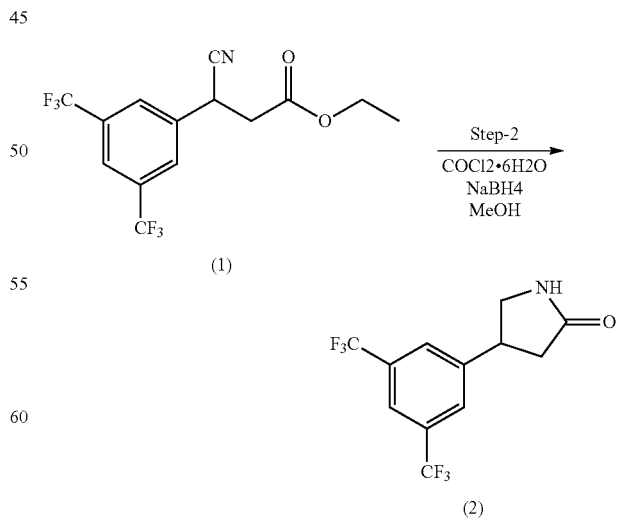

In a 100-mL, 3N RBF equipped with nitrogen inlet, a Thermometer pocket and stopper, Intermediate-1 (1.2 g, 1.0 eq.) was dissolved in MeOH (48 mL, 40V). Dichlorocobalt hexahydrate (1.68 g, 2.0 eq.) was added portion wise. The reaction mixture was cooled to 20° C. NaBH$_4$ (1.98 g, 15 eq.) was added portion wise slowly by maintaining temperature below 25° C. in this reaction mixture. Then the reaction mixture was stirred for 18 hrs at 25° C. The progress of the reaction was followed by TLC analysis using 50% Ethyl acetate-hexane as mobile phase. The reaction mixture was concentrated under reduce pressure and residue was partitioned between ethyl acetate (25 mL) and water (25 mL). Reaction mixture was filtered through celite and organic layer separated, dried over Na$_2$SO$_4$, filtered, and concentrated by rotary evaporation. This crude compound was triturated with pet ether to afford 0.5 g of pure compound. (Yield 47.61%).

Synthesis of Intermediate (3)

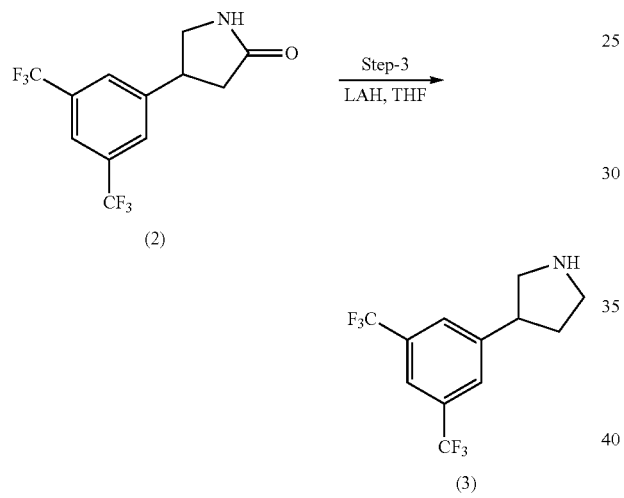

In a 100-mL, 3N RBF equipped with nitrogen inlet, a Thermometer pocket and stopper, Intermediate-2 (1.0 g, 1.0 eq.) was dissolved in THF (20 mL, 20V). The reaction mixture was cooled to 0° C. To this reaction mixture LAH (6.7 mL, 2.0 eq.) was added dropwise by maintaining temperature 0° C. After completion of addition, temperature of reaction mixture was brought to room temperature and then refluxed to 70° C. for 1 h. The progress of the reaction was followed by TLC analysis using 5% MeOH:DCM as mobile phase. The reaction mixture was cooled to 0° C. Reaction mixture was quenched by addition of 1.5 mL of 5% KOH solution. Then reaction mass was filtered through celite and washed with EtOAc (20 mL). Filtrate was concentrated by rotary evaporation to afford 1.0 g of crude compound. The crude compound was purified by column chromatography using 60/120 mesh silica and MeOH:DCM as mobile phase. The column was packed in DCM and started eluting in MeOH in gradient manner starting with fraction collection (25-mL fractions). The compound started eluting from 4% to 6% MeOH in DCM. Fractions containing such TLC profile were collected together to obtain pure compound 0.18 gm Yield (19%).

Synthesis of (Z)-3-(3-(3,5-bis(trifluoromethyl)phenyl)pyrrolidin-1-yl)-1-(3,3-difluoroazetidin-1-yl)prop-2-en-1-one

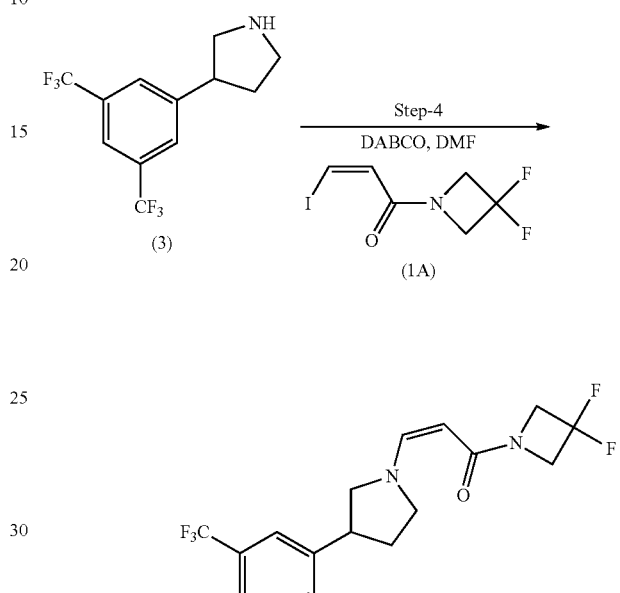

In a 50 mL 3-neck round bottom flask equipped with septum, Nitrogen bubbler and thermometer pocket, Intermediate -3 (0.050 g, 1.0 eq.) in DMF (2.0 mL) were added. Then DABCO (0.039 g, 2.0 eq.) was added at room temperature. Reaction mixture was stirred at room temperature for 30 min Intermediate-1A (0.053 g, 1.1 eq.) was added at room temperature drop wise. Reaction mixture was stirred for 30 min. The progress of the reaction was followed by TLC analysis using 5% MeOH: DCM as mobile phase and visualization with UV, SM Rf=0.20 and product Rf=0.70. The reaction mixture was poured into water (50 mL) and extracted with EtOAc (2×50 mL). The combined organic layer was washed with brine solution (50 mL), dried over anhydrous Na$_2$SO$_4$, filtered, and concentrated by rotary evaporation (25° C., 20 mmHg) to afford crude compound 50 mg. The crude material was purified by Prep.TLC using 2% MeOH: DCM as mobile phase. It was again purified by Prep.TLC using 50% EtOAc: Hexane as mobile phase to obtained 0.018 g of pure compound (Yield-24%).

(Z)-3-(3-(3,5-bis(trifluoromethyl)phenyl)pyrrolidin-1-yl)-1-(3,3-difluoroazetidin-1-yl)prop-2-en-1-one $^1$H NMR (400 MHz, CDCl$_3$) δ, 7.82 (s, 1H), 7.73 (s, 1H), 7.69 (s, 2H), 4.43-4.46 (d, J=12.4 Hz, 1H), 4.32-4.38 (t, J=12 Hz, 4H), 3.61 (s, 2H), 2.47 (s, 1H), 2.18 (s, 1H), 2.16 (s, 1H), 1.27 (s, 1H); LCMS for $C_{18}H_{16}F_8N_2O$ [M+1]$^+$ 428.3 found 429.09 at RT 3.047 min purity (95.45%).

Example 44

3,5-Bis(trifluoromethyl)-phenylacetonitrile (1.4 mL, 1.0 eq.) was dissolved in THF (20 mL). The reaction mixture was cooled to −78° C. where a solution of NaHMDS (35% in THF) (4.34 mL, 1.05 eq.) was added dropwise. The reaction mixture was allowed to warm to 10° C. and stirred

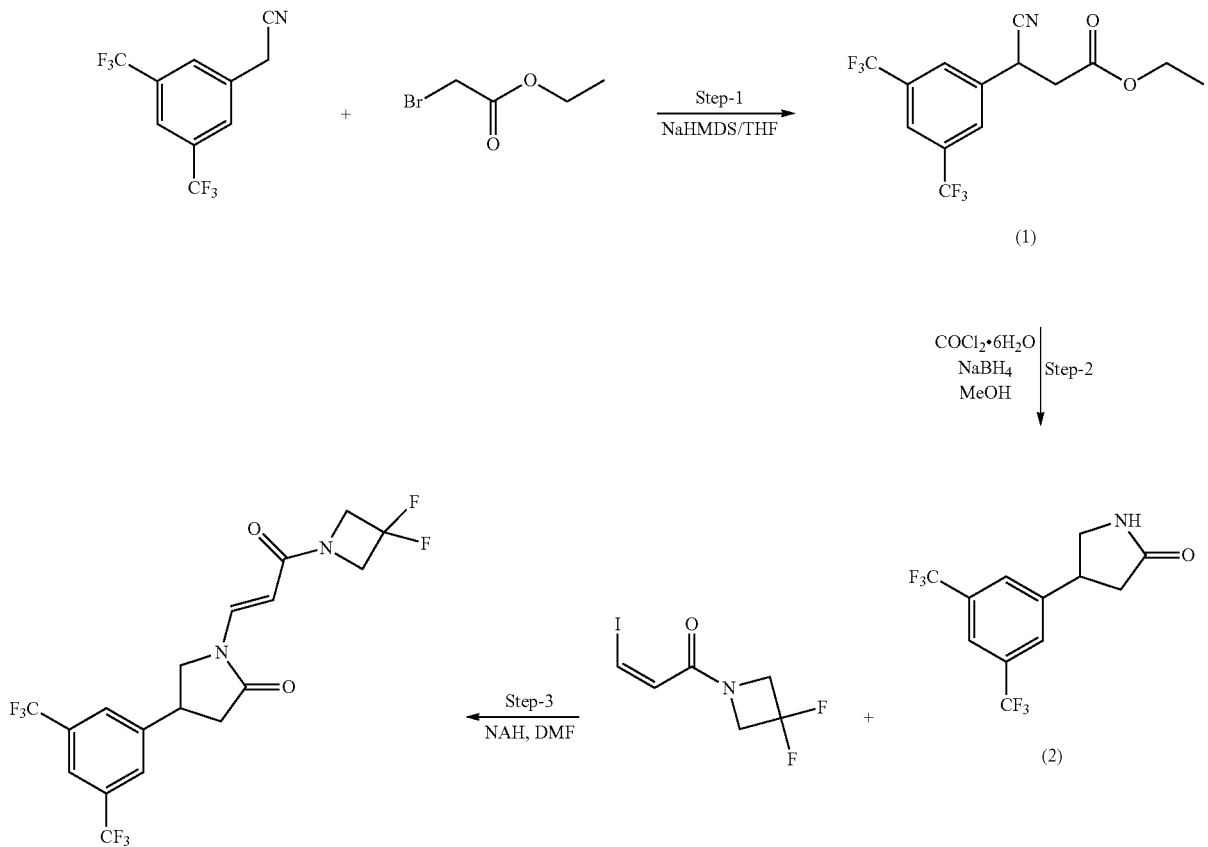

Synthesis of ethyl 3-(3,5-bis(trifluoromethyl)phenyl)-3-cyanopropanoate (1)

for 15 min. Then it was cooled to −78° C. where ethyl bromoacetate (0.87 mL, 1.0 eq.) was added. The reaction mixture was then allowed to warm to room temperature where it was stirred for 16 h. Reaction mixture was poured into water (50 mL) and was extracted with EtOAc (3×20 mL) The combined organic layers were washed with brine solution (3×50 mL), dried over $Na_2SO_4$, filtered, and concentrated under reduced pressure to afford 3.5 g of crude product, which was purified by chromatography (4% ethyl acetate in hexane) to give 1.2 g of ethyl 3-(3,5-bis(trifluoromethyl)phenyl)-3-cyanopropanoate (Yield 44.94%).

Synthesis of 4-(3,5-bis(trifluoromethyl)phenyl)pyrrolidin-2-one (2)

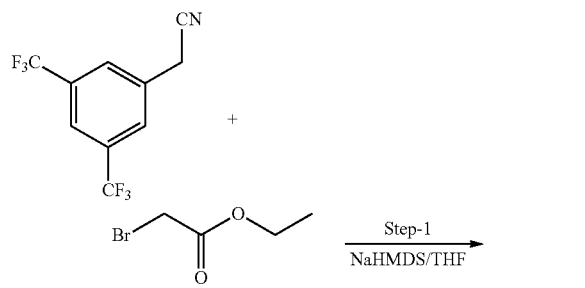

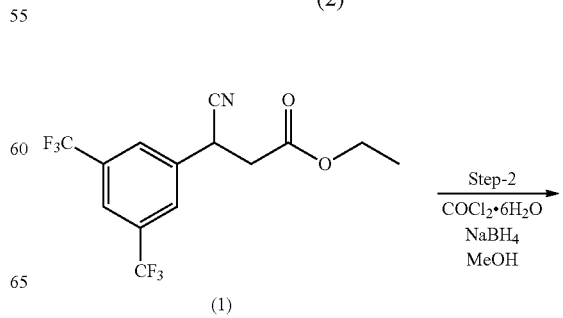

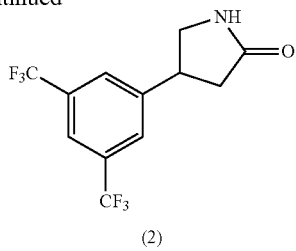

Ethyl 3-(3,5-bis(trifluoromethyl)phenyl)-3-cyanopropanoate (1.2 g, 1.0 eq.) was dissolved in MeOH (48 mL). Dichlorocobalt hexahydrate (1.68 g, 2.0 eq.) was added and the reaction mixture was cooled to 20° C. $NaBH_4$ (1.98 g, 15 eq.) was added portion wise by maintaining temperature below 30° C. After completion of addition, this reaction mixture was stirred for 18 h at 25° C. The reaction mixture was concentrated under reduced pressure and the residue was partitioned between ethyl acetate (25 mL) and water (25 mL). The reaction mixture was filtered through Celite™ and the organic layer was separated, dried over $Na_2SO_4$, filtered, and concentrated under reduced pressure to afford 0.65 g of crude product, which after trituration with petroleum ether gave 0.5 g of 4-(3,5-bis(trifluoromethyl)phenyl)pyrrolidin-2-one (Yield 47.61%).

Synthesis of (E)-4-(3,5-bis(trifluoromethyl)phenyl)-1-(3-(3,3-difluoroazetidin-1-yl)-3-oxoprop-1-enyl)pyrrolidin-2-one

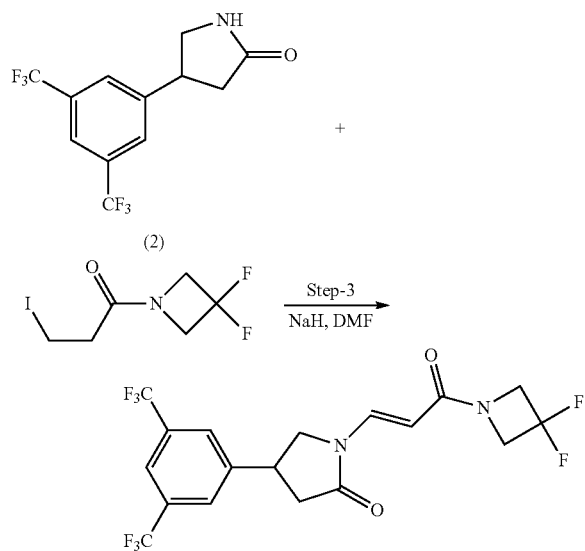

4-(3,5-bis(trifluoromethyl)phenyl)pyrrolidin-2-one (0.5 g, 1.0 eq.) was dissolved in DMF (5 mL) and cooled to 0° C. A solution of NaH in DMF (0.133 g, 2.0 eq.) was added at 0° C. (Z)-1-(3,3-difluoroazetidin-1-yl)-3-iodoprop-2-en-1-one (0.689 g, 1.5 eq.) was then introduced. The reaction mixture was stirred for 30 min at room temp. The reaction mixture was poured into water (50 mL) and extracted with EtOAc (3×20 mL). The combined organic layers were washed with brine (3×50 mL), dried over $Na_2SO_4$, filtered, and concentrated under reduced pressure to afford 0.502 g of crude product, which was purified by chromatography (1% Methanol in DCM) to give 0.030 g of (E)-4-(3,5-bis(trifluoromethyl)phenyl)-1-(3-(3,3-difluoroazetidin-1-yl)-3-oxoprop-1-enyl)pyrrolidin-2-one (Yield 4.03%). $^1$H NMR (400 MHz, $CDCl_3$) δ 8.15-8.19 (d, J=14 Hz, 1H), 7.69-7.87 (m, 3H), 5.27-5.31 (d, J=14 Hz, 1H), 4.05-4.47 (m, 4H), 3.89-3.93 (s, 1H), 3.73-3.77 (s, 1H), 3.60-3.62 (s, 1H), 3.08-3.13 (s, 1H), 2.78-2.90 (s, 1H); LCMS calcd. for $C_{18}H_{14}F_8N_2O_2$ $[M+H]^+$. found 443.44 at retention time 2.97 min.

Example 51

Synthesis of (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one

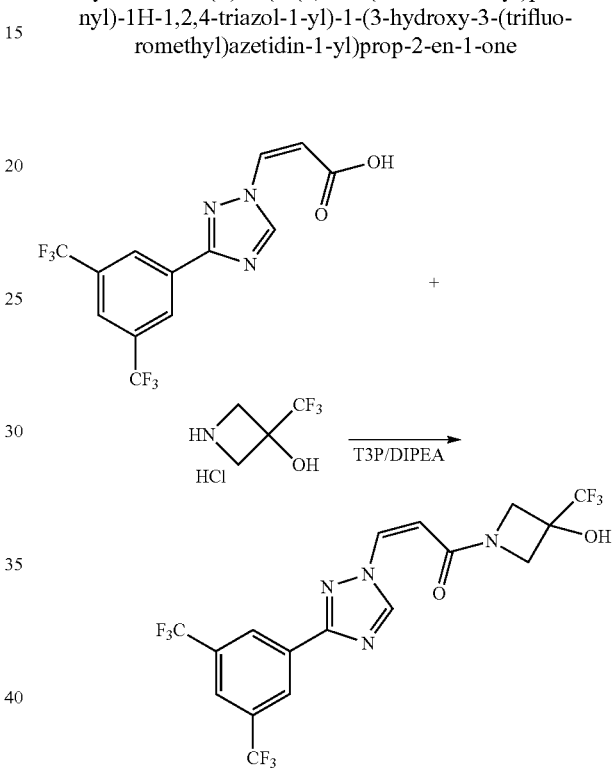

(Z)-3-(3-(3,5-bis(trifluoromethyl)phenyl)-1H-1,2,4-triazol-1-yl)acrylic acid (0.10 g, 1.0 eq.) and 3-(trifluoromethyl)azetidin-3-ol hydrochloride (0.055 g, 1.1 eq.) were dissolved in DCM (3.0 mL) The reaction mixture was cooled to −30° C. where $T_3P$ (0.3 mL, 1.5 eq.) and DIPEA (0.12 mL, 2.5 eq.) were added. The reaction mixture was stirred at −30° C. for 30 min. and diluted by DCM, washed with water. The combined organic layers were dried over sodium sulfate and distilled under reduce pressure (250° C., 20 mmHg) to obtain crude product. The crude product was purified by preparative TLC (70% ethyl acetate-Hexane) to yield to 0.020 g of (Z)-3-(3-(3,5-bis(trifluoromethyl)phenyl)-1H-1,2,4-triazol-1-yl)-1-(3-hydroxy-3-(trifluoromethyl)azetidin-1-yl)prop-2-en-1-one. (Yield: 14.8%). $^1$H NMR (400 MHz, MeOD) δ 9.20 (s, 1H), 8.65 (s, 2H), 8.09 (s, 1H), 7.40-7.43 (d, J=10 Hz, 1H), 5.95-5.93 (d, J=10.6 Hz, 1H), 4.42-4.43 (m, 2H), 4.33-4.05 (m, 2H); LCMS calcd for $C_{17}H_{11}F_9N_4O_2$ $[M+H]^+$474.3. Found: 475.14 Retention time: 2.872 min,

189

Synthesis of
1-benzhydryl-3-(trifluoromethyl)azetidin-3-ol (1A)

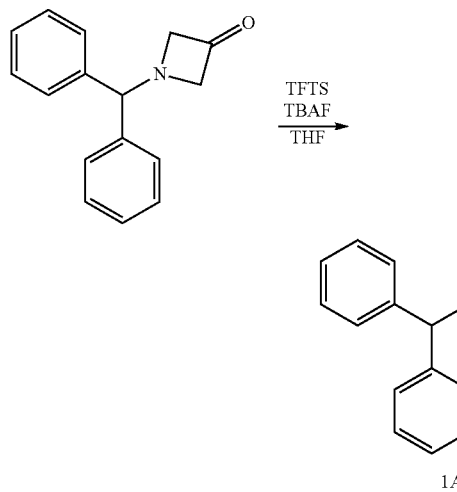

1A

1-Benzhydrylazetidin-3-one (5.0 g, 1.0 eq.) was dissolved in THF (50 mL). Trifluoromethyl trimethylsilane was added at 5-10° C. The reaction mixture was stirred at 10° C. for 10 min. Tetrabutyl ammonium fluoride was then added. The reaction mixture was allowed to warm to room temperature and stirred for 1 h. The reaction mixture was diluted with ethyl acetate, and washed with water and brine. The organic layer was dried over sodium sulfate and concentrated under reduced pressure to give the crude product, which was purified by chromatography (6% ethyl acetate-hexane) to give 3 g of 1-benzhydryl-3-(trifluoromethyl)azetidin-3-ol (Yield: 46.32%).

Synthesis of 3-(trifluoromethyl)azetidin-3-ol hydrochloride (2a)

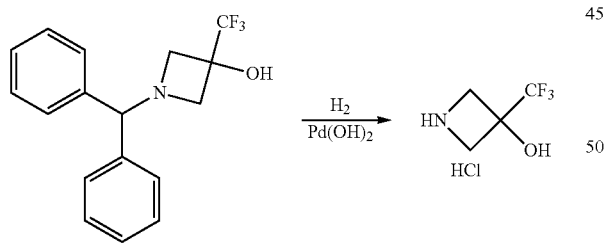

1-Benzhydryl-3-(trifluoromethyl)azetidin-3-ol (0.25 g) was dissolved in ethanol (3 mL). Palladium hydroxide on carbon (0.25 g) was added and hydrogen gas was purged in to the reaction mixture. The reaction mixture was maintained at 25-30° C. for 2 h. The solid formed was removed by filtration and ethanolic HCl was added to the filtrate at 0° C. and further stirred for 30 min. The reaction mixture was concentrated under reduced pressure to give an oily residue, which was triturated with ether to give 3-(trifluoromethyl) azetidin-3-ol hydrochloride as solid product, which was used in the next step without further purification. $^1$H-NMR (400 MHz, MeOD) δ=4.39-4.43 (d, 2H), 4.13-4.16 (d, 2H).

190

Example 52

Synthesis of (Z)-tert-butyl 6-(3-(3-(3,5-bis(trifluoromethyl)phenyl)-1H-1,2,4-triazol-1-yl)acryloyl)-2,6-diazaspiro[3.3]heptane-2-carboxylate

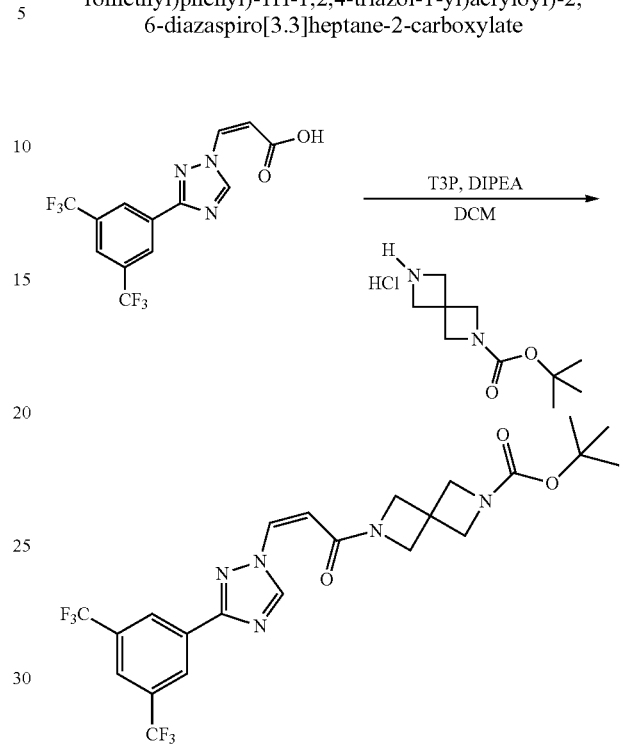

(Z)-3-(3-(3,5-bis(trifluoromethyl)phenyl)-1H-1,2,4-triazol-1-yl)acrylic acid (0.50 g, 1.0 eq.) was dissolved in DCM (5 mL). tert-Butyl 2,6-diazaspiro[3.3]heptane-2-carboxylate hydrochloride (0.40 g, 1.2 eq.) was added and the reaction mixture was cooled to −70° C. T3P (1.02 mL, 1.2 eq.) was added dropwise followed by DIPEA (0.73 mL, 3.0 eq.). The reaction mixture was quenched with 50 mL of water and extracted by DCM. The organic layer was concentrated under reduced pressure (35° C., 20 mmHg) to afford 0.603 g of crude product which was purified by chromatography (1% Methanol in DCM) to give 0.350 g of (Z)-tert-butyl 6-(3-(3-(3,5-bis(trifluoromethyephenyl)-1H-1,2,4-triazol-1-yl)acryloyl)-2,6-diazaspiro[3.3]heptane-2-carboxylate. (Yield 46.29%).

Synthesis of (Z)-3-(3-(3,5-bis(trifluoromethyl)phenyl)-1H-1,2,4-triazol-1-yl)-1-(2,6-diazaspiro[3.3]heptan-2-yl)prop-2-en-1-one 2,2,2-trifluoroacetate

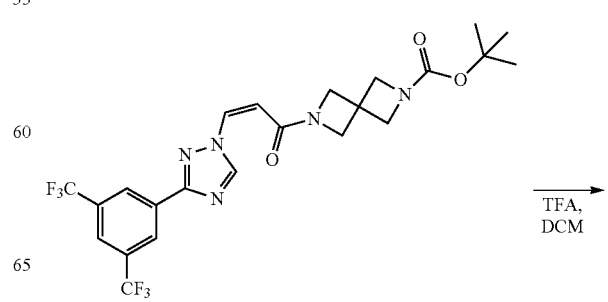

-continued

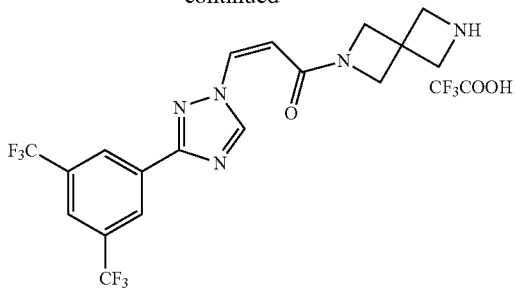

Chemical Formula: $C_{18}H_{15}F_6N_5O$
Molecular Weight: 431.34

(Z)-tert-butyl 6-(3-(3-(3,5-bis(trifluoromethyl)phenyl)-1H-1,2,4-triazol-1-yl)acryloyl)-2,6-diazaspiro[3.3]heptane-2-carboxylate (0.13 g) was dissolved in DCM (1.5 mL). The reaction mixture was cooled to 0° C. and CF$_3$COOH (1.5 mL) was added. The reaction mixture was allowed to warm to room temp. where it was stirred for 4 h. The reaction mixture was concentrated under reduced pressure (35° C., 20 mmHg) to afford 0.100 g of (Z)-3-(3-(3,5-bis(trifluoromethyl)phenyl)-1H-1,2,4-triazol-1-yl)-1-(2,6-diazaspiro[3.3]heptan-2-yl)prop-2-en-1-one 2,2,2-trifluoroacetate (Yield 95.23%). $^1$H NMR (400 MHz, DMSO) δ 9.49 (s, 1H), 8.52-8.5 (m, 3H), 8.32 (s, 1H), 7.44-7.42 (d, 1H, J=10.4 Hz), 5.97-5.94 (d, J=10.4 Hz, 1H), 4.37-3.93 (m, 8H); LCMS calcd for $C_{18}H_{16}F_6N_5O$ [M+H]$^+$ 432.34. found 432.29 at retention time 2.256 min.

Example 53

Synthesis of (Z)-3-(3-(3,5-bis(trifluoromethyl)phenyl)-1H-1,2,4-triazol-1-yl)-1-(3-hydroxyazetidine-1-yl)prop-2-en-1-one

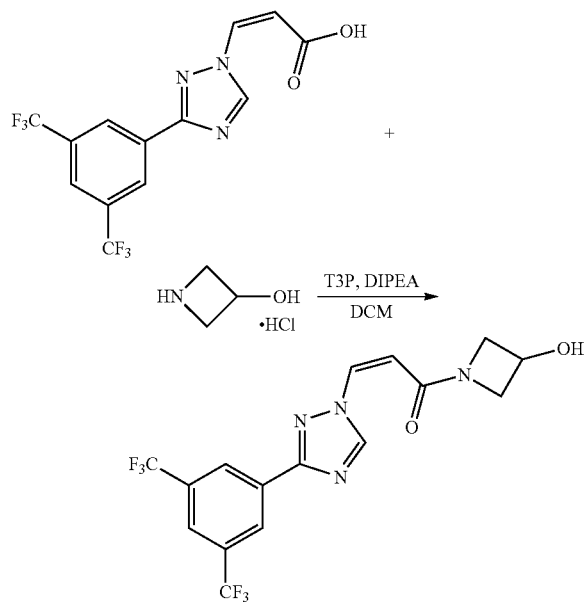

(Z)-3-(3-(3,5-bis(trifluoromethyephenyl)-1H-1,2,4-triazol-1-yl)acrylic acid (0.2 g, 1.0 eq.) was dissolved in DCM (20 mL) The reaction mixture was cooled to −60° C. where azetidin-3-ol hydrochloride (0.075 g, 1.2 eq), T3P (50% in EtOAc) (0.4 mL, 1.2 eq) followed by DIPEA (0.2 mL, 2 eq) were added dropwise. The clear reaction mixture was stirred at −60° C. for 45 min. The reaction mixture was concentrated under reduced pressure (25° C., 20 mm Hg) to afford the crude product, which was purified by chromatography (5% Methanol in DCM with ammonia) to obtain 30 mg of (Z)-3-(3-(3,5-bis(trifluoromethyl)phenyl)-1H-1,2,4-triazol-1-yl)-1-(3-hydroxyazetidine-1-yl)prop-2-en-1-one Yield (13%). $^1$H NMR (400 MHz, DMSO) δ=9.4 (s, 1H), 8.56 (s, 2H), 8.29 (s, 1H), 7.48-7.40 (d, J=10.4 Hz, 1H), 5.95-5.97 (d, J=10 Hz, 1H), 5.77-5.79 (d, J=5.6, 1H, D$_2$O exchangeable), 4.47-4.48 (d, J=5.6, 1H), 4.25-4.29 (t, 1H), 4.15-4.19 (m, 1H), 3.8-3.84 (m, 1H), 3.70-3.73 (m, 1H); LCMS calcd. for $C_{16}H_{13}F_6N4O_2$ [M+H]$^+$ 407.28. found: 407.14, at 2.462 min retention time.

Example 54

Synthesis of (Z)-1-(3-(3-(3,5-bis(trifluoromethyl)phenyl)-1H-1,2,4-triazol-1-yl)acryloyl)azetidine-3-carbonitrile

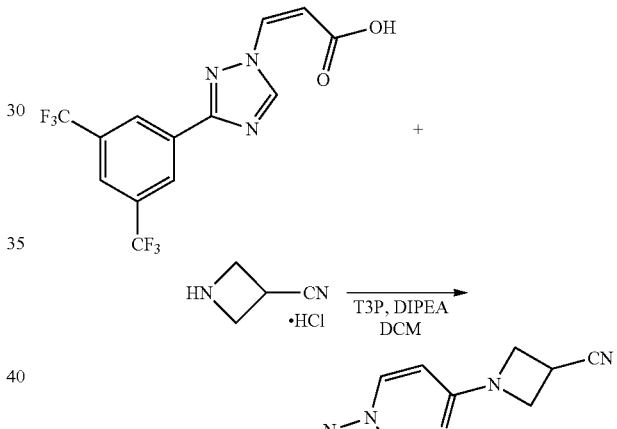

(Z)-3-(3-(3,5-bis(trifluoromethyl)phenyl)-1H-1,2,4-triazol-1-yl)acrylic acid (0.2 g, 1.0 eq.) was dissolved in DCM (20 mL). The reaction mixture was cooled to −60° C. where azetidine-3-carbonitrile hydrochloride (0.08 g, 1.2 eq), T3P (50% in EtOAc) (0.4 mL, 1.2 eq) followed by DIPEA (0.2 mL, 2 eq) were added dropwise. The clear reaction mixture was stirred at −60° C. for 45 min. The reaction mixture was concentrated under reduced pressure (25° C., 20 mm Hg) to afford the crude product, which was purified by chromatography (3-5% Methanol in DCM). to obtain (Z)-1-(3-(3-(3,5-bis(trifluoromethyl)phenyl)-1H-1,2,4-triazol-1-yl)acryloyl)azetidine-3-carbonitrile (0.14 g, 60% yield). $^1$H NMR (400 MHz, DMSO) δ=9.36 (s, 1H), 8.54 (s, 2H), 8.30 (s, 1H), 7.45-7.43 (d, J=10 Hz, 1H), 5.95-5.92 (d, J=10 Hz, 1H), 4.39-4.37 (t, 1H), 4.29-4.11 (m, 3H), 3.84-3.82 (m, 1H); LCMS calcd. for $C_{17}H_{12}F_6N_5O$ [M+H]$^+$ 416.29. found 416.14, at 2.64 min retention time

Example 55

Synthesis of methyl azetidine-3-carboxylate hydrochloride

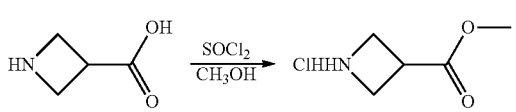

A suspension of azetidine-3-carboxylic acid (1 g, 9.8 mmol) in MeOH (10 mL) was cooled to 5° C. Thionyl chloride (5.83 g, 49.45 mmol) was added dropwise maintaining the reaction temperature below 30° C. The mixture was then heated to 65° C. for 10-12 h. The reaction mixture was concentrated under reduced pressure to yield methyl azetidine-3-carboxylate hydrochloride as viscous brown oil (1.3 g, 90%), which was used without further purification.

Synthesis of (Z)-methyl 1-(3-(3-(3,5-bis(trifluoromethyl)phenyl)-1H-1,2,4-triazol-1-yl)acryloyl)azetidine-3-carboxylate

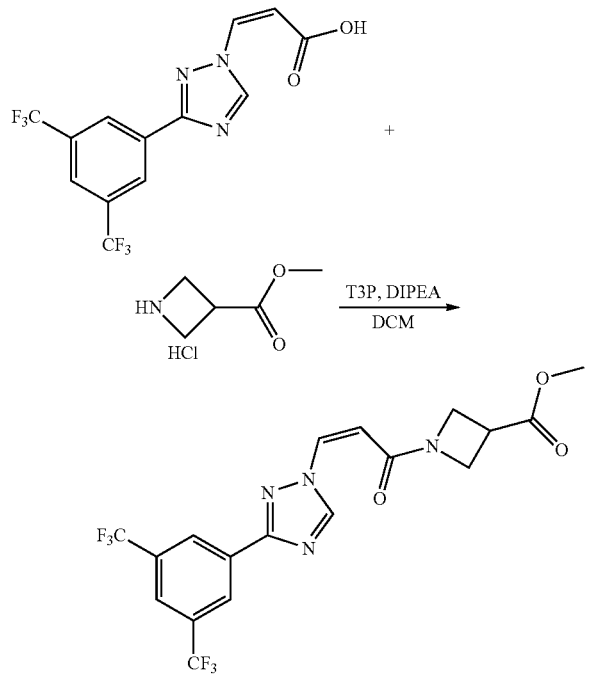

(Z)-3-(3-(3,5-bis(trifluoromethyl)phenyl)-1H-1,2,4-triazol-1-yl)acrylic acid (0.5 g, 1.0 eq.) was dissolved in DCM (20 mL). The reaction mixture was cooled to −60° C. where methylazetidine-3-carboxylate hydrochloride (0.25 g, 1.2 eq.), T3P (50% in EtOAc) (1.0 mL, 1.2 eq.) followed by DIPEA (0.48 mL, 2 eq.) were added. The clear reaction mixture was stirred at −60° C. for 45 min. The reaction mixture was concentrated under reduced pressure (25° C., 20 mm Hg) to afford the crude product, which was purified by chromatography (2-3% Methanol in DCM) to give (Z)-methyl 1-(3-(3-(3,5-bis(trifluoromethyl)phenyl)-1H-1,2,4-triazol-1-yl)acryloyl)azetidine-3-carboxylate (0.15 g, 24% yield).

Synthesis of (Z)-1-(3-(3-(3,5-bis(trifluoromethyl)phenyl)-1H-1,2,4-triazol-1-yl)acryloyl)azetidine-3-carboxylic acid

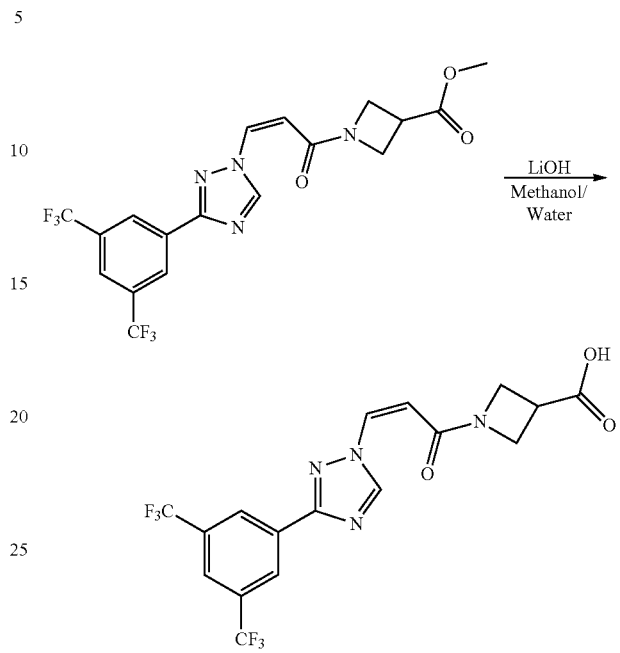

(Z)-methyl 1-(3-(3-(3,5-bis(trifluoromethyl)phenyl)-1H-1,2,4-triazol-1-yl)acryloyl)azetidine-3-carboxylate (0.1 g, 1.0 eq.) was dissolved in methanol:water (10 mL, 1:1). LiOH (0.010 g, 1.0 eq.) was added. The reaction mixture was stirred at room temperature for 1-2 h. The reaction mixture was quenched with 10 mL water and acidified with dilute HCl until pH=2-3. The aqueous layer was extracted with ethyl acetate (10 mL×3). The organic layer was washed with brine, dried over sodium sulphate and concentrated under reduced pressure to afford 0.060 g of (Z)-1-(3-(3-(3,5-bis(trifluoromethyl)phenyl)-1H-1,2,4-triazol-1-yl)acryloyl)azetidine-3-carboxylic acid (62.5% yield). $^1$H NMR (400 MHz, DMSO) δ=9.38 (s, 1H), 8.54 (s, 2H), 8.29 (s, 1H), 7.40-7.42 (d, J=10.4 Hz, 1H), 5.93-5.96 (d, J=10.4 Hz, 1H), 4.23-4.27 (m, 2H), 4.12-4.16 (m, 3H). LCMS calcd. for $C_{17}H_{13}F_6N_4O_3$ [M+H]$^+$: 435.29. Found: 435.14, at 2.55 min retention time.

Example 56

Synthesis of (Z)-tert-butyl 6-(3-(3-(3,5-bis(trifluoromethyl)phenyl)-1H-1,2,4-triazol-1-yl)acrylamido)-3-azabicyclo[3.1.0]hexane-3-carboxylate

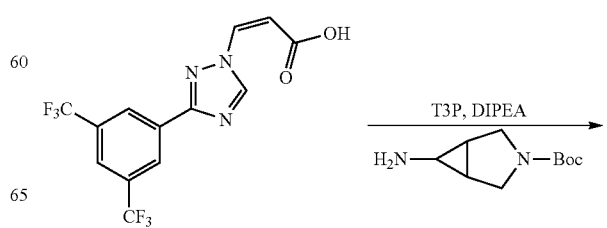

-continued

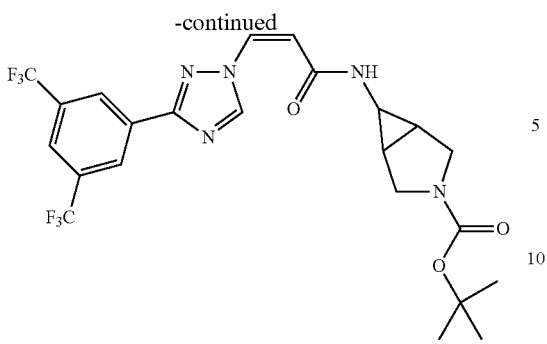

(Z)-3-(3-(3,5-bis(trifluoromethyl)phenyl)-1H-1,2,4-triazol-1-yl)acrylic acid (0.250 g, 1.0 eq.) was dissolved in DCM (12 mL). tert-butyl 6-amino-3-azabicyclo[3.1.0]hexane-3-carboxylate (0.17 g, 1.2 eq.) was added and the reaction mixture was cooled to −60° C. $T_3P$ (0.51 mL, 1.2 eq.), followed by DIPEA (0.24 mL, 2.0 eq.) was then added at the same temperature. The reaction mixture was stirred for 30 min. and transferred into water (50 mL) and extracted with DCM (2×50 mL). The combined organic layer was washed with brine (50 mL), dried over anhydrous $MgSO_4$, filtered, and concentrated under reduced pressure (25° C., 20 mmHg) to afford crude product, which was purified by chromatography (0-5% MeOH in DCM) to give (Z)-tert-butyl 6-(3-(3-(3,5-bis(trifluoromethyl)phenyl)-1H-1,2,4-triazol-1-yl)acrylamido)-3-azabicyclo[3.1.0]hexane-3-carboxylate (0.28 g; 66.1% yield).

Synthesis of (Z)—N-(3-azabicyclo[3.1.0]hexan-6-yl)-3-(3-(3,5-bis(trifluoromethyl)phenyl)-1H-1,2,4-triazol-1-yl)acrylamide hydrochloride

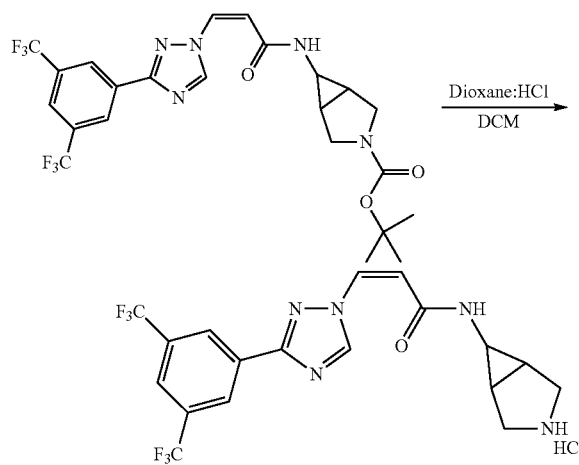

(Z)-tert-butyl 6-(3-(3-(3,5-bis(trifluoromethyl)phenyl)-1H-1,2,4-triazol-1-yl)acrylamido)-3-azabicyclo[3.1.0]hexane-3-carboxylate (0.05 g, 1.0 eq.) was dissolved in DCM (3 mL) and cooled to 0° C. where dioxane:HCl (0.2 mL) was added dropwise and stirred for 30 min. The reaction was allowed to warm to room temperature and stirred for 30 min, concentrated under reduced pressure. The crude product was triturated with ether to afford (Z)—N-(3-azabicyclo[3.1.0]hexan-6-yl)-3-(3-(3,5-bis(trifluoromethyl)phenyl)-1H-1,2,4-triazol-1-yl)acrylamide hydrochloride (0.015 g, 37.5% yield). $^1$H NMR (400 MHz, DMSO) δ, 9.61 (s, 1H), 8.75 (s, 2H), 8.60 (s, 2H), 8.30 (s, 1H), 7.38-7.40 (d, J=10.4 Hz, 1H), 5.87-5.89 (d, J=10.4 Hz, 1H), 2.91 (s, 1H), 2.14 (s, 2H), 1.23 (s, 3H); LCMS for Chemical Formula: $C_{18}H_{16}F_6N_5O$ [M+H]$^+$ 432.34 found 432.19 at retention time 2.302 min.

Example 57

Synthesis of tert-butyl 6-((((9H-fluoren-9-yl)methoxy)carbonyl)amino)-3-azabicyclo[3.1.0]hexane-3-carboxylate

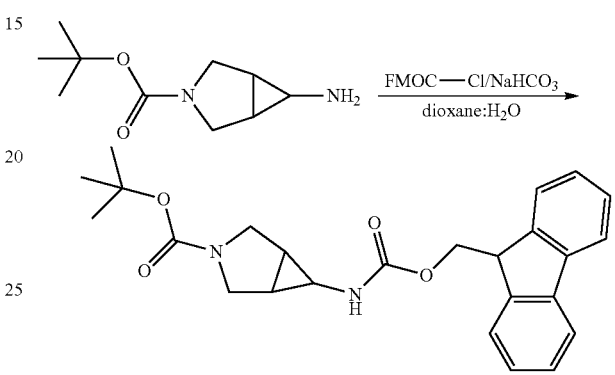

tert-Butyl 6-amino-3-azabicyclo[3.1.0]hexane-3-carboxylate (1 g, 1.0 eq.) was added to a solution of sodium bicarbonate (0.84 g, 2.0 eq.) in water (5 ml) at 5° C. FMOC—Cl (1.56 g, 1.2 eq.) in 1,4-dioxane (10 ml) was added dropwise. The reaction mixture was stirred at room temperature for 3 h, transferred into iced water (50 mL), and extracted with EtOAc (2×100 mL). The combined organic layers was washed with brine (2×50 mL), dried over $Na_2SO_4$, filtered, and concentrated under reduced pressure (25° C., 20 mmHg) to afford 1.9 g of tert-butyl 6-((((9H-fluoren-9-yl)methoxy)carbonyl)amino)-3-azabicyclo[3.1.0]hexane-3-carboxylate (yield 90%).

Synthesis of (9H-fluoren-9-yl)methyl 3-azabicyclo[3.1.0]hexan-6-ylcarbamate

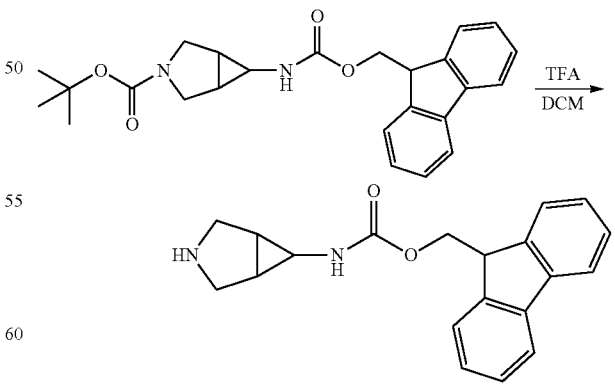

tert-Butyl 6-((((9H-fluoren-9-yl)methoxy)carbonyl)amino)-3-azabicyclo[3.1.0]hexane-3-carboxylate (1.9 g, 1.0 eq.) was dissolved in DCM (20 mL) TFA (1.38 mL, 4 eq) was added dropwise at 0° C. and the reaction mixture was stirred at room temperature for 4 h. The reaction mixture was cooled to 0° C. and neutralized by saturated NaHCO$_3$. The solid precipitated out was collected by filtration to afford 1.0 g of (9H-fluoren-9-yl)methyl 3-azabicyclo[3.1.0]hexan-6-ylcarbamate (69% yield).

Synthesis of (Z)-(9H-fluoren-9-yl)methyl (3-(3-(3-(3,5-bis(trifluoromethyl)phenyl)-1H-1,2,4-triazol-1-yl)acryloyl)-3-azabicyclo[3.1.0]hexan-6-yl)carbamate Synthesis of (Z)-1-(6-amino-3-azabicyclo[3.1.0]hexan-3-yl)-3-(3-(3,5-bis(trifluoromethyl)phenyl)-1H-1,2,4-triazol-1-yl)prop-2-en-1-one

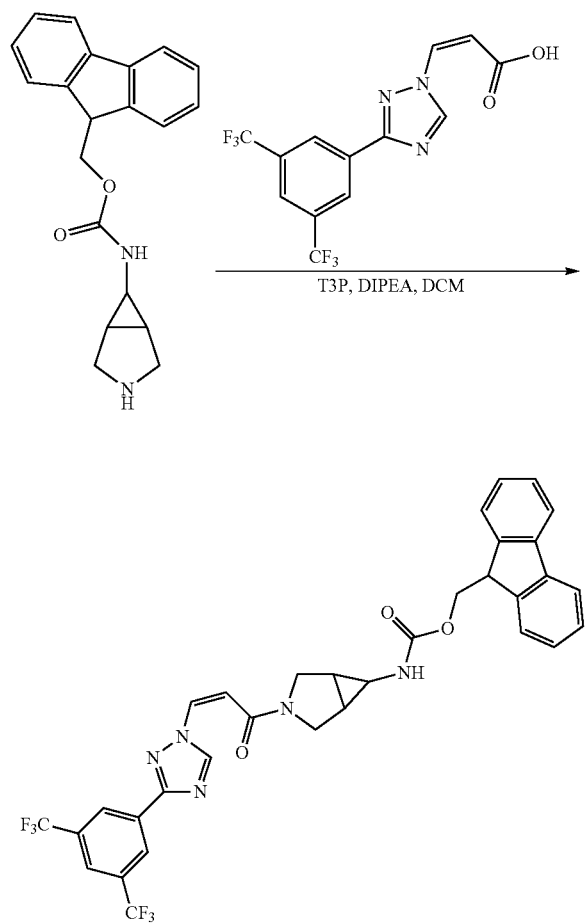

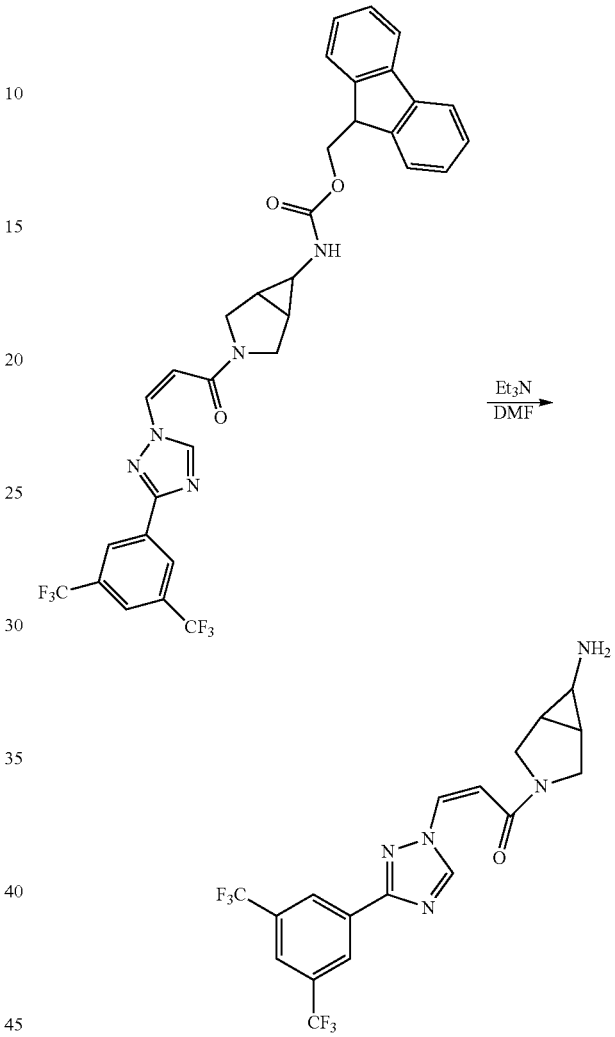

(Z)-3-(3-(3,5-Bis(trifluoromethyl)phenyl)-1H-1,2,4-triazol-1-yl)acrylic acid (1.0 g, 1.0 eq.) was dissolved in DCM (50 mL) and cooled to −60° C. where (9H-fluoren-9-yl)methyl 3-azabicyclo[3.1.0]hexan-6-ylcarbamate (1.09 g, 1.2 eq.), T3P (50% in EtOAc) (2.02 mL, 1.2 eq.) and DIPEA (0.95 mL, 2 eq.) was added. The clear reaction mixture was stirred at −60° C. for 1 h, quenched with water, and extracted with DCM. The organic layer was dried over sodium sulphate, concentrated under reduced pressure (25° C., 20 mm Hg) to afford the crude product, which was purified by chromatography (2% Methanol in DCM) to yield (Z)-(9H-fluoren-9-yl)methyl (3-(3-(3-(3,5-bis(trifluoromethyl)phenyl)-1H-1,2,4-triazol-1-yl)acryloyl)-3-azabicyclo[3.1.0]hexan-6-yl)carbamate (1.26 g, 69% yield).

(Z)-(9H-Fluoren-9-yl)methyl (3-(3-(3-(3,5-bis(trifluoromethyl)phenyl)-1H-1,2,4-triazol-1-yl)acryloyl)-3-azabicyclo[3.1.0]hexan-6-yl)carbamate (0.3 g, 1.0 eq.) in was dissolved in DMF (0.75 ml). TEA (0.75 ml) was added dropwise and the reaction mixture was stirred at room temperature for 4 h, quenched with water (10 mL) and extracted with ethyl acetate (3×50 mL). The combined organic layers was washed with brine (50 mL), dried over Na$_2$SO$_4$, filtered, and concentrated under reduced pressure (25° C., 20 mmHg) to afford 0.2 g of the crude product, which was purified by chromatography (10% Methanol in DCM) to obtain (Z)-1-(6-amino-3-azabicyclo[3.1.0]hexan-3-yl)-3-(3-(3,5-bis(trifluoromethyl)phenyl)-1H-1,2,4-triazol-1-yl)prop-2-en-1-one (0.1 g; 50% yield). $^1$H NMR (400 MHz, DMSO) δ=9.10 (s, 1H), 8.49 (s, 2H), 8.30 (s, 1H), 7.30-7.32 (d, J=10 Hz, 1H), 6.07-6.09 (d, J=10 Hz, 1H), 3.65-3.68 (d, 1H), 3.48 (s, 1H), 3.35-3.45 (m, 1H), 3.29-3.30 (d, 1H), 2.28 (s, 1H), 1.48-1.49 (m, 2H), 1.22 (s, 1H); LCMS calcd. for C$_{18}$H$_{16}$F$_6$N$_5$O [M+H]$^+$ 432.34. found 432.19 at 2.1 min retention time.

Example 58

Synthesis of (Z)-tert-butyl 6-(3-(3-(3,5-bis(trifluoromethyl)phenyl)-1H-1,2,4-triazol-1-yl)acryloyl)-2,6-diazaspiro[3.4]octane-2-carboxylate

Synthesis of (Z)-3-(3-(3,5-bis(trifluoromethyl)phenyl)-1H-1,2,4-triazol-1-yl)-1-(2,6-diazaspiro[3.4]octan-6-yl)prop-2-en-1-one 2,2,2-trifluoroacetate

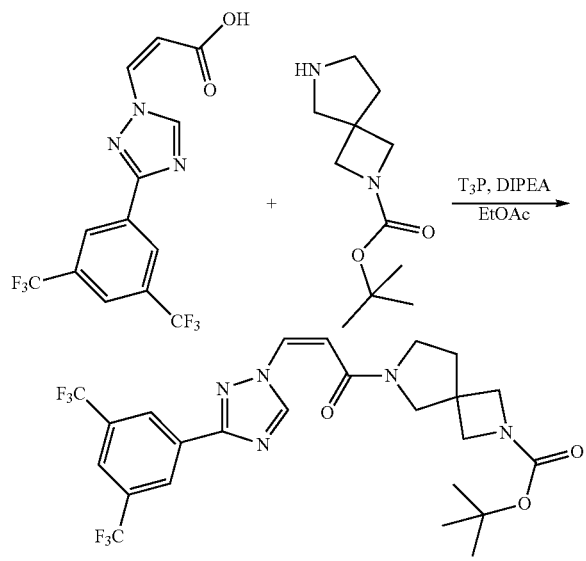

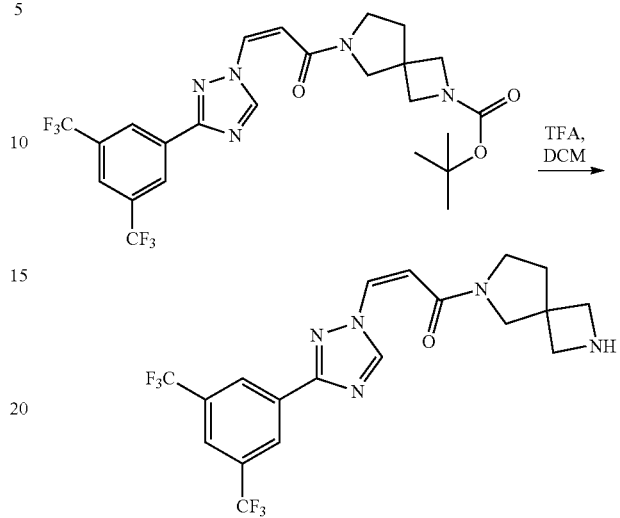

(Z)-3-(3-(3,5-Bis(trifluoromethyl)phenyl)-1H-1,2,4-triazol-1-yl)acrylic acid (0.3 g, 1 eq.) dissolved in ethylacetate (20 mL) and cooled to −70° C. where tert-butyl-2,6-diazaspiro[3.4]octane-2-carboxylate (0.22 g, 1.2 eq.), T3P (50% in EtOAc) (0.61 mL, 1.2 eq.), followed by DIPEA (0.6 mL, 4 eq) were added. The clear reaction mixture was stirred at −60° C. for 1 h, concentrated under reduced pressure (25° C., 20 mm Hg) to afford the crude product, which was purified by chromatography (3-4% Methanol in DCM) to yield (Z)-tert-butyl 6-(3-(3-(3,5-bis(trifluoromethyl)phenyl)-1H-1,2,4-triazol-1-yl)acryloyl)-2,6-diazaspiro[3.4]octane-2-carboxylate (0.2 g; 43% yield).

(Z)-tert-Butyl 6-(3-(3-(3,5-bis(trifluoromethyl)phenyl)-1H-1,2,4-triazol-1-yl)acryloyl)-2,6-diazaspiro[3.4]octane-2-carboxylate (0.05 g) was dissolved in DCM (20 mL), cooled to 0° C. and $CF_3COOH$ (0.5 mL) was added. The reaction mixture was stirred at room temperature for 4 h, concentrated under reduced pressure (35° C., 20 mmHg) to give (Z)-3-(3-(3,5-bis(trifluoromethyl)phenyl)-1H-1,2,4-triazol-1-yl)-1-(2,6-diazaspiro[3.4]octan-6-yl)prop-2-en-1-one 2,2,2-trifluoroacetate (0.03 g, 95% yield). $^1$H NMR (400 MHz, DMSO) δ=9.25 (s, 1H), 8.77 (brs, 1H), 8.59 (s, 2H), 8.30 (s, 1H), 7.39-7.37 (d, 1H, J=10.4 Hz), 6.15-6.12 (d, J=10.4 Hz, 1H), 3.86-3.65 (brs, 4H), 2.14 (s, 2H), 1.49 (s, 2H), 0.85-1.23 (m, 2H); LCMS calcd. for $C_{19}H_{18}F_6N_5O$ [M+H]$^+$ 446.36. found 446.12 at retention time 2.161 min.

Example 59

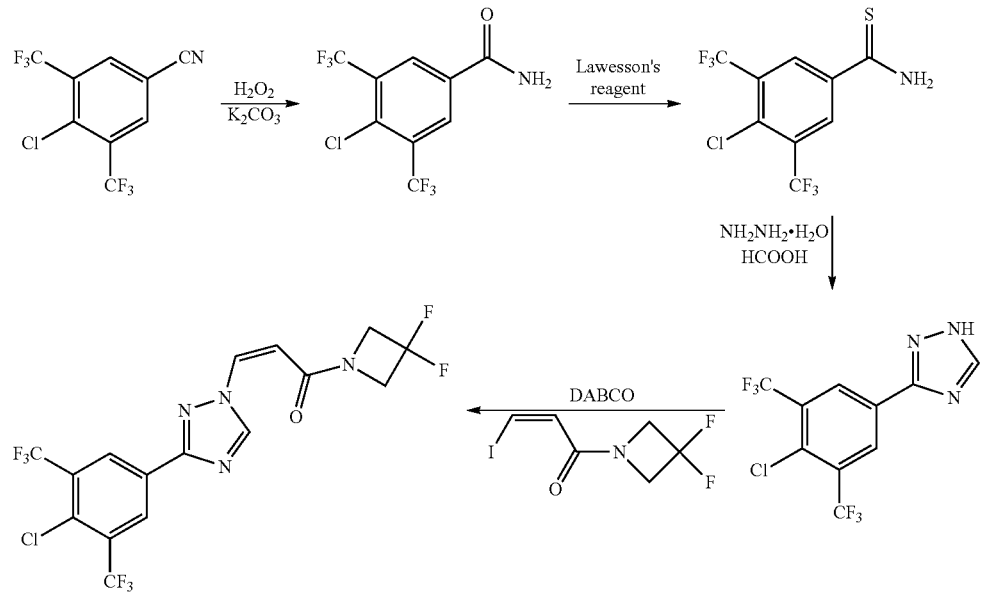

Synthesis of 4-chloro-3,5-bis(trifluoromethyl)benzamide

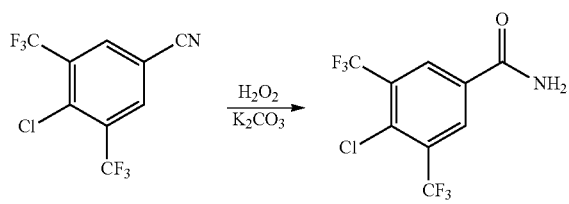

4-Chloro-3,5-bis(trifluoromethyl)benzonitrile (1 g, 1.0 eq.) was dissolved in DMSO (10 mL). K$_2$CO$_3$ (0.55 g, 1.1 eq.) and H$_2$O$_2$ (1 mL) were added to the reaction mixture and stirred at room temperature for 2-3 h, then poured into ice water (20 mL). The precipitate formed was collected by filtration and washed with petroleum ether to afford 1.0 g of crude product (90% yield), which was used without further purification in the next step.

Synthesis of 4-chloro-3,5-bis(trifluoromethyl)benzothioamide

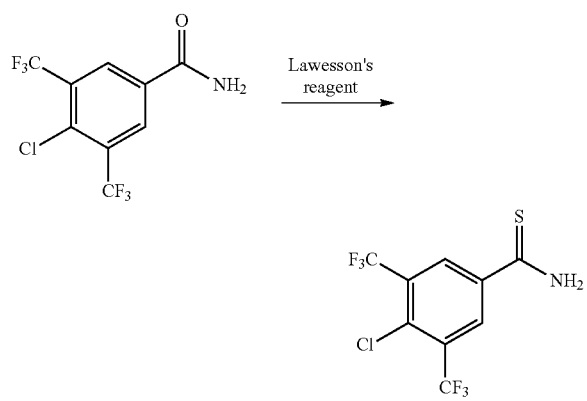

4-Chloro-3,5-bis(trifluoromethyl)benzamide (1.2 g, 1.0 eq.) was dissolved in toluene (20 mL) and Lawesson's reagent (3.32 g, 2.0 eq.) was added. The reaction mixture was stirred at 90° C. for 8 h then filtered. The filtrate was poured into water. The compound was extracted with EtOAc (3×100 mL). The combined organic layers was washed with brine (3×50 mL), dried over Na$_2$SO$_4$, filtered, and concentrated under reduced pressure (25° C., 20 mmHg) to afford 2 g of 4-chloro-3,5-bis(trifluoromethyl)benzothioamide (95% yield), which was used in the next step with no further purification.

Synthesis of 3-(4-chloro-3,5-bis(trifluoromethyl)phenyl)-1H-1,2,4-triazole

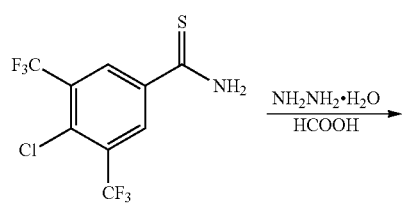

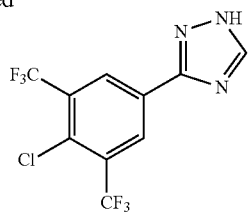

4-Chloro-3,5-bis(trifluoromethyl)benzothioamide (1 g, 1.0 eq.) was dissolved in DMF (10 mL). Hydrazine hydrate (0.32 g, 2.0 eq.) was added and the reaction mixture was stirred at room temperature for 1 h. Formic acid (3 mL) was then added and the reaction mixture was heated to 90° C. for 2-3 h. The reaction mixture was poured into saturated sodium bicarbonate solution slowly maintaining the temperature at 25-30° C. The desired product was extracted with EtOAc (3×50 mL). The combined organic layers was washed with brine (50 mL), dried over Na$_2$SO$_4$, filtered, and concentrated under reduced pressure (25° C., 20 mmHg) to afford 1.5 g of crude product, which was purified by chromatography (40% ethyl acetate in Hexane) to afford 0.150 g of 3-(4-chloro-3,5-bis(trifluoromethyephenyl)-1H-1,2,4-triazole (15% yield)

Synthesis of (Z)-3-(3-(4-chloro-3,5-bis(trifluoromethyl)phenyl)-1H-1,2,4-triazol-1-yl)-1-(3,3-difluoroazetidin-1-yl)prop-2-en-1-one

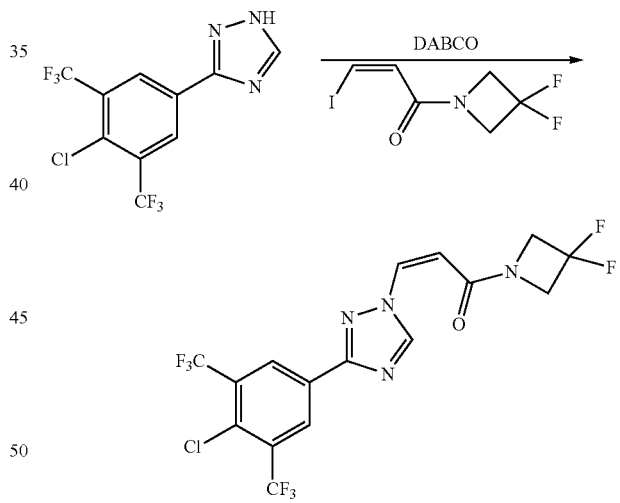

3-(4-Chloro-3,5-bis(trifluoromethyl)phenyl)-1H-1,2,4-triazole (0.1 g, 1.0 eq.) was dissolved in DMF (5 mL). DABCO (0.071 g, 2 eq.) was added and stirred for 30 min. (Z)-1-(3,3-difluoroazetidin-1-yl)-3-iodoprop-2-en-1-one (0.095 g, 1.1 eq.) was then added. The reaction mixture was stirred at room temperature for 5 h and then poured into iced water (50 mL). Product was extracted with EtOAc (3×15 mL). The combined organic layers was washed with brine, (20 mL), dried over Na$_2$SO$_4$, filtered, and concentrated by rotary evaporation (25° C., 20 mmHg) to afford 0.150 g of crude product, which was purified by chromatography to obtain (Z)-3-(3-(4-chloro-3,5-bis(trifluoromethyl)phenyl)-1H-1,2,4-triazol-1-yl)-1-(3,3-difluoroazetidin-1-yl)prop-2-en-1-one (0.004 g, 3% yield). $^1$H NMR (400 MHz, DMSO)

δ=9.32 (s, 1H), 8.46 (s, 1H), 8.32 (s, 1H), 7.47-7.49 (d, J=10.4 Hz, 1H), 6.00-5.04 (d, J=10.4 Hz, 1H), 4.55-4.58 (m, 2H), 4.33-4.36 (m, 2H) LCMS calcd for $C_{16}H_{10}ClF_8N_4O$ [M+H]$^+$: 461.7. Found: 461.14, at 2.99 min retention time.

Example 60

Synthesis of (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one

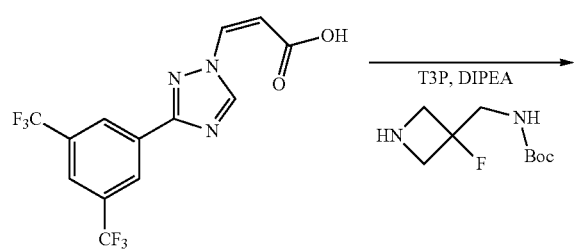

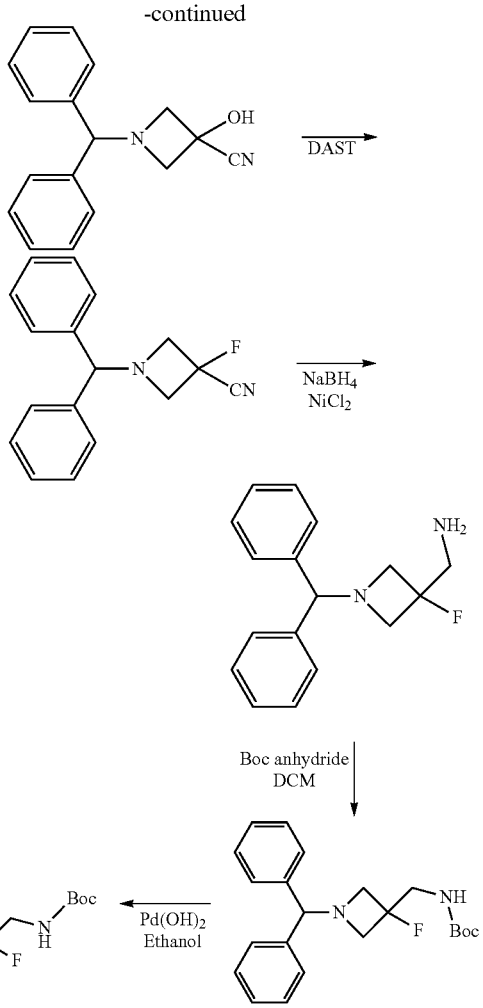

Synthesis of 1-benzhydryl-3-hydroxyazetidine-3-carbonitrile

Synthesis of tert-butyl((3-fluoroazetidin-3-yl)methyl)carbamate

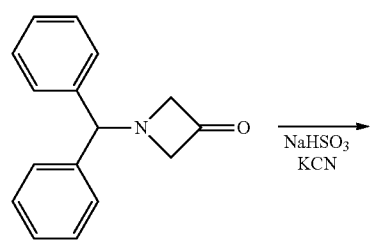

1-Benzhydrylazetidin-3-one (50 g, 210 mmol) was dissolved in methanol (250 mL) KCN (15 g, 316 mmol) and NaHSO$_3$ (32.86 g, 316 mmol) was added at 25° C. and the reaction mixture was stirred at rt for 16 h. The reaction mixture was acidified with dilute HCl and the product was extracted with ethyl acetate (200 mL×3). Organic layers were washed with brine, dried over anhydrous Na₂SO₄ and concentrated under reduced pressure to obtain 45.0 g crude product, which was purified by chromatography to give 10.5 g of 1-benzhydryl-3-hydroxyazetidine-3-carbonitrile (18% yield). ¹H NMR (400 MHz, CDCl₃, ppm) δ=7.5-7.2 (m, 10H); 4.43 (s, 1H); 3.73-3.71 (d, 2H); 3.27-3.24 (t, 2H).

Synthesis of
1-benzhydryl-3-fluoroazetidine-3-carbonitrile

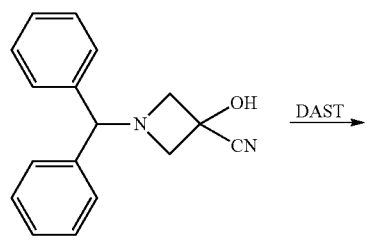

1-Benzhydryl-3-hydroxyazetidine-3-carbonitrile (10.5 g, 39.7 mmol) was dissolved in DCM and cooled to −78° C. DAST (12.80 g, 79.45 mmol) was slowly added and the reaction mixture was allowed to warm to rt where it was further stirred for 5 h. Reaction mixture was cooled to 0° C. and transferred into 500 mL NaHCO₃ solution and extracted with (100 mL×3) DCM. Combined organic layers were washed with brine, dried over Na₂SO₄, and concentrated under reduced pressure to obtain 15.0 g of crude product, which was purified by chromatography to obtain 6.0 g of 1-benzhydryl-3-fluoroazetidine-3-carbonitrile. (57.14% yield). ¹H NMR (400 MHz, CDCl₃, ppm) δ=7.6-7.1 (m, 10H); 4.46 (s, 1H); 3.9-3.6 (m, 2H); 3.5-3.2 (m, 2H).

Synthesis of
(1-benzhydryl-3-fluoroazetidin-3-yl)methanamine

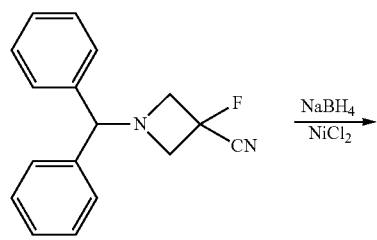

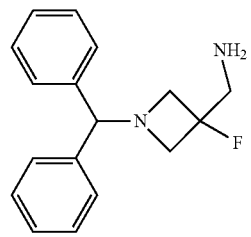

1-Benzhydryl-3-fluoroazetidine-3-carbonitrile (0.5 g, 1.88 mmol) was dissolved in methanol (25 mL). NaBH₄ (0.49 g, 13.14 mmol) and NiCl₂ (0.044 g, 0.34 mmol) were added at 0° C. and the reaction mixture was stirred at rt for 14 h. The solids formed were removed by filtration and the filtrate was concentrated under reduced pressure. The crude product was purified by chromatography (0-5% methanol-DCM) to give 0.15 g of (1-benzhydryl-3-fluoroazetidin-3-yl)methanamine (30% yield). ¹H NMR (400 MHz, CDCl₃, ppm) δ=7.46-7.19 (m, 10H); 4.48 (s, 1H); 3.38-3.34 (t, 2H); 3.26-3.09 (m, 4H).

Synthesis of tert-butyl (1-benzhydryl-3-fluoroazetidin-3-yl)methylcarbamate

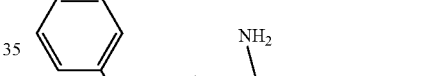

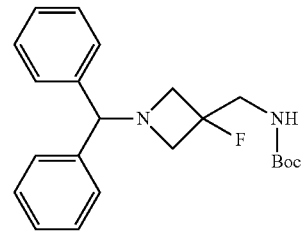

(1-Benzhydryl-3-fluoroazetidin-3-yl)methanamine (0.5 g, 1.85 mmol) was dissolved in DCM (20 mL) and Boc anhydride (0.20 g, 0.924 mmol) was added at 0° C. The reaction mixture was allowed to warm to rt, at which temperature it was stirred for 4 h. The reaction mixture was concentrated under reduced pressure to afford 0.5 g of tert-butyl (1-benzhydryl-3-fluoroazetidin-3-yl)methylcarbamate (100% yield). ¹H NMR (400 MHz, CDCl₃, ppm) δ=7.44-7.19 (m, 10H); 5.32 (s, 1H); 4.84 (s, 1H); 3.69-3.61 (m, 2H); 3.38-3.033 (m, 2H); 3.18-3.10 (m, 2H).

Synthesis of tert-butyl (3-fluoroazetidin-3-yl)methylcarbamate

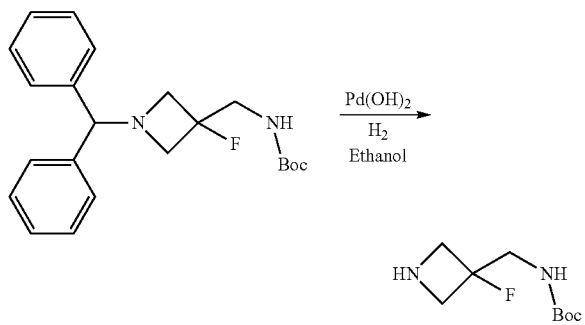

tert-Butyl (1-benzhydryl-3-fluoroazetidin-3-yl)methylcarbamate (0.6 g, 1.35 mmol) was dissolved in ethanol and Pd(OH)$_2$ (0.38 gm, 2.7 mmol) was added. The reaction mixture was stirred at rt for 14 h under H$_2$ atmosphere. The solids were removed by filtration and the filtrate was concentrated under reduced pressure to afford 0.2 g of tert-butyl (3-fluoroazetidin-3-yl)methylcarbamate (66% yield).

Synthesis of (Z)-tert-butyl (1-(3-(3-(3,5-bis(trifluoromethyl)phenyl)-1H-1,2,4-triazol-1-yl)acryloyl)-3-fluoroazetidin-3-yl)methylcarbamate

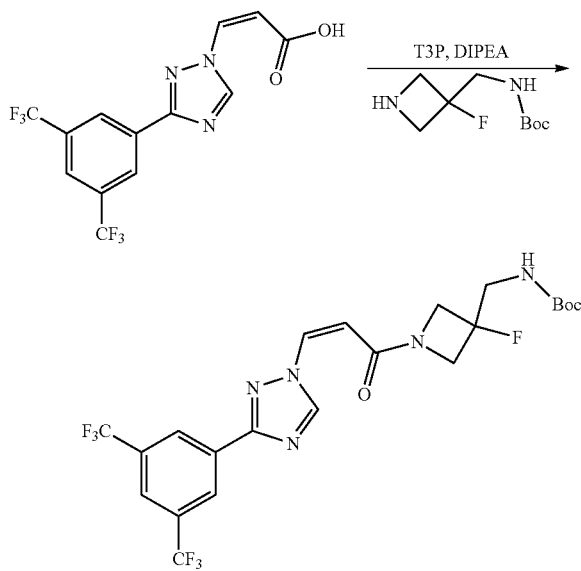

(Z)-3-(3-(3,5-Bis(trifluoromethyl)phenyl)-1H-1,2,4-triazol-1-yl)acrylic acid (0.20 g, 0.56 mmol) was dissolved in DCM (10 mL). The reaction mixture was cooled to −60° C., at which temperature tert-butyl(3-fluoroazetidin-3-yl)methylcarbamate (0.127 g, 0.62 mmol), was added, followed by T$_3$P (50% in EtOAc) (0.434 g, 0.67 mmol). DIPEA (0.144 g, 1.11 mmol) was then introduced slowly. The clear reaction mixture was stirred at −60° C. for a further 45 min. The reaction mixture was concentrated under reduced pressure to obtain crude product, which was purified by column chromatography (0-15% ethyl actetate-hexane) to afford 150 mg of (Z)-tert-butyl(1-(3-(3-(3,5-bis(trifluoromethyl)phenyl)- 1H-1,2,4-triazol-1-yl)acryloyl)-3-fluoroazetidin-3-yl)methylcarbamate (Yield 50%). $^1$H NMR (400 MHz, CDCl$_3$, ppm) δ=9.7 (s, 1H); 8.63 (s, 2H); 7.94 (s, 1H); 7.24-7.21 (d, J=10.8 Hz, 1H); 5.67-5.64 (d, J=10.8, 1H); 4.41-4.16 (m, 4H); 3.76-3.54 (m, 3H).

Synthesis of (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one

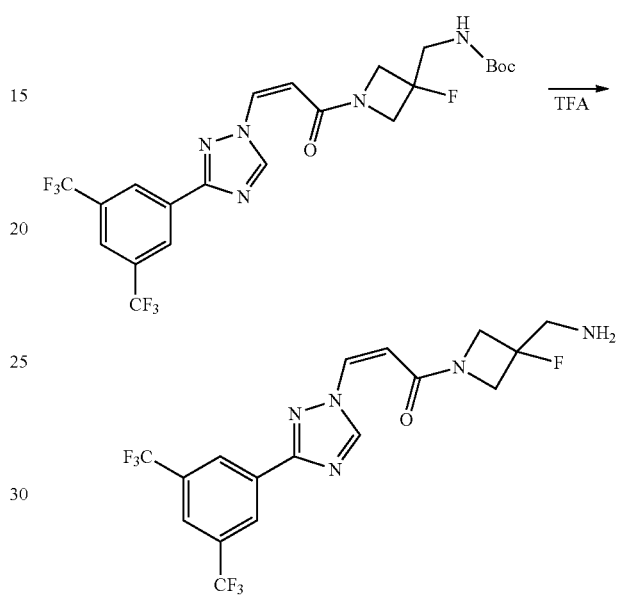

(Z)-tert-Butyl(1-(3-(3-(3,5-bis(trifluoromethyl)phenyl)-1H-1,2,4-triazol-1-yl)acryloyl)-3-fluoroazetidin-3-yl)methylcarbamate (0.15 g, 0.279 mmol) was dissolved in DCM (10 mL) and TFA (0.1 mL) was added at 0° C. The reaction mixture was stirred at rt for 4 h and concentrated under reduced pressure to afford 0.5 g of crude product, which was purified by chromatography (0-5% methanol in DCM) to afford 15 mg of (Z)-1-(3-(aminomethyl)-3-fluoroazetidin-1-yl)-3-(3-(3,5-bis(trifluoromethyl)phenyl)-1H-1,2,4-triazol-1-yl)prop-2-en-1-one (Yield 15%). $^1$H NMR (400 MHz, CDCl$_3$, ppm) δ=9.4 (s, 1H); 8.54 (s, 2H); 8.32 (s, 1H); 8.13 (s, 3H); 7.49-7.46 (d, J=10 Hz, 1H); 6.0-5.97 (d, J=10 Hz, 1H); 4.41-4.06 (m, 4H); 3.49-3.36 (m, 3H). LCMS calcd for C$_{17}$H$_{15}$F$_7$N$_5$O [M+H]$^+$ 438.3. found: 438.19 (retention time 2.298 min).

Example 61

Synthetic scheme for methyl 3-fluoroazetidine-3-carboxylate hydrochloride

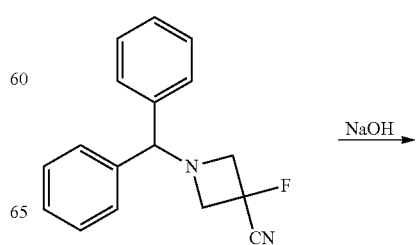

-continued

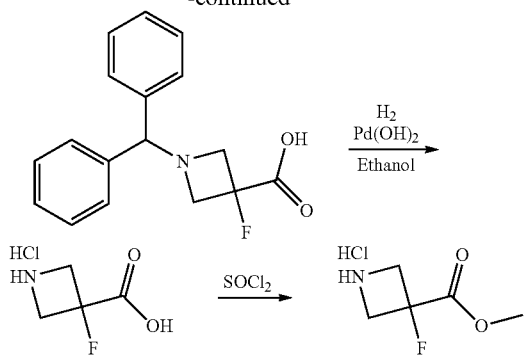

Synthesis of
1-benzhydryl-3-fluoroazetidine-3-carboxylic acid

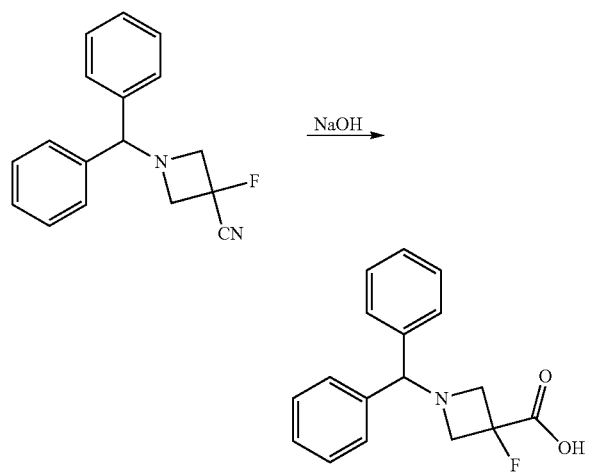

1-Benzhydryl-3-fluoroazetidine-3-carbonitrile (3.5 g, 1.0 eq.) was dissolved in ethanol, and aq. NaOH solution (1N) was added. The reaction mixture was refluxed for 5 h, then was allowed to cool to room temperature, at which temperature, it was acidified with dilute HCl (pH=3) and extracted with ethyl acetate (50 mL×3). The combined organic layers were washed with brine, dried over sodium sulfate and concentrated under reduced pressure to obtain 0.5 g of 1-benzhydryl-3-fluoroazetidine-3-carboxylic acid (13% yield). The product was used in the next step without further purification.

Synthesis of 3-fluoroazetidine-3-carboxylic acid hydrochloride

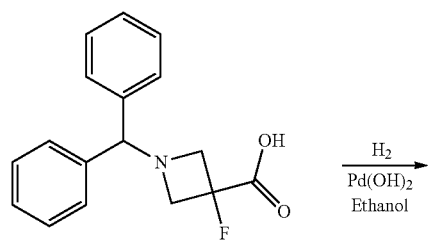

-continued

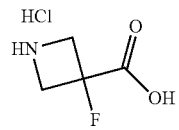

1-Benzhydryl-3-fluoroazetidine-3-carboxylic acid (0.5 g, 1.0 eq.) was dissolved in ethanol. Pd(OH)$_2$ (0.5 g) was added and the reaction mixture was stirred for 14 h at room temperature under H$_2$ atmosphere. The solids were removed by filtration and the filtrate was concentrated under reduced pressure to afford 150 mg of 3-fluoroazetidine-3-carboxylic acid hydrochloride (30% yield). The product was used in the next step without further purification.

Synthesis of methyl 3-fluoroazetidine-3-carboxylate hydrochloride

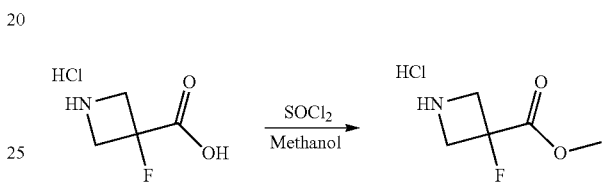

3-Fluoroazetidine-3-carboxylic acid hydrochloride (0.10 g, 8.4 mmol) was dissolved in methanol (2 mL) and cooled to 5° C. Thionyl chloride (0.05 g, 4.2 mmol) was added dropwise. The reaction mixture was heated at 65° C. overnight and concentrated under reduced pressure to afford methyl 3-fluoroazetidine-3-carboxylate hydrochloride. The product was used in the next step without further purification.

Synthesis of (Z)-methyl 1-(3-(3-(3,5-bis(trifluoromethyl)phenyl)-1H-1,2,4-triazol-1-yl)acryloyl)-3-fluoroazetidine-3-carboxylate

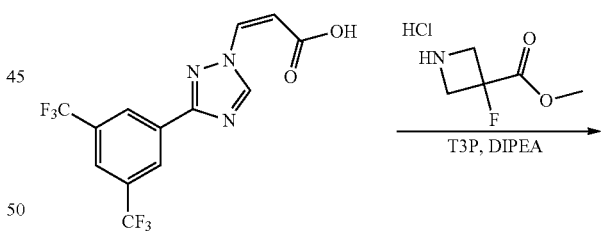

(Z)-3-(3-(3,5-Bis(trifluoromethyl)phenyl)-1H-1,2,4-triazol-1-yl)acrylic acid (0.20 g, 1.0 eq.) was dissolved in DCM (4 mL). The reaction mixture was cooled to −60° C., at which temperature methyl 3-fluoroazetidine-3-carboxylate hydrochloride (0.09 g, 1.2 eq.) and T3P (50% in EtOAc) (0.427 g, 1.2 eq.) were added, followed by DIPEA (0.146 g, 2 eq.). The clear reaction mixture was stirred at −60° C. for 45 min and concentrated under reduced pressure (25° C., 20 mm Hg) to afford the crude product, which was purified by chromatography (20-30% ethyl acetate in hexane) to give (Z)-methyl-1-(3-(3-(3,5-bis(trifluoromethyl)phenyl)-1H-1,2,4-triazol-1-yl)acryloyl)-3-fluoroazetidine-3-carboxylate. (40 mg; 24% yield). $^1$H NMR (400 MHz, CDCL3) δ 9.51 (S, 1H), 8.62 (s, 2H), 7.96 (s, 1H), 7.20-7.18 (d, J=10.8, 1H), 5.70-5.68 (d, J=10.8 Hz, 1H), 4.15-3.82 (m, 4H), 3.82 (s, 3H).

Example 62

Synthesis of (Z)-1-(3-(3-(3,5-bis(trifluoromethyl)phenyl)-1H-1,2,4-triazol-1-yl)acryloyl)-3-fluoroazetidine-3-carboxylic acid

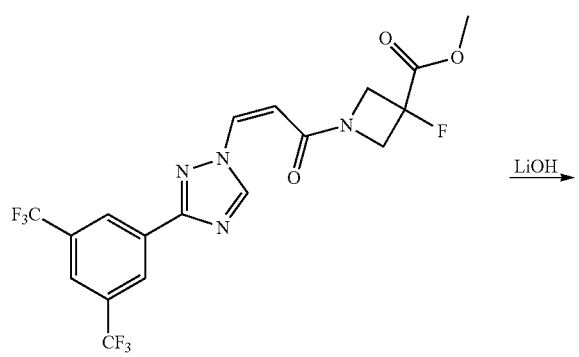

(Z)-Methyl 1-(3-(3-(3,5-bis(trifluoromethyl)phenyl)-1H-1,2,4-triazol-1-yl)acryloyl)-3-fluoroazetidine-3-carboxylate (0.01 g, 1.0 eq.) was dissolved in methanol:water (0.2 mL, 1:1), and LiOH (1.0 mg, 1.0 eq) was added. The reaction mixture was stirred at room temperature for 2 h. The reaction mixture was quenched with 10 mL of water and acidified with dilute HCl to pH 2-3. The aqueous layer was extracted with ethyl acetate (10 mL×3). The combined organic layers were then washed with brine, dried over sodium sulfate and concentrated under reduced pressure to afford 0.002 g of (Z)-1-(3-(3-(3,5-bis(trifluoromethyl)phenyl)-1H-1,2,4-triazol-1-yl)acryloyl)-3-fluoroazetidine-3-carboxylic acid. Yield (20.83%). $^1$H NMR (400 MHz, CDCL3) δ 8.92 (S, 1H), 8.54 (s, 2H), 8.29 (s, 1H), 7.45-7.42 (d, J=10.4, 1H), 6.00-5.98 (d, J=10.4 Hz, 1H), 3.73 (m, 4H).

Example 63

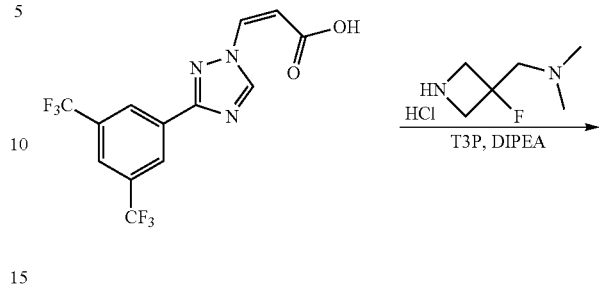

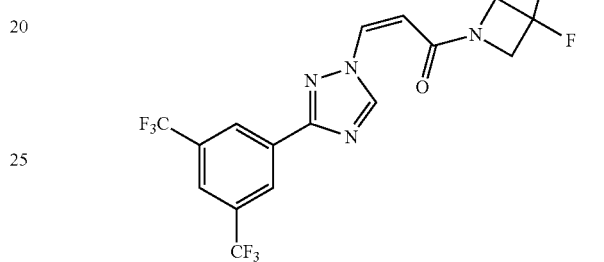

Synthesis of 1-(1-benzhydryl-3-fluoroazetidin-3-yl)-N,N-dimethylmethanamine

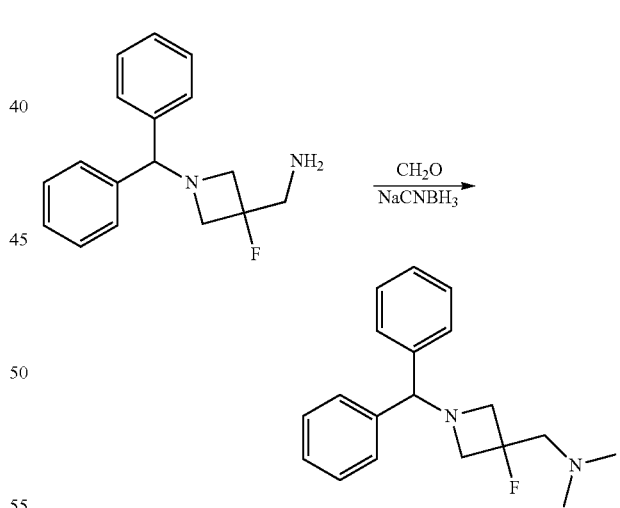

(1-Benzhydryl-3-fluoroazetidin-3-yl)methanamine (0.5 g, 1.0 eq.) was dissolved in methanol and HCHO (0.138 g, 2.5 eq.) and NaCNBH$_3$ (0.47 g, 4.0 eq.) were added at 0° C. The reaction mixture was stirred for 14 h at room temperature, then quenched with aqueous ammonium chloride solution and extracted with DCM. The organic layer was washed with brine, dried over sodium sulfate, and concentrated under reduced pressure to afford 150 mg of 1-(1-benzhydryl-3-fluoroazetidin-3-yl)-N,N-dimethylmethanamine (100%), which was used in the next step without further purification.

Synthesis of 1-(3-fluoroazetidin-3-yl)-N,N-dimethylmethanamine

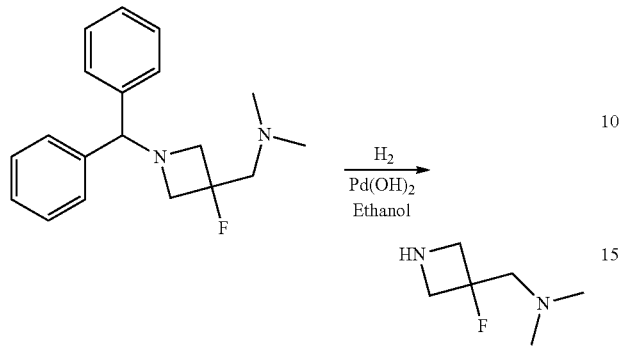

1-(1-Benzhydryl-3-fluoroazetidin-3-yl)-N,N-dimethylmethanamine (0.6 g, 1.0 eq.) was dissolved in ethanol. Pd(OH)$_2$ (0.6 g) was added. The reaction mixture was stirred for 14 h at room temperature under H$_2$ atmosphere. The solids were removed by filtration and the filtrate was concentrated under reduced pressure to afford 300 mg of 1-(3-fluoroazetidin-3-yl)-N,N-dimethylmethanamine (68% yield), which was used in the next step without further purification.

Synthesis of (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one

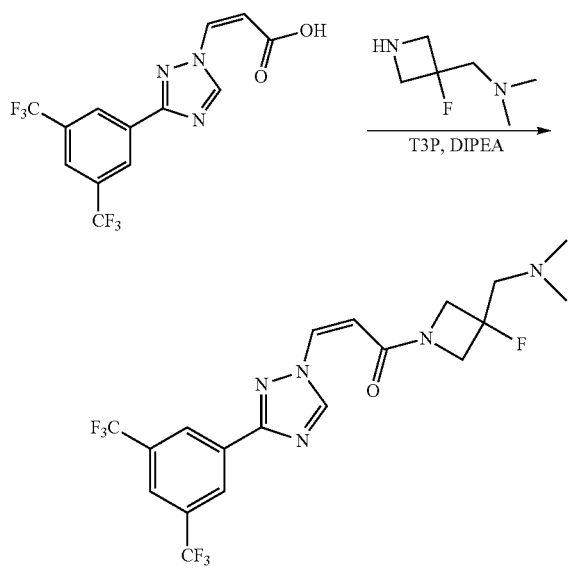

(Z)-3-(3-(3,5-Bis(trifluoromethyl)phenyl)-1H-1,2,4-triazol-1-yl)acrylic acid (0.50 g, 1.0 eq.) was dissolved in DCM (10 mL). The reaction mixture was cooled to −60° C., at which temperature 1-(3-fluoroazetidin-3-yl)-N,N-dimethylmethanamine (0.22 g, 1.2 eq) and T3P (50% in EtOAc) (1.08 g, 1.2 eq.) were added, followed by DIPEA (0.36 g, 2 eq.). The clear reaction mixture was stirred at −60° C. for 45 min. The reaction mixture was concentrated under reduced pressure (25° C., 20 mm Hg) to afford the crude product, which was purified by chromatography to give 12 mg of (Z)-3-(3-(3,5-bis(trifluoromethyl)phenyl)-1H-1,2,4-triazol-1-yl)-1-(3-((dimethylamino)methyl)-3-fluoroazetidin-1-yl)prop-2-en-1-one (3% yield). $^1$H NMR (400 MHz, CDCl$_3$) δ=9.75 (s, 1H), 8.62 (s, 2H), 7.94 (s, 1H), 7.24-7.21 (d, J=10.8 Hz, 1H), 5.69-5.66 (d, J=10.8 Hz, 1H), 4.37-4.25 (m, 2H), 4.22-4.15 (m, 2H), 2.82-2.76 (d, 2H), 2.35 (s, 2.35, 1H); LCMS for C$_{19}$H$_{19}$F$_7$N$_5$O [M+H]$^+$ 466.4 found 466.3 at retention time 2.263 min

Example 64

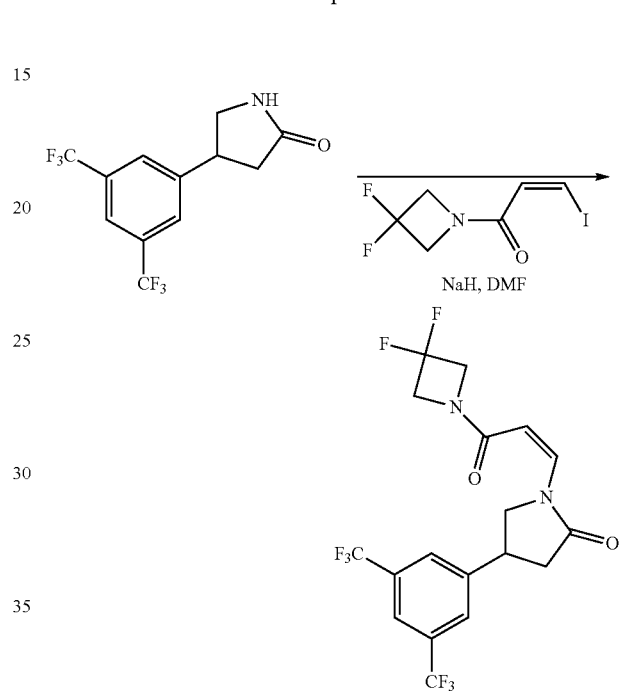

THF (5 mL) and sodium hydride (0.08 g, 2.02 mmol) were added under nitrogen atmosphere to a 25-mL sealed tube equipped with septum. The reaction mixture was cooled to 0° C. and 4-(3,5-bis(trifluoromethyl)phenyl)pyrrolidin-2-one (0.3 g, 1.01 mmol) was added portionwise, maintaining a temperature below 0° C. The reaction mixture was refluxed for 3.5 h and later cooled to −10° C. To this reaction mixture, (Z)-isopropyl 3-iodoacrylate (0.33 g, 1.21 mmol) was added dropwise. Reaction mixture was further stirred at −10° C. for another 30 min. The reaction mixture was transferred into water (50 mL) and extracted with EtOAc (2×50 mL). The combined organic layers were washed with saturated brine solution (50 mL), dried over anhydrous Na$_2$SO$_4$, filtered, and concentrated under reduced pressure to obtain crude compound. The crude material was purified by column chromatography (silica 60/120, EtOAc-hexane gradient) and again purified by preparative TLC using 60% EtOAc-hexane as mobile phase to afford 0.015 g (Z)-4-(3,5-bis(trifluoromethyl)phenyl)-1-(3-(3,3-difluoroazetidin-1-yl)-3-oxoprop-1-enyl)pyrrolidin-2-one (Yield 3.3%). $^1$H NMR (400 MHz, CDCl$_3$) δ, 7.83 (s, 1H); 7.73 (s, 2H); 7.16-7.19 (d, J=10.4 Hz, 1H); 5.08-5.11 (d, J=10.4 Hz, 1H); 4.43-4.51 (m, 3H); 4.30-4.36 (t, J=12 Hz, 2H); 3.96-4.01 (m, 1H); 3.75-3.79 (m, 1H); 2.95-3.02 (m, 1H); 2.68-2.75 (m, 1H); LCMS for C$_{18}$H$_{15}$F$_8$N$_2$O$_2$ [M+1]$^+$ 442.3 found 443.14 at RT 2.932 min.

Example 65

Synthesis of (Z)-3-(2-(3,5-bis(trifluoromethyl)phenyl)-1H-pyrrol-1-yl)-1-(3,3-difluoroazetidin-1-yl)prop-2-en-1-one

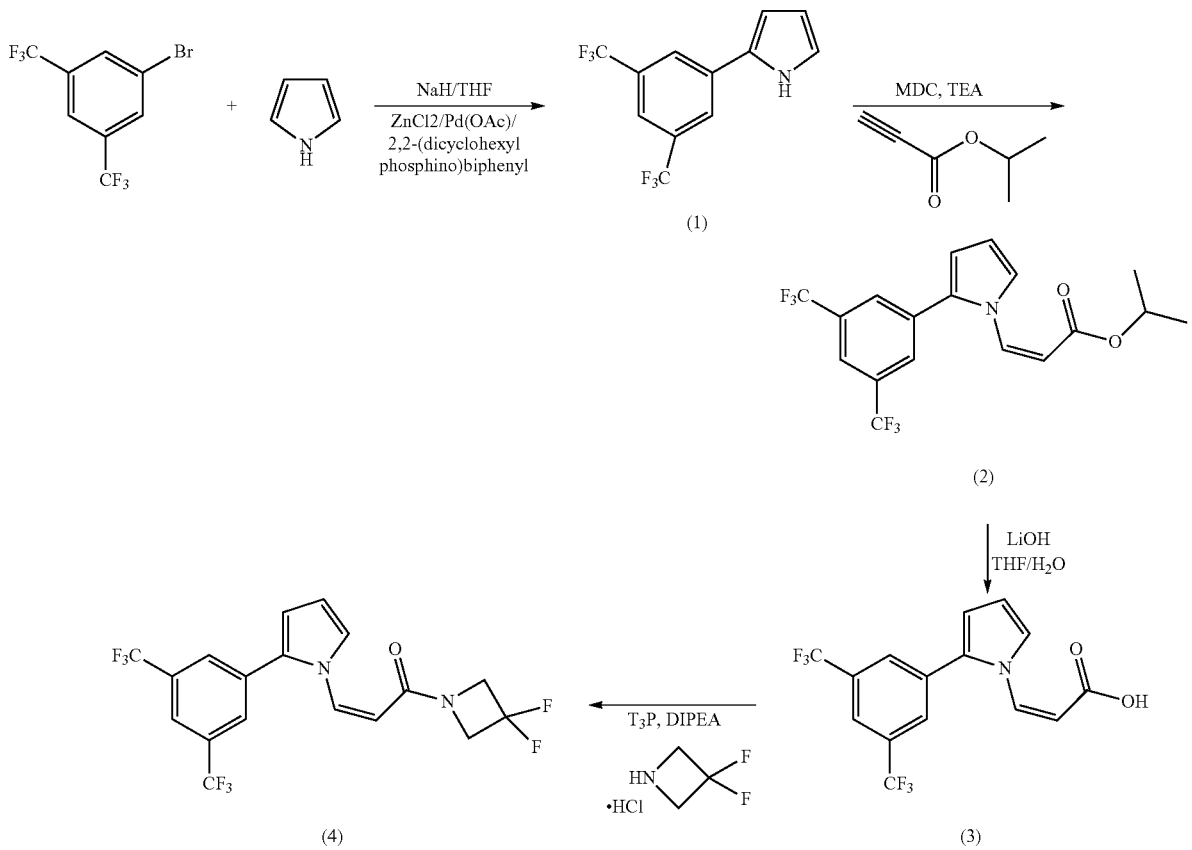

Synthesis of 2-(3,5-bis(trifluoromethyl)phenyl)-1H-pyrrole

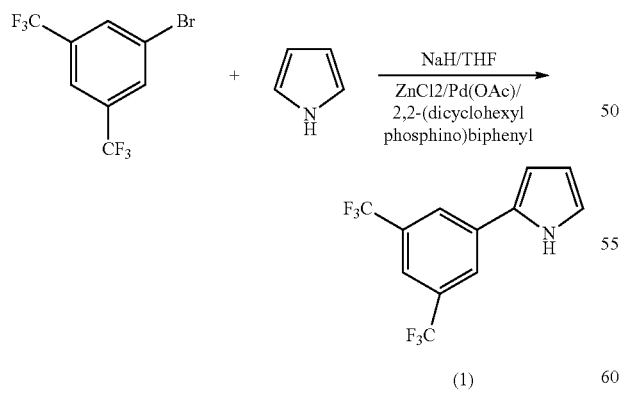

A 500 mL 3-neck round-bottomed flask was charged with a solution of pyrrole (5.15 g, 76.79 mmol) in THF (120 mL) at rt and cooled to 0° C. NaH(2.21 g, 92.12 mmol) was added portionwise and the reaction mixture was stirred at 0° C. for 1 h. To this reaction mixture, ZnCl₂ (10.4 g, 77 mmol) was added and stirred at 0° C. for 1 h. 1-Bromo-3,5-bis(trifluoromethyl)benzene (5.0 g, 17.0 mmol) was added and reaction was properly degassed for 10 min and palladium diacetate (0.172 g, 0.76 mmol) and 2-(dicyclohexyl phosphino)biphenyl (0.269 g, 0.76 mmol) were added and reaction was refluxed for 48 h. Reaction mixture was transferred into water (100 mL) and extracted with EtOAc (3×300 mL) and the combined organic layers were washed with saturated brine solution (3×150 mL), dried over MgSO₄, filtered, and concentrated under reduced pressure to afford 7 g of crude 2-(3,5-bis(trifluoromethyl)phenyl)-1H-pyrrole which was purified by chromatography to afford 0.8 g of pure product. LCMS calcd for: $C_{12}H_6F_6N$ [M−H]⁻ 278.18. found 278.19 (retention time 3.383 min)

Synthesis of (Z)-isopropyl 3-(2-(3,5-bis(trifluoromethyl)phenyl)-1H-pyrrol-1-yl)acrylate

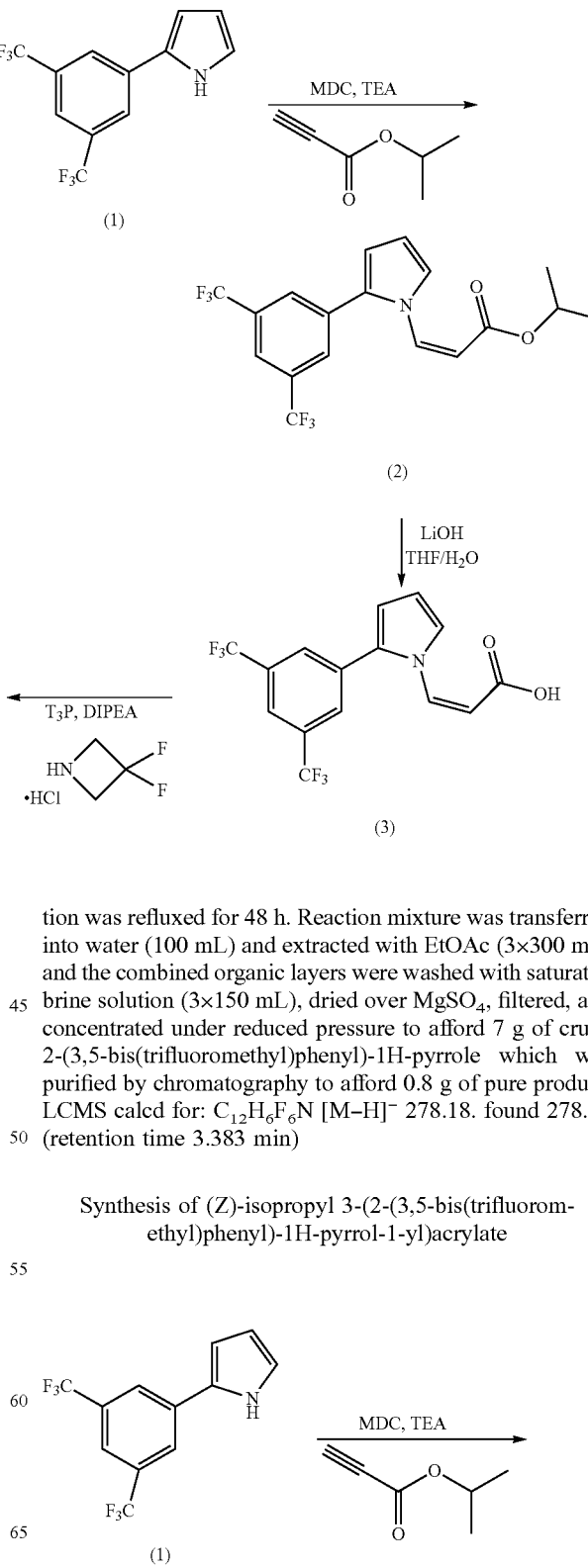

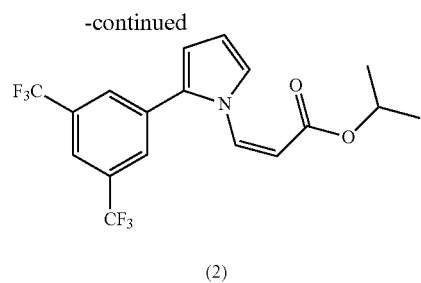

(2)

A 100 mL 3-neck round-bottomed flask was charged with a solution of 2-(3,5-bis(trifluoromethyl)phenyl)-1H-pyrrole (1) (0.7 g, 2.50 mmol)) in DCM (14 mL) and reaction mixture was cooled to 0° C. TEA (0.379 g, 3.76 mmol) and isopropyl acrylate (0.421 g, 3.76 mmol) were added simultaneously at 0° C. and stirred for 1.5 h. Reaction mixture was transferred into water (50 mL), extracted with EtOAc (3×20 mL) and combined organic layers were washed with saturated brine solution (3×50 mL), dried over MgSO$_4$, filtered, and concentrated under reduced pressure to afford 1.5 g of crude compound which was purified by column chromatography to obtain 0.150 g of (Z)-isopropyl 3-(2-(3,5-bis(trifluoromethyl)phenyl)-1H-pyrrol-1-yl)acrylate (Yield 15%). $^1$H NMR (400 MHz, CDCl$_3$, ppm) δ=1.279-1.318 (m, 6H); 5.106 (m, 1H); 5.521-545 (d, J=9.6 Hz, 1H); 6.377 (s, 1H); 6.494 (s, 1H); 6.643-6.763 (d, J=10 Hz, 1H); 7.800-7.831 (m, 3H): LCMS calcd for: C$_{18}$H$_{16}$F$_6$NO$_2$ [M+H]$^+$ 392.31. found 392.4 (retention time 3.820 min).

Synthesis of (Z)-3-(2-(3,5-bis(trifluoromethyl)phenyl)-1H-pyrrol-1-yl)acrylic acid

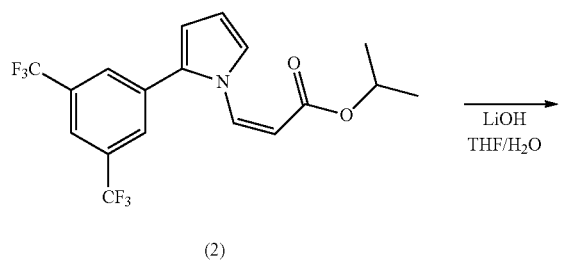

A 100 mL 3-neck round-bottomed flask was charged with a solution of (Z)-isopropyl 3-(2-(3,5-bis(trifluoromethyl) phenyl)-1H-pyrrol-1-yl)acrylate (0.15 g, 0.383 mmol) in THF (10 mL) and water (10 mL) and stirred at rt. To this reaction mixture, LiOH.H$_2$O (0.027 g, 1.15 mmol) was added and reaction was further stirred for 16 h. Reaction mixture was acidified by dilute HCl and extracted with EtOAc (3×20 mL). The combined organic layers were washed with brine solution (3×50 mL), dried over MgSO$_4$, filtered, and concentrated under reduced pressure to afford 0.15 g of (Z)-3-(2-(3,5-bis(trifluoromethyl)phenyl)-1H-pyrrol-1-yl)acrylic acid (3) (Yield: 88%) which was used for next step without purification. LCMS calcd for: C$_{15}$H$_{10}$F$_6$NO$_2$ [M+H]$^+$ 350.23. found 350.39 (retention time 3.129 min)

Synthesis of (Z)-3-(2-(3,5-bis(trifluoromethyl)phenyl)-1H-pyrrol-1-yl)-1-(3,3-difluoroazetidin-1-yl)prop-2-en-1-one

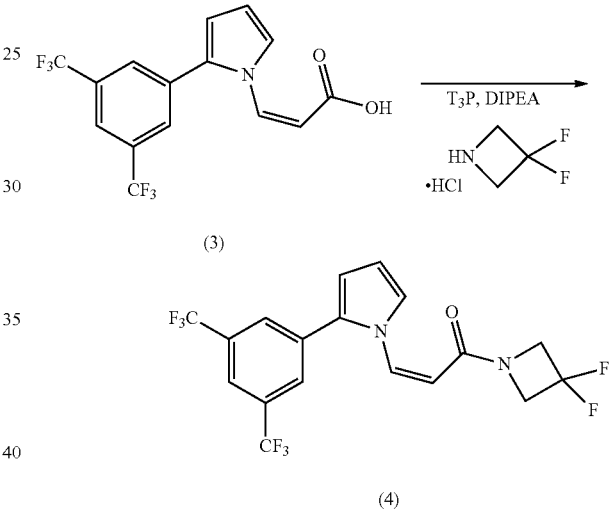

A 100 mL 3-neck round-bottomed flask was charged with a solution of (Z)-3-(2-(3,5-bis(trifluoromethyl)phenyl)-1H-pyrrol-1-yl)acrylic acid (0.15 g, 0.429 mmol) in DCM (10 mL) and cooled to 0° C. and 3,3-difluoroazetidine hydrochloride (0.052 g, 0.558 mmol) was added dropwise. T3P (50% in EtOAc) (0.163 g, 0.514 mmol) was added dropwise followed by DIPEA (0.11 g, 0.858 mmol) and the reaction mixture was stirred for 1 h at 0° C. The reaction mixture was concentrated under reduced pressure to afford 0.2 g of crude product which was purified by column chromatography (60/120 silica gel, 0-3% ethylacetate:n-hexane gradient) to afford 0.01 g of (Z)-3-(2-(3,5-bis(trifluoromethyl)phenyl)-1H-pyrrol-1-yl)-1-(3,3-difluoro azetidin-1-yl)prop-2-en-1-one (Yield 6.6%). $^1$H NMR (400 MHz, CDCl$_3$, ppm) δ=4.307-4.425 (m, 4H); 5.523-5.443 (d, J=10 Hz, 1H); 6.387-6.404 (t, 1H); 6.500-6.509 (t, 1H); 6.765-6.790 (d, J=10 Hz, 1H); 7.704-7.715 (t, 1H); 7.811-7.845 (m, 3H). LCMS calcd for: C$_{18}$H$_{13}$F$_8$N$_2$O [M+H]$^+$435.29. found 425.49 (retention time 3.292 min).

Example 66

Synthesis of (Z)-3-(3-(3,5-bis(trifluoromethyl)phenyl)-1H-1,2,4-triazol-1-yl)-1-(4-hydroxypiperidin-1-yl)prop-2-en-1-one

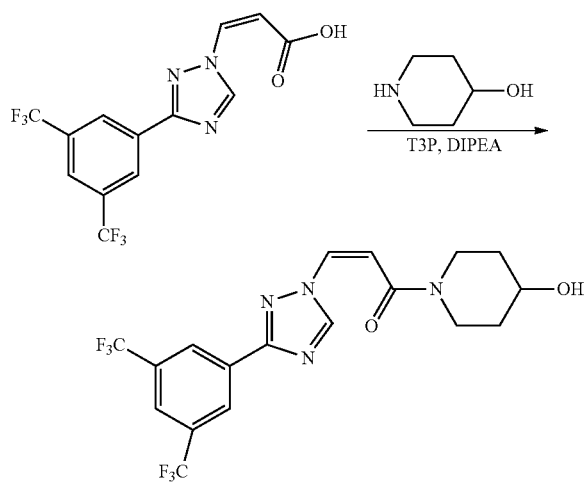

(Z)-3-(3-(3,5-Bis(trifluoromethyl)phenyl)-1H-1,2,4-triazol-1-yl)acrylic acid (0.20 g, 1.0 eq.) was dissolved in DCM (10 mL). Piperidin-4-ol (0.07 g, 1.2 eq.) was added and the reaction mixture was cooled to −60° C. T$_3$P (propyl phosphonic anhydride) (0.40 mL, 1.2 eq.) and DIPEA (0.19 mL, 2.0 eq.) were added. Reaction mixture was stirred for 30 min. The reaction mixture was then transferred into water (50 mL) and extracted with DCM (2×50 mL). The combined organic layers were washed with brine (50 mL), dried over anhydrous MgSO$_4$, filtered, and concentrated under reduced pressure (25° C., 20 mmHg) to afford crude product, which was purified by chromatography (0-3% MeOH in DCM) to obtain 0.025 g of (Z)-3-(3-(3,5-bis(trifluoromethyl)phenyl)-1H-1,2,4-triazol-1-yl)-1-(4-hydroxypiperidin-1-yl)prop-2-en-1-one (Yield: 10%). $^1$H NMR (400 MHz, CDCl$_3$) δ, 8.75 (s, 1H), 8.58 (s, 1H), 7.93 (s, 1H), 7.08-7.11 (d, J=10.4 Hz, 1H), 6.01-6.04 (d, J=10.4 Hz, 1H), 4.02-4.14 (m, 1H), 3.98-4.01 (m, 1H), 3.78-3.85 (m, 1H), 3.47-3.52 (s, 1H), 3.32-3.38 (s, 1H), 1.96 (s, 1H), 1.83 (s, 1H), 1.27 (s, 1H), 0.90 (s, 1H); LCMS for Chemical Formula: C$_{18}$H$_{17}$F$_6$N$_4$O$_2$ [M+H]$^+$ 435.34 found 435.24 at RT 2.408 min.

Inhibition of Nuclear Export

The ability of exemplary compounds of the invention to inhibit CRM1-mediated nuclear export was assessed in a RevGFP assay. Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/CRM1 pathway (Neville et al. 1997). Nuclear accumulation of Rev can be observed in cells treated with specific inhibitors of CRM1, such as LMB (Kau et al. 2003).

In this assay, U2OS-RevGFP cells were seeded onto clear-bottomed, black, 384-well plates the day before the experiment. Compounds were serially diluted 1:2 in DMEM, starting from 40 µM in a separate, 384-well plate, and then transferred onto the cells. The cells were incubated with compound for about 1 hr before fixation with 3.7% formaldehyde and nuclei staining with Hoechst 33258. The amount of GFP in cell nuclei was measured and the IC$_{50}$ of each compound was determined (Kau et al. 2003). Compounds of the invention are considered active in the RevGFP assay outlined above if they have an IC$_{50}$ of less than about 10 µM, with the most preferred compounds having an IC$_{50}$ of less than about 1 µM. The results of the RevGFP assay appear in Table 3.

Cell Proliferation Assay

The CellTiter 96® AQueous One Solution cell proliferation assay (Promega) was used on MM.1S multiple myeloma cell line to study the cytotoxic and cytostatic properties of the compounds. The assay is based on the cleavage of the tetrazolium salt, MTS, in the presence of an electron-coupling reagent PES (phenazine ethosulfate). The MTS tetrazolium compound is bioreduced by cells into a colored formazan product that is soluble in tissue culture medium. This conversion is presumably accomplished by NADPH or NADH produced by dehydrogenase enzymes in metabolically active cells. Assays are performed by adding a small amount of the CellTiter 96® AQueous One solution reagent directly to culture wells, incubating for 1-4 hours and then recording the absorbance at 490 nm with a 96-well plate reader. The absorbance revealed directly correlates to the cell number and their metabolic activity.

The cells were seeded at 5×10$^3$ to 1.5×10$^4$ cells (depending on cell type) in each well of a 96-well plate in 100 µL of fresh culture medium and adherent cells were allowed to attach overnight. The stock solutions of the compounds were diluted in cell culture medium to obtain eight concentrations of each drug, ranging from 1 nM to 30 µM and DMSO at less than 1% v/v was used as a negative control. The resulting drug solutions were transferred onto the cells. After 72 h of treatment, 20 µl of CellTiter 96® AQueous reagent was added into each well of the 96-well assay plates and the plate was incubated at 37° C. for 1-4 hours in a humidified, 5% CO$_2$ atmosphere. Then the absorbance of each well was recorded at 490 nm using a 96-well plate reader. In most cases, the assay was performed in triplicate and the results were presented as half maximal inhibitory concentration (IC$_{50}$). Optical density versus compound concentration was plotted and analyzed using non-linear regression equations (IDBS XLfit) and the IC$_{50}$ for each compound was calculated.

Pharmacokinetic (PK) Assay and Brain:Plasma Ratio Determination

Pharmacokinetics (PK) play an increasing role in drug discovery and development. Pharmacokinetics is the quantitative study of the time course of drug absorption, distribution, metabolism and/or excretion. When a drug is administered, it distributes rapidly from its administration site into the systemic blood circulation. One measure of the extent of a therapeutic agent's distribution is the area under the plasma concentration-time curve (AUC), calculated to the last measured concentration (AUC$_t$) and extrapolated to infinity (AUC$_{Inf}$). AUC is thus a useful metric to quantitate drug exposure.

Generally, the higher the exposure of a therapeutic agent, the greater the effects of the agent. However, high exposure of a therapeutic agent may have deleterious effects on certain tissues such as the brain. While the blood-brain barrier (BBB), a protective network consisting of tight junctions between endothelial cells, restricts the diffusion of hydrophilic and/or large molecules, drugs with high AUC are still capable of penetrating the BBB and/or cerebrospinal fluid. Such penetration can lead to unwanted side effects. Current drug discovery efforts are aimed, in part, at striking a balance between maximizing drug exposure (e.g., AUC), while minimizing brain penetration.

The brain to plasma (B:P) ratio is one method of quantifying the relative distribution of a therapeutic agent in brain tissue to that in circulation and, as such, provides one indication of the brain penetration of a given therapeutic agent. A high brain to plasma ratio is preferred when targeting diseases localized in the central nervous system (CNS), including the brain and the cerebrospinal fluid. However, a lower brain to plasma ratio is generally preferable for non-CNS therapeutic agents to minimize brain penetration and avoid potential side effects caused by unwanted accumulation of the therapeutic agents in the brain and CNS tissue.

AUC.

Blood was collected from mice (N=3) to contribute to the total of 10 time points (pre-dose, 5 min, 15 min, 30 min, 1 hour, 2 hours, 4 hours, 8 hours, 12 hours and 24 hours post dose). Mice were bled on a rotating basis, each mouse contributing 3 time points to the blood collection. At the designated time points, animals were anaesthetized under isoflurane, and approximately 110 μL of blood per time point was collected via retro-orbital puncture into pre-cooled $K_2EDTA$ (anti-coagulant) tubes. Blood samples were put on wet ice and centrifuged (2000 g, 5 min at 4° C.) to obtain plasma within 30 minutes of sample collection. All samples were stored frozen at approximately −80° C. until analysis. Prior to analysis, samples were mixed with internal standard (dexamethasone) in acetonitrile, vortexed, centrifuged, and supernatant was injected for analysis. Concentration of compounds in plasma was determined using LC-MS-MS instrumentation (API 4000, Triple Quadruple with electrospray ionization; Acuity Ultra Performance Liquid Chromatography column C18, with MeOH and formic acid as organic solvents). AUC values were calculated using WinNonlin Professional 6.2 software package, non-compartmental pharmacokinetic model NCA200.

Brain to Plasma (B:P) Ratio.

A separate group of mice (N=3) were dosed (PO at 10 mg/kg) and then sacrificed at the time of maximal plasma concentration (estimated at 2 hours post-dose), at which time terminal plasma and brain tissue were collected. Following collection, brain tissue was rinsed with cold saline, dried on filter paper, weighed and snap-frozen by placing on dry ice. All samples were stored frozen at approximately −80° C. until analysis. At the time of analysis, brain tissue was homogenized (homogenizing solution PBS, pH 7.4), mixed with internal standard (dexamethasone) in acetonitrile, vortexed, centrifuged, and supernatant was injected for analysis of compound concentration using LC-MS-MS methodology (API 4000, Triple Quadruple with electrospray ionization; Acuity Ultra Performance Liquid Chromatography column C18, with MeOH and formic acid as organic solvents). Plasma samples were treated with the identical method (except homogenization step) and the concentration of compound in each matrix was calculated based on generated standard curves. The results of the PK assay and the B:P ratio determination are presented in Table 3.

TABLE 3

Assay Results for Exemplary Compounds of the Invention (A = <1 μM; B = 1-10 μM; C = >10 μM; NT = not tested).

| Cmpd. No. | Structure | $AUC_{Inf}$ hr*ng/mL (mouse, PO, 10 mpk) | B/P | Rev Export [$IC_{50}$] | Cytotoxicity [EC50] |
|---|---|---|---|---|---|
| 1 | 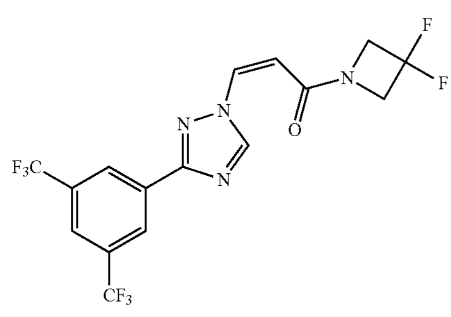 [SMILES: O=C(/C=C\n1cnc(-c2cc(C(F)(F)F)cc(C(F)(F)F)c2)n1)N1CC(F)(F)C1] | 12300 | 5 | A | A |
| 2 | 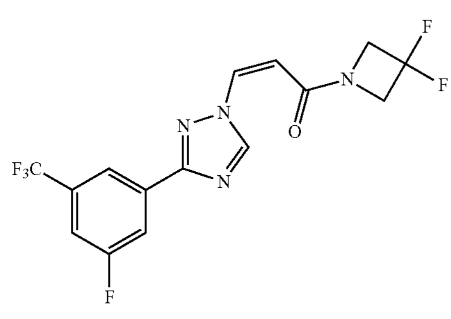 [SMILES: O=C(/C=C\n1cnc(-c2cc(F)cc(C(F)(F)F)c2)n1)N1CC(F)(F)C1] | 396 | NT | NT | A |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 3 | 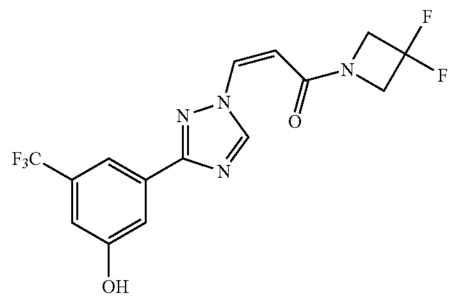 [SMILES: O=C(/C=C\n1cnc(-c2cc(O)cc(C(F)(F)F)c2)n1)N1CC(F)(F)C1] | NT | NT | NT | A |
| 4 | 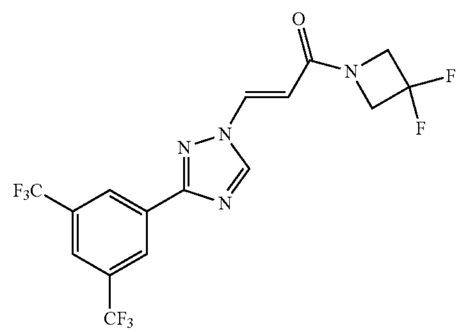 [SMILES: O=C(/C=C/n1cnc(-c2cc(C(F)(F)F)cc(C(F)(F)F)c2)n1)N1CC(F)(F)C1] | NT | NT | A | A |
| 5 | 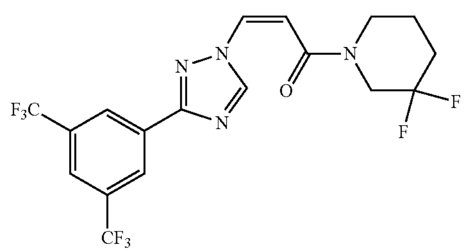 [SMILES: O=C(/C=C\n1cnc(-c2cc(C(F)(F)F)cc(C(F)(F)F)c2)n1)N1CCCC(F)(F)C1] | NT | NT | NT | B |
| 6 | 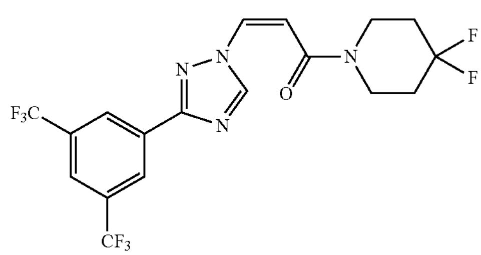 [SMILES: O=C(/C=C\n1cnc(-c2cc(C(F)(F)F)cc(C(F)(F)F)c2)n1)N1CCC(F)(F)CC1] | NT | NT | NT | B |
| 7 | 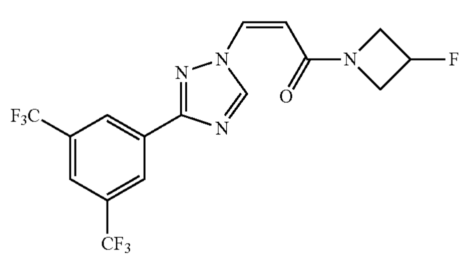 [SMILES: O=C(/C=C\n1cnc(-c2cc(C(F)(F)F)cc(C(F)(F)F)c2)n1)N1CC(F)C1] | 2510 | NT | NT | A |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
| --- | --- | --- | --- | --- | --- |
| 8 | 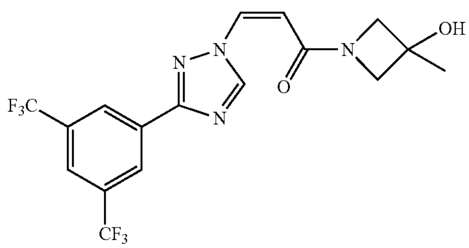 [SMILES: CC1(O)CN(C(=O)/C=C\n2cnc(-c3cc(C(F)(F)F)cc(C(F)(F)F)c3)n2)C1] | 9050^ | 3.16 | NT | A |
| 9 | 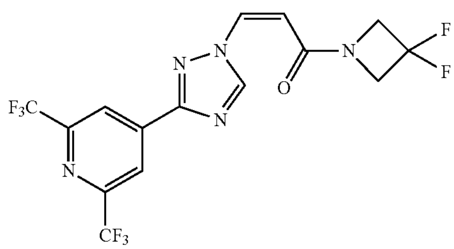 [SMILES: O=C(/C=C\n1cnc(-c2cc(C(F)(F)F)nc(C(F)(F)F)c2)n1)N1CC(F)(F)C1] | NT | NT | NT | A |
| 10 | 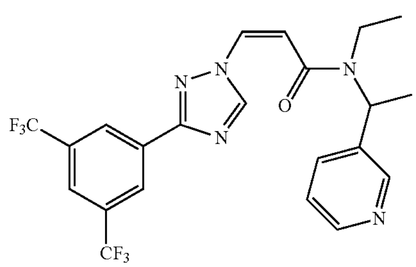 [SMILES: CCN(C(=O)/C=C\n1cnc(-c2cc(C(F)(F)F)cc(C(F)(F)F)c2)n1)C(C)c1cccnc1] | NT | NT | NT | B |
| 11 | 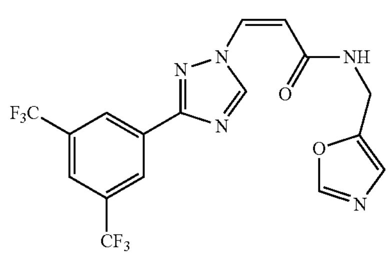 [SMILES: O=C(/C=C\n1cnc(-c2cc(C(F)(F)F)cc(C(F)(F)F)c2)n1)NCc1cnco1] | 3080^ | NT | NT | A |
| 12 | 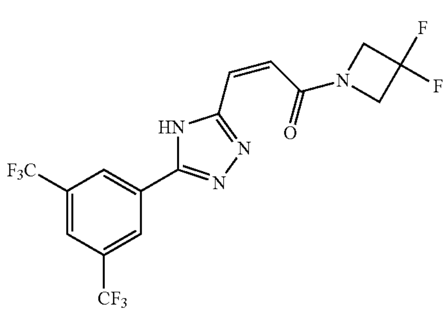 [SMILES: O=C(/C=C\c1nnc(-c2cc(C(F)(F)F)cc(C(F)(F)F)c2)[nH]1)N1CC(F)(F)C1] | NT | NT | NT | B |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 13 | 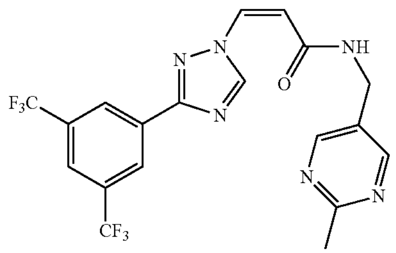 [SMILES: Cc1ncc(CNC(=O)/C=C\n2cnc(-c3cc(C(F)(F)F)cc(C(F)(F)F)c3)n2)cn1] | NT | NT | NT | B |
| 14 | 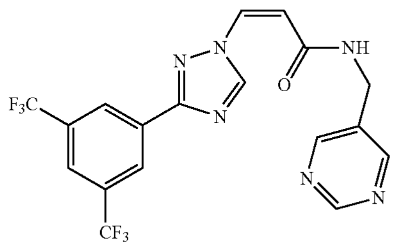 [SMILES: O=C(/C=C\n1cnc(-c2cc(C(F)(F)F)cc(C(F)(F)F)c2)n1)NCc1cncnc1] | NT | NT | NT | A |
| 15 | 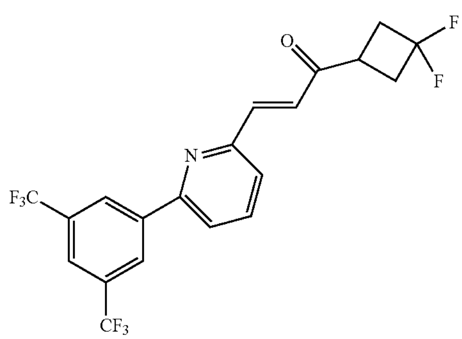 [SMILES: O=C(/C=C/c1cccc(-c2cc(C(F)(F)F)cc(C(F)(F)F)c2)n1)C1CC(F)(F)C1] | NT | NT | NT | C |
| 16 | 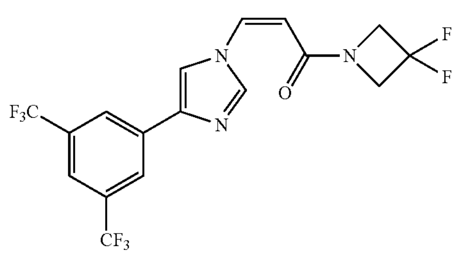 | NT | NT | NT | A |
| 17 | 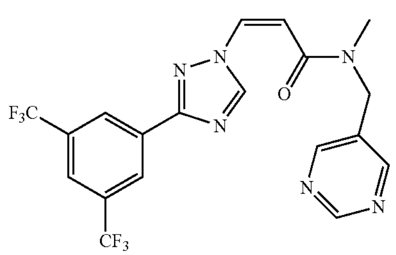 [SMILES: CN(Cc1cncnc1)C(=O)/C=C\n1cnc(-c2cc(C(F)(F)F)cc(C(F)(F)F)c2)n1] | NT | NT | NT | B |

TABLE 3-continued

Assay Results for Exemplary Compounds of the Invention (A = <1 µM; B = 1-10 µM; C = >10 µM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 18 | 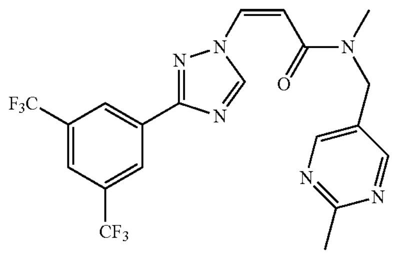 [SMILES: Cc1ncc(CN(C)C(=O)/C=C\n2cnc(-c3cc(C(F)(F)F)cc(C(F)(F)F)c3)n2)cn1] | NT | NT | NT | B |
| 19 | 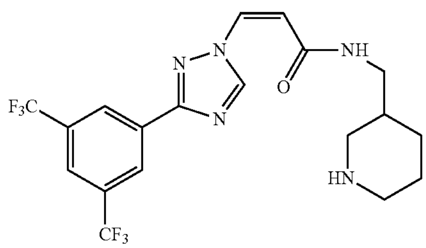 [SMILES: O=C(/C=C\n1cnc(-c2cc(C(F)(F)F)cc(C(F)(F)F)c2)n1)NCC1CCCNC1] | NT | NT | NT | B |
| 20 | 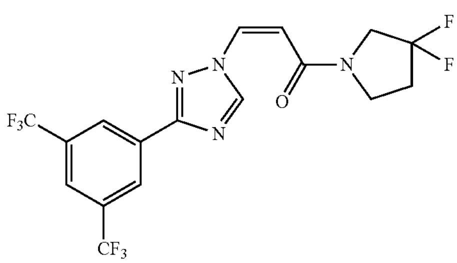 [SMILES: O=C(/C=C\n1cnc(-c2cc(C(F)(F)F)cc(C(F)(F)F)c2)n1)N1CCC(F)(F)C1] | NT | NT | NT | A |
| 21 | 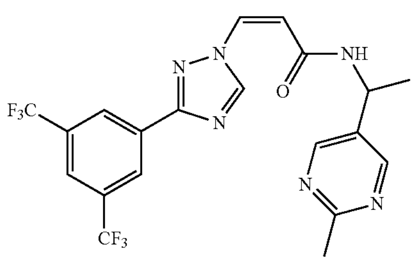 [SMILES: Cc1ncc(C(C)NC(=O)/C=C\n2cnc(-c3cc(C(F)(F)F)cc(C(F)(F)F)c3)n2)cn1] | NT | NT | NT | B |
| 22 | 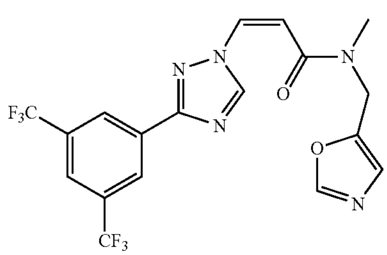 [SMILES: CN(Cc1cnco1)C(=O)/C=C\n1cnc(-c2cc(C(F)(F)F)cc(C(F)(F)F)c2)n1] | NT | NT | NT | B |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 23 | 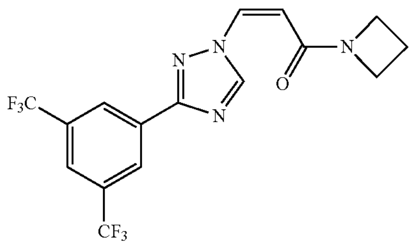 [SMILES: O=C(/C=C\n1cnc(-c2cc(C(F)(F)F)cc(C(F)(F)F)c2)n1)N1CCC1] | 521 | NT | NT | A |
| 24 | 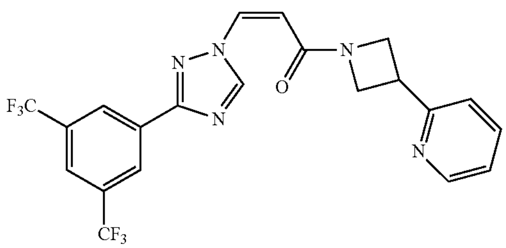 [SMILES: O=C(/C=C\n1cnc(-c2cc(C(F)(F)F)cc(C(F)(F)F)c2)n1)N1CC(c2ccccn2)C1] | NT | NT | NT | A |
| 25 | 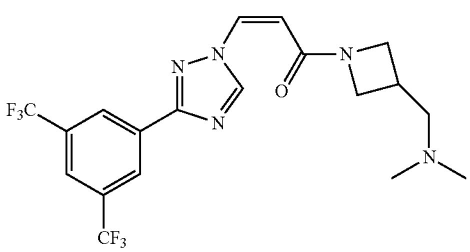 [SMILES: CN(C)CC1CN(C(=O)/C=C\n2cnc(-c3cc(C(F)(F)F)cc(C(F)(F)F)c3)n2)C1] | 2640 | NT | NT | A |
| 26 | 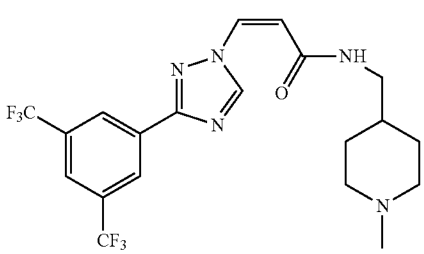 [SMILES: CN1CCC(CNC(=O)/C=C\n2cnc(-c3cc(C(F)(F)F)cc(C(F)(F)F)c3)n2)CC1] | NT | NT | NT | A |
| 27 | 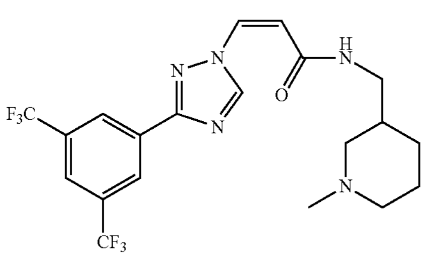 [SMILES: CN1CCCC(CNC(=O)/C=C\n2cnc(-c3cc(C(F)(F)F)cc(C(F)(F)F)c3)n2)C1] | NT | NT | NT | A |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 28 | 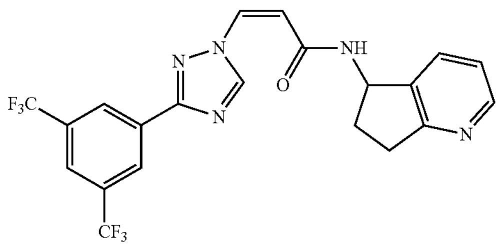 [SMILES: O=C(/C=C\n1cnc(-c2cc(C(F)(F)F)cc(C(F)(F)F)c2)n1)NC1CCc2ncccc21] | NT | NT | NT | B |
| 29 | 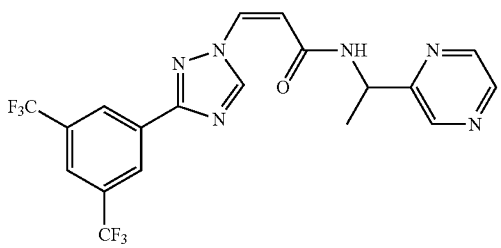 [SMILES: CC(NC(=O)/C=C\n1cnc(-c2cc(C(F)(F)F)cc(C(F)(F)F)c2)n1)c1cnccn1] | NT | NT | NT | B |
| 30 | 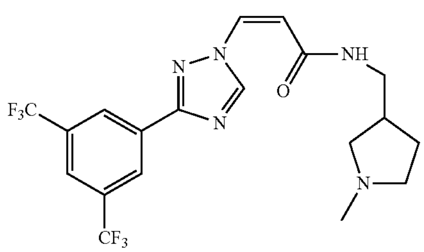 [SMILES: CN1CCC(CNC(=O)/C=C\n2cnc(-c3cc(C(F)(F)F)cc(C(F)(F)F)c3)n2)C1] | NT | NT | NT | A |
| 31 | 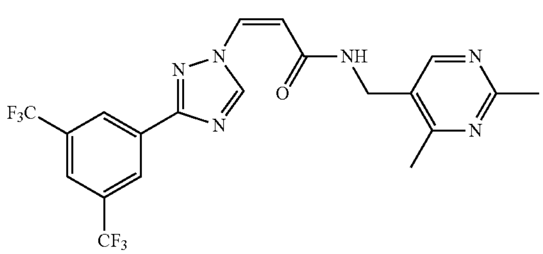 [SMILES: Cc1ncc(CNC(=O)/C=C\n2cnc(-c3cc(C(F)(F)F)cc(C(F)(F)F)c3)n2)c(C)n1] | NT | NT | NT | A |
| 32 | 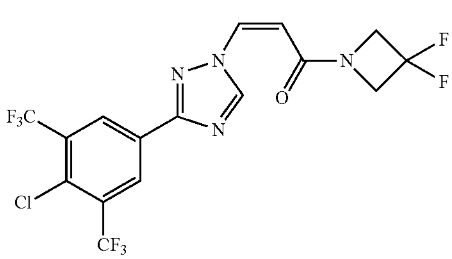 | NT | NT | NT | A |

TABLE 3-continued

Assay Results for Exemplary Compounds of the Invention (A = <1 μM; B = 1-10 μM; C = >10 μM; NT = not tested).

| Cmpd. No. | Structure | $AUC_{Inf}$ hr*ng/mL (mouse, PO, 10 mpk) | B/P | Rev Export [$IC_{50}$] | Cytotoxicity [EC50] |
|---|---|---|---|---|---|
| 33 | 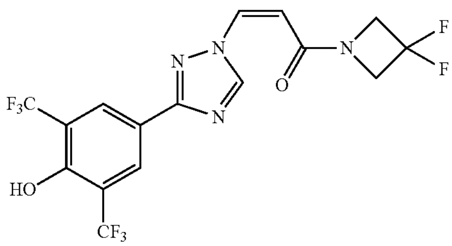 | NT | NT | NT | NT |
| 34 | 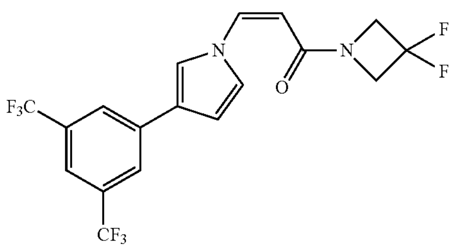 | NT | NT | NT | NT |
| 35 | 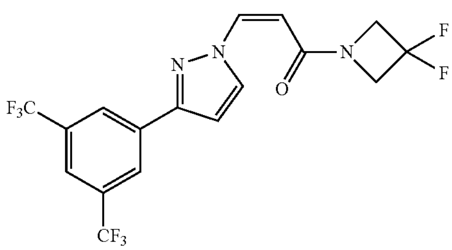 | NT | NT | NT | A |
| 36 | 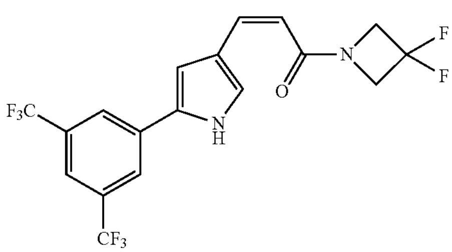 | NT | NT | NT | N/T |
| 37 | 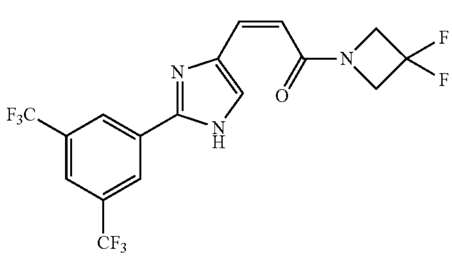 | NT | NT | NT | NT |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 38 | 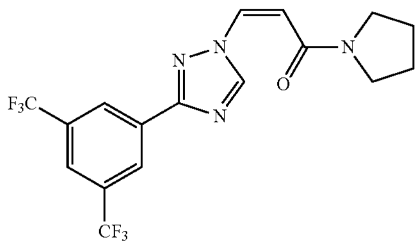 [SMILES: O=C(/C=C\n1cnc(-c2cc(C(F)(F)F)cc(C(F)(F)F)c2)n1)N1CCCC1] | NT | NT | NT | NT |
| 39 | 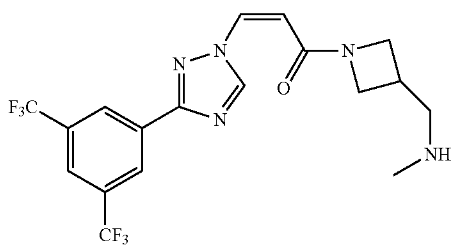 [SMILES: CNCC1CN(C(=O)/C=C\n2cnc(-c3cc(C(F)(F)F)cc(C(F)(F)F)c3)n2)C1] | NT | NT | NT | NT |
| 40 | 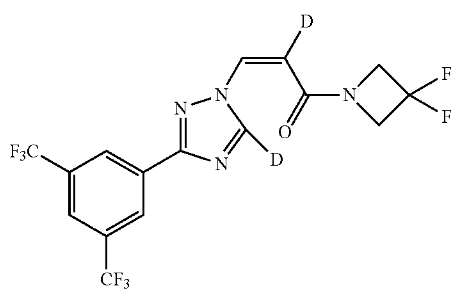 [SMILES: [2H]/C(=C/n1nc(-c2cc(C(F)(F)F)cc(C(F)(F)F)c2)nc1[2H])C(=O)N1CC(F)(F)C1] | NT | NT | NT | A |
| 41 | 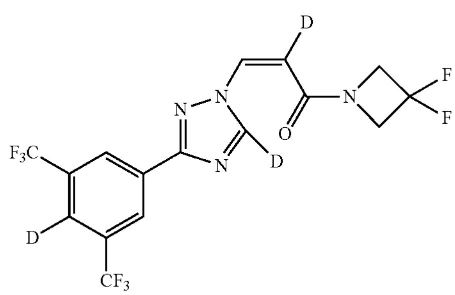 [SMILES: [2H]/C(=C/n1nc(-c2cc(C(F)(F)F)c([2H])c(C(F)(F)F)c2)nc1[2H])C(=O)N1CC(F)(F)C1] | NT | NT | NT | NT |
| 42 | 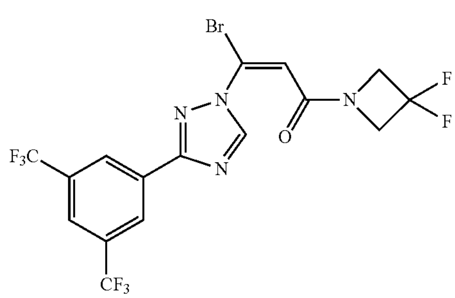 [SMILES: O=C(/C=C(/Br)n1cnc(-c2cc(C(F)(F)F)cc(C(F)(F)F)c2)n1)N1CC(F)(F)C1] | NT | NT | NT | NT |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 43 | 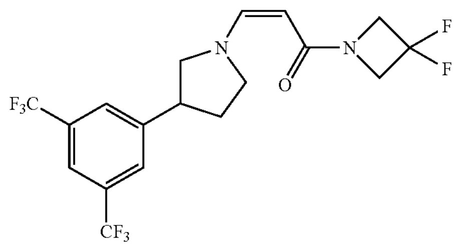 [SMILES: O=C(/C=C\N1CCC(c2cc(C(F)(F)F)cc(C(F)(F)F)c2)C1)N1CC(F)(F)C1] | NT | NT | NT | C |
| 44 | 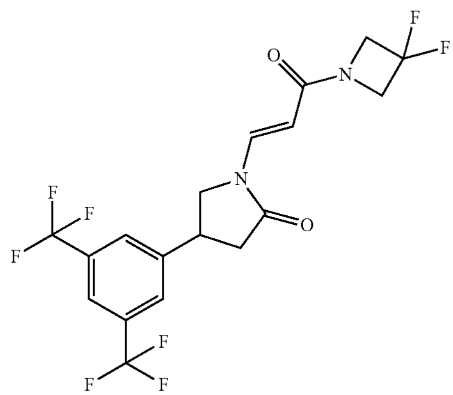 [SMILES: O=C1CC(c2cc(C(F)(F)F)cc(C(F)(F)F)c2)CN1/C=C/C(=O)N1CC(F)(F)C1] | NT | NT | NT | C |
| 45 | 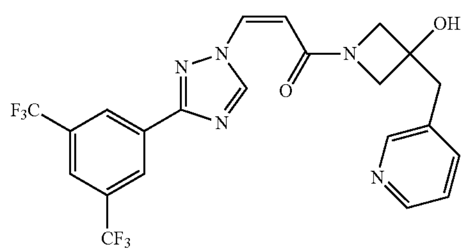 | NT | NT | NT | NT |
| 46 | 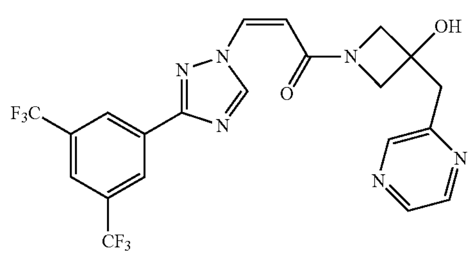 | NT | NT | NT | NT |
| 47 | 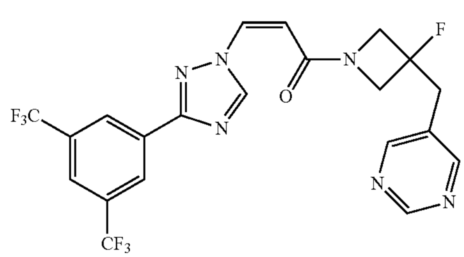 | NT | NT | NT | NT |

TABLE 3-continued

Assay Results for Exemplary Compounds of the Invention (A = <1 µM; B = 1-10 µM; C = >10 µM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 48 | 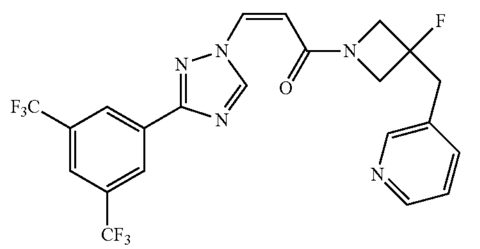 | NT | NT | NT | NT |
| 49 | 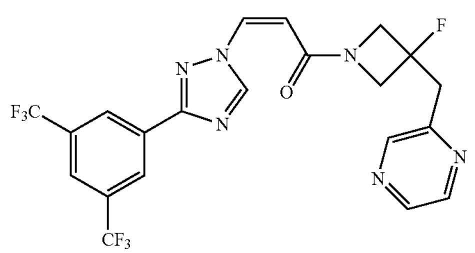 | NT | NT | NT | NT |
| 50 | 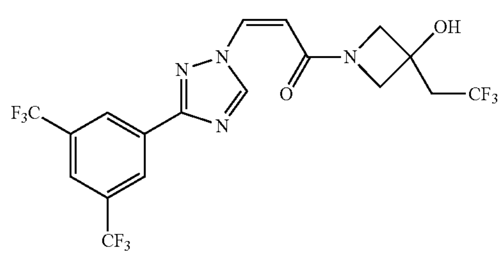 [SMILES: O=C(/C=C\n1cnc(-c2cc(C(F)(F)F)cc(C(F)(F)F)c2)n1)N1CC(O)(CC(F)(F)F)C1] | NT | NT | NT | NT |
| 51 | 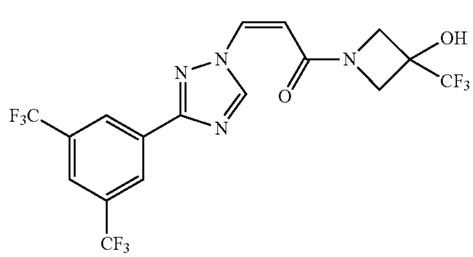 [SMILES: O=C(/C=C\n1cnc(-c2cc(C(F)(F)F)cc(C(F)(F)F)c2)n1)N1CC(O)(C(F)(F)F)C1] | NT | NT | NT | A |
| 52 | 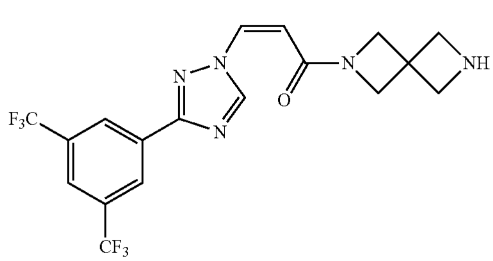 [SMILES: O=C(/C=C\n1cnc(-c2cc(C(F)(F)F)cc(C(F)(F)F)c2)n1)N1CC2(CNC2)C1] | NT | NT | NT | A |

TABLE 3-continued

Assay Results for Exemplary Compounds of the Invention (A = <1 µM; B = 1-10 µM; C = >10 µM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 53 | 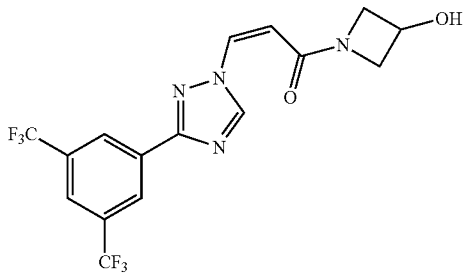 | NT | NT | NT | A |
| 54 | 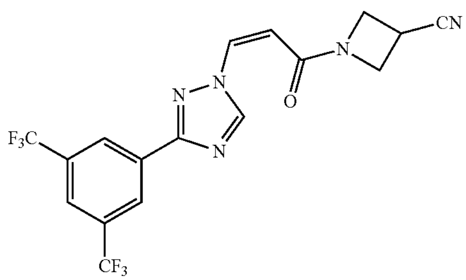 | NT | NT | NT | A |
| 55 | 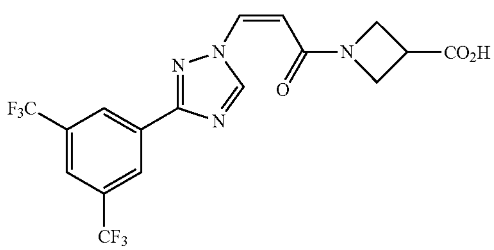 [SMILES: O=C(O)C1CN(C(=O)/C=C\n2cnc(-c3cc(C(F)(F)F)cc(C(F)(F)F)c3)n2)C1] | NT | NT | NT | B |
| 56 | 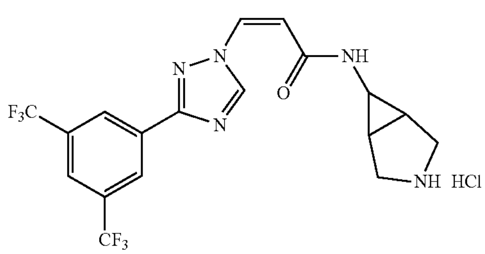 [SMILES: O=C(/C=C\n1cnc(-c2cc(C(F)(F)F)cc(C(F)(F)F)c2)n1)NC1C2CNCC21 ; Cl] | NT | NT | A | A |
| 57 | 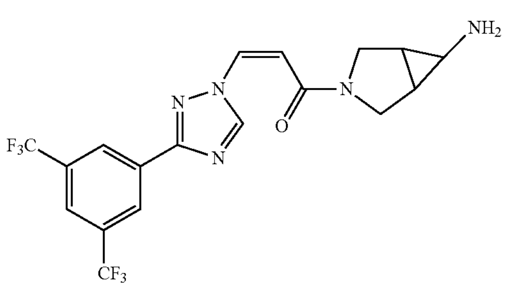 [SMILES: NC1C2CN(C(=O)/C=C\n3cnc(-c4cc(C(F)(F)F)cc(C(F)(F)F)c4)n3)CC12] | NT | NT | NT | A |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 58 | 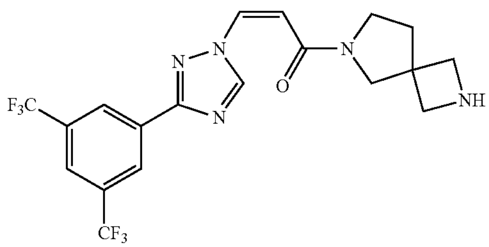 [SMILES: O=C(/C=C\n1cnc(-c2cc(C(F)(F)F)cc(C(F)(F)F)c2)n1)N1CCC2(CNC2)C1] | NT | NT | NT | A |
| 59 | 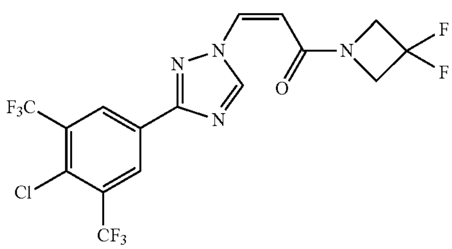 | NT | NT | NT | A |
| 60 | 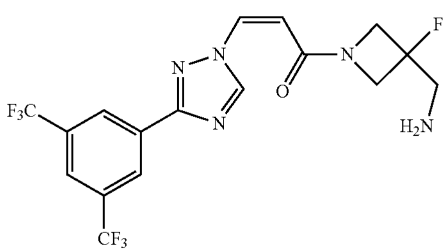 | 1240 | 13.3 | NT | A |
| 61 | 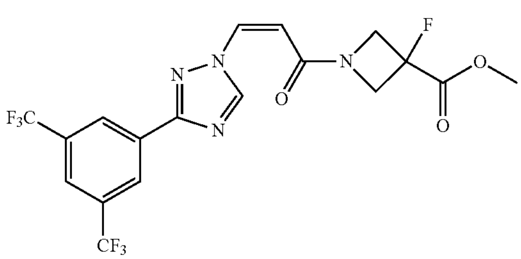 [SMILES: COC(=O)C1(F)CN(C(=O)/C=C\n2cnc(-c3cc(C(F)(F)F)cc(C(F)(F)F)c3)n2)C1] | NT | NT | NT | A |
| 62 | 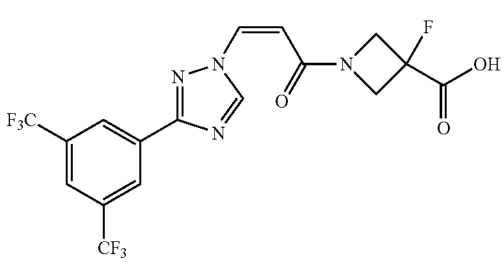 [SMILES: O=C(/C=C\n1cnc(-c2cc(C(F)(F)F)cc(C(F)(F)F)c2)n1)N1CC(F)(C(=O)O)C1] | NT | NT | NT | B |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 63 | 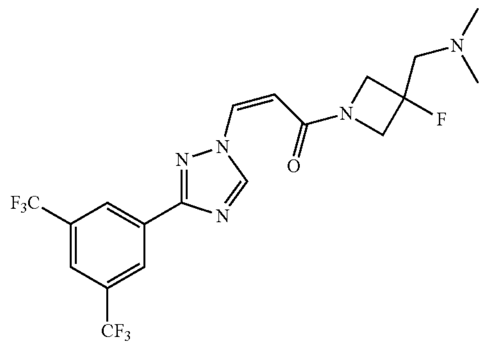 [SMILES: CN(C)CC1(F)CN(C(=O)/C=C\n2cnc(-c3cc(C(F)(F)F)cc(C(F)(F)F)c3)n2)C1] | NT | NT | NT | A |
| 64 | 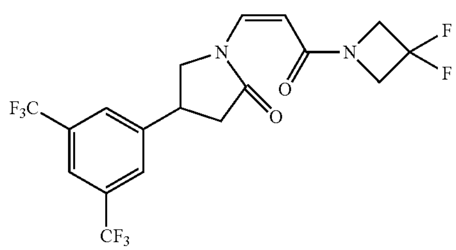 [SMILES: O=C1CC(c2cc(C(F)(F)F)cc(C(F)(F)F)c2)CN1/C=C\C(=O)N1CC(F)(F)C1] | NT | NT | NT | C |
| 65 | 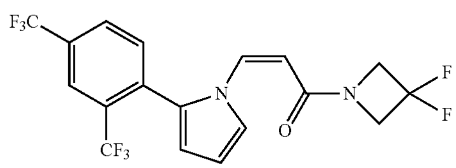 [SMILES: O=C(/C=C\n1cccc1-c1ccc(C(F)(F)F)cc1C(F)(F)F)N1CC(F)(F)C1] | NT | NT | NT | C |
| 66 | 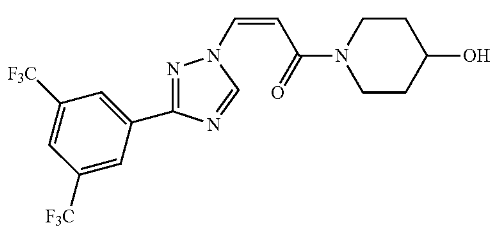 [SMILES: O=C(/C=C\n1cnc(-c2cc(C(F)(F)F)cc(C(F)(F)F)c2)n1)N1CCC(O)CC1] | NT | NT | NT | A |
| 67 | 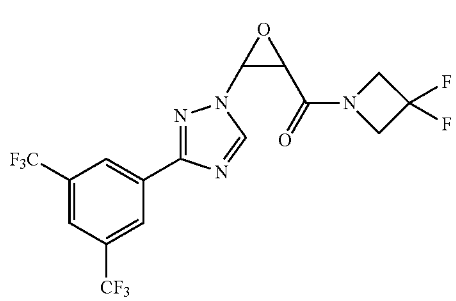 [SMILES: O=C(C1OC1n1cnc(-c2cc(C(F)(F)F)cc(C(F)(F)F)c2)n1)N1CC(F)(F)C1] | | | | |

TABLE 3-continued

Assay Results for Exemplary Compounds of the Invention (A = <1 μM; B = 1-10 μM; C = >10 μM; NT = not tested).

| Cmpd. No. | Structure | AUC$_{Inf}$ hr*ng/mL (mouse, PO, 10 mpk) | B/P | Rev Export [IC$_{50}$] | Cytotoxicity [EC50] |
|---|---|---|---|---|---|
| 68 | 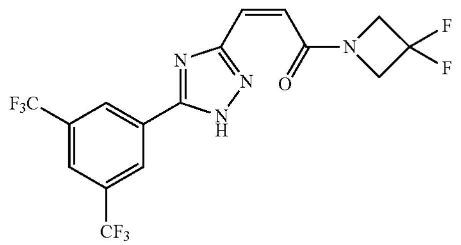 [SMILES: O=C(/C=C\c1n[nH]c(-c2cc(C(F)(F)F)cc(C(F)(F)F)c2)n1)N1CC(F)(F)C1] | NT | NT | NT | NT |
| 69 | 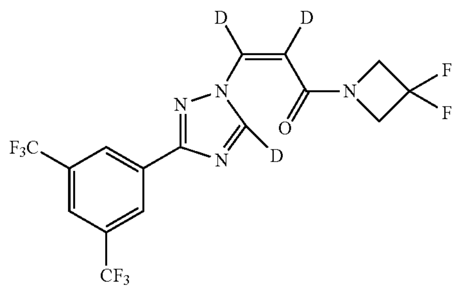 [SMILES: [2H]/C(C(=O)N1CC(F)(F)C1)=C(\[2H])n1nc(-c2cc(C(F)(F)F)cc(C(F)(F)F)c2)nc1[2H]] | NT | NT | NT | NT |
| 70 | 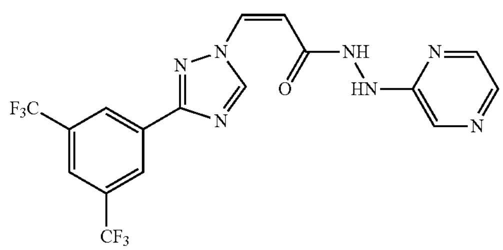 [SMILES: O=C(/C=C\n1cnc(-c2cc(C(F)(F)F)cc(C(F)(F)F)c2)n1)NNc1cnccn1] | 10100 | 0.71 | A | A |
| 71 | 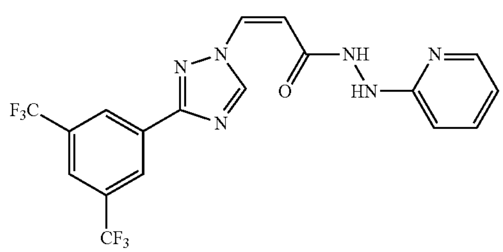 [SMILES: O=C(/C=C\n1cnc(-c2cc(C(F)(F)F)cc(C(F)(F)F)c2)n1)NNc1ccccn1] | 10800 | 1.8 | A | A |

*tested at 5 mpk.

Inhibition of HCT-116 Xenografts In Vivo

Mice were inoculated on the hind flank with HCT-116 cell line and the HCT-116 xenografts were grown to approximately 150 mm³, at which time treatment was initiated. Treatment groups were as follows:
  Vehicle SC;
  50 mg/kg 5-FU IP, days 1-3;
  25 mg/kg Compound 1 compound QDx5 SC (low dose);
  75 mg/kg Compound 1 compound QDx5 SC (high dose).

FIG. 1 is a graph of tumor volume as a percentage of the initial tumor volume versus time and shows that treatment with Compound 1 inhibited tumor growth, and showed superior anti-tumor effects compared to 5-FU. Compound 1 compound was well-tolerated at both the low and high doses.

Induction of p21, p53 and Apoptosis in HCT-116 Cells

HCT-116 cells were incubated with 10 μM Compound 1 for 24 hours, at which time the cells were fixed and stained with antibodies to p21 or p53, or the DNA stain, DAPI. Subsequent analysis by immunofluorescence showed that both p21 and p53 were concentrated in the nucleus in cells treated with Compound 1, while cells treated with vehicle only (DMSO) contained only low levels of p53 and p21 in cytoplasm and nucleus.

This experiment showed that Compound 1 inhibited the nuclear export function of CRM1, altering the subcellular localization of the tumor suppressor gene protein p53 and the cyclin dependent kinase inhibitor, p21.

Figure 2A:
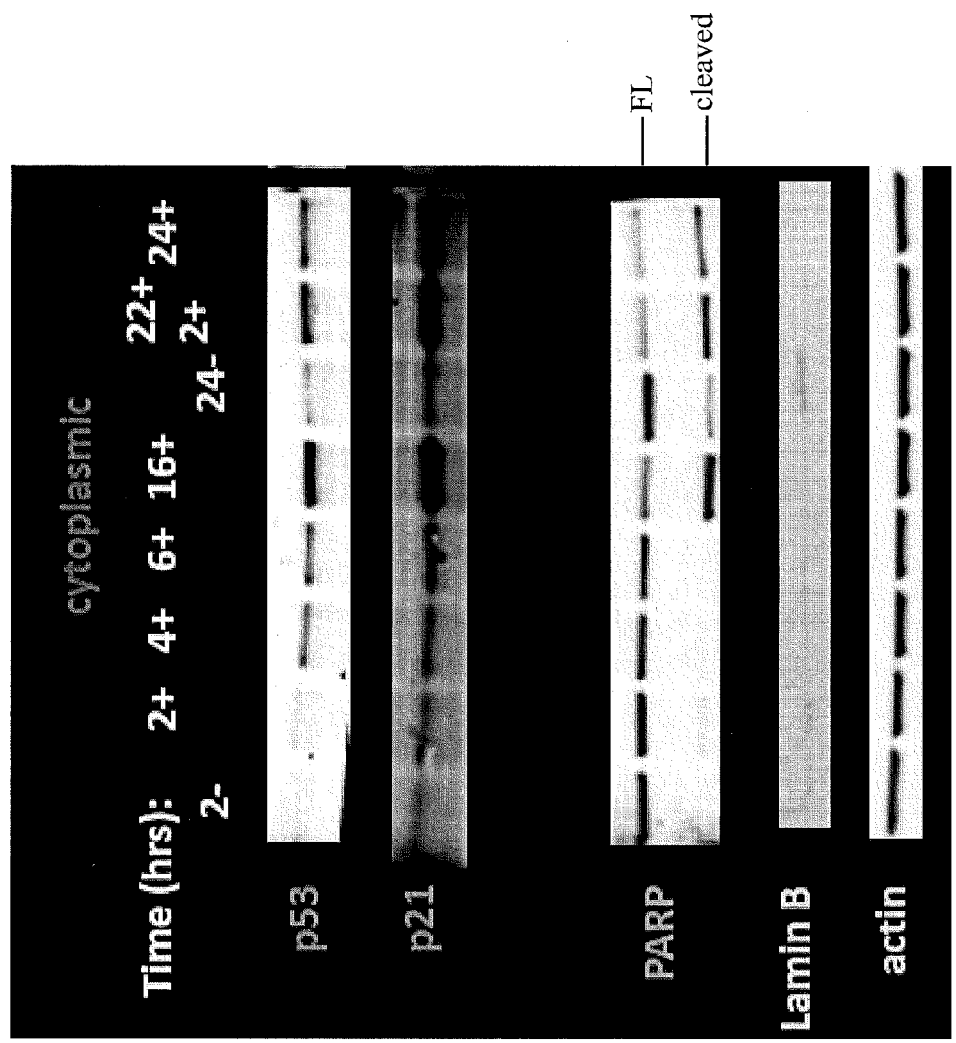
FIG. 2A is images of Western blots and shows the amount of p53, p21, full-length (FL) PARP and cleaved PARP, and lamin B in the cytoplasmic fraction of a protein extract from HCT-116 cells at various times before and after treatment with Compound 1.
Figure 2B:
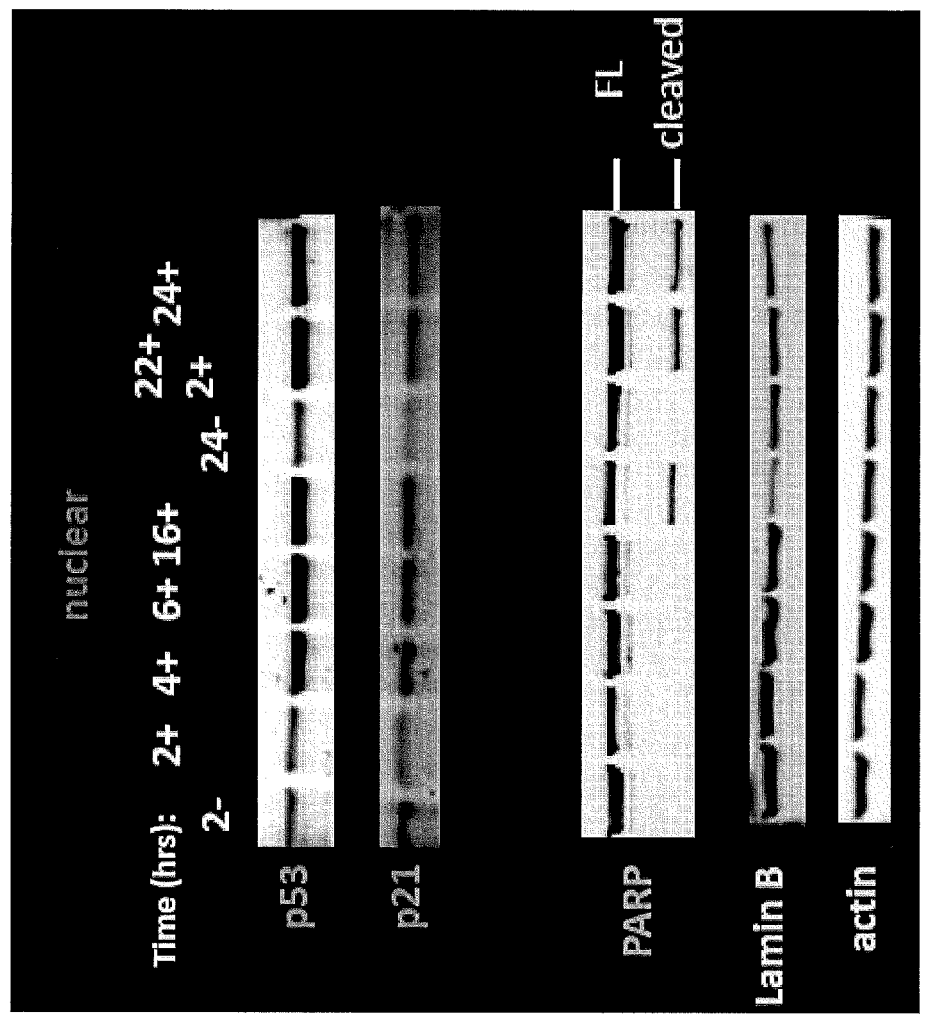
FIG. 2B is images of Western blots and shows the amount of p53, p21, full-length (FL) PARP and cleaved PARP, and lamin B in the nuclear fraction of a protein extract from HCT-116 cells at various times before and after treatment with Compound 1.

HCT-116 cells were incubated with 10 μM Compound 1 for 2, 4, 6, 16, or 24 hours (indicated in FIGS. 2A and 2B as "2+," 4+," etc.), or with 10 µM Compound 1 for 22 hours and an additional 1 µM Compound 1 for another 2 hours (indicated in FIGS. 2A and 2B as "22+2+"). At the end of the incubation period, total protein extracts were prepared. In addition, protein cell extracts were made from cells incubated with vehicle (DMSO) for 2 and 24 hours (indicated in FIGS. 2A and 2B as "−"). Cytoplasmic and nuclear proteins were separated, immunoblotted and reacted with antibodies to p53, p21, full-length (FL) PARP, cleaved PARP and lamin B.

FIGS. 2A and 2B are images of Western blots obtained from the experiment and show that Compound 1 induces p21 and p53 in both cytoplasmic and nuclear fractions. Particularly strong induction of p53 was observed in the nuclear fraction of cells treated with Compound 1. In addition, FIGS. 2A and 2B show that Compound 1 induces apoptosis in HCT-116 cells after 24 hours, as indicated by the decrease in PARP, an apoptosis marker, and the increase in cleaved PARP. Cleaved PARP marks the initiation of cell death following 16 hrs of incubation, lamin is a marker for nuclear proteins and actin is a loading control.

Induction of pRb Nuclear Localization and Phosphorylation in HCT-116 Cells

HCT-116 cells were incubated with 10 µM Compound 1 for 24 hours, at which time the cells were fixed and stained with antibodies to pRb or DAPI. Subsequent analysis by immunofluorescence showed that treatment with Compound 1 induced nuclear localization of the tumor suppressor gene protein, pRb.

Figure 3A:
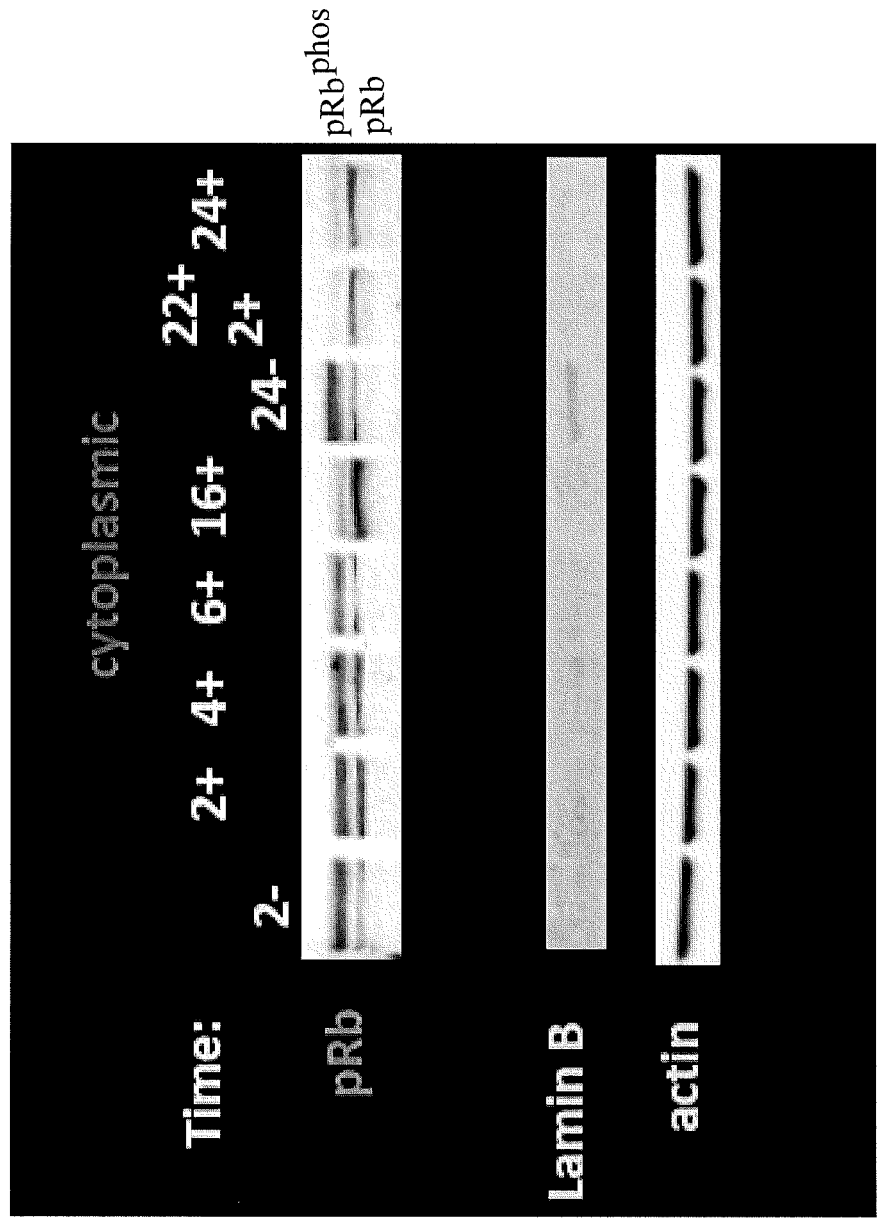
FIG. 3A is images of Western blots and shows the amount of pRb, phosphorylated pRB ($pRb^{phos}$), and lamin B in the cytoplasmic fraction of a protein extract from HCT-116 cells at various times before and after treatment with Compound 1.
Figure 3B:
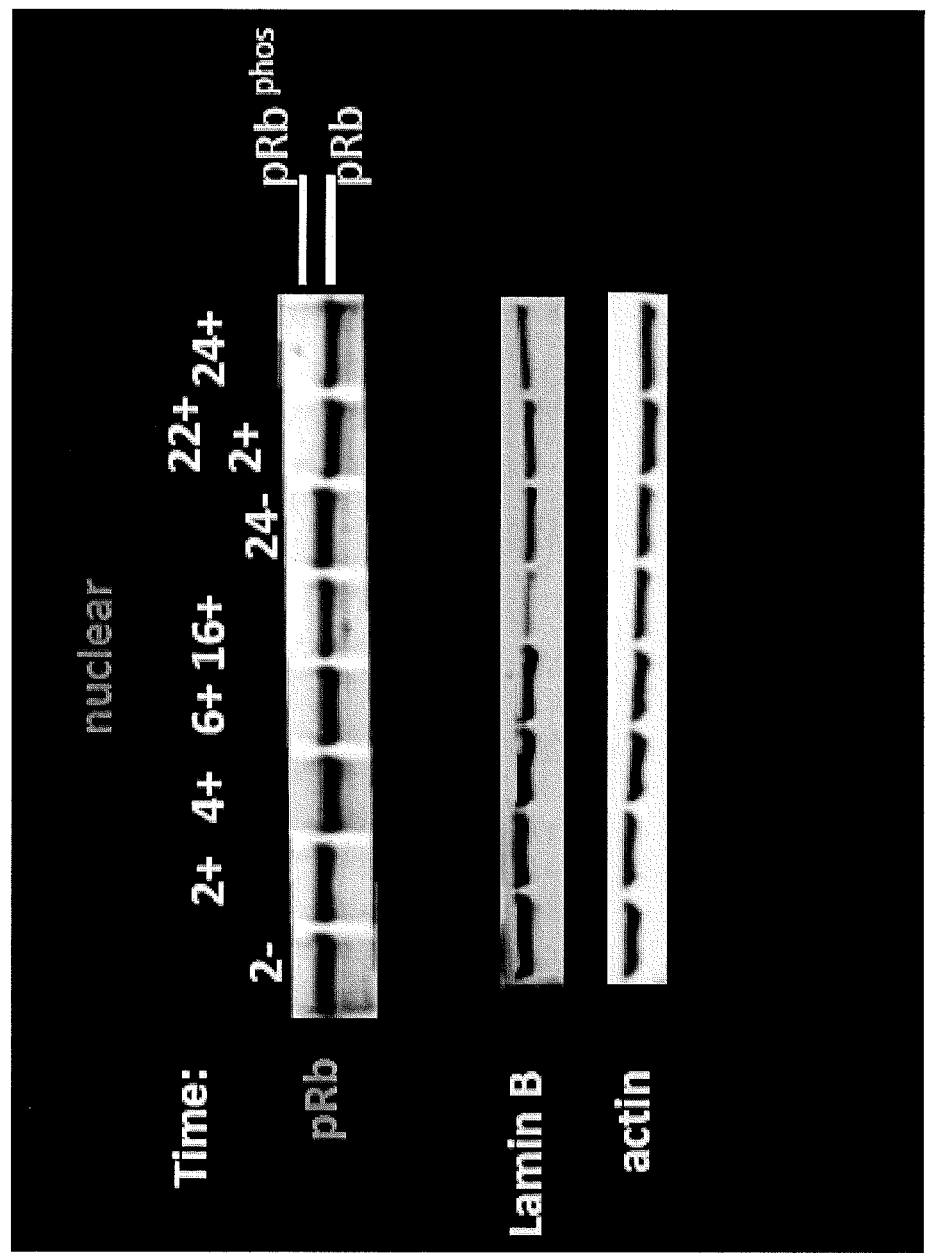
FIG. 3B is images of Western blots and shows the amount of pRb, phosphorylated pRB ($pRb^{phos}$), and lamin B in the nuclear fraction of a protein extract from HCT-116 cells at various times before and after treatment with Compound 1.

HCT-116 cells were incubated with 10 µM Compound 1 for 2, 4, 6, 16, or 24 hours (indicated in FIGS. 3A and 3B as "2+," 4+," etc.), or with 10 µM Compound 1 for 22 hours and an additional 1 µM Compound 1 for another 2 hours (indicated in FIGS. 3A and 3B as "22+2+"). At the end of the incubation period, total protein extracts were prepared. In addition, protein cell extracts were made from cells incubated with vehicle (DMSO) for 2 and 24 hours (indicated in FIGS. 3A and 3B as "−"). Cytoplasmic and nuclear proteins were separated, immunoblotted and reacted with antibodies to phosphorylated pRb (pRb$^{phos}$), pRb, actin and lamin B.

FIGS. 3A and 3B are images of Western blots obtained from the experiment and show higher levels of pRb in the nuclear fraction and a loss of the upper band of pRb protein in samples treated with Compound 1 for more than 6 hours. The upper pRb bands correspond to the inactive, phosphorylated protein and the lower bands correspond to the unphosphorylated, active form of the protein that induces cell cycle arrest. FIGS. 3A and 3B show that Compound 1 induces dephosphorylation of pRb in both cytoplasmic and nuclear fractions.

Induction of APC and IκB Nuclear Localization in HCT-116 Cells

HCT-116 cells were incubated with 10 µM Compound 1 for 24 hours, at which time the cells were fixed and stained with antibodies to APC or IκB, or DAPI. Subsequent analysis by immunofluorescence shows that treatment with Compound 1 induced the nuclear localization of the tumor suppressor proteins, APC and IκB, respectively, in HCT-116 cells. Cells treated with vehicle only showed clear cytoplasmic (ring-like staining) of both, APC and IκB.

Experimental Autoimmune Encephalomyelitis (EAE) Model

The EAE Model is an accepted model for the study of human CNS demyelinating diseases such as multiple sclerosis. The model described herein used 5-8-week-old female C57BL/6 or CD40−/− mice (13-16-week-old BM chimeric mice). The mice were immunized subcutaneously with 200 µg of MOG35-55 peptide (peptide 35-55 of myelin oligodendrocyte glycoprotein) emulsified in CFA (Complete Freund's Adjuvant) supplemented with 500 µg of *Mycobacterium tuberculosis* (DIFCO). The mice received intraperitoneal injections with 250 ng of pertussis toxin (Sigma-Aldrich) at the time of immunization and 48 h later to increase the permeability of the blood brain barrier. After 7 days, the mice received an identical boost immunization with MOG/CFA without pertussis toxin. Clinical disease commenced between days 13 and 18 after immunization. The administration of Compound 1 started when all mice displayed flaccid tail and weakness of hind limbs. The study design was as described below and all dosing was performed in a blinded fashion.

The study consisted of 3 groups: (i) vehicle-treated; (ii) 25 mg/kg of Compound 1; and (iii) 75 mg/kg Compound 1 (oral gavage, 3 days per week—Monday, Wednesday, Friday). Each group had 16-18 animals and was color coded. Body weight and condition and clinical score were recorded daily by two independent investigators. The clinical scoring of the mice was conducted four times per week as follows: 0, no detectable signs of EAE; 0.5, distal limp tail; 1, complete limp tail; 1.5, limp tail and hind limb weakness; 2, unilateral partial hind limb paralysis; 2.5, bilateral partial hind limb paralysis; 3, complete bilateral hind limb paralysis; 3.5, complete hind limb paralysis and unilateral forelimb paralysis; 4, total paralysis of fore and hind limbs (score >4 to be sacrificed); 5, death. During the course of the experiment, supplementation of soft and palatable food such as gelatin and Nutrical was provided.

Figure 4A:
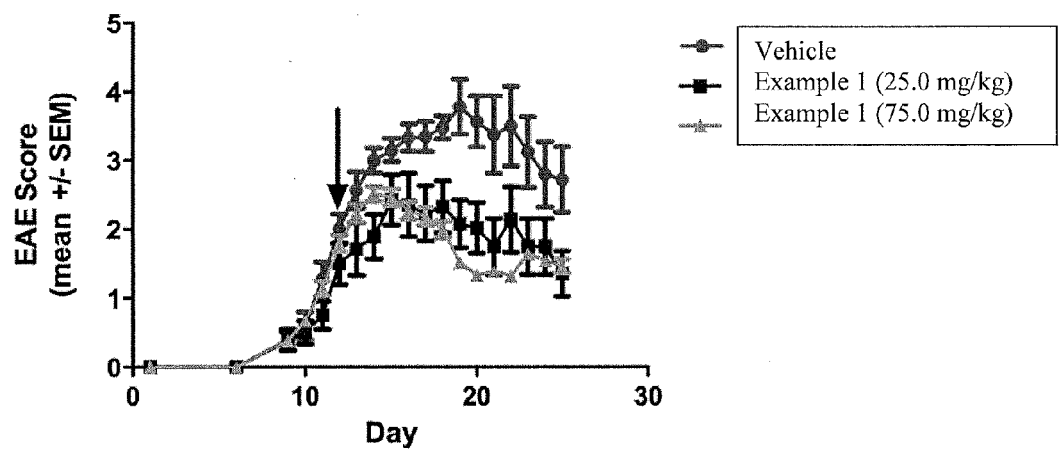
FIG. 4A is a graph of EAE score a function of time and shows the effect of various amounts of Compound 1 on EAE score in the EAE model of multiple sclerosis.
Figure 4B:
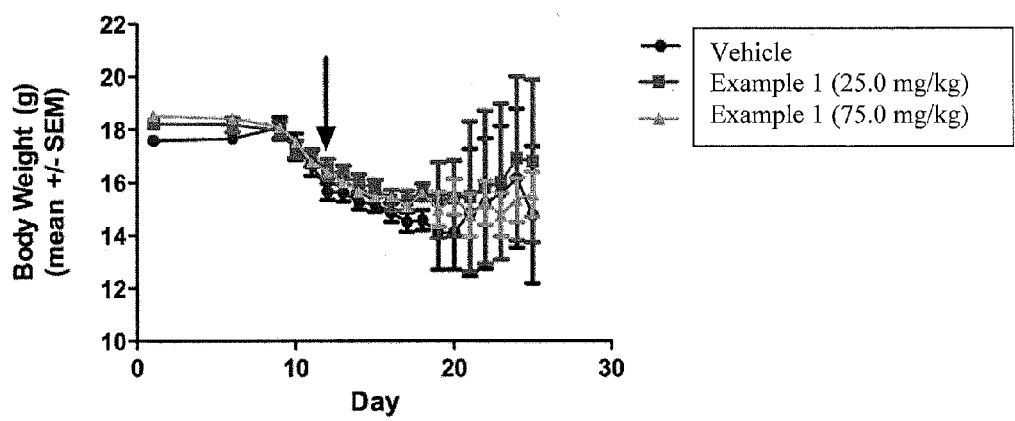
FIG. 4B is a graph of body weight as a function of time and shows the effect of various amounts of Compound 1 on body weight in the EAE model of multiple sclerosis.

FIG. 4A is a graph of EAE score as a function of time and shows that administration of Compound 1 in the above-described regimen reduced the clinical score in a statistically significant manner for both the 25 mg/kg (low dose) and 75 mg/kg (high dose) groups. FIG. 4B is a graph of body weight as a function of time and shows that administration of Compound 1 in the above-described regimen did not dramatically affect body weight.

Figure 5:
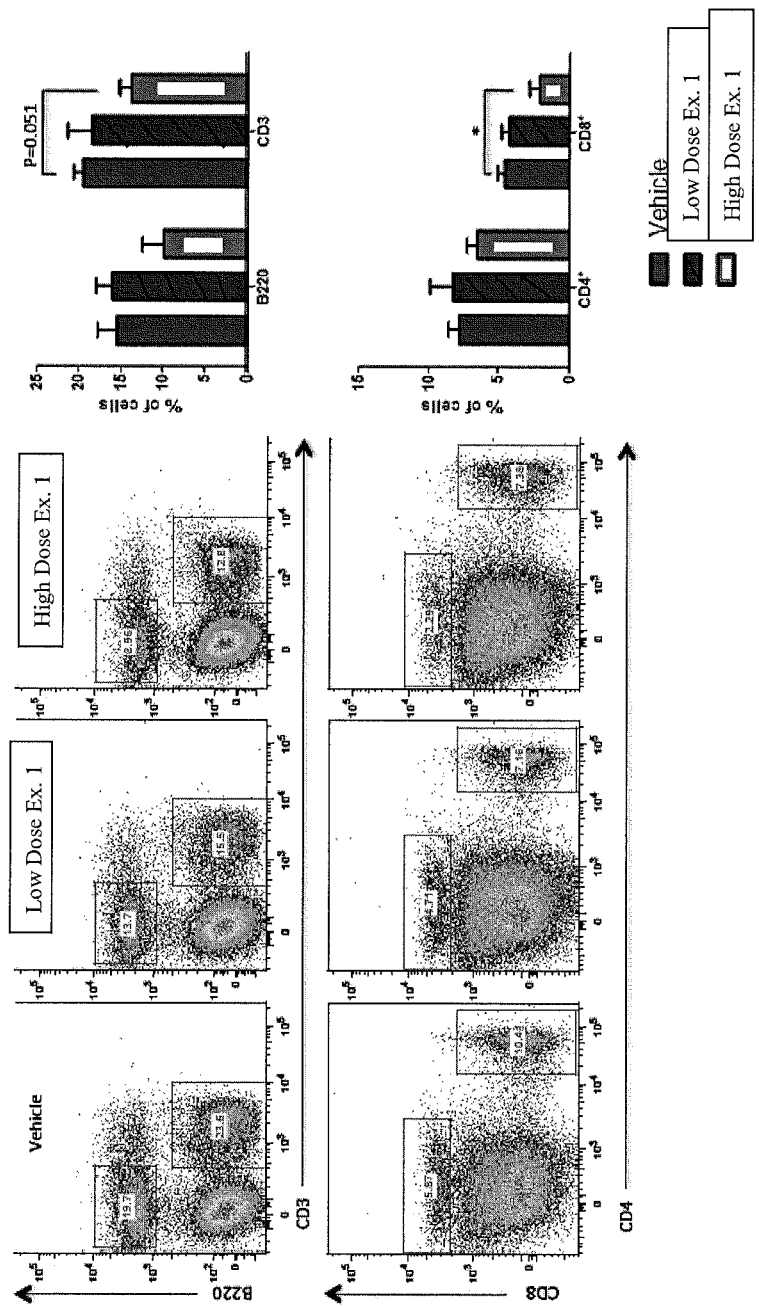
FIG. 5 shows the results of FACS sorting of lymphocytes for a subset of mice at day 26 of the EAE Model described herein.

On day 26, a subset of mice was sacrificed and immune cells were subjected to fluorescence-activated cell sorting (FACS) using standard methods. FIG. 5 shows the results of the FACS experiment, which indicated a modest decrease in the number of splenocytes and circulating CD8 cells associated with the high dose of Compound 1.

Compound 1 and Example 1 are used interchangeably herein and refer to Compound 1 of Table 2 having the chemical name (Z)-3-(3-(3,5-bis(trifluoromethyl)phenyl)-1H-1,2,4-triazol-1-yl)-1-(3,3-difluoroazetidin-1-yl)prop-2-en-1-one.

BIBLIOGRAPHY

1. Cronshaw J M and Matunis M J. 2004. The nuclear pore complex: disease associations and functional correlations TRENDS Endocrin Metab. 15:34-39
2. Falini B et al. 2006. Both carboxy-terminus NES motif and mutated tryptophan(s) are crucial for aberrant nuclear export of nucleophosmin leukemic mutants in NPMc+ AML Blood. 107:4514-4523
3. Cai X and Liu X. 2008 Inhibition of Thr-55 phosphorylation restores p53 nuclear localization and sensitizes cancer cells to DNA damage. PNAS. 105:16958-16963.
4. Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517

5. Davis J R et al. 2007. Controlling protein compartmentalization to overcome disease Pharmaceut Res. 24:17-27
6. Freundt E, Yu L, Park E, et al 2009 Molecular determinants for subcellular localization of the severe acute respiratory syndrome coronavirus open reading frame 3b protein. J Virol 83(13):6631-40
7. Ghildyal R, Ho A, Dias M, et al 2009 The respiratory syncytial virus matrix protein possesses a Crm1-mediated nuclear export mechanism. J Virol 83(11):5353-62
8. Ghosh C C et al 2008 Analysis of nucleocytoplasmic shuttling of NF kappa B proteins in human leukocytes. Methods Mol. Biol. 457:279-92.
9. Gupta N et al 2008 Retinal tau pathology in human glaucomas Can J Ophthalmol. 2008 February; 43(1):53-60
10. HoshinoL et al. 2008. Combined effects of p53 gene therapy and leptomycin B in human esophageal squamous cell carcinoma. Oncology. 75:113-119.
11. Lain S et al. 1999a An inhibitor of nuclear export activates the p53 response and induces the localization of HDM2 and p53 to U1A-positive nuclear bodies associated with the PODs Exp Cell Res. 248:457-472.
12. Lain S et al. 1999b. Accumulating active p53 in the nucleus by inhibition of nuclear export: a novel strategy to promote the p53 tumor suppressor function Exp Cell Res. 253:315.
13. Muller P A et al. 2009 Nuclear-cytosolic transport of COMMD1 regulates NF-kappaB and HIF-1 activity. Traffic on-line publication
14. Mutka S 2007 Nuclear Export Inhibitors (NEIs) as novel cancer therapies AACR Annual Meeting. Poster 5609.
15. Mutka S, Yang W, Dong S, et al. 2009. Identification of nuclear export inhibitors with potent anticancer activity in vivo. Cancer Res. 69: 510-7.
16. Nakahara J et al. 2009. Abnormal expression of TIP30 and arrested nucleocytoplasmic transport within oligodendrocyte precursor cells in multiple sclerosis J Clin Invest. 119:169-181
17. Noske A et al. 2008. Expression of the nuclear export protein chromosomal region maintenance/exportin 1/Xpo1 is a prognostic factor in human ovarian cancer
18. Cancer. 112:1733-1743
19. Pollard V & Malim M. 1998 The HIV-1 Rev protein 52:491-532.
20. Rawlinson S, Pryor M, Wright P, Jans D 2009 CRM1-mediated nuclear export of dengue virus RNA polymerase NS5 modulates interleukin-8 induction and virus production J Biol Chem 284(23):15589-97
21. Sanchez V, Mahr J, Orazio N, et al 2007 Nuclear export of the human cytomegalovirus tegument protein pp 65 requires cyclin-dependent kinase activity and the Crm1 exporter J Virol 81(21):11730-6.
22. Sorokin A V et al. 2007. Nucleocytoplasmic transport of proteins Biochemistry. 72:1439-1457.
23. Terry L J et al. 2007. Crossing the nuclear envelope: hierarchical regulation of nucleocytoplasmic transport Science. 318:1412-1416
24. Van der Watt P J et al. 2008. The Karyopherin proteins, Crm1 and Karyopherin beta1, are overexpressed in cervical cancer and are critical for cancer cell survival and proliferation Int J Canc. 124:1829-1840
25. Walsh M D et al. 2008 Exportin 1 inhibition attenuates nuclear factor-kappaB-dependent gene expression. Shock 29:160-166
26. Williams P, Verhagen J, Elliott G 2008 Characterization of a CRM1-dependent nuclear export signal in the C terminus of herpes simplex virus type 1 tegument protein UL47 J Virol 82(21):10946-52.
27. Yang W 2007 Anti-tumor activity of novel nuclear export inhibitors (NEIs) in multiple murine leukemia models AACR Annual Meeting. Poster 5597.
28. Yao Y et al. 2009. The expression of CRM1 is associated with prognosis in human osteosarcoma Oncol Rep. 21:229-35.
29. Zimmerman T L et al 2006 Nuclear export of retinoid X receptor alpha in response to interleukin-1beta-mediated cell signaling: roles for JNK and SER260J Biol Chem 281:15434-15440

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:
1. A compound of formula I:

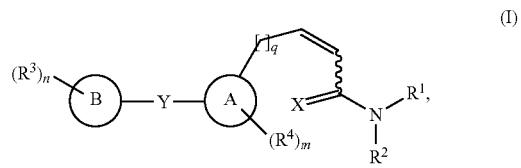

or a pharmaceutically acceptable salt thereof, wherein:
Ring A is an optionally substituted triazolyl ring;
Ring B is represented by the following structural formula:

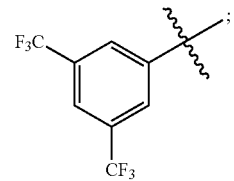 [SMILES: *c1cc(C(F)(F)F)cc(C(F)(F)F)c1]

X is O;
Y is a covalent bond;
$R^1$ and $R^2$ are taken together with their intervening atoms to form a heterocyclic ring represented by the following structural formula:

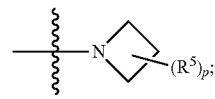

each of m, and p is independently an integer selected from 0, 1, 2, 3 and 4;
q is 0;
each of $R^4$, and $R^5$ is independently halogen, —$NO_2$, —CN, —$N_3$, -L-$R^6$, or an optionally substituted group selected from $C_{1-6}$ aliphatic, a 3-8 membered saturated or partially unsaturated monocyclic carbocyclic ring, phenyl, an 8-10 membered bicyclic aryl ring, a 3-8 membered saturated or partially unsaturated monocyclic heterocyclic ring having 1-2 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur, or:

two $R^4$ groups on Ring A are taken together with their intervening atoms to form a fused 4-8 membered saturated, partially unsaturated, or aryl ring having 0-3 heteroatoms independently selected from nitrogen, oxygen, and sulfur; or:

two $R^5$ groups on the ring formed by $R^1$ and $R^2$ are taken together with their intervening atoms to form a fused 4-8 membered saturated, partially unsaturated, or aryl ring having 0-3 heteroatoms independently selected from nitrogen, oxygen, and sulfur;

L is a covalent bond or an optionally substituted bivalent $C_{1-6}$ hydrocarbon group, wherein one or two methylene units of L is optionally and independently replaced by -Cy-, —O—, —S—, —N($R^6$)—, —C(O)—, —C(S)—, —C(O)N($R^6$)—, —N($R^6$)C(O)N($R^6$)—, —N($R^6$)C(O)—, —N($R^6$)C(O)O—, —OC(O)N($R^6$)—, —S(O)—, —S(O)$_2$—, —S(O)$_2$N($R^6$)—, —N($R^6$)S(O)$_2$—, —OC(O)— or —C(O)O—;

-Cy- is an optionally substituted bivalent ring selected from a 3-7 membered saturated or partially unsaturated cycloalkylenylene ring, a 4-7-membered saturated or partially unsaturated heterocycloalkylene ring having 1-4 heteroatoms independently selected from nitrogen, oxygen, and sulfur, phenylene, a 5-6 membered monocyclic heteroarylene having 1-4 heteroatoms independently selected from nitrogen, oxygen, and sulfur, an 8-10 membered bicyclic arylene, and an 8-10 membered bicyclic heteroarylene having 1-4 heteroatoms independently selected from nitrogen, oxygen, and sulfur; and each $R^6$ is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl carbocyclic ring, a 4-7-membered saturated or partially unsaturated heterocyclic ring having 1-4 heteroatoms independently selected from nitrogen, oxygen, and sulfur, a 5-6 membered monocyclic heteroaryl ring having 1-4 heteroatoms independently selected from nitrogen, oxygen, and sulfur, and an 8-10 membered bicyclic heteroaryl ring having 1-4 heteroatoms independently selected from nitrogen, oxygen, and sulfur; or:

two $R^6$ on the same nitrogen are taken together with their intervening atoms to form a 4-7 membered saturated, partially unsaturated, or aromatic heterocyclic ring having 1-2 heteroatoms independently selected from nitrogen, oxygen, and sulfur.

2. The compound according to claim 1, wherein Ring A is selected from:

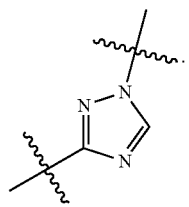 [SMILES: *c1ncn(*)n1]

3. The compound according to claim 1, wherein the heterocyclic ring formed by $R^1$, $R^2$ and their intervening atoms is represented by the following structural formula:

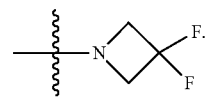

4. The compound according to claim 1, wherein the compound is represented by the following structural formula:

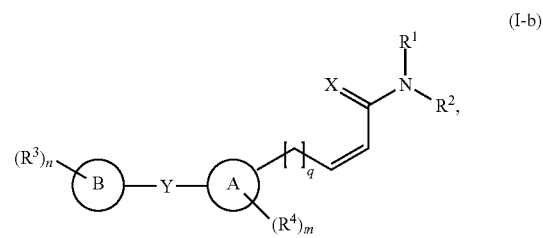

(I-b)

or a pharmaceutically acceptable salt thereof.

5. The compound according to claim 1, wherein the compound is represented by any one of the following structural formulas, or a pharmaceutically acceptable salt thereof:

| Compound | Structure |
|---|---|
| 1 | 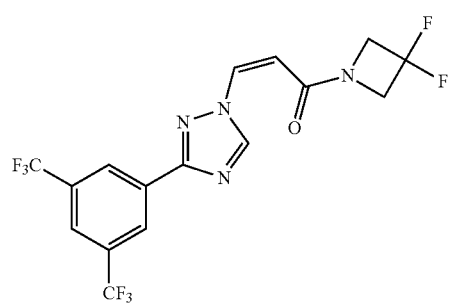 |
| 2 | |
| 3 | |

-continued
| Compound | Structure |
|---|---|
| 4 | 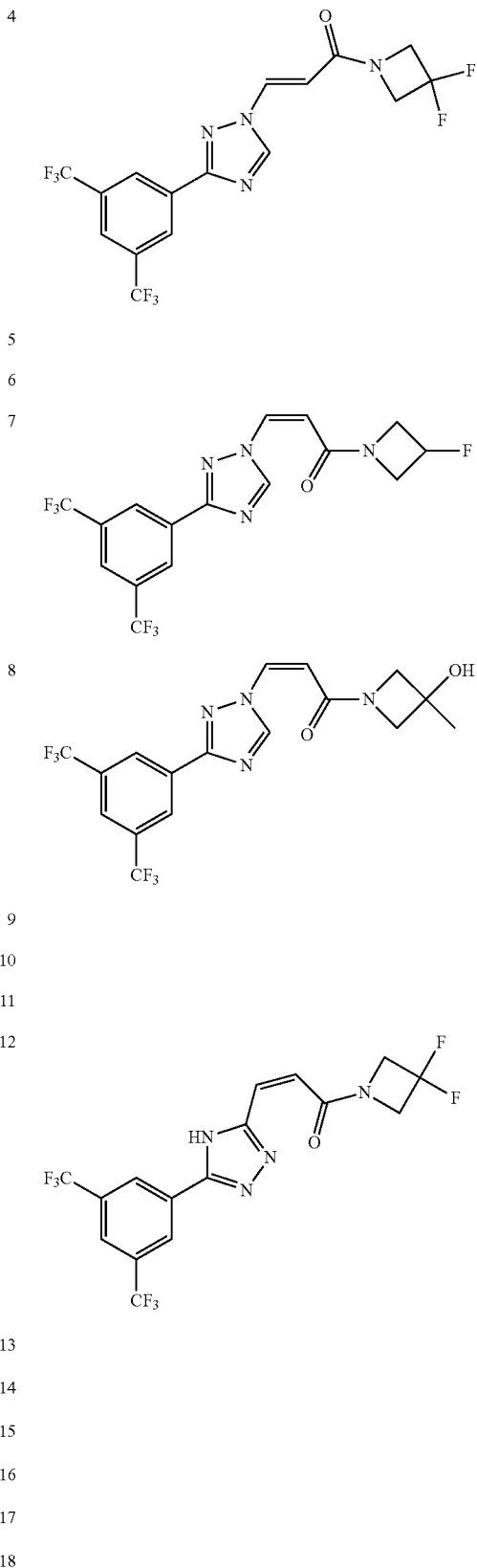 |
| 5 | |
| 6 | |
| 7 | 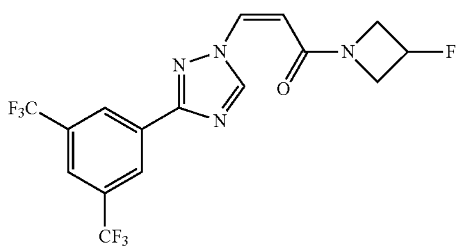 [SMILES: O=C(/C=C\n1cnc(-c2cc(C(F)(F)F)cc(C(F)(F)F)c2)n1)N1CC(F)C1] |
| 8 | 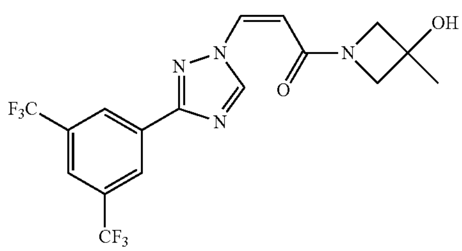 |
| 9 | |
| 10 | |
| 11 | |
| 12 | 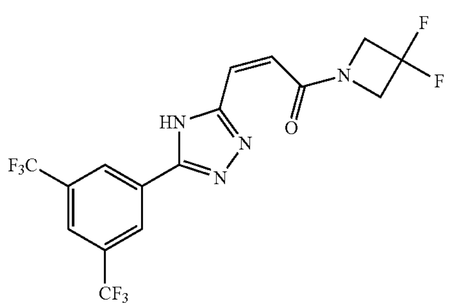 [SMILES: O=C(/C=C\c1nnc(-c2cc(C(F)(F)F)cc(C(F)(F)F)c2)[nH]1)N1CC(F)(F)C1] |
| 13 | |
| 14 | |
| 15 | |
| 16 | |
| 17 | |
| 18 | |
-continued
| Compound | Structure |
|---|---|
| 5 | |
| 19 | |
| 20 | |
| 21 | |
| 22 | |
| 23 | 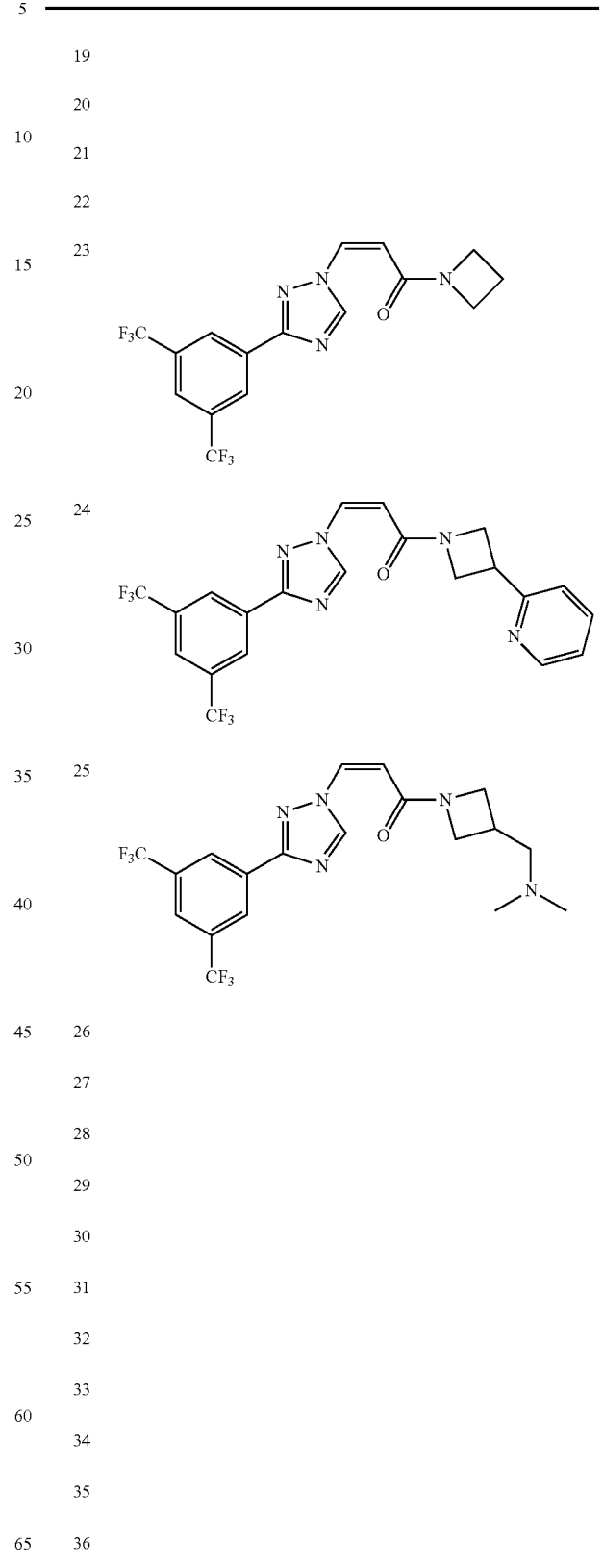 |
| 24 | 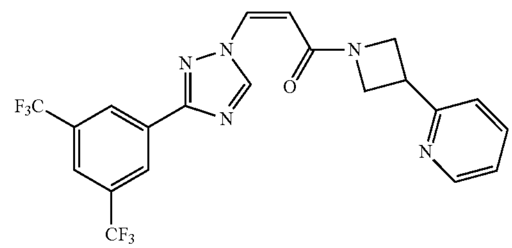 [SMILES: O=C(/C=C\n1cnc(-c2cc(C(F)(F)F)cc(C(F)(F)F)c2)n1)N1CC(c2ccccn2)C1] |
| 25 | 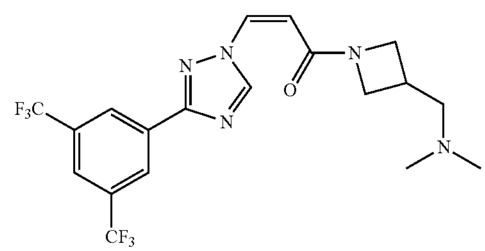 [SMILES: CN(C)CC1CN(C(=O)/C=C\n2cnc(-c3cc(C(F)(F)F)cc(C(F)(F)F)c3)n2)C1] |
| 26 | |
| 27 | |
| 28 | |
| 29 | |
| 30 | |
| 31 | |
| 32 | |
| 33 | |
| 34 | |
| 35 | |
| 36 | |

| Compound | Structure |
|---|---|
| 37 | [structure: 2-(3,5-bis(trifluoromethyl)phenyl)-1H-imidazole linked via cis-acrylamide to 3,3-difluoroazetidine] |
| 38 | |
| 39 | [structure: 3-(3,5-bis(trifluoromethyl)phenyl)-1,2,4-triazole linked via cis-acrylamide to 3-((methylamino)methyl)azetidine] |
| 40 | |
| 41 | |
| 45 | [structure: 3-(3,5-bis(trifluoromethyl)phenyl)-1,2,4-triazole linked via cis-acrylamide to 3-hydroxy-3-(pyridin-3-ylmethyl)azetidine] |
| 46 | [structure: 3-(3,5-bis(trifluoromethyl)phenyl)-1,2,4-triazole linked via cis-acrylamide to 3-hydroxy-3-(pyrazin-2-ylmethyl)azetidine] |
| 47 | [structure: 3-(3,5-bis(trifluoromethyl)phenyl)-1,2,4-triazole linked via cis-acrylamide to 3-fluoro-3-(pyrimidin-5-ylmethyl)azetidine] |

| Compound | Structure |
|---|---|
| 48 | [structure: 3-(3,5-bis(trifluoromethyl)phenyl)-1,2,4-triazole linked via cis-acrylamide to 3-fluoro-3-(pyridin-3-ylmethyl)azetidine] |
| 49 | [structure: 3-(3,5-bis(trifluoromethyl)phenyl)-1,2,4-triazole linked via cis-acrylamide to 3-fluoro-3-(pyrazin-2-ylmethyl)azetidine] |
| 50 | [structure: 3-(3,5-bis(trifluoromethyl)phenyl)-1,2,4-triazole linked via cis-acrylamide to 3-hydroxy-3-(2,2,2-trifluoroethyl)azetidine] |
| 51 | |
| 53 | |
| 54 | |
| 55 | |
| 57 | |
| 59 | |
| 60 | |
| 61 | |
| 62 | |
| 63 | |
| 65 | |
| 66 | |
| 68 | |
| 69. | |

6. The compound of claim 1, wherein the compound is represented by the following structural formula:

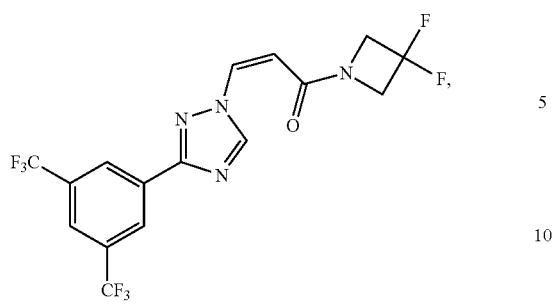
or a pharmaceutically acceptable salt thereof.
7. A composition comprising the compound of claim 1, or a pharmaceutically acceptable salt thereof, and a pharmaceutically acceptable carrier, adjuvant, or vehicle.
8. A method for modulating CRM1, the method comprising contacting CRM1 with an amount of the compound of claim 1 effective for modulating CRM1.
* * * * *